US012767945B2

(12) United States Patent
Gonatopoulos-Pournatzis et al.

(10) Patent No.: US 12,767,945 B2
(45) Date of Patent: Oct. 20, 2026

(54) METHODS AND COMPOSITIONS FOR MULTIPLEX GENE EDITING

(71) Applicant: THE GOVERNING COUNCIL OF THE UNIVERSITY OF TORONTO, Toronto (CA)

(72) Inventors: Thomas Gonatopoulos-Pournatzis, Toronto (CA); Michael Aregger, Toronto (CA); Jason Moffat, Toronto (CA); Benjamin J. Blencowe, Toronto (CA); Kevin Brown, Toronto (CA); Shaghayegh Farhangmehr, North York (CA)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 1269 days.

(21) Appl. No.: 17/615,007

(22) PCT Filed: Jun. 1, 2020

(86) PCT No.: PCT/IB2020/055181
§ 371 (c)(1),
(2) Date: Nov. 29, 2021

(87) PCT Pub. No.: WO2020/240523
PCT Pub. Date: Dec. 3, 2020

(65) Prior Publication Data

US 2022/0348910 A1 Nov. 3, 2022

(30) Foreign Application Priority Data

May 31, 2019 (GB) ..................................... 1907733

(51) Int. Cl.
*C12N 15/11* (2006.01)
*C12N 9/22* (2006.01)
(Continued)

(52) U.S. Cl.
CPC .......... *C12N 15/11* (2013.01); *C12N 15/1089* (2013.01); *C12N 15/64* (2013.01);
(Continued)

(58) Field of Classification Search
None
See application file for complete search history.

(56) References Cited

U.S. PATENT DOCUMENTS 9,688,972 B2 * 6/2017 May ........................ C12N 9/16
10,266,851 B2 * 4/2019 Chen ....................... C12N 9/22
(Continued)

FOREIGN PATENT DOCUMENTS

WO WO-2016196361 A1 * 12/2016 ............ C12N 15/63

OTHER PUBLICATIONS

Jinek et al. (A Programmable Dual-RNA-Guided DNA endonuclease in adaptive bacterial immunity, Science, 2012), (Year: 2012).*
(Continued)

*Primary Examiner* — Heather Calamita
*Assistant Examiner* — Elizabeth Rose Lafave
(74) *Attorney, Agent, or Firm* — SMART & BIGGAR LP

(57) ABSTRACT

A hybrid guide RNA (hgRNA) comprising a proximal spacer, a distal spacer, a type II CRISPR-Cas tracrRNA, and a type V CRISPR-Cas direct repeat. Also provided herein are further multiplexed hgRNAs comprising additional direct repeats and spacers as well as methods of making and using thereof. Libraries comprising said hgRNAs or components thereof, cells, kits and reagents employed in the making or use thereof are also provided.

10 Claims, 47 Drawing Sheets

Figure 1A:
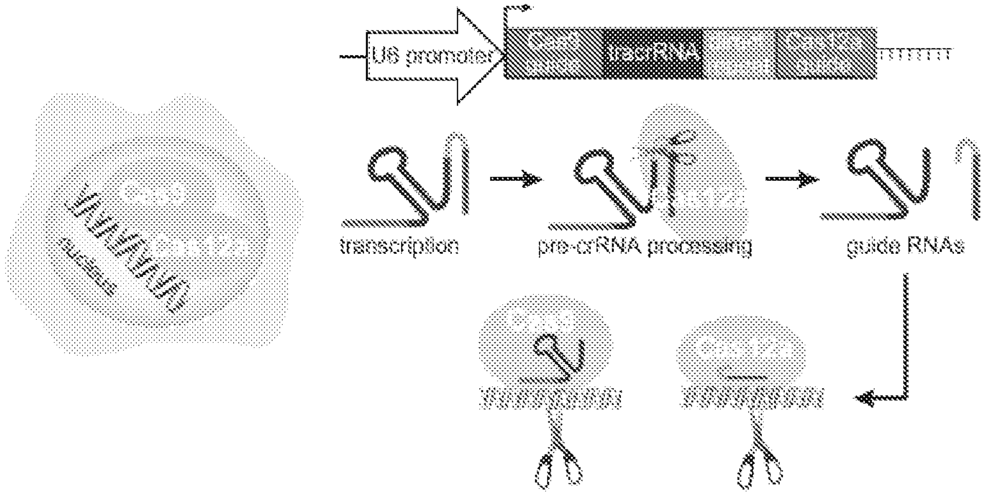

Specification includes a Sequence Listing.

(51) Int. Cl.

| | |
|---|---|
| ***C12N 15/10*** | (2006.01) |
| ***C12N 15/64*** | (2006.01) |
| ***C40B 40/06*** | (2006.01) |
| ***G16B 30/00*** | (2019.01) |
| ***G16B 40/20*** | (2019.01) |
| *C12N 15/90* | (2006.01) |

(52) U.S. Cl.

CPC ................ *G16B 30/00* (2019.02); *C12N 9/22* (2013.01); *C12N 15/1079* (2013.01); *C12N 15/111* (2013.01); *C12N 15/907* (2013.01); *C12N 2310/20* (2017.05); *C12N 2310/3519* (2013.01); *C12N 2330/31* (2013.01); *C12N 2740/16043* (2013.01); *C40B 40/06* (2013.01); *G16B 40/20* (2019.02)

(56) References Cited

U.S. PATENT DOCUMENTS

2016/0208243 A1* 7/2016 Zhang ................ C12N 15/8201
2019/0218547 A1* 7/2019 Lee ...................... C12N 15/907

OTHER PUBLICATIONS

Pineda-Lucena, A., Ho, C.S.W., Mao, D.Y.L., Sheng, Y., Laister, R.C., Muhandiram, R., Lu, Y., Seet, B.T., Katz, S., Szyperski, T., et al. (2005). A Structure-based Model of the c-Myc/Bin1 Protein Interaction Shows Alternative Splicing of Bin1 and c-Myc Phosphorylation are Key Binding Determinants. J. Mol. Biol. 351, 182-194.

Quesnel-Vallières, M., Weatheritt, R.J., Cordes, S.P., and Blencowe, B.J. (2019). Autism spectrum disorder: insights Into convergent mechanisms from transcriptomics. Nat. Rev. Genet. 20, 51-63.

Raj, B., Irimia, M., Braunschweig, U., Sterne-Weiler, T., O'Hanlon, D., Lin, Z.-Y., Chen, G.I., Easton, L.E., Ule, J., Gingras, A.-C., et al. (2014). A Global Regulatory Mechanism for Activating an Exon Network Required for Neurogenesis. Mol. Cell 56, 90-103.

Sack, L.M., Davoli, T., Xu, Q., Li, M.Z., and Elledge, S.J. (2016). Sources of Error in Mammalian Genetic Screens. G3: 6, 2781-2790.

Sakamuro, D., Elliott, K.J., Wechsler-Reya, R., and Prendergast, G.C. (1996). BIN1 is a novel MYC-interacting protein with features of a tumour suppressor. Nat. Genet. 14, 69-77.

Saxton, R.A., and Sabatini, D.M. (2017). mTOR Signaling in Growth, Metabolism, and Disease. Cell 168, 960-976.

Scotti, M.M., and Swanson, M.S. (2016). RNA mis-splicing in disease. Nat. Rev. Genet. 17, 19-32.

Shalem, O., Sanjana, N.E., Hartenian, E., Shi, X., Scott, D.A., Mikkelsen, T.S., Heckl, D., Ebert, B.L., Root, D.E., Doench, J.G., et al. (2014). Genome-scale CRISPR-Cas9 knockout screening in human cells. Science 343, 84-87.

Shen, J.P., Zhao, D., Sasik, R., Luebeck, J., Birmingham, A., Bojorquez-Gomez, A., Licon, K., Klepper, K., Pekin, D., Beckett, A.N., et al. (2017a). Combinatorial CRISPR-Cas9 screens for de novo mapping of genetic interactions. Nat. Methods 14, 573-576.

Shen, J.P., Zhao, D., Sasik, R., Luebeck, J., Birmingham, A., Bojorquez-Gomez, A., Licon, K., Klepper, K., Pekin, D., Beckett, A.N., et al. (2017b). Combinatorial CRISPR-Cas9 screens for de novo mapping of genetic interactions. Nat. Methods.

Shifrut, E., Carnevale, J., Tobin, V., Roth, T.L., Woo, J.M., Bui, C.T., Li, P.J., Diolaiti, M.E., Ashworth, A., and Marson, A. (2018). Genome-wide CRISPR Screens in Primary Human T Cells Reveal Key Regulators of Immune Function. Cell 175, 1958-1971.e15.

Shu, L., and Houghton, P.J. (2009). The mTORC2 Complex Regulates Terminal Differentiation of C2C12 Myoblasts. Mol. Cell. Biol. 29, 4691-4700.

Singh, P.P., Arora, J., and Isambert, H. (2015). Identification of Ohnolog Genes Originating from Whole Genome Duplication in Early Vertebrates, Based on Synteny Comparison across Multiple Genomes. PLOS Comput. Biol. 11, e1004394.

Slovackova, J., Smarda, J., and Smardova, J. (2012). Roscovitine-induced apoptosis of H1299 cells depends on functional status of p53. Neoplasma 59, 606-612.

Stockman, V.B., Ghamsari, L., Lasso, G., Honig, B., Shapira, S.D., and Wang, H.H. (2016). A High-Throughput Strategy for Dissecting Mammalian Genetic Interactions. PLoS One 11, e0167617.

Tapial, J., Ha, K.C.H., Sterne-Weiler, T., Gohr, A., Braunschweig, U., Hermoso-Pulido, A., Quesnel-Vallières, M., Permanyer, J., Sodaei, R., Marquez, Y., et al. (2017). An atlas of alternative splicing profiles and functional associations reveals new regulatory programs and genes that simultaneously express multiple major isoforms. Genome Res. 27, 1759-1768.

Thoreen, C.C., Kang, S. a, Chang, J.W., Liu, Q., Zhang, J., Gao, Y., Reichling, L.J., Sim, T., Sabatini, D.M., and Gray, N.S. (2009). An ATP-competitive mammalian target of rapamycin inhibitor reveals rapamycin-resistant functions of mTORC1. J. Biol. Chem. 284, 8023-8032.

Tsang, C.K., Bertram, P.G., Ai, W., Drenan, R., and Zheng, X.F.S. (2003). Chromatin-mediated regulation of nucleolar structure and RNA Pol I localization by TOR. EMBO J. 22, 6045-6056.

Valvezan, A.J., and Manning, B.D. (2019). Molecular logic of mTORC1 signalling as a metabolic rheostat. Nat. Metab. 1, 321-333.

Varier, R.A., de Santa Pau, E.C., van der Groep, P., Lindeboom, R.G.H., Matarese, F., Mensinga, A., Smits, A.H., Edupuganti, R.R., Baltissen, M.P., Jansen, P.W.T.C., et al. (2016). Recruitment of the Mammalian Histone-modifying EMSY Complex to Target Genes Is Regulated by ZNF131. J. Biol. Chem. 291, 7313-7324.

Vidigal, J.A., and Ventura, A. (2015). Rapid and efficient one-step generation of paired gRNA CRISPR-Cas9 libraries. Nat. Commun. 6, 8083.

Viswanathan, S.R., Nogueira, M.F., Buss, C.G., Krill-Burger, J.M., Wawer, M.J., Malolepsza, E., Berger, A.C., Choi, P.S., Shih, J., Taylor, A.M., et al. (2018). Genome-scale analysis identifies paralog lethality as a vulnerability of chromosome 1p loss in cancer. Nat. Genet. 50, 937-943.

Wang, G., Zimmermann, M., Mascall, K., Lenoir, W.F., Moffat, J., Angers, S., Durocher, D., and Hart, T. (2017). Identifying drug-gene interactions from CRISPR knockout screens with drugZ. bioRxiv 232736.

Wang, T., Wei, J.J., Sabatini, D.M., and Lander, E.S. (2014). Genetic screens in human cells using the CRISPR-Cas9 system. Science 343, 80-84.

Wang, T., Birsoy, K., Hughes, N.W., Krupczak, K.M., Post, Y., Wei, J.J., Lander, E.S., and Sabatini, D.M. (2015). Identification and characterization of essential genes in the human genome. Science 350, 1096-1101.

Wong, A.S.L., Choi, G.C.G., Cui, C.H., Pregernig, G., Milani, P., Adam, M., Perli, S.D., Kazer, S.W., Gaillard, A., Hermann, M., et al. (2016). Multiplexed barcoded CRISPR-Cas9 screening enabled by CombiGEM. Proc. Natl. Acad. Sci. 113, 2544-2549.

Wright, A.V., Nuñez, J.K., and Doudna, J.A. (2016). Biology and Applications of CRISPR Systems: Harnessing Nature's Toolbox for Genome Engineering. Cell 164, 29-44.

Xu, H., Xiao, T., Chen, C.-H., Li, W., Meyer, C.A., Wu, Q., Wu, D., Cong, L., Zhang, F., Liu, J.S., et al. (2015). Sequence determinants of improved CRISPR sgRNA design. Genome Res. 25, 1147-1157.

Zetsche, B., Gootenberg, J.S., Abudayyeh, O.O., Slaymaker, I.M., Makarova, K.S., Essletzbichler, P., Volz, S.E., Joung, J., van der Oost, J., Regev, A., et al. (2015). Cpf1 Is a Single RNA-Guided Endonuclease of a Class 2 CRISPR-Cas System. Cell 163, 759-771.

Zetsche, B., Heidenreich, M., Mohanraju, P., Fedorova, I., Kneppers, J., DeGennaro, E.M., Winblad, N., Choudhury, S. R., Abudayyeh, O.O., Gootenberg, J.S., et al. (2016). Multiplex gene editing by CRISPR-Cpf1 using a single crRNA array. Nat. Biotechnol. 35, 31-34.

Zhu, H., Shyh-Chang, N., Segre, A. V, Shinoda, G., Shah, S.P., Einhorn, W.S., Takeuchi, A., Engreitz, J.M., Hagan, J. P., Kharas, M.G., et al. (2011). The Lin28/let-7 axis regulates glucose metabolism. Cell 147, 81-94.

Zhu, S., Li, W., Liu, J., Chen, C.-H., Liao, Q., Xu, P., Xu, H., Xiao, T., Cao, Z., Peng, J., et al. (2016). Genome-scale deletion screening

(56) References Cited

OTHER PUBLICATIONS of human long non-coding RNAs using a paired-guide RNA CRISPR-Cas9 library. Nat. Biotechnol. 34, 1279-1286.
Gonatopoulos-Pournatzis et al. Genetic interation mapping and exon-resolution functional genomics with a hybrid Cas9-Cas12a platform. Nature Biotechnology. May 2020. vol. 38, pp. 638-648.
Kweon et al. Fusion guide RNAs for orhogonal gene manipulation with Cas9 and Cpf1. Nature Communications, 2017, vol. 8, No. 1723, pp. 1-6.
Adamson, B., Norman, T.M., Jost, M., Cho, M.Y., Nuñez, J.K., Chen, Y., Villalta, J.E., Gilbert, L.A., Horlbeck, M.A., Hein, M.Y., et al. (2016). A Multiplexed Single-Cell CRISPR Screening Platform Enables Systematic Dissection of the Unfolded Protein Response. Cell 167, 1867-1882.e21.
Ashworth, A., Lord, C.J., and Reis-Filho, J.S. (2011). Genetic Interactions in Cancer Progression and Treatment. Cell 145, 30-38.
Bassik, M.C., Kampmann, M., Lebbink, R.J., Wang, S., Hein, M.Y., Poser, I., Weibezahn, J., Horlbeck, M.A., Chen, S., Mann, M., et al. (2013a). A systematic mammalian genetic interaction map reveals pathways underlying ricin susceptibility. Cell 152, 909-922.
Berriz, G. F., King, O. D., Bryant, B., Sander, C. & Roth, F. P. Characterizing gene sets with FuncAssociate. Bioinformatics 19, 2502-2504 (2003).
Boettcher, M., Tian, R., Blau, J.A., Markegard, E., Wagner, R.T., Wu, D., Mo, X., Biton, A., Zaitlen, N., Fu, H., et al. (2018). Dual gene activation and knockout screen reveals directional dependencies in genetic networks. Nat. Biotechnol. 36, 170-178.
Brake, O. ter, Hooft, K. 't, Liu, Y.P., Centlivre, M., Jasmijn von Eije, K., and Berkhout, B. (2008). Lentiviral Vector Design for Multiple shRNA Expression and Durable HIV-1 Inhibition. Mol. Ther. 16, 557-564.
Breinig, M., Schweitzer, A.Y., Herianto, A.M., Revia, S., Schaefer, L., Wendler, L., Cobos Galvez, A., and Tschaharganeh, D.F. (2019). Multiplexed orthogonal genome editing and transcriptional activation by Cas12a. Nat. Methods 16, 51-54.
Chow, R.D., Wang, G., Codina, A., Ye, L., and Chen, S. (2017). Mapping in vivo genetic interactomics through Cpf1 crRNA array screening. bioRxiv 153486.
Cock, P.J.A., Antao, T., Chang, J.T., Chapman, B.A., Cox, C.J., Dalke, A., Friedberg, I., Hamelryck, T., Kauff, F., Wilczynski, B., et al. (2009). Biopython: freely available Python tools for computational molecular biology and bioinformatics. Bioinformatics 25, 1422-1423.
Cong, L., Ran, F.A., Cox, D., Lin, S., Barretto, R., Habib, N., Hsu, P.D., Wu, X., Jiang, W., Marraffini, L.A., et al. (2013). Multiplex genome engineering using CRISPR/Cas systems. Science 339, 819-823.
Costanzo, M., VanderSluis, B., Koch, E.N., Baryshnikova, A., Pons, C., Tan, G., Wang, W., Usaj, M., Hanchard, J., Lee, S.D., et al. (2016). A global genetic interaction network maps a wiring diagram of cellular function. Science 353, aaf1420-aaf1420.
Costanzo, M., Kuzmin, E., van Leeuwen, J., Mair, B., Moffat, J., Boone, C., and Andrews, B. (2019). Global Genetic Networks and the Genotype-to-Phenotype Relationship. Cell 177, 85-100.Dang, Y. et al. Optimizing sgRNA structure to improve CRISPR-Cas9 knockout efficiency. Genome Biol. 16, 280 (2015).
Doench, J.G. (2018). Am i ready for Crispr? A user's guide to genetic screens. Nat. Rev. Genet. 19, 67-80.
Doench, J.G., Fusi, N., Sullender, M., Hegde, M., Vaimberg, E.W., Donovan, K.F., Smith, I., Tothova, Z., Wilen, C., Orchard, R., et al. (2016). Optimized sgRNA design to maximize activity and minimize off-target effects of CRISPR-Cas9. Nat. Biotechnol. 34, 184-191.
Dominguez, D., Tsai, Y.-H., Weatheritt, R., Wang, Y., Blencowe, B.J., and Wang, Z. (2016). An extensive program of periodic alternative splicing linked to cell cycle progression. Elife 5.
Dvinge, H., Kim, E., Abdel-Wahab, O., and Bradley, R.K. (2016). RNA splicing factors as oncoproteins and tumour suppressors. Nat. Rev. Cancer 16, 413-430.
Ewen-Campen, B., Mohr, S.E., Hu, Y., and Perrimon, N. (2017). Accessing the Phenotype Gap: Enabling Systematic Investigation of Paralog Functional Complexity with CRISPR. Dev. Cell 43, 6-9.
Fonfara, I., Richter, H., Bratovic, M., Le Rhun, A., and Charpentier, E. (2016). The CRISPR-associated DNA-cleaving enzyme Cpf1 also processes precursor CRISPR RNA. Nature 532, 517-521.
Ge, K., DuHadaway, J., Du, W., Herlyn, M., Rodeck, U., and Prendergast, G.C. (1999). Mechanism for elimination of a tumor suppressor: aberrant splicing of a brain-specific exon causes loss of function of Bin1 in melanoma. Proc. Natl. Acad. Sci. U. S. A. 96, 9689-9694.
Gonatopoulos-Pournatzis, T., Wu, M., Braunschweig, U., Roth, J., Han, H., Best, A.J., Raj, B., Aregger, M., O'Hanlon, D., Ellis, J.D., et al. (2018). Genome-wide CRISPR-Cas9 Interrogation of Splicing Networks Reveals a Mechanism for Recognition of Autism-Misregulated Neuronal Microexons. Mol. Cell 72, 510-524.e12.
Gu, Z., Steinmetz, L.M., Gu, X., Scharfe, C., Davis, R.W., and Li, W.-H. (2003). Role of duplicate genes in genetic robustness against null mutations. Nature 421, 63-66.
Gueroussov, S., Gonatopoulos-Pournatzis, T., Irimia, M., Raj, B., Lin, Z.-Y., Gingras, A.-C., and Blencowe, B.J. (2015). An alternative splicing event amplifies evolutionary differences between vertebrates. Science 349, 868-873.
Guschin, D.Y., Waite, A.J., Katibah, G.E., Miller, J.C., Holmes, M.C., and Rebar, E.J. (2010). A rapid and general assay for monitoring endogenous gene modification. Methods Mol. Biol. 649, 247-256.
Haapaniemi, E., Botla, S., Persson, J., Schmierer, B., and Taipale, J. (2018). CRISPR-Cas9 genome editing induces a p53-mediated DNA damage response. Nat. Med. 24, 927-930.
Han, K., Jeng, E.E., Hess, G.T., Morgens, D.W., Li, A., and Bassik, M.C. (2017). Synergistic drug combinations for cancer identified in a CRISPR screen for pairwise genetic interactions. Nat. Biotechnol. 35, 463-474.
Haney, M.S., Bohlen, C.J., Morgens, D.W., Ousey, J.A., Barkal, A.A., Tsui, C.K., Ego, B.K., Levin, R., Kamber, R.A., Collins, H., et al. (2018). Identification of phagocytosis regulators using magnetic genome-wide CRISPR screens. Nat. Genet. 50, 1716-1727.
Hart, T., Chandrashekhar, M., Aregger, M., Steinhart, Z., Brown, K.R., Macleod, G., Mis, M., Zimmermann, M., Fradet-Turcotte, A., Sun, S., et al. (2015). High-Resolution CRISPR Screens Reveal Fitness Genes and Genotype-Specific Cancer Liabilities. Cell 163, 1515-1526.
Hart, T., Tong, A.H.Y., Chan, K., Van Leeuwen, J., Seetharaman, A., Aregger, M., Chandrashekhar, M., Hustedt, N., Seth, S., Noonan, A., et al. (2017). Evaluation and Design of Genome-Wide CRISPR/SpCas9 Knockout Screens. G3: 7, 2719-2727.
Horlbeck, M.A., Xu, A., Wang, M., Bennett, N.K., Park, C.Y., Bogdanoff, D., Adamson, B., Chow, E.D., Kampmann, M., Peterson, T.R., et al. (2018). Mapping the Genetic Landscape of Human Cells. Cell 174, 953-967.e22.
Hubbard, K.S., Gut, I.M., Lyman, M.E., and McNutt, P.M. (2013). Longitudinal RNA sequencing of the deep transcriptome during neurogenesis of cortical glutamatergic neurons from murine ESCs. F1000Research 2, 35.
Jinek, M., Chylinski, K., Fonfara, I., Hauer, M., Doudna, J.A., and Charpentier, E. (2012). A Programmable Dual-RNA-Guided DNA Endonuclease in Adaptive Bacterial Immunity. Science 337, 816-821.
Kafri, R., Springer, M., and Pilpel, Y. (2009). Genetic Redundancy: New Tricks for Old Genes. Cell 136, 389-392.
Ke, M., Mo, L., Li, W., Zhang, X., Li, F., and Yu, H. (2017). Ubiquitin ligase SMURF1 functions as a prognostic marker and promotes growth and metastasis of clear cell renal cell carcinoma. FEBS Open Bio 7, 577-586.
Kim, H.K., Song, M., Lee, J., Menon, A.V., Jung, S., Kang, Y.-M., Choi, J.W., Woo, E., Koh, H.C., Nam, J.-W., et al. (2017). In vivo high-throughput profiling of CRISPR-Cpf1 activity. Nat. Methods 14, 153-159.
Kim, H.K., Min, S., Song, M., Jung, S., Choi, J.W., Kim, Y., Lee, S., Yoon, S., and Kim, H.H. (2018). Deep learning Improves prediction of CRISPR-Cpf1 guide RNA activity. Nat. Biotechnol. 36, 239-241.

(56) References Cited

OTHER PUBLICATIONS

Koo, J., Yue, P., Gal, A.A., Khuri, F.R., and Sun, S.-Y. (2014). Maintaining Glycogen Synthase Kinase-3 Activity Is Critical for mTOR Kinase Inhibitors to Inhibit Cancer Cell Growth. Cancer Res. 74, 2555-2568.

Koo, J., Yue, P., Deng, X., Khuri, F.R., and Sun, S.-Y. (2015). mTOR Complex 2 Stabilizes Mcl-1 Protein by Suppressing Its Glycogen Synthase Kinase 3-Dependent and SCF-FBXW7-Mediated Degradation. Mol. Cell. Biol. 35, 2344-2355.

Kuzmin, E., VanderSluis, B., Wang, W., Tan, G., Deshpande, R., Chen, Y., Usaj, M., Balint, A., Mattiazzi Usaj, M., van Leeuwen, J., et al. (2018). Systematic analysis of complex genetic interactions. Science 360, eaao1729.

Li, M., Yu, J.S.L., Tilgner, K., Ong, S.H., Koike-Yusa, H., and Yusa, K. (2018). Genome-wide CRISPR-KO Screen Uncovers mTORC1-Mediated Gsk3 Regulation in Naive Pluripotency Maintenance and Dissolution. Cell Rep. 24, 489-502.

Listgarten, J., Weinstein, M., Kleinstiver, B.P., Sousa, A.A., Joung, J.K., Crawford, J., Gao, K., Hoang, L., Elibol, M., Doench, J.G., et al. (2018). Prediction of off-target activities for the end-to-end design of CRISPR guide RNAs. Nat. Biomed. Eng. 2, 38-47.

Liu, Y., Yu, C., Daley, T.P., Wang, F., Cao, W.S., Bhate, S., Lin, X., Still, C., Liu, H., Zhao, D., et al. (2018). CRISPR Activation Screens Systematically Identify Factors that Drive Neuronal Fate and Reprogramming. Cell Stem Cell 23, 758-771.e8.

Lorenz, R., Bernhart, S.H., Honer zu Siederdissen, C., Tafer, H., Flamm, C., Stadler, P.F., and Hofacker, I.L. (2011). ViennaRNA Package 2.0. Algorithms Mol. Biol. 6, 26.

Lynch, M., and Conery, J.S. (2000). The evolutionary fate and consequences of duplicate genes. Science 290, 1151-1155.

Mali, P., Yang, L., Esvelt, K.M., Aach, J., Guell, M., DiCarlo, J.E., Norville, J.E., and Church, G.M. (2013). RNA-Guided Human Genome Engineering via Cas9. Science 339, 823-826.

Martin, T.D., Chen, X.-W., Kaplan, R.E.W., Saltiel, A.R., Walker, C.L., Reiner, D.J., and Der, C.J. (2014). Ral and Rheb GTPase Activating Proteins Integrate mTOR and GTPase Signaling in Aging, Autophagy, and Tumor Cell Invasion. Mol. Cell 53, 209-220.

Meyer, C., Garzia, A., Mazzola, M., Gerstberger, S., Molina, H., and Tuschl, T. (2018). The TIA1 RNA-Binding Protein Family Regulates EIF2AK2-Mediated Stress Response and Cell Cycle Progression. Mol. Cell 69, 622-635.e6.

Najm, F.J., Strand, C., Donovan, K.F., Hegde, M., Sanson, K.R., Vaimberg, E.W., Sullender, M.E., Hartenian, E., Kalani, Z., Fusi, N., et al. (2017a). Orthologous CRISPR-Cas9 enzymes for combinatorial genetic screens. Nat. Biotechnol. 36, 179-189.

Park, R.J., Wang, T., Koundakjian, D., Hultquist, J.F., Lamothe-Molina, P., Monel, B., Schumann, K., Yu, H., Krupzcak, K.M., Garcia-Beltran, W., et al. (2016). A genome-wide CRISPR screen identifies a restricted set of HIV host dependency factors. Nat. Genet. 49, 193-203.

Patel, S.J., Sanjana, N.E., Kishton, R.J., Eidizadeh, A., Vodnala, S.K., Cam, M., Gartner, J.J., Jia, L., Steinberg, S.M., Yamamoto, T.N., et al. (2017). Identification of essential genes for cancer immunotherapy. Nature 548, 537-542.

Peterson, T.R., Laplante, M., Van Veen, E., Van Vugt, M., Thoreen, C.C., and Sabatini, D.M. (2015). mTORC1 regulates cytokinesis through activation of Rho-ROCK signaling.

* cited by examiner

Fig. 14

CHyMErA Cas9-Cas12a Hybrid gRNA System

Cas9 target sequence:

NNNNNNNNNNNNNNNNNNNVNGG
NNNNNNNNNNNNNNNNNNNBNCC

20nt guide

Cas12a target sequence:

TTTVNNNNNNNNNNNNNNNNNNNNNNN
AAABNNNNNNNNNNNNNNNNNNNNNNN

23nt guide

Library Cloning Strategy

1. PCR amplify hybrid gRNA oligos
2. Digest pLCHKO vector backbone and amplified hybrid oligos with BfuAI
3. Ligate hybrid oligo pool into pLCHKO
4. Digest pLCHKO-hybrid oligo vector and the TOPO tracrRNA-DR fragment with BsmBI
5. Ligate tracrRNA-DR fragment into pLCHKO-hybrid oligo vector

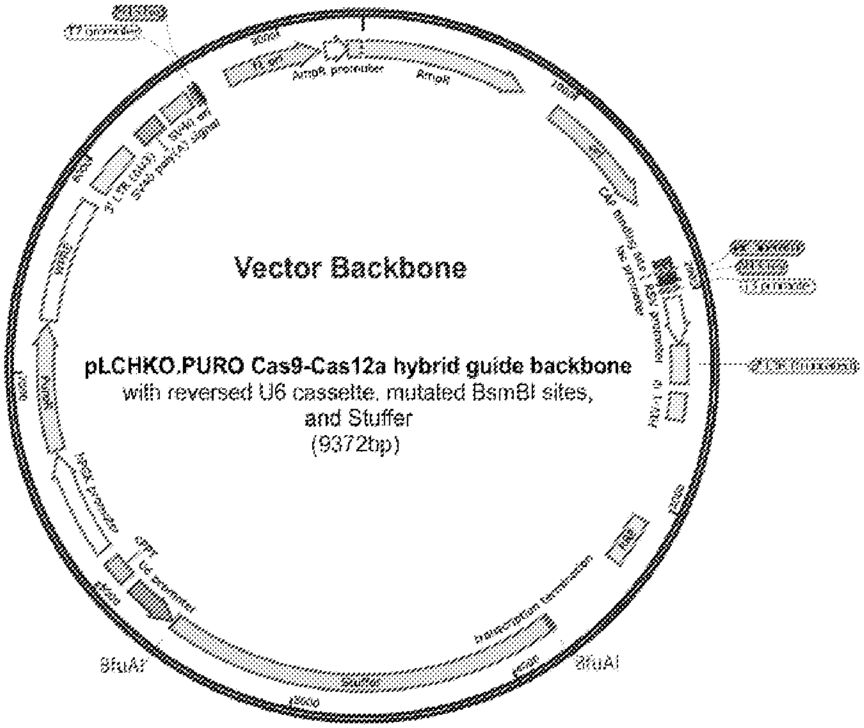

Fig. 16C

| Criteria | CHyMErA | BigPapi | dual Cas9 |
|---|---|---|---|
| | *This study* | *(Najm et al.)* | *(e.g. Hahn et al., Shen et al.)* |
| Nuclease(s) | Sp-Cas9 & Lb-Cas12a (As-Cas12a) | Sp-Cas9 & Sa-Cas9 | Sp-Cas9 |
| PAM site(s) | NGG & TTTV | NGG & NNGRRT | NGG |
| gRNA expression | Single promoter | Multiple promoters | Multiple promoters |
| tracrRNA diversity | Yes | Yes | No |
| Gene sets used for gRNA optimization | >480 core essential genes (for both human and mouse) | 1. EEF and CD81<br>2. 9 genes | N/A |
| gRNA design rules | Yes (CNN score) | Yes | Established |
| Higher-order multiplexing | Yes | No | No |
| Programmable libraries | Yes | No (random assortment) | No (random assortment) |
| Exon deletion | Yes | No | No |
| Dual gene targeting | Yes | No | No |
| Paralog targeting | Yes | No | No |
| Genetic interaction mapping | Yes | Yes | Yes |
| Potential for combination of Cas modalities | Yes | Yes | No |
| Vector component | 3 (Cas9; Cas12a;hgRNA) | 2 (Sp-Cas9; Sa-Cas9 & sgRNAs) | 2 (Sp-Cas9; sgRNAs) |

METHODS AND COMPOSITIONS FOR MULTIPLEX GENE EDITING

CROSS REFERENCE TO RELATED APPLICATION

The present application is a national phase entry of Patent Cooperation Treaty Application PCT/IB2020/055181, filed 1 Jun. 2020, which claims the benefit of priority of GB provisional patent application No. GB1907733.8 entitled "Methods and compositions for multiplex gene editing", filed 31 May 2019, each of which is incorporated herein by reference in their entirety.

INCORPORATION OF SEQUENCE LISTING

A computer readable form of the Sequence Listing "P56951US00_Sequence_Listing_Revised" (37,923 bytes) created on Jun. 6, 2022, is herein incorporated by reference.

FIELD

The present disclosure relates to reagents and methods for multiplex gene targeting and in particular to CRISPR-based reagents and methods for multiplex gene targeting.

INTRODUCTION

Breakthroughs in gene editing technologies over the past several years have transformed mammalian cell genetics and disease research by enabling fastidious genome engineering and genome-scale genetic screens (Cong et al., 2013; Jinek et al., 2012; Mali et al., 2013; Wright et al., 2016). The development of high-complexity genome-scale CRISPR (clustered regularly interspaced short palindromic repeats) libraries have started delivering insight into genotype-to-phenotype relationships (Doench, 2018). For example, genome-wide pooled CRISPR-Cas9 screens have defined a core set of essential genes that are required for human cell proliferation and that share functional, evolutionary and physiological properties with essential genes in other model organisms (Hart et al., 2015; Shalem et al., 2014; Wang et al., 2014, 2015). These studies have laid the groundwork for a new era of functional genomics for systematically characterizing genes that underlie critical biological processes such as stem cell pluripotency, neuronal differentiation, T cell function, cancer immunotherapy, viral infection, phagocytosis and alternative splicing regulation (Mair et al., 2019., Gonatopoulos-Pournatzis et al., 2018; Haney et al., 2018; Li et al., 2018; Liu et al., 2018; Park et al., 2016; Patel et al., 2017; Shifrut et al., 2018). Despite these advances, major challenges in functional genomics include the development of tools for the phenotypic interrogation of gene segments, such as the myriad of previously uncharacterized alternative exons associated with normal biology and disease, and the mapping of genetic interactions.

Systematic efforts to identify genetic interactions or 'GIs' (i.e. deviations from expected phenotypes when combining multiple genetic mutations) are crucial for advancing knowledge of gene function and how genome alterations contribute to human diseases and disorders (Ashworth et al., 2011). Studies using the budding yeast as a model system have led to the creation of global genetic interaction networks and wiring diagrams of cellular function (Costanzo et al., 2016, 2019). Current efforts in functional genomics are directed towards exploiting CRISPR-Cas screening platforms to systematically map genetic interactions in mammalian cells. In this regard, an important question is the extent to which paralogous mammalian genes contribute to phenotypic robustness. Functional redundancy between genes or pathways is widespread in higher organisms as a consequence of whole genome duplication events during vertebrate evolution, as well as smaller scale events that gave rise to paralogous genes (Lynch and Conery, 2000). Redundant gene functions have been preserved across many cellular processes including signalling, developmental regulation and metabolism, enabling buffering of cellular systems and adaptations to environmental changes (Kafri et al., 2009). However, it is unclear to what extent paralog genes have retained redundant functions and which of these redundancies impact cell proliferation in human cells. Similarly, it is also not known to what extent annotated alternative exons contribute to critical cell functions.

Key to addressing the above questions is the generation of a functional genomics tool for combinatorial genetic perturbation. Although several screening systems employing expression of two or more Cas9 guides from multiple promoters have been described (Han et al., 2017; Najm et al., 2017a; Shen et al., 2017a; Wong et al., 2016; Zhu et al., 2016), a limitation of these approaches is reduced editing efficiency, as a consequence of recombination between expression cassettes (Adamson et al., 2016; Brake et al., 2008; Han et al., 2017; Sack et al., 2016; Vidigal and Ventura, 2015). Cas12a (formerly known as Cpf1) enzymes contain intrinsic RNAse activity and can generate multiple guide (g)RNAs from a single concatemeric guide RNA transcript (Fonfara et al., 2016; Zetsche et al., 2015, 2016), making this an attractive option for combinatorial gene targeting. However, the reported efficiency of generating multiple indels in the same cell with Cas12a is <15% (Zetsche et al., 2016), and it is thought that distinct gRNAs may compete for loading into the common effector enzyme leading to decreased overall efficiency (Stockman et al., 2016). Nevertheless, Cas12a has been exploited in positive selection screens to identify pairwise genetic interactions between tumor suppressor genes that, when ablated, accelerate tumor growth in lung metastases models (Chow et al., 2017). However, targeting efficiency has been a major limitation in screens where phenotypes are being scored in the absence of selection.

Additional screening approaches are needed.

SUMMARY

A system that uses co-expression of orthologous class II monomeric Cas enzymes such as Cas9 and Cas12a nucleases, together with "hybrid guide" (hg) RNAs, generated from fusion constructs comprising Cas9 and Cas12a gRNAs expressed from a single promoter is described herein. It is demonstrated herein that an embodiment of the system, referred to as Cas Hybrid for Multiplexed Editing and Screening Applications or CHyMErA, is among other uses, an effective platform for the large-scale analysis of exon function, by identifying alternative exons that are important for cell fitness.

Also described herein are optimized hgRNAs designed using a deep learning framework, for example as shown for both the human and mouse genomes, through iterative rounds of pooled hgRNA library construction and screening in both human and mouse cells. As demonstrated herein, optimized Cas12a gRNA efficiencies are comparable to the most efficient Cas9 gRNAs. An optimized genome-scale, high-complexity hgRNA library that targets 672 human paralog pairs representing 1344 genes, or >90% of predicted paralogs in the human genome, was used to identify genetic interactors (GIs) and chemical-GIs. The results demonstrate a previously unappreciated complexity of GIs and chemical-GIs involving paralogous genes in human cells.

Accordingly, one aspect of the disclosure includes a hybrid guide RNA (hgRNA) comprising from 5' to 3' a proximal spacer RNA, a type II CRISPR-Cas tracrRNA, a type V CRISPR-Cas direct repeat, and a distal spacer RNA, wherein the proximal spacer is configured to target a type II CRISPR target site and the distal spacer is configured to target a type V CRISPR target site.

Another aspect of the disclosure includes a construct comprising an hgRNA expression cassette. A further aspect of the disclosure includes a nucleic acid library comprising a multiplicity of hgRNAs or a nucleic acid library comprising a multiplicity of constructs comprising an hgRNA expression cassette.

In another embodiment, the hgRNA is capable of being processed by a type V Cas protein, preferably a Cas12a protein, into a first and a second mature guide RNA.

In another embodiment, the hgRNA further comprises one or more additional direct repeats and one or more additional spacers, wherein the one or more additional spacers are capable of being processed into mature guide RNAs by a type V Cas protein, preferably a Cas12a protein.

In an embodiment, the type II Cas is a Cas9. In an embodiment, the Cas9 is from *Streptococcus pyogenes* and/or comprises an amino acid sequence with at least 80%, at least 90%, at least 95%, at least 99% or 100% sequence identity to a protein encoded by SEQ ID NO: 19 and having Cas9 activity (e.g. binding the gRNA and the target site).

In an embodiment, the type V Cas is a Cas12a. In an embodiment, the Cas12a is from *Acidaminococcus* sp. BV3L6 (As-Cas12a) or preferably from *Lachnospiraceae bacterium* (Lb-Cas12a). In an embodiment, the Cas12a is a protein comprising an amino acid sequence with at least 80%, at least 90%, at least 95%, at least 99% or 100% sequence identity to a protein encoded by SEQ ID NO: 20 or SEQ ID NO 21 and having Cas12a activity (e.g. binding the gRNA and the target site). In an embodiment, the type V Cas protein possesses DNA and/or RNA processing activity. Preferably the type V Cas protein possesses RNA processing activity.

In another embodiment, the proximal spacer is configured to target a Cas9 target site and/or the distal spacer is configured to target a Cas12a target site.

In another embodiment, the proximal spacer is 15 to 25, 16 to 24, 17 to 23, 18 to 22, or 19 to 21 nucleotides in length, optionally 20 nucleotides in length.

In another embodiment, the distal spacer is 15 to 28, 16 to 27, 17 to 26, 18 to 25, or 19 to 24 nucleotides in length, optionally 20, 21, 22, or 23 nucleotides in length.

In another embodiment, the tracrRNA has the sequence as set out in SEQ ID NO: 5. In another embodiment, the direct repeat is an Lb-Cas12a direct repeat, optionally having a sequence as set out in SEQ ID NO: 6, or an As-Cas12a direct repeat, optionally having a sequence as set out in SEQ ID NO: 7. In another embodiment, the hgRNA has a sequence as set out in SEQ ID NO: 8 or SEQ ID NO: 9.

Another aspect is a construct comprising an hgRNA expression cassette, the expression cassette comprising a DNA sequence encoding the hgRNA, wherein the DNA sequence is operably linked to a promoter and a transcription termination site.

In another embodiment, the promoter is a U6 promoter.

In another embodiment, the construct is a lentiviral vector having a (+) strand and a (−) strand and the hgRNA expression cassette is inverted so as to be encoded on the (−) strand.

Another aspect is a nucleic acid library comprising a multiplicity of hgRNAs described herein. Another aspect is a nucleic acid library, comprising a multiplicity of nucleic acid constructs encoding a multiplicity of hgRNAs described herein.

Also described herein is an hgRNA library comprising a plurality of hgRNAs capable of targeting a plurality of target sequences in a genome. Described herein are the spacer pairs listed in tables 1, 2, 3, 4, 5, 6, or 9, wherein the "Cas9.Guide" (Tables 1, 2, 3, 4, 5, and 6) or "Cas9 Guide" (Table 9) corresponds to the proximal spacer, and the "Cas12a.Guide" (Tables 1, 2, 3, 4, 5, and 6) or "Cas12a Guide" (Table 9) corresponds to the distal spacer.

In another embodiment, the library is an exon-targeting library wherein the each hgRNA or encoded hgRNA comprises: a) a proximal spacer that targets an intronic site flanking a target exon, optionally that is at least or about 100 base pairs from a splice site flanking the target exon, and a distal spacer that targets an intronic site flanking the target exon, optionally that is at least or about 100 base pairs from another splice site flanking the target exon or another target exon; b) a proximal spacer that targets an intronic site flanking the target exon optionally that is at least or about 100 base pairs from a splice site flanking the target exon and a distal spacer that targets an intergenic region; c) a proximal spacer that targets an intergenic region and a distal spacer that targets an intronic site flanking the target exon, optionally that is at least or about 100 base pairs from a splice site flanking the target exon; d) a proximal spacer that targets an exonic region and a distal spacer that targets an intergenic region; e) a proximal spacer that targets an intergenic region and a distal spacer that targets an exonic region; f) a proximal spacer that targets an intergenic region and a distal spacer that targets a different intergenic region on the same or a different chromosome; and/or g) a proximal spacer and/or a distal spacer that are non-targeting spacers.

In another embodiment, for each exon targeted, each subset of hgRNAs comprises: a) at least two proximal spacers that each target an intronic site flanking a target exon, optionally that is at least or about 100 base pairs from a splice site flanking the target exon; b) at least four distal spacers that each target an intronic site optionally that is at least or about 100 base pairs from a splice site flanking the target exon.

In another embodiment, the exon-targeting library comprises: a) a subset of hgRNAs that are configured to generate frame-altering genetic alterations; and b) a subset of hgRNAs that are configured to generate frame-preserving genetic alterations.

The libraries described herein can be directed to human genome, mouse genome or other mammalian genomes or other genomes (e.g. vertebrate).

In another embodiment, the library targets one or more core fitness genes.

In another embodiment, the library comprises: a) at least or about 1,000, 2,000, 3,000, 4,000, 5,000, 10,000, 15,000, 20,000, 25,000, 30,000, 35,000, 40,000, 45,000, 50,000, or 55,000 or for example at least 61,888 hgRNAs where one or two spacers target one of a minimal set of genes, for example, at least or about 100, 200, 300, 400, 500, 600, 750, 1,000, 1,500, 2,000, 2,500, 3,000, 3,500, 4,000 or 4,500 genes, for example at least 4,993 genes, for example, genes defined as having the highest expression levels across a panel of for example five commonly used cell lines, optionally human cell lines; b) at least or about 100, 200, 300, 400, 500, 1,000, 1,500, 2,000, 2,500 or 3,000 or for example at least 3,566 control hgRNAs targeting intergenic or exogenous sequences for assessing single-versus dual-cutting effects; c) at least or about 1,000, 2,000, 3,000, 4,000, 5,000, 10,000, 15,000, 20,000, 25,000 or 30,000 or for example at least 30848 combinatorial- and single-targeting hgRNAs targeting at least or about 100, 200, 300, 400, 500, 600, 750, 900, 1,100, or 1,300 human paralogs, for example at least 1344 human paralogs; and/or d) one or more hand-selected gene-gene pairs of interest. Exogenous sequences refer to sequences not existing in the genome targeted by the library, for example human or mouse genomes. Examples are hgRNAs targeting sequences such as eGFP, mClover, mCherry, LacZ, renilla Luciferase, firefly Luciferase, nano Luciferase.

In another embodiment, the library comprises any whole number of hgRNAs or encoded hgRNAs between for example 100 and 61,888.

In some embodiments the library is an exon-targeting library, an intron-targeting library, a 5' and/or 3' UTR targeting library, a paralog targeting library, a chromosome targeting library, gene pair targeting library, dual-targeting of individual genes library, enhancer targeting library, promoter targeting library and/or a non-coding RNA (ncRNA) targeting library.

In another embodiment, the library comprises the pairs of spacer sequences shown in Table 1, 2, 3, 4, 5, 6, or 9.

Another aspect is a paired guide oligonucleotide comprising a 5' restriction enzyme recognition sequence or a compatible 5' end, a proximal spacer, a stuffer segment comprising one or more internal restriction enzyme sites, a distal spacer, and a 3' restriction enzyme recognition sequence or a compatible 3' end.

In an embodiment, the stuffer segment is 25 to 45, 28 to 40, 30 to 35, or 31 to 33 nucleotides in length, optionally 32 nucleotides in length. In another embodiment, the proximal spacer is 15 to 25, 16 to 24, 17 to 23, 18 to 22, or 19 to 21 nucleotides in length, optionally 20 nucleotides in length. In another embodiment, the distal spacer is 15 to 28, 16 to 27, 17 to 26, 18 to 25, or 19 to 24 nucleotides in length, optionally 20, 21, 22, or 23 nucleotides in length.

In another embodiment, the oligonucleotide has a sequence of SEQ ID NO: 12 or SEQ ID NO: 13.

A further aspect of the disclosure includes a method of generating an hgRNA expression construct, or a library of hgRNA expression constructs, the method comprising: a) obtaining a paired guide oligonucleotide, optionally one or more paired guide oligonucleotides as described herein; b) cloning the paired guide or one or more oligonucleotides into one or more vectors between a promoter sequence and a transcription termination site to generate one or more intermediate constructs; c) obtaining a second oligonucleotide optionally one or more second oligonucleotides comprising or encoding a tracrRNA and a direct repeat sequence, and having 5' and 3' ends that are capable of interfacing with the one or more internal restriction enzyme sites of the paired guide oligonucleotide; and d) cloning the one or more second oligonucleotides into the intermediate construct between the proximal guide and the distal guide.

In another embodiment, the vector is a lentiviral vector having a (+) strand and a (−) strand and the hgRNA expression cassette is inverted so as to be encoded on the (−) strand. In another embodiment, the vector is a pLCKO-based vector, such as pLCHKO. In another embodiment, the second oligonucleotide comprises the sequence of SEQ ID NO: 15 or SEQ ID NO: 16.

Another aspect is a method of generating a library of constructs encoding a multiplicity of hgRNAs, the method comprising: a) obtaining a multiplicity of paired guide oligonucleotides; b) cloning the multiplicity of paired guide oligonucleotides into a plurality of vectors between a promoter sequence and a transcription termination site to generate a multiplicity of intermediate constructs; c) obtaining a plurality of second oligonucleotides each comprising or encoding a tracrRNA and a direct repeat sequence, and having 5' and 3' ends that are capable of interfacing with one or more processed internal restriction enzyme sites of the paired guide oligonucleotide; and d) cloning the plurality of second oligonucleotides into the multiplicity of intermediate constructs between the proximal guide and the distal guide.

Another aspect is a library of constructs encoding a multiplicity of hgRNAs obtained using a method described herein.

Another aspect of the disclosure is a method of generating a targeted genetic deletion, the method comprising: a) introducing into a cell an hgRNA as described herein, wherein the proximal guide is configured to target a CRISPR target site on a chromosome at one end of the desired deletion and the distal guide is configured to target another CRISPR target site on the chromosome at the other end of the desired deletion, and wherein the cell expresses a type II Cas protein and a type V Cas protein; b) culturing the cell under suitable conditions such that: i) the hgRNA is processed into mature guide RNAs, ii) the mature guide RNAs associate with their respective Cas protein and guide the Cas proteins to their respective CRISPR target sites; iii) the Cas proteins each introduce a double-stranded break at the target site on the chromosome; and iv) the double-stranded breaks are repaired by a DNA repair process such that a targeted genetic deletion is generated.

Another aspect is a method of generating a targeted genetic deletion, the method comprising: a) introducing into a cell a construct according to the invention, wherein the proximal guide has been designed to target a site on a chromosome at one end of the desired deletion and the distal guide has been designed to target a target site on the chromosome at the other end of the desired deletion, and wherein the cell expresses a nuclear localized type II Cas protein and a nuclear localized type V Cas protein; b) culturing the cell under suitable conditions such that: i) the hgRNA is expressed and processed into mature guide RNAs, ii) the mature guide RNAs associate with their respective Cas protein and guide the Cas proteins to their respective target sites; iii) the Cas proteins each introduce a double-stranded break at the target site on the chromosome; and iv) the double-stranded breaks are repaired by a DNA repair process such that a targeted genetic deletion is generated.

In another embodiment, the type II Cas protein is Cas9 and/or the type V Cas protein is Cas12a. In an embodiment the Cas9 is spCas9, or optionally is a protein comprising an amino acid sequence with at least 80%, at least 90%, at least 95%, at least 99% or 100% sequence identity to a protein encoded by SEQ ID NO: 19 and having Cas9 activity (e.g. bind the gRNA and the target site). In an embodiment, the Cas9 has DNA processing activity.

In another embodiment, the type V Cas protein is Lb-Cas12a or As-Cas12a. Optionally the Cas12a is a protein comprising an amino acid sequence with at least 80%, at least 90%, at least 95%, at least 99% or 100% sequence identity to a protein encoded by SEQ ID NO: 20 or SEQ ID NO 21 and having Cas12a activity (e.g. binding the gRNA and the target site). In an embodiment, the type V Cas protein has DNA and/or RNA processing activity.

In another embodiment, the type II Cas protein and/or the type V Cas protein comprises one or more nuclear localization signals, optionally wherein the type II Cas protein comprises two nuclear localization signals and/or the type V Cas protein comprises two nuclear localization signals. In an embodiment a nuclear localization signal comprises a nucleoplasmin nuclear localization signal.

Another aspect of the disclosure is a cell expressing a Cas9 protein, a Cas12a protein, and an hgRNA as described herein.

In an embodiment, the Cas12a protein is Lb-Cas12a or As-Cas12a. In an embodiment, the Cas9 protein and/or the Cas12a protein comprise one or more nuclear localization signals, optionally a nucleoplasmin nuclear localization signal and/or an SV40 nuclear localization signal. In another embodiment, the cell is a cell line. The cell line is not particularly limited and can be for example any vertebrate or mammalian cell line. In another embodiment, the cell line is selected from the list consisting of HAP1, hTERT, RPE1, Neuro2a, and CGR8. In another embodiment, the cell is stably transduced with virus or viruses carrying a Cas9 and/or a Cas12a expression cassette.

Another aspect of the disclosure is a method of genetic interaction screening, the method comprising: a) introducing into a plurality of cells the hgRNA library as described herein, wherein the plurality of cells each express a type II Cas protein and a type V Cas protein; b) culturing the plurality of cells such that: i) the multiplicity of hgRNAs are processed into mature guide RNAs, ii) the mature guide RNAs associate with their respective Cas protein and guide the Cas proteins to their respective target sites; iii) the Cas proteins each introduce a double-stranded break at the target site on the chromosome; and iv) the double-stranded breaks are repaired by a DNA repair process such that a genetic alteration is generated at the target site; c) culturing the plurality of cells for a period of time to allow for hgRNA dropout or enrichment; d) collecting the plurality of cells; and optionally e) identifying one or more hgRNAs that are over- or under-represented in the plurality of cells.

A related aspect of the disclosure is a chemical-genetic interaction screening method, the method comprising: a) introducing into a plurality of cells the hgRNA library as described herein, wherein the plurality of cells each express a type II Cas protein and a type V Cas protein; b) culturing the plurality of cells such that: i) the multiplicity of hgRNAs are processed into mature guide RNAs, ii) the mature guide RNAs associate with their respective Cas protein and guide the Cas proteins to their respective target sites; iii) the Cas proteins each introduce a double-stranded break at the target site on the chromosome; and iv) the double-stranded breaks are repaired by a DNA repair process such that a genetic alteration is generated at the target site; c) treating with an amount of a test drug; d) culturing the plurality of cells under drug selection for a period of time to allow for hgRNA dropout; e) collecting the plurality of cells; and optionally f) identifying one or more targets that suppress or sensitize the plurality of cells to the test drug.

In an embodiment, in step b) iii) the type II Cas and/or the type V Cas introduces a double-stranded break at the target site on the chromosome; and optionally the double-stranded break is repaired by a DNA repair process such that a genetic alteration is generated at the target site. In another embodiment, the type II Cas and/or the type V Cas protein is a catalytically dead Cas protein and in step b) iii) the catalytically dead Cas protein binds the CRISPR target site and alters transcription. In another embodiment, the type II Cas and/or the type V Cas protein is a base editor and in step b) iii) the Cas protein binds the CRISPR target site and creates a genetic alteration at the target site. In another embodiment, sufficient numbers of cells are retained during culturing such that at least or about a 250-fold library coverage is retained over the time course of the screen.

In an embodiment, the method includes one or more of the steps or reagents described in an Example section disclosed herein. In an embodiment, the method is a method described in the Examples section.

Another aspect of the disclosure is a computer implemented method of training a convolutional neural network for optimizing guide design, the method comprising: a) collecting a set of guide target sequences and corresponding activity category from a database, wherein each guide target region sequence is n nucleotides in length and comprises the spacer sequence, PAM sequence, and flanking upstream and downstream sequences, and the activity category is either "active" or "inactive"; b) applying one or more transformations to each guide target sequence, including generating a 4 by n binary matrix E such that element $e_{ij}$ represents the indicator variable for nucleotide i at position j, to create a training set; c) training the neural network using the training set by: i) passing the first training set into a convolutional layer of 52 filters of length 4 to generate an activated score set; ii) passing the activated score set through a pooling layer to generate an average score set; iii) passing the average score set through a dropout layer to generate a summarized feature score set; iv) passing the summarized feature score set through a fully connected hidden layer and another dropout layer; and v) passing the set generated in step iv) through an output layer.

In an embodiment, the activity category is "active" when the False Discovery Rate (FDR)<5% and the Log Fold Change (FC)<−1; and "inactive" when FDR>=5% and FC=(−0.5 to 0.5).

A further aspect of the disclosure is a method of designing a guide RNA, the method comprising: a) identifying a PAM sequence in a DNA target region; b) determining a guide target region sequence for each PAM sequence, wherein the guide target region sequence is n nucleotides in length and comprises a spacer sequence, PAM sequence, and flanking upstream and downstream sequences; c) submitting the guide target region sequence through the trained convolutional neural network described herein to obtain one or more prediction scores; and d) identifying a guide RNA sequence on the basis of the one or more prediction scores obtained in step c), and optionally producing the guide RNA.

A further aspect of the disclosure is a spacer library comprising a multiplicity of CRISPR-Cas12a spacers designed using a method described herein that are capable of targeting a multiplicity of target regions or genes in a genome, wherein each of the multiplicity of CRISPR-Cas12a spacers are 15-28, 16 to 27, 17 to 26, 18 to 25, or 19 to 24 nucleotides in length, optionally 20, 21, 22, or 23 nucleotides in length. The spacer library can comprise the distal spacer or distal spacers where there is more than one Cas12a spacer. In an embodiment, the spacer library comprises a multiplicity of spacers that are capable of targeting 100, 200, 300, 400, 500, 600, 750, 1,000, 1,500, 2,000, 2,500, 3,000, 3,500, 4,000 or 4,500 genomic loci, for example at least 4,993 genes, or any number of genes or other genomic loci, or for example each gene in the genome or a desired subset thereof, wherein the library comprises one, two, three, four, five, or more spacers per target gene or genomic locus. In an embodiment, the library is capable of (e.g. designed for) targeting a desired subset of genes or genomic loci in the genome and comprises one, two, three, four, five, or more different spacers per gene or genomic locus.

Also described herein are the CRISPR-Cas12a spacers listed in Tables 1, 2, 3, 4, 5, and 6 as "Cas12a.Guide" and in Table 9 as "Cas12a Guide". In an embodiment, the library comprises at least or about 1,000, 2,000, 3,000, 4,000, 5,000, 10,000, 15,000, 20,000, 25,000, 30,000, 35,000, 40,000, 45,000, 50,000, or 55,000 Cas12a spacers, optionally each spacer capable of targeting a target region having a prediction score of greater than 0.6, greater than 0.7, greater than 0.8, or greater than 0.9 as determined by a method described herein (e.g. CNN/CHyMErA-Net) and/or as listed in Table 5 or 6 as "CNN.Score" or in Table 9 as "Cas12a Score". These libraries are disclosed in priority GB provisional application GB1907733.8 entitled "Methods and compositions for multiplex gene editing", filed 31 May 2019, in the Tables filed therein.

As shown herein, active guides are neutral with respect to GC content (e.g. have 40-60% GCs), with a preference for G at the first position proximal to the PAM sequence, depletion of T at the first nine positions, and depleted for a C at the PAM-distal 23rd nucleotide. Similar nucleotide preferences were observed in the filters learned by the CNN classifier.

Accordingly, in an embodiment, the multiplicity of spacers, or a subset of the multiplicity, optionally each spacer having a sequence of 23 nucleotides or longer, is designed or selected preferentially to include spacers that have one or more of the following properties: are neutral for GC content (e.g. have 40-60%, 45-55% or approximately 50% GC content), have a G at the first nucleotide (position one), do not have a T at one or more of each of the first nine nucleotides (positions 1 to 9), and/or do not have a C at the 23rd nucleotide (position 23). The multiplicity of spacers, or subset thereof, may therefore be neutral for GC content, enriched for G at position 1, depleted for T at each of positions 1 to 9, and/or depleted for C at position 23. For example, spacers that have a GC content of between 40-60% are preferred, spacers that have a G at position one are preferred for example at a ratio of greater than 1:3, spacers that have any nucleotide that is not T at one or more of positions 1, 2, 3, 4, 5, 6, 7, 8 or 9 are preferred for example at a ratio of greater than 3:1 and/or spacers that have any nucleotide that is not C at position 23 are preferred for example at a ratio of greater than 3:1. Taking into account the above preferences, it may be that each of the multiplicity of spacers has for example a greater than 25% likelihood of nucleotide G being at position 1, has for example less than 25% likelihood of nucleotide T being at positions 1-9, independently, and/or for example has less than 25% likelihood of nucleotide C being at position 23. In an embodiment, selection of each of the multiplicity of spacers is neutral for GC content. Overall GC content of each of the multiplicity of spacers can be about 40-60%, 45-55%, or preferentially approximately 50% (see FIG. 2*c*).

An aspect provides a kit comprising one or more of: a paired guide; a construct comprising a paired guide; a library of paired guides; a library of constructs comprising paired guides; a cell expressing a Cas9 protein, a Cas12a protein, and a paired guide or a construct comprising a paired guide; or a library of CRISPR-Cas12a spacers; and optionally one or more of a type II Cas expression construct, and a type V expression construct, and/or instructions for carrying out a method described herein. The kit can comprise one or more buffers or other reagents described herein.

Also described herein are libraries and methods as described in "*Genetic interaction mapping and exon-resolution functional genomics with a hybrid Cas9-Cas12a platform*", Thomas Gonatopoulos-Pournatzis, Michael Aregger, Kevin R. Brown, Shaghayegh Farhangmehr, Ulrich Braunschweig, Henry N. Ward, Kevin C. H. Ha, Alexander Weiss, Maximilian Billmann, Tanja Durbic, Chad L. Myers, Benjamin J. Blencowe, and Jason Moffat., Nature Biotechnology (2020) 38, 638-648, including all and any disclosure thereof and all and any disclosure from the corresponding supplementary materials available from the publisher, including supplementary materials made available online.

The preceding section is provided by way of example only and is not intended to be limiting on the scope of the present disclosure and appended claims. Additional objects and advantages associated with the compositions and methods of the present disclosure will be appreciated by one of ordinary skill in the art in light of the instant claims, description, and examples. For example, the various aspects and embodiments of the disclosure may be utilized in numerous combinations, all of which are expressly contemplated by the present description. These additional advantages objects and embodiments are expressly included within the scope of the present disclosure. The publications and other materials used herein to illuminate the background of the disclosure, and in particular cases, to provide additional details respecting the practice, are incorporated by reference, and for convenience are listed in the appended reference section.

DRAWINGS

Further objects, features and advantages of the disclosure will become apparent from the following detailed description taken in conjunction with the accompanying figures showing illustrative embodiments of the disclosure, in which:

FIG. 1 shows the development of a screening platform for combinatorial genetic perturbations. FIG. 1A shows a schematic overview of CHyMErA, in which an hgRNA consisting of a fusion of Cas9 and Cas12a sgRNAs is expressed under a single U6 promoter and Cas12a RNA processing activity cleaves the hgRNA to generate functional Cas9 and Cas12a sgRNA. FIG. 1B shows PCR assays monitoring of Ptbp1 exon 8 deletion efficiency using paired Cas9 intronic guides (left panel), paired Cas12a intronic guides (middle panel) or CHyMErA (right panel). Data are representative from two to four independent experiments. FIG. 1C shows HAP1 cells expressing Cas9 and Cas12a (Lb or As) transduced with lentiviral expression cassettes for multiplexed hgRNAs encoding an increasing number of targets as indicated. For all hgRNA constructs, the first and last positions encode for a TK1-targeting Cas9 and HPRT1-targeting Cas12a gRNA respectively, while the intervening positions encode for intergenic Cas12a sgRNAs (left panel). To assay resistance to thymidine and 6-thioguanine cells were either control-treated (Con) or challenged with 250 μM thymidine or 6 μM 6-thioguanine. Cell viability was measured by AlamarBlue staining 4 days post treatment relative to the non-targeting control. Western blot was performed to detect HPRT1 levels and β-Actin was used as a loading control (right panel). FIG. 1D shows a schematic of hgRNA constructs designed to delete exons by targeting flanking intronic sequences (top panel) and a schematic diagram of positive selection screens by treating cells with 6-thioguanine (6-TG) (bottom panel). FIG. 1E is a scatterplot depicting fold change of paired guides targeting HPRT1 for exon deletion (dark grey) or gene knockout (black=Cas9, medium grey=Cas12a) in 6-TG treated (6 μM) (y-axis) vs. non-treated (x-axis) cells. Other guides are shown in light grey. The screen results performed with Lb-Cas12a and As-Cas12a are depicted in the left and right panels respectively. FIG. 1F is an overview of library generation and experimental setup for negative and positive selection screens. FIG. 1G shows fold change distributions from normalized hgRNA read counts for Cas9 sgRNAs (upper panel) or Cas12a sgRNAs (lower panel) targeting essential genes for each of the indicated time points in HAP1 cells. The Lb-Cas12a screen is depicted in the left panel while the As-Cas12a screen in the right panel.

FIG. 2 shows Machine-learning-based prediction of efficient Lb-Cas12a guides. FIG. 2A is an evaluation of different machine learning algorithms predictions of active Lb-Cas12a guides using the area under the receiver operating characteristic curve (AUC) (left) and average precision (right). Active guides are defined as those that displayed a Log 2FC<−1 at T18 compared to T0 (likelihood-ratio test, FDR of <0.05 with Benjamini-Hochberg multiple testing correction), and were chosen from three independent screens with three biological replicates each. Inactive guides are defined as those with Log 2FC between −0.5 and 0.5. Machine learning classifiers were trained using only the Cas12a gRNA target (n=5,097 unique sequences) and flanking sequence (39 nt), or with the addition of secondary structure and melting temperature (+). FIG. 2B shows a performance evaluation of the CNN classifier via cross-validation. FIG. 2C is a boxplot depicting fold change distributions of exonic Lb-Cas12a guides binned by their GC content. Throughout the disclosure, whisker plots are showing the interquartile range with the 25th percentile at the bottom, 75th percentile at the top and the line indicates the median. The whiskers extend to the quartile+/−1.5× interquartile range. FIG. 2D is the sequence composition of active exonic Lb-Cas12a guides from human and mouse optimization screens as determined by a logistic regression (LR) model. FIG. 2E shows Pearson correlation coefficients between LFC and CHyMErA-Net score for Lb-Cas12a exonic guides in HAP1 (left, n=4,268 guides) and CGR8 (right, n=3,338 guides) cells. FIG. 2F shows boxplots of LFC distributions of 4,268 guides as a function of CHyMErA-Net (left) and DeepCpf1 scores (right).

FIG. 3 shows dual Cas9-Cas12a gene targeting compared with single Cas9 editing. FIG. 3A shows Log 2FC distribution plots of Lb-Cas12a exonic guides from optimization and 2$^{nd}$ generation CHyMErA libraries at the endpoint. Guides targeting intergenic regions or non-expressed genes are included as negative controls. FIG. 3B is a schematic of single vs. dual gene targeting. FIG. 3C shows box plots depicting log 2FC depletion of single vs. dual-targeting hgRNAs in HAP1 (T18, left) or RPE1 cells (T24, right) as indicated. Subsets were compared using two-tailed Mann-Whitney U-tests. Tests were performed only between groups with indicated P values. hgRNA guides per group: 3,310 (Cas9 exonic-Cas12a exonic), 1,148 (Cas9 exonic-Cas12a intergenic) and 1,676 (Cas9 intergenic-Cas12a exonic) targeting core essential genes; 25,578 (Cas9 exonic-Cas12a exonic), 8,753 (Cas9 exonic-Cas12a intergenic) and 12,874 (Cas9 intergenic-Cas12a exonic) targeting other protein-coding genes; and 4,993 (Cas9 intergenic-Cas12a intergenic) controls. FIG. 3D shows scatterplots displaying the correlation of gene-level beta scores as calculated by the MAGeCK algorithm for genes targeted by dual- (y-axis) or single-targeting (x-axis) hgRNAs in HAP1 (T18, left) and RPE1 cells (T24, right). FIG. 3E shows bar plots showing the number of essential genes identified by the MAGeCK algorithm by analyzing single- and dual-targeting hgRNAs at the indicated time points (T12 and T18).

FIG. 4. shows mapping GIs among gene paralog pairs in human cells. FIG. 4A shows schematic hgRNA constructs for interrogating digenic interactions. FIG. 4B shows bar plots depicting log 2FC of single or combinatorial gene ablations as indicated. FIG. 4C-D show scatter plots of expected vs observed log 2FC of paralog pairs in HAP1 (C) or RPE1 (D) cells. In (C) GI T12 is shown in dark grey; GI T12+T18 is shown in black. In (D) GI T18 is shown in dark grey; GI T18+T24 is shown in black. Other guides are shown in light grey. Two-tailed Wilcoxon rank-sum test, Benjamini-Hochberg multiple testing correction, n=3 independent technical replicates. FIG. 4E-F show bar plots depicting log 2FC of single or combinatorial gene ablations of paralog pairs in HAP1 (E) or RPE1 (F) cells at the indicated time points. Bars show mean±2×s.e.m. derived from three independent experiments. Each gene was targeted by eight hgRNA constructs (except LDHA and LDHB, which were targeted by 16 and 12 hgRNAs, respectively), while the gene pair was targeted with 30 hgRNA constructs (20 for LDHA:LDHB). FIG. 4G shows scatterplots of expression changes following siRNA-mediated depletion of RBM26 (left) or RBM27 (right) versus RBM26/RBM27 co-depletion in HAP1 cells, as assessed by RNA-seq. Differentially expressed genes were identified using exactTest from the Bioconductor package edgeR, and were defined as those with RPKM>5, a twofold change compared to control treatment and FDR<0.05, and are highlighted. n=2 independent biological replicates. FIG. 4H shows a Venn diagram of the number of genes regulated in response to depletion of RBM26, RBM27 or both, as defined above.

FIG. 5 shows dual gene targeting and combinatorial perturbation of paralogs identifies chemical-genetic interactions in response to inhibition of mTOR with the active site inhibitor Torin. FIG. 5A shows the number of Torin1 sensitizer and suppressor gene hits detected by single- or dual-targeting (top panel) or using single- or combinatorial-targeting of paralogous genes (lower panel) (FDR<0.01, two-tailed Wilcoxon rank-sum test with Benjamini-Hochberg multiple testing correction, n=3 independent technical replicates). FIG. 5B shows differential log 2 fold-change of genes perturbed by single-(left panel) and dual-targeting (right panel) hgRNAs upon Torin1 treatment in HAP1 cells at the late time point (T18). Sensitizer (bottom) and suppressor gene hits (top) are highlighted (FDR<0.01, two-tailed Wilcoxon rank-sum test, Benjamini-Hochberg multiple testing correction, n=3 independent technical replicates) and the top 10 as well as selected genes from the top 20 significant hits are listed. FIG. 5C shows differential log 2 fold-change of paralogs perturbed by single-(left panel) and combinatorial-targeting (right panel) hgRNAs upon Torin1 treatment in HAP1 cells at the late time point (T18). Sensitizer (bottom) and suppressor gene hits (top) are highlighted (FDR<0.01, Wilcoxon rank-sum test with Benjamini-Hochberg multiple testing correction, n=3 independent technical replicates) and the top 10 as well as selected genes from the top 20 significant hits are listed. FIG. 5D-E show differential $\log_2$ fold-change of selected complex members perturbed by single- or dual-targeting hgRNAs, or perturbed in a combinatorial manner as a paralog pair as indicated at the early (T12) and late (T18) time points. Statistical analysis using a two-tailed Wilcoxon rank-sum test with Benjamini-Hochberg multiple testing correction, n=3 independent technical replicates. In (D) the mTORC2 and Rho pathways are predominantly suppressors while RALGTPases are predominantly sensitizers. In (E) the PRC2 complex and EMSY complex components are predominantly suppressors, while Hippo pathway (with the exception of AMOTL1, WWTR1 and YAP1) and PBAF complex components are predominantly sensitizers.

FIG. 6 shows the identification of fitness exons in RPE1 cells using an exon-targeting CHyMErA library. FIG. 6A shows a cumulative distribution graph of the percentage of interrogated alternative exons with a fitness phenotype across the fraction of significant exon deletion intronic-intronic (left panel) or intronic-intergenic (right panel) hgRNA pairs targeting each exon. FIG. 6B is a bar plot showing the percentage of exons with a phenotype determined by having at least 18% of targeting guides displaying significant depletion in essential and non-essential genes (exon deletion, P=0.02, n=26; single cut, P=0.16, n=132; both, two-sided Fisher's exact test). FIG. 6C shows all hgRNA constructs targeting frame-disruptive exons in MMS19 or RFT1 (depicted above the gene model (x-axis)), with the observed $\log_2$ fold-change value for each hgRNA (y-axis). Exon deletion (i.e. intronic-intronic), single-targeting (i.e. intronic-intergenic), and exon-targeting (exonic-intergenic) hgRNAs are indicated and significantly depleted hgRNAs are highlighted. FIG. 6D is a visualization of frame-preserving alternative exons with a fitness phenotype. All exons targeted in the library are ranked based on the mean $\log_2$ fold-change depletion of exonic guides targeting the corresponding genes and the genes that contain fitness exons are indicated. FIG. 6E shows the average LFC distribution of hgRNAs causing gene knockout by targeting exonic regions in genes that contain alternative exons interrogated in the library. Genes with exons identified as significant screen hits are indicated (Mann-Whitney U test, p=0.00012).

FIG. 7 shows the generation of dual Cas9 sgRNA expression vectors for exon deletions. FIG. 7A is a schematic of Ptbp1 exon 8 deletion targeting (top panel) and of dual Cas9 sgRNA expression cassettes (bottom panel). FIG. 7B shows PCR monitoring of Ptbp1 exon 8 deletion in CGR8 cells transiently transfected (left panel) or transduced (right panel) with dual Cas9 guides (see FIG. 7A). FIG. 7C shows immunofluorescence analysis of N2A cells transiently transfected or stably transduced with lenti Lb- or As-Cas12a containing 1 nuclear localization signal (left panel). Immunofluorescence analysis of stably transduced N2A cells with lenti Lb- or As-Cas12a containing 2 nuclear localization signals (right panel). Scale corresponds to 27 μm. FIG. 7D shows western blot analysis of Cas9 and Cas12a in N2A, CGR8, HAP1 and RPE1 cells as indicated. Asterisk indicates non-specific signal. FIG. 7E is a bar plot showing hgRNA pre-RNA processing based on qRT-PCR analysis. The strategy used for the quantification is indicated below the panel. All data are represented as means±standard deviation (n=3 replicates). FIG. 7F shows PCR monitoring of exon deletion from Parp6 and HPRT1 genes in the indicated cell lines using CHyMErA. Independent pLCHKO constructs expressing Cas9 and Cas12a gRNAs targeting flanking intronic sites for exon deletions or controls were used as indicated. FIG. 7G shows enrichment of intergenic, exonic and intronic HPRT1 targeting hgRNAs in non-treated (NT) or 6-TG treated HAP1 cells (pairwise two-tailed Mann-Whitney U test with Holm multiple testing correction). FIG. 7H is a scatterplot depicting fold change of paired guides targeting TK1 for exon deletion (medium grey) or knockout (black=Cas9, dark grey=Cas12a) in double-thymidine block treated (y-axis) vs. non-treated (x-axis) cells. Other guides are shown in light grey. The screen results performed with Lb-Cas12a and As-Cas12a are depicted in the top and bottom panels respectively. FIG. 7I shows relative cell viability following sequential drug treatments (thymidine and 6-thioguanine) of HAP1 cells transduced with pLCHKO vectors expressing hgRNAs targeting TK1 and HPRT1, as indicated in the schematic on the left. For all hgRNA constructs, the first and last positions encode a TK1-targeting Cas9 and HPRT1-targeting Cas12a gRNA, respectively, while the intervening positions encode intergenic Cas12a gRNAs. After subjecting cells to the first drug treatment, cells were passaged at an equal ratio and challenged with the second drug treatment. Cell viability was assessed following both treatments using an AlamarBlue assay. Data represented as mean±SD, n=3 independent biological replicates.

FIG. 8 is a feature analysis of Cas12a guides. FIG. 8A is a schematic of exon targeting hgRNA libraries with CHyMErA. FIG. 8B shows hgRNA screening libraries generated by performing two rounds of Golden Gate assembly. During the first step the synthesized 113-nt oligos containing both Cas9 and Cas12a guides were introduced into a modified pLCHKO vector (see main text). During the second step, the spacer sequence between the two oligos was replaced with a hybrid scaffold consisting of the Cas9 tracrRNA followed by the Lb- or As-Cas12a direct repeat (DR). Schematic of Cas9 and Cas12a guide length, PAM sequence and double stranded DNA cutting pattern is indicated at the bottom. FIG. 8C shows the fold change distributions from normalized hgRNA read counts for Cas9 sgRNAs or Cas12a sgRNAs targeting essential genes in CGR8 cells. FIG. 8D shows exonic Lb-Cas12a guides grouped based on $\log_2$ fold-change cut-offs in the HAP1 and CGR8 optimization screens. Strongly depleting guides were used as positive, and neutral guides as negative cases. FIG. 8E shows precision recall (left panel) and receiver operating characteristic (right panel) curves of different machine-learning approaches for predicting Cas12a guide performance in HAP1 and CGR8 cells. CNN: convolutional neural networks; L1Logit: lasso regularized logistic regression; RF: random forest. FIG. 8F depicts weblogos of filters learned by CNN/CHyMErA-Net in the convolutional layer. FIG. 8G is a boxplot depicting fold change distributions of exonic Lb-Cas12a grouped according to their PAM sequence. FIG. 8H is an enrichment analysis of active and inactive Lb-Cas12a guides based on chromatin accessibility from K562 cells.

FIG. 9 shows second generation CHyMErA screens display increased dropout sensitivity. FIG. 9A is a scatter plot showing the correlation of mean log 2FC scores of hgRNA targeted genes in HAP1 and RPE1 cells. HgRNAs targeting core fitness genes are indicated in medium grey and all other hgRNAs are indicated in dark grey. FIG. 9B shows box plots depicting Log 2 fold-change distribution of hgRNAs targeting intergenic and/or non-targeting (NT) regions in HAP1 and RPE1 cells. * q<0.001,  q<0.01 and * q<0.05; Wilcoxon rank-sum test followed by Benjamini-Hochberg multiple testing correction. FIG. 9C shows the distribution of the LFC differences between the dual-targeting hgRNA and the single-Cas9 targeting guides. FIG. 9D shows dropout profiles of dual-targeting hgRNAs, as measured by the LFC at T18 in the HAP1 cell line, were binned into ten equal sized bins (n=1,093-1,097) according to the distance between Cas9 and Cas12a target sites. Data derived from n=3 independent technical replicates. FIG. 9E shows western blot depicting p53, pRb and p21 protein levels following camptothecin treatment in RPE1 CHyMErA cells transduced or not with hgRNA constructs. Representative data of two independent experiments. FIG. 9F shows CERES scores from the DepMap CRISPR screens are shown for CEG2 essential (Essential) and non-essential (Non-essential) genes, genes discovered by both single-(ST) and dual-targeting (DT) (Overlapping ST/DT Hits), or genes discovered only through dual-targeting by CHyMErA (Novel HAP1 DT hits). Lower CERES scores correspond to greater depletion through the screens. CERES scores for each gene set across all 558 screens were aggregated together for plotting: Essential—367,164 scores corresponding to 658 genes, Overlapping ST/DTt Hits—990,450 scores from 1,775 genes, Novel HAP1 DT Hits—313,038 scores from 561 genes, Non-essential—435,798 scores from 781 genes. CERES score distributions for CHyMErA DT-only genes (n=313,038) and non-essential genes (n=435,798) were compared using a two-tailed Wilcoxon rank-rum test.

FIG. 10 shows that CHyMErA reveals widespread non-additive fitness phenotypes upon combinatorial perturbation of paralogous genes. FIG. 10A-B show bar plots depicting log 2FC of single or combinatorial gene ablations as indicated. The expected combinatorial effect size based on single perturbation is indicated with dotted bars. All data are represented as means±standard error. FIG. 10C-D show scatter plots of expected vs observed log 2FC of paralog pairs in HAP1 (C) or RPE1 (D) cells. Paralogs displaying significant genetic interaction at both or only at the late time point are highlighted in dark grey and light grey respectively (clustered to the lower right). Other paralogs are shown in grey. FIG. 10E-F show bar plots depicting log 2FC of single or combinatorial gene ablations in HAP1 (E) or RPE1 (F) as indicated. FIG. 10G-H show scatter plots depicting the expression of paralog pairs in HAP1 (G) or RPE1 (H) cells (left panel). Paralogs with significant genetic interactions at the early, late or both time points are highlighted in light grey, and dark grey, respectively (clustered to the lower left). The density of FDR values for all gene pairs in both orientations are also displayed and the significance threshold of 0.1 is indicated as a dashed line (right panel). FIG. 10I shows real-time RT-PCR quantification of RBM26 and RBM27 knock-down efficiency in HAP1 cells. All data are represented as means±standard deviation (n=3 replicates). * p<0.001;  p<0.01; two-tailed unpaired t-test. FIG. 10J shows cell viability of HAP1 and RPE1 cells as measured by AlamarBlue staining 3 days post-transfection of siRNAs targeting RBM26, RBM27 or both. *p<0.001, p<0.01, and *p<0.05; two-tailed unpaired t test. FIG. 10K shows cell viability of WT and single knockout HAP1 clones as measured by AlamarBlue staining 6 days post-transduction of the indicated lentiCRISPRv2 sgRNA expression cassettes targeting the indicated genes. Cell viability was normalized to intergenic-targeting control sgRNAs. *p<0.001, p<0.01, and *p<0.05; two-tailed unpaired t test (n=3). FIG. 10L shows gene ontology enrichment analysis for genes with significantly decreased expression upon co-depletion of RBM26 and RBM27 following siRNA treatment. (n=2 independent biological replicates. FDR was calculated using FuncAssociate (Berriz et al., *Bioinformatics,* 2003).

FIG. 11 shows CHyMErA compared with single Cas9 targeting chemogenetic screens. FIG. 11A shows the differential $\log_2$ fold-change of genes perturbed by single-(left panel) and dual-targeting (right panel) hgRNAs upon Torin1 treatment in HAP1 cells at the early time point (T12). Sensitizer (bottom) and suppressor gene hits (top) are highlighted (FDR<0.01, two-tailed Wilcoxon rank-sum test with Benjamini-Hochberg multiple testing correction, n=3 independent technical replicates) and the top 10 as well as selected genes from the top 20 significant hits are listed. FIG. 11B shows the differential $\log_2$ fold-change of paralogs perturbed by single-(left panel) and combinatorial-targeting (right panel) hgRNAs upon Torin1 treatment in HAP1 cells at the early time point (T12). Sensitizer (bottom) and suppressor gene hits (top) are highlighted (FDR<0.01, two-tailed Wilcoxon rank-sum test with Benjamini-Hochberg multiple testing correction, n=3 independent technical replicates) and the top 10 as well as selected genes from the top 20 significant hits are listed. FIG. 11C depicts gene ontology enrichment of sensitizer (upper panel) or suppressor hits (lower panel) called at an FDR<0.1 across both time points. FDR was calculated using GOrilla (Eden et al., *BMC Bioinformatics,* 2009). FIG. 11D shows the Torin1 IC50 values (drug concentration resulting in 50% reduction of cell viability) in HAP1 WT and EED knockout cell clones. IC50 values were calculated based on dose response curves in the respective HAP1 cell lines (n=4 independent biological replicates; p=0.026, two-tailed unpaired t test). FIG. 11E shows the differential $\log_2$ fold-change of diphthamide biosynthesis genes perturbed by single- or dual-targeting hgRNAs as indicated. Two-tailed Wilcoxon rank-sum test with Benjamini-Hochberg multiple testing correction, n=3 independent technical replicates.

FIG. 12 shows the use of CHyMErA for exon deletion phenotypic screens. FIG. 12A shows the length distribution of the alternative exons targeted by CHyMErA exon deletion library. FIG. 12B shows bar plots depicting the percentage of alternative exons that overlap a modular protein domain. FIG. 12C shows PCR monitoring of exon deletion from PDPR, MDM4 and SRFS7 genes in RPE1 cells using hgRNAs guides with different phenotypic scores. FIG. 12D shows representative examples of hgRNA constructs targeting frame-disruptive exons in BIN1, FUZ, FHOD3, MEGF8, TNRC6A or C1orf77 (depicted above the gene model (x-axis)), with the observed $\log_2$ fold-change value for each hgRNA (y-axis). Exon deletion (i.e. intronic-intronic) and single-targeting control (i.e. intronic-intergenic) hgRNAs are indicated, while significantly depleted hgRNAs are highlighted. FIG. 12E shows the LFC of exon-deletion hgRNAs (intronic/intronic) vs. control hgRNAs in which only the Cas9 (left) or Cas12a guide (right) is targeting an intronic region, while the other nuclease is targeting an intergenic region. The dark grey dots represent exon-deletion hgRNAs that are significantly depleted, while light grey dots represent all other exon-deletion hgRNAs. Significant depletion was scored against the empirical null distribution of 1,647 intergenic-intergenic control pairs (refer to Methods for details). Marginal histograms indicate the density distribution of control guide pairs corresponding to significant and non-significant exon-deletion pairs, respectively. FIG. 12F shows the density of exonic "hits" (light) compared to all other exons (grey) from the exon-deletion screen as a function of PSI (percent spliced in). p-value is from a two-tailed Mann-Whitney U test (n=91 for hits, 1,514 for background).

Figure 13A:
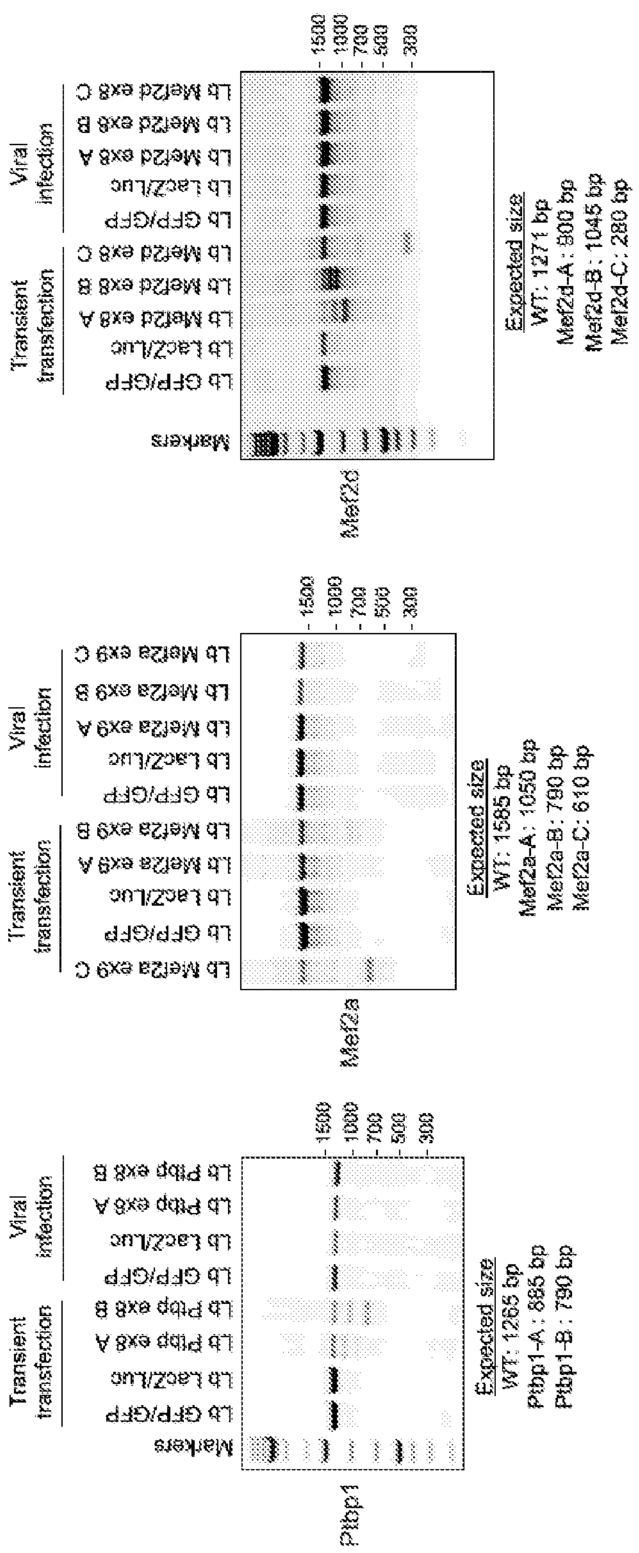
Figure 13B:
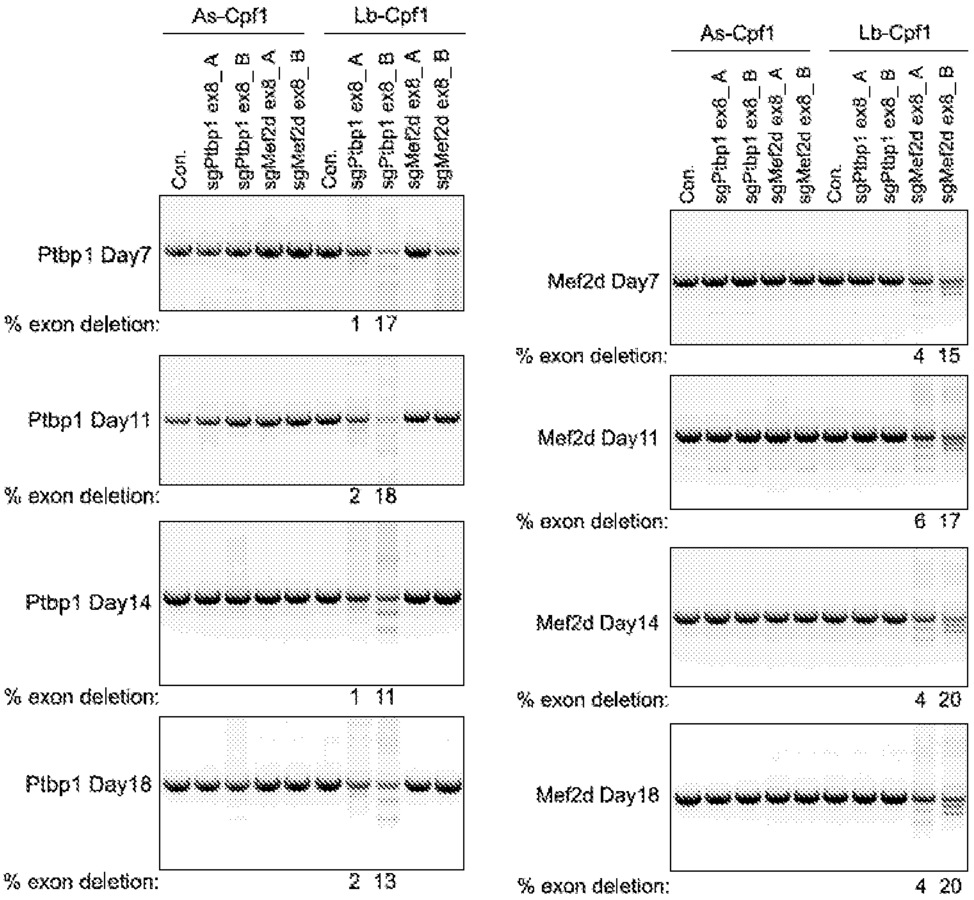

FIG. 13 shows Cas12a alone only results in modest combinatorial editing. FIG. 13A shows PCR monitoring of exon deletion from the indicated genes after transient transfection of CGR8 cells with lenti-LbCas12a construct expressing dual guides. FIG. 13B shows PCR monitoring of exon deletion from the indicated genes after lentiviral delivery of CGR8 cells with lenti-LbCas1 a constructs expressing dual guides.

Figure 14:
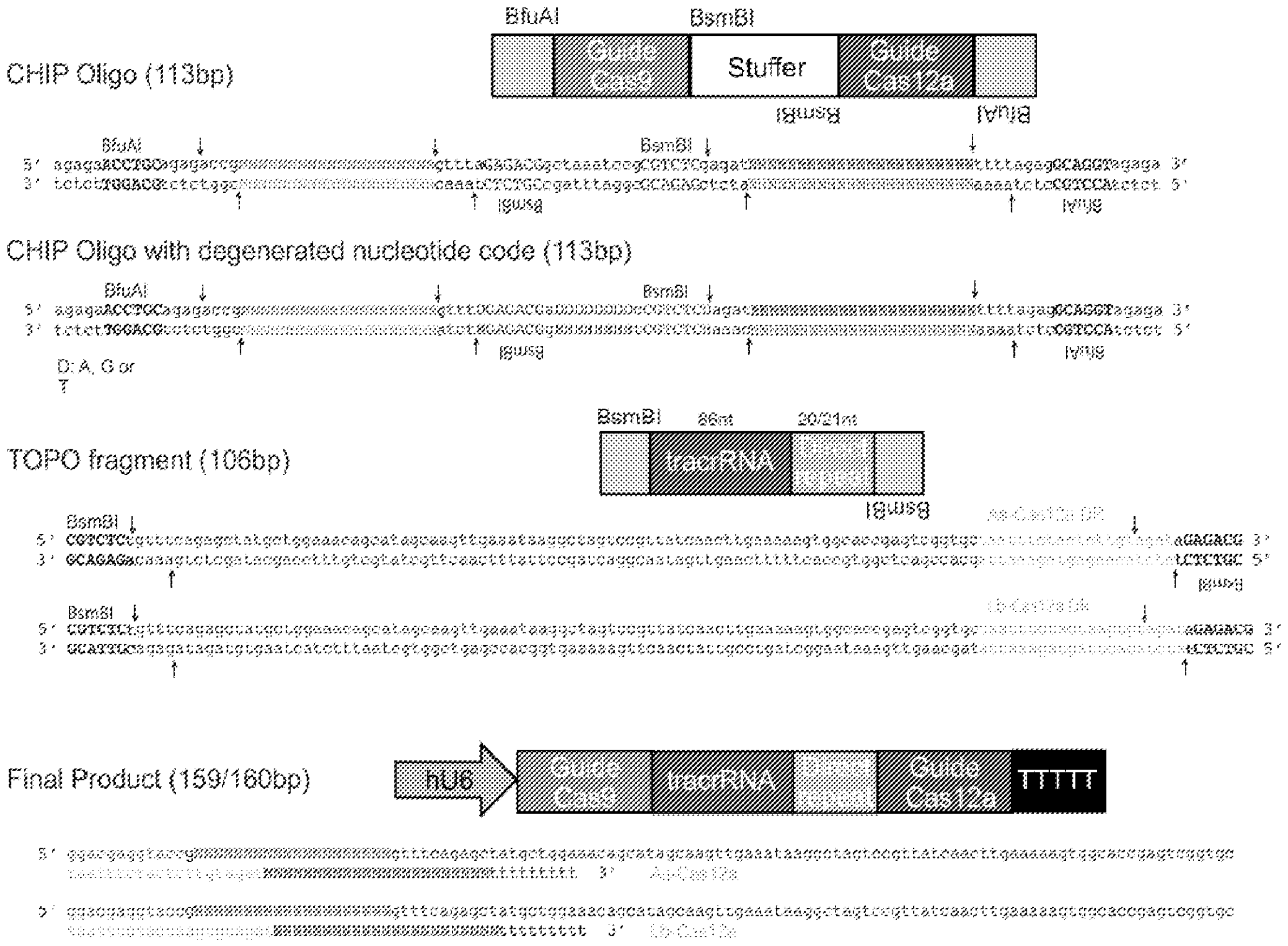

FIG. 14 is a schematic of the HgRNA cloning strategy, describing the cloning strategy and nucleotide sequences for the generation of hgRNA expression cassettes to be used with Cas9 and Cas12a nucleases.

Figure 15A:
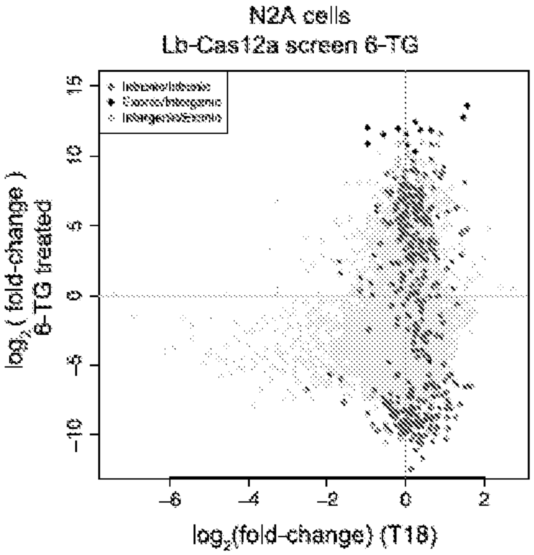
Figure 15B:
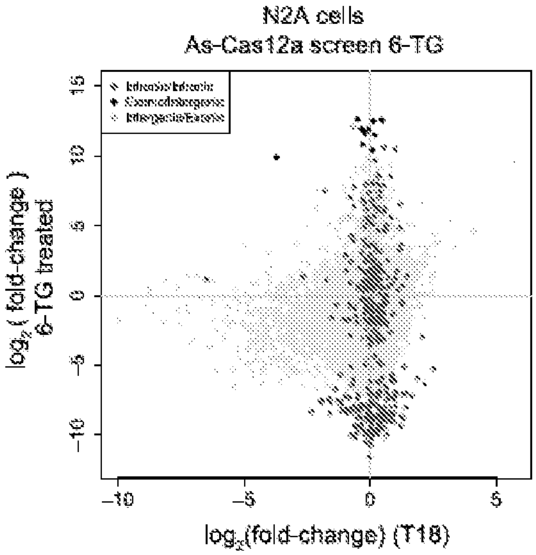

FIG. 15 shows results of Hprt exon deletion experiments in mouse N2A cells. FIG. 15A-B show enrichment of paired hgRNAs targeting exons in Hprt1 for deletion (medium grey), or gene knockout (black=Cas9, dark grey=Cas12a) in 6-TG treated (6 mM)(y-axis) versus non-treated (x-axis) N2A cells. Other paired hgRNAs are shown in light grey. The screens were performed with either (A) Lb-Cas12a or (B) As-Cas12a.

Figure 15C:
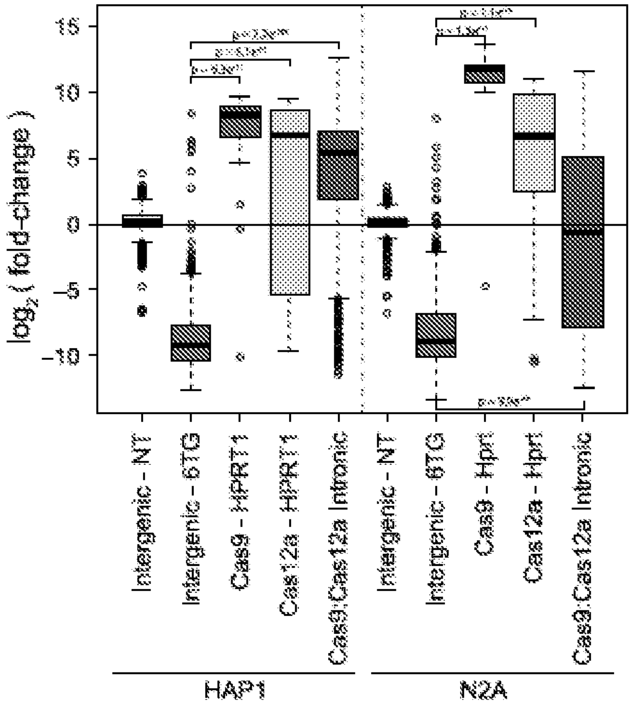

FIG. 15C shows enrichment of intergenic, exonic and intronic human HPRT1 or mouse Hprt1 targeting hgRNAs in non-treated (NT) or 6-TG treated HAP1 (left panel) or N2A cells (right panel), respectively (Wilcoxon rank-sum test).

Figure 16A:
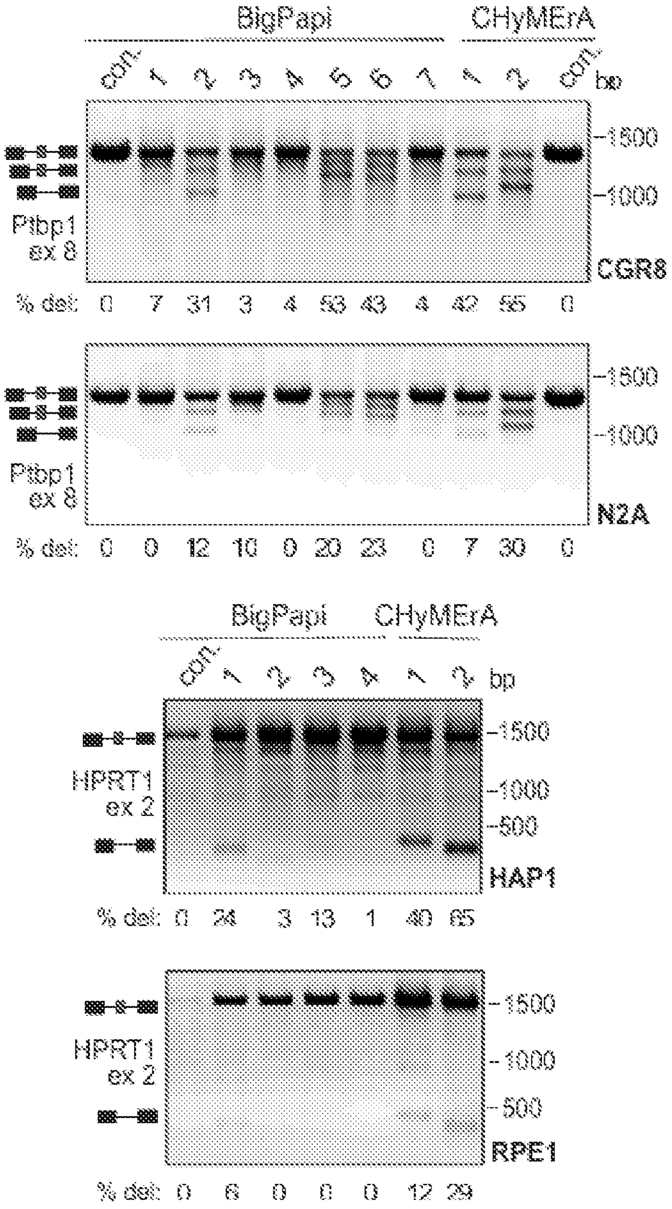
Figure 16B:
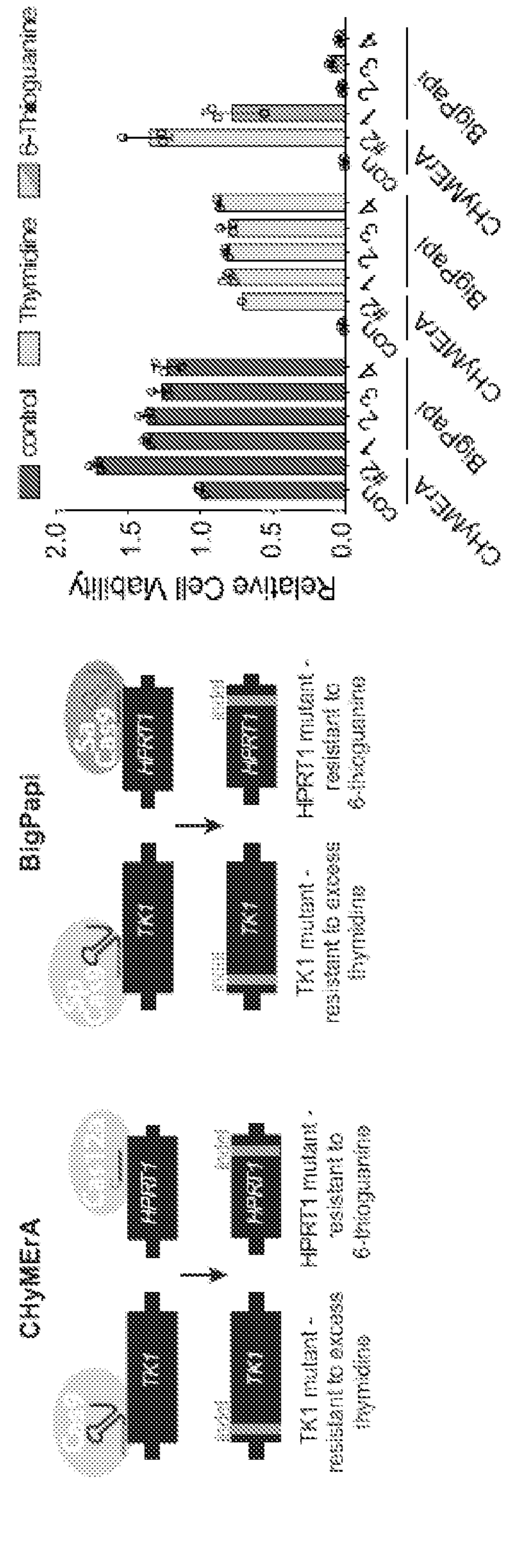

FIG. 16 shows a comparison of CHyMErA with other dual-targeting screening systems. FIG. 16A shows PCR monitoring of exon deletion from Ptbp1 and HPRT1 genes in the indicated cell lines using CHyMErA or BigPapi. Independent pLCHKO and pPapi constructs expressing Sp-Cas9 and Cas12a (CHyMErA) or Sa-Cas9 (BigPapi) gRNAs targeting flanking intronic sites for exon deletions or controls were used as indicated. Representative data of two independent experiments. FIG. 16B shows a schematic of combinatorial gene targeting by CHyMErA (left panel) or BigPapi (middle panel). Comparison between CHyMErA and the BigPapi system for the combinatorial targeting of TK1 and HPRT1, as determined by resistance to thymidine and 6-thioguanine treatments, respectively (right panel). The same Cas9 guide targeting TK1 was used for CHyMErA and all BigPapi constructs. Data represented as mean±SD, n=3 independent biological replicates. FIG. 16C shows a summary of the key characteristics and applications of dual-targeting CRISPR screening systems.

GB patent application GB1907733, from which this application claims priority, expressly refers to a lengthy table section. The following Tables are described in priority GB application GB1907733.8 entitled "Methods and compositions for multiplex gene editing", filed 31 May 2019, which is hereby incorporated herein by reference in its entirety including each of the following tables and may be employed in the practice of the invention:

Table 1. Human hgRNA optimization library listing spacer pairs, wherein the "Cas9. Guide" corresponds to the proximal (Cas9) spacer and the "Cas12a.Guide" corresponds to the distal (Cas12a) spacer.

Table 2. Mouse hgRNA optimization library listing spacer pairs, wherein the "Cas9. Guide" corresponds to the proximal (Cas9) spacer and the "Cas12a.Guide" corresponds to the distal (Cas12a) spacer.

Table 3. Human hgRNA optimization library screening results including listing of spacer pairs, wherein the "Cas9. Guide" corresponds to the proximal (Cas9) spacer and the "Cas12a.Guide" corresponds to the distal (Cas12a) spacer.

Table 4. Mouse hgRNA optimization library screening results including listing of spacer pairs, wherein the "Cas9. Guide" corresponds to the proximal (Cas9) spacer and the "Cas12a.Guide" corresponds to the distal (Cas12a) spacer.

Table 5. Human 2nd generation library listing spacer pairs, wherein the "Cas9. Guide" corresponds to the proximal (Cas9) spacer and the "Cas12a.Guide" corresponds to the distal (Cas12a) spacer; and a prediction score ("CNN score") for each corresponding Cas12a guide. Also included are RNA-seq data across 5 cell lines.

Table 6. Human 2nd generation library screening results including a listing of spacer pairs, wherein the "Cas9. Guide" corresponds to the proximal (Cas9) spacer and the "Cas12a.Guide" corresponds to the distal (Cas12a) spacer; and a prediction score ("CNN score") for each corresponding Cas12a guide.

Table 7. Paralog scoring.

Table 8. Torin1 drug sensitivity scoring.

Table 9. Human exon targeting library listing spacer pairs, wherein the "Cas9 Guide" corresponds to the proximal (Cas9) spacer and the "Cas12a Guide" corresponds to the distal (Cas12a) spacer, and a prediction score ("Cas12a score") for each corresponding Cas12a guide.

Table 10. Human exon targeting library screening results.

Table 11. Primers and oligos.

Table 12. Sequences

Copies of the Tables have been submitted with the UKIPO on May 31, 2019 in connection with the filing of GB1907733.8.

DESCRIPTION OF VARIOUS EMBODIMENTS

The following is a detailed description provided to aid those skilled in the art in practicing the present disclosure. Unless otherwise defined, all technical and scientific terms used herein have the same meaning as commonly understood by one of ordinary skill in the art to which this disclosure belongs. The terminology used in the description herein is for describing particular embodiments only and is not intended to be limiting of the disclosure. All publications, patent applications, patents, figures and other references mentioned herein are expressly incorporated by reference in their entirety.

I. Definitions

As used herein, the following terms may have meanings ascribed to them below, unless specified otherwise. However, it should be understood that other meanings that are known or understood by those having ordinary skill in the art are also possible, and within the scope of the present disclosure. All publications, patent applications, patents, and other references mentioned herein are incorporated by reference in their entirety. In the case of conflict, the present specification, including definitions, will control. In addition, the materials, methods, and examples are illustrative only and not intended to be limiting.

The terms "nucleic acid", "oligonucleotide", "primer" as used herein means two or more covalently linked nucleotides. Unless the context clearly indicates otherwise, the term generally includes, but is not limited to, deoxyribonucleic acid (DNA) and ribonucleic acid (RNA), which may be single-stranded (ss) or double stranded (ds). For example, the nucleic acid molecules or polynucleotides of the disclosure can be composed of single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically double-stranded or a mixture of single- and double-stranded regions. In addition, the nucleic acid molecules can be composed of triple-stranded regions comprising RNA or DNA or both RNA and DNA. The term "oligonucleotide" as used herein generally refers to nucleic acids up to 200 base pairs in length and may be single-stranded or double-stranded. The sequences provided herein may be DNA sequences or RNA sequences, however it is to be understood that the provided sequences encompass both DNA and RNA, as well as the complementary RNA and DNA sequences, unless the context clearly indicates otherwise. For example, the sequence 5'-GAATCC-3', is understood to include 5'-GAAUCC-3', 5'-GGATTC-3', and 5'GGAUUC-3'.

The term "CRISPR-Cas" as used herein refers a CRISPR Clustered Regularly Interspaced Short Palindromic Repeats-CRISPR associated (CRISPR-Cas) protein that binds RNA and is targeted to a specific DNA sequence by the RNA to which it is bound. The CRISPR-Cas is a class II monomeric Cas protein for example a type II Cas, or a type V Cas. The type II Cas protein may be a Cas9 protein, such as Cas9 from *Streptococcus pyogenes, Francisella novicida, A. Naeslundii, Staphylococcus aureus* or *Neisseria meningitidis*. Optionally the Cas9 is from *S. pyogenes*. Optionally the Cas9 is a protein comprising an amino acid sequence with at least 80%, at least 90%, at least 95%, at least 99% or 100% sequence identity to a protein encoded by SEQ ID NO: 19 and having Cas9 activity (e.g. binding the gRNA and the target site). The Cas9 protein may possess DNA processing activity. The type V Cas protein may be a Cas12a (formerly Cpf1) Cas protein, such as a Cas12a from *Lachnospiraceae bacterium* (Lb-Cas12a) or from *Acidaminococcus* sp. BV3L6 (As-Cas12a). Optionally the Cas12a is a protein comprising an amino acid sequence with at least 80%, at least 90%, at least 95%, at least 99% or 100% sequence identity to a protein encoded by SEQ ID NO: 20 or SEQ ID NO 21 and having Cas12a activity (e.g. binding the gRNA and the target site). The type V Cas protein may possess DNA and/or RNA processing activity. Preferably the type V Cas protein possesses RNA processing activity. The terms "Cpf1" and "Cas12a" are used interchangeably throughout. Optionally the Cas12a is Lb-Cas12a.

It will be understood that type II and type V Cas proteins may possess DNA endonuclease activity, or may be modified in such a way as to generate altered activities. For example, Cas9n is a modified Cas9 that generates a DNA nick rather than a double-stranded break. As a further example, Cas9n may be fused with for example a cytidine and adenine deaminase to generate a DNA base editor that generates specific genetic alterations at or near the CRISPR target site. As another example, dCas9 is a modified Cas9 that lacks DNA endonuclease activity but retains target DNA binding activity. dCas9 may be fused with for example a transcriptional activator or a transcriptional repressor to alter gene expression from the CRISPR target site. Other modified CRISPR-Cas proteins can be used within the scope of the present disclosure.

The terms "guide RNA," "guide," or "gRNA" as used herein refer to an RNA molecule that hybridizes with a specific DNA sequence and minimally comprises a spacer sequence. The guide RNA may further comprise a protein binding segment that binds a CRISPR-Cas protein. The portion of the guide RNA that hybridizes with a specific DNA sequence is referred to herein as the nucleic acid-targeting sequence, or spacer sequence. The protein binding segment of the guide may comprise for example a tracrRNA and/or a direct repeat. The term "guide" or "guide RNA" may refer to a spacer sequence alone, or an RNA molecule comprising a spacer sequence and a protein binding segment, according to the context. The guide RNA can be represented by the corresponding DNA sequence.

The term "spacer" or "spacer sequence" as used herein refers to the portion of the guide that forms, or is capable of forming, an RNA-DNA duplex with the target sequence or a portion thereof. The spacer sequence may be complementary or correspond to a specific CRISPR target sequence. The nucleotide sequence of the spacer sequence may determine the CRISPR target sequence and may be designed or configured to target a desired CRISPR target site. A "non-targeting spacer" is a spacer that is designed to target a DNA sequence that is not present in the target DNA.

The terms "CRISPR target site" or "CRISPR-Cas target site" as used herein mean a nucleic acid to which an activated CRISPR-Cas protein will bind under suitable conditions. A CRISPR target site comprises a protospacer-adjacent motif (PAM) and a CRISPR target sequence (i.e. corresponding to the spacer sequence of the guide to which the activated CRISPR-Cas protein is bound). The sequence and relative position of the PAM with respect to the CRISPR target sequence will depend on the type of CRISPR-Cas protein. For example, the CRISPR target site of type II CRISPR-Cas protein such as Cas9 may comprise, from 5' to 3', a 15 to 25, 16 to 24, 17 to 23, 18 to 22, or 19 to 21 nucleotide, optionally a 20 nucleotide target sequence followed by a 3 nucleotide PAM having the sequence NGG (SEQ ID NO: 1). Accordingly, a type II CRISPR target site may have the sequence 5'-NiNGG-3' (SEQ ID NO: 2), where $N_1$ is 15 to 25, 16 to 24, 17 to 23, 18 to 22, or 19 to 21 nucleotides in length, optionally 20 nucleotides in length. As another example, the CRISPR-target site of a type V CRISPR-Cas protein such as Cpf1 may comprise, from 5' to 3', a 4 nucleotide PAM having the sequence TTTV (SEQ ID NO: 3), followed by a 15 to 28, 16 to 27, 17 to 26, 18 to 25, or 19 to 24 nucleotide, optionally a 20, 21, 22, or 23 nucleotide target sequence. Accordingly, a type V CRISPR target site may have the sequence 5'-TTTV-$N_1$-3' (SEQ ID NO: 4) where $N_1$ is 15 to 28, 16 to 27, 17 to 26, 18 to 25, or 19 to 24 nucleotides, optionally 20, 21, 22, or 23 nucleotides in length.

The CRISPR target site can be in any suitable genomic locus. For example, the CRISPR target site can be in a gene, optionally an intron or exon, in a promoter or other regulatory element, or in an intergenic region.

The term "active CRISPR-Cas effector protein" as used herein refers to a CRISPR-Cas protein bound to a guide RNA and which is capable of binding and optionally modifying a CRISPR target site. CRISPR-Cas proteins may modify the nucleic acid to which they are bound for example by cleaving one or more strands of the nucleic acid. The term "cleaving" or "cleavage" as used herein means breaking or severing the covalent bond between two adjacent nucleotides. In some cases this means breaking the covalent bond between two adjacent nucleotides in both strands of a double-stranded nucleic acid. Where cleavage occurs in both strands of a double stranded nucleic acid, the resulting ends may be blunt or may have overhanging ends. Accordingly, the term "CRISPR-sensitive" as used herein means a nucleic acid comprising a CRISPR target site that may be modified by an active CRISPR-Cas effector protein.

Target DNA located in the nucleus of a cell requires a CRISPR-Cas protein that can enter the nucleus. Accordingly, the CRISPR-Cas protein may be nuclear-localized and/or may comprise for example one or more nuclear localization signals, optionally a nucleoplasmin nuclear localization signal. Optionally the CRISPR-Cas protein comprises two or more nuclear localization signals.

The term "tracrRNA" as used herein refers to a "trans-encoded crRNA" which may, for example, interact with a CRISPR-Cas protein such as Cas9 and may be connected to, or form part of, a guide RNA. The tracrRNA may be a tracrRNA from for example *S. pyogenes*. A tracrRNA may have for example the sequence of 5'-gtttcagagctatgctggaaacagcatagcaagttgaaataaggctagtccgttatcaacttgaaaaagtggcaccgagtcggtgc-3' (SEQ ID NO: 5). Other tracrRNAs may also be used. Suitable tracrRNAs can be identified by a person skilled in the art based on the teaching of the present application.

The terms "direct repeat" as used herein refers to an RNA that forms a stem-loop and may, for example, interact with a CRISPR-Cas protein such as Cas12a and may be connected to, or form part of, a guide RNA. The direct repeat may be a direct repeat from for example *Lachnospiraceae bacterium* or *Acidaminococcus* sp. BV3L6. A direct repeat may have for example the sequence of 5'-taatttctactcttgtagat-3' (for Lb-Cas12a) (SEQ ID NO: 6) or 5'-taatttctactaagtgtagat-3' (for As-Cas12a) (SEQ ID NO: 7). Other direct repeats may also be used. Suitable direct repeats can be identified by a person skilled in the art based on the teaching of the present application.

The terms "hybrid guide" or "hgRNA" as used herein refers to a guide RNA comprising two or more guide RNAs that are capable of interacting with orthologous CRISPR-Cas proteins under suitable conditions. For example, the hybrid guide may comprise a proximal spacer, a tracrRNA, a direct repeat, and a distal spacer, and the proximal spacer and tracrRNA may interact with a type II Cas protein such as Cas9, and the direct repeat and distal spacer may interact with a type V Cas protein such as Cas12a. The hybrid guide may comprise additional components for example an additional direct repeat and additional spacer.

The terms "proximal spacer" and "distal spacer" as used herein refer to the relative positions of the respective spacers in the hybrid guide, wherein a proximal spacer refers to a spacer at or near the 5' end of the hybrid guide, and a distal spacer refers to a spacer at or near the 3' end of the hybrid guide.

The term "hgRNA of the disclosure" as used herein means a hybrid guide comprising a proximal spacer RNA, a distal spacer RNA, a type II CRISPR-Cas tracrRNA, and a type V CRISPR-Cas direct repeat. The hgRNA may be oriented as follows, from 5' to 3', a proximal spacer RNA, a type II CRISPR-Cas tracrRNA, a type V CRISPR-Cas direct repeat, and a distal spacer RNA. Other orientations are contemplated.

The term "mature guide RNA" as used herein refers to a hgRNA which is processed into individual Cas9 and Cas12a guide RNAs.

The proximal spacer and distal spacer of the hybrid guide may be configured or paired for example to generate one or more desired genetic perturbations. Accordingly, the terms "paired guide" or "paired oligonucleotide" as used herein refer to a combination of two or more spacers that are configured to generate a desired genetic perturbation. The paired guide may for example be configured to target an exon in a gene of interest. Accordingly, the term "exon-targeting" as used herein refers to a paired guide configured to target one intronic site upstream of the target exon and another intronic site downstream of the target exon. In some cases, the paired guide may be configured to generate a frame-altering genetic alteration. In some cases the paired guide may be configured to generate a frame-preserving genetic alteration. In another example, the paired guide may be configured to target two or more paralogous or ohnologous genes. The paired guide may be configured to target two or more genes of interest. Other configurations are also possible. Suitable configurations will depend on the desired genetic perturbation, and can be identified by a person skilled in the art based on the teaching of the present application.

The term "guide target region" or "extended target region" as used herein refers to the CRISPR target site and flanking upstream and downstream regions of the target site. For example, the guide target region may comprise the spacer sequence, the PAM sequence, and flanking upstream and downstream sequences. The target guide region may comprise for example a 23 bp spacer sequence, a 4 bp upstream PAM sequence and 6 bp each of flanking upstream and downstream sequences, resulting in a total guide target region of 39 bp.

The term "core essential gene" as used herein refers to genes whose knockout results in a fitness defect across various mammalian cell lines and as described for human cell lines in the core essential gene 2 (CEG2) data set in Hart et al., 2017.

Where a range of values is provided, it is understood that each intervening value, to the tenth of the unit of the lower limit unless the context clearly dictates otherwise, between the upper and lower limit of that range and any other stated or intervening value in that stated range is encompassed within the description. Ranges from any lower limit to any upper limit are contemplated. The upper and lower limits of these smaller ranges which may independently be included in the smaller ranges is also encompassed within the description, subject to any specifically excluded limit in the stated range. Where the stated range includes one or both of the limits, ranges excluding either both of those included limits are also included in the description.

It must be noted that as used herein and in the appended claims, the singular forms "a", "an", and "the" include plural references unless the context clearly dictates otherwise.

All numerical values within the detailed description and the claims herein are modified by "about" or "approximately" the indicated value, and take into account experimental error and variations that would be expected by a person having ordinary skill in the art.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of" will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively As used herein in the specification and in the claims, the phrase “at least one,” in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase “at least one” refers, whether related or unrelated to those elements specifically identified.

The term “about” as used herein means plus or minus 10%-15%, 5-10%, or optionally about 5% of the number to which reference is being made.

It should also be understood that, in certain methods described herein that include more than one step or act, the order of the steps or acts of the method is not necessarily limited to the order in which the steps or acts of the method are recited unless the context indicates otherwise.

II. Materials and Methods

A system that uses co-expression of orthologous Cas9 and Cas12a nucleases, together with “hybrid guide” (hg) RNAs, generated from fusion constructs comprising Cas9 and Cas12a gRNAs expressed off of a single promoter is described herein. As demonstrated in the Examples, the hgRNAs may be processed by intrinsic Cas12a RNAse activity. As further demonstrated in the Examples, a hgRNA can be used for example for generating a targeted genetic deletion such as an exon deletion in a gene of interest.

Accordingly, one aspect of the disclosure includes a hybrid guide RNA (hgRNA) comprising, from 5' to 3', a proximal spacer RNA, a type II CRISPR-Cas tracrRNA, a type V CRISPR-Cas direct repeat, and a distal spacer RNA. In one embodiment the hgRNA may be capable of being processed into a first and a second mature guide RNA, optionally by a type V Cas protein, preferably a Cas12a protein. In another embodiment, the proximal spacer may be configured to target a type II CRISPR target site, optionally a Cas9 target site. In a further embodiment, the distal spacer may be configured to target a type V CRISPR target site, preferably a Cas12a target site.

It has been reported that the Cas9 tracrRNA can be modified to improve the expression of the RNA transcript and/or to minimize transcription termination due to the T-rich tracrRNA sequence (Dang et al., 2015). Accordingly, in one embodiment the tracrRNA may have a sequence as set out in SEQ ID NO: 5.

In one embodiment the proximal spacer may be 19-21, or optionally 20 nucleotides in length. In another embodiment the distal spacer may be 19 to 24, or optionally 23 nucleotides in length. In a further embodiment, the hgRNA may have a sequence as set out in SEQ ID NO: 8 or SEQ ID NO: 9.

As demonstrated in the Examples, an hgRNA may be suitable for further multiplexing by increasing the number of Cas12a guides in the hgRNA. Accordingly, in one embodiment, the hgRNA further comprises one or more additional direct repeats and one or more additional spacers, wherein the one or more additional spacers are capable of being processed into mature guide RNAs by a type V Cas protein.

As demonstrated in the Examples, an hgRNA may be encoded in a construct and/or expressed from an expression cassette. Accordingly, one aspect of the disclosure is a construct comprising an hgRNA expression cassette, the expression cassette comprising a DNA sequence encoding an hgRNA, wherein the DNA sequence is operably linked to a promoter and a transcription termination site. Any suitable promoter may be used. Suitable promoters can be identified by a person skilled in the art, and may include RNA polymerase III promoters such as U6 and H1 (from human mouse or other species), or any RNA polymerase II promoters for higher-order multiplex hgRNAs (such as CMV, EF1A, PGK or any other promoter suitable for efficient expression including inducible promoters such as doxycycline responsive promoters). Optionally the promoter is a U6 promoter.

In one embodiment, the construct is a vector. Any suitable vector may be used. Suitable vectors can be identified by a person skilled in the art, and may include a viral vector, optionally a lentiviral vector. It has been reported that Cas12a RNA processing activity targets and inactivates lentiviral particles designed to deliver Cas12a sgRNAs into cells (Zetsche et al., 2016). This limitation was overcome by inverting the orientation of the sgRNA expression cassette such as not to be recognized in the (+) RNA strand of lentivirus but still to be expressed after integration into the host genome (Zetsche et al., 2016). Accordingly, in one embodiment the construct is a lentiviral vector having a (+) strand, and the hgRNA expression cassette is inverted so as not to be recognized in the (+) strand of lentivirus.

Also described herein are optimized hgRNAs designed using a deep learning framework, for both the human and mouse genomes, through iterative rounds of pooled hgRNA library construction and screening in both human and mouse cells. As demonstrated herein, the modified Cas12a gRNA efficiencies are comparable to the most efficient Cas9 gRNAs. An optimized genome-scale, high-complexity hgRNA library was used to identify fitness genes. The hgRNA library comprised the following sets of Cas9 and Cas12a hgRNA expression cassettes: (1) 58332 hgRNAs where one or two guides target one of 4993 genes, defined as having the highest expression levels across a panel of five commonly used human cell lines; (2) 3566 control hgRNAs targeting intergenic or exogenous sequences for assessing single-versus dual-cutting effects; and (3) 30848 combinatorial- and single-targeting hgRNAs directed at 1344 human paralogs and 22 hand-selected gene-gene pairs of interest.

Accordingly, another aspect of the disclosure includes a nucleic acid library comprising a multiplicity of hgRNAs or a multiplicity of constructs that encode a multiplicity of hgRNAs. The hgRNA library may include any number of hgRNAs or any number of constructs that encode any number of hgRNAs. In one embodiment, the library comprises: a) at least or about 1,000, 2,000, 3,000, 4,000, 5,000, 10,000, 15,000, 20,000, 25,000, 30,000, 35,000, 40,000, 45,000, 50,000, or 55,000 or for example at least 58,332 hgRNAs where one or two spacers target one of a set of genes or genomic loci, for example, at least or about 100, 200, 300, 400, 500, 600, 750, 1,000, 1,500, 2,000, 2,500, 3,000, 3,500, 4,000 or 4,500 genes or genomic loci, for example at least 4,993 genes or genomic loci.

The nucleic acid library can comprise a targeted collection of hgRNAs for targeting a desired set or type of genes or genomic loci. For example, the nucleic acid library can comprise hgRNAs designed for exon-targeting, intron targeting, 5' and/or 3' UTR targeting, gene pair targeting library, dual-targeting of individual genes library, enhancer targeting library, promoter targeting library and/or non-coding RNA targeting. Accordingly, on one embodiment, the nucleic acid library is selected from an exon-targeting library, an intron-targeting library, a 5' and/or 3' UTR targeting library, a paralog targeting library, a chromosome targeting library, gene pair targeting library, dual-targeting of individual genes library, enhancer targeting library, promoter targeting library and/or a non-coding RNA (ncRNA) targeting library and the like. (e.g. a selected set for example based on gene function or pathway).

For example, genes or genomic loci defined as having the highest expression levels across a panel of for example five commonly used cell lines, optionally human cell lines; b) at least or about 100, 200, 300, 400, 500, 1,000, 1,500, 2,000, 2,500 or 3,000 or for example at least 3,566 control hgRNAs targeting intergenic or exogenous sequences for example for assessing single-versus dual-cutting effects; c) at least or about 1,000, 2,000, 3,000, 4,000, 5,000, 10,000, 15,000, 20,000, 25,000 or 30,000 or for example at least 30,848 combinatorial- and single-targeting hgRNAs targeting at least or about 100, 200, 300, 400, 500, 600, 750, 900, 1,100, or 1,300 human paralogs, for example at least 1,344 human paralogs; and/or d) one or more hand-selected gene-gene pairs of interest. In some embodiments, the library comprises one or more of the guide sequences set out in Tables herein, such as any one or combinations in Tables 1-6 and/or 9, optionally Tables 1, 2, 5 and/or 9.

In some embodiments, the nucleic acid library is optimized for the preferential inclusion of hgRNAs that comprise a distal spacer (Cas12a spacer) that have one or more of the following properties: is neutral with respect to GC content, has a G at the first position, does not have a T at one or more of the first nine positions, and/or does not have a C at the 23rd nucleotide (e.g. where the distal spacer comprises a 23rd nucleotide). Accordingly, the nucleic acid library may be enriched for Cas12a spacers that are neutral for GC content (e.g. have 40-60%, 45-55%, or approximately 50% GC content); enriched for spacers that have a G in the first position; depleted for spacers that have a T at one or more of the first nine positions; and/or depleted for spacers that have a C at the $23^{rd}$ position.

In some embodiments the library is an exon-targeting library wherein each hgRNA encoded hgRNA comprises: a) a proximal spacer that targets (e.g. is complementary in sequence to) an intronic site flanking a target exon, optionally that is at least or about 100 base pairs from a splice site flanking the target exon, and a distal spacer that targets an intronic site flanking the target exon, optionally that is at least or about 100 base pairs from another splice site flanking the target exon or another target exon; b) a proximal spacer that targets an intronic site flanking a target exon optionally that is at least or about 100 base pairs from a splice site flanking the target exon and a distal spacer that targets an intergenic region; c) a proximal spacer that targets an intergenic region and a distal spacer that targets an intronic site flanking a target exon, optionally that is at least or about 100 base pairs from a splice site flanking the target exon; d) a proximal spacer that targets an exonic region and a distal spacer that targets an intergenic region; and/or e) a proximal spacer that targets an intergenic region and a distal spacer that targets an exonic region. Optionally for each exon targeted, each subset of hgRNAs comprises: a) at least two proximal spacers that each target an intronic site flanking a target exon, optionally that is at least or about 100 base pairs from a splice site flanking the target exon; and b) at least four distal spacers that each target an intronic site optionally that is at least or about 100 base pairs from a splice site flanking each target exon. Optionally, an intronic site flanking a target exon will be absent for any known functional genetic elements such as for example lncRNAs, snoRNAs, or enhancers.

Exon-targeting hgRNAs can be designed to generate frame-altering exon deletions or frame-preserving exon deletions. Accordingly, in one embodiment, the exon-targeting library comprises a subset of hgRNAs that are configured to generate frame-altering genetic alterations; and a subset of hgRNAs that are configured to generate frame-preserving genetic alterations.

In some embodiments the library is an exon-targeting library, an intron-targeting library, a 5' and/or 3' UTR targeting library, a paralog targeting library, a chromosome targeting library, gene pair targeting library, dual-targeting of individual genes library, enhancer targeting library, promoter targeting library and/or a non-coding RNA (ncRNA) targeting library.

As described herein, a construct encoding an hgRNA may be generated in a two-step process using a paired guide oligonucleotide. Accordingly, one aspect of the disclosure is a paired guide oligonucleotide comprising a 5' restriction enzyme site or a compatible overhang, a proximal spacer, a stuffer segment comprising one or more internal restriction enzyme sites, a distal spacer, and a 3' restriction enzyme site or a compatible overhang. It will be understood that any suitable restriction enzyme sites may be used. Optionally, the restriction enzyme sites will be recognized by restriction enzymes that cut at a distance from the recognition sequence. Suitable restriction enzyme sites are commonly used in the art and can be identified. In some embodiments the 5' and/or 3' restriction enzyme sites may be a BfuAI site. In some embodiments the one or more internal restriction enzyme sites may be a BsmBI site. Alternately, the 5' and 3' ends comprise overhangs that are compatible with overhangs generated by a restriction digest of the construct into which the guide will be cloned. It will be understood that suitable compatible overhangs may be generated by restriction digest or by annealing forward and reverse oligonucleotides having overhanging ends.

In some embodiments, for example large-scale hgRNA library cloning, paired guide oligonucleotides may be polymerase chain reaction (PCR) amplified before being cloned into the suitable construct. Further, it will be understood that restriction enzyme cleavage may be more efficient for internal restriction enzyme sites, i.e. where the nucleic acid extends in both the 5' and 3' directions from the recognition sequence. Accordingly, in some embodiments, the paired-guide nucleotide further comprises 5' and/or 3' extensions of 1, 2, 3, 4, 5 base pairs or more beyond the restriction enzyme recognition sequence.

In some embodiments the stuffer segment is 25 to 45, 28 to 40, 30 to 35, or 31 to 33 nucleotides in length, optionally 32 nucleotides in length. In some embodiments the stuffer segment has a sequence of SEQ ID NO: 10. In some embodiments the stuffer segment is a degenerate stuffer segment having a sequence of SEQ ID NO: 11. In some embodiments the proximal spacer is 15 to 25, 16 to 24, 17 to 23, 18 to 22, or 19 to 21 nucleotides in length, optionally 20 nucleotides in length. In some embodiments the distal spacer is 15 to 28, 16 to 27, 17 to 26, 18 to 25, or 19 to 24 nucleotides in length, optionally 20, 21, 22, or 23 nucleotides in length. Optionally the paired guide oligonucleotide has a sequence of SEQ ID NO: 12 or SEQ ID NO: 13.

Another aspect of the disclosure includes a method of generating an hgRNA expression construct, the method comprising: a) obtaining a paired guide oligonucleotide as described herein; b) cloning the oligonucleotide into a vector between a promoter sequence and a transcription termination site to generate an intermediate construct; c) obtaining a second oligonucleotide comprising or encoding a tracrRNA and a direct repeat sequence, and having 5' and 3' ends that are capable of interfacing with the one or more processed internal restriction enzyme sites of the paired guide oligonucleotide; and d) cloning the second oligonucleotide into the intermediate construct between the proximal guide and the distal guide.

Suitable cloning techniques are routinely practiced in the art and can be identified by the skilled person and may include one or more of the following steps: performing a restriction digest using a suitable restriction enzyme, purifying desired fragments using any suitable method, and combining and ligating the desired fragments. Other cloning techniques are also known in the art and are specifically contemplated in the disclosure. Any suitable vector may be used. In some embodiments the vector is a viral vector, for example a lentiviral vector. Optionally the lentiviral vector is a pLCKO based vector, optionally having the sequence of SEQ ID NO: 14.

The second oligonucleotide may be flanked by any suitable restriction enzyme sites so as to be compatible with the internal restriction enzyme sites of the paired guide oligonucleotide. In some embodiments the second oligonucleotide has 5' and 3' ends that are capable of interfacing with a BsmBI restriction enzyme site. In some embodiments the second oligonucleotide has a Lb-Cas12a direct repeat or a As-Cas12a direct repeat. Optionally the second oligonucleotide has a sequence of SEQ ID NO: 15 or SEQ ID NO: 16.

The paired guide oligonucleotides of the disclosure can be used to generate a library of constructs encoding a multiplicity of hgRNAs. Accordingly, one aspect of the disclosure is a method of generating a library of constructs encoding a multiplicity of hgRNAs, the method comprising: a) obtaining a multiplicity of discrete paired guide oligonucleotides; b) cloning the multiplicity of paired guide oligonucleotides into a plurality of vectors between a promoter sequence and a transcription termination site to generate a multiplicity of intermediate constructs; c) obtaining a plurality of second oligonucleotides each comprising or encoding a tracrRNA and a direct repeat sequence, and having 5' and 3' ends that are capable of interfacing with the one or more internal restriction enzyme sites of the paired guide oligonucleotide; and d) cloning the plurality of second oligonucleotides into the multiplicity of intermediate constructs between the proximal guide and the distal guide. A further aspect of the disclosure includes a library of constructs encoding a multiplicity of hgRNAs obtained using the method described above.

As demonstrated in the Examples, an hgRNA of the disclosure may be used to generate a targeted genetic deletion by introducing an hgRNA of the disclosure into a cell expressing a type II Cas protein and a type V Cas protein. Accordingly, one aspect of the disclosure includes a method of generating a targeted genetic deletion, the method comprising: a) introducing into a cell an hgRNA of the disclosure, wherein the proximal guide is configured to target a CRISPR target site on a chromosome at one end of the desired deletion and the distal guide is configured to target another CRISPR target site on the chromosome at the other end of the desired deletion, and wherein the cell expresses a type II Cas protein and a type V Cas protein; b) culturing the cell under suitable conditions such that: i) the hgRNA is processed into mature guide RNAs, ii) the mature guide RNAs associate with their respective Cas protein and guide the Cas proteins to their respective CRISPR target sites; iii) the Cas proteins each introduce a double-stranded break at the target site on the chromosome; and iv) the double-stranded breaks are repaired by a DNA repair process such that a targeted genetic deletion is generated.

The hgRNA may be introduced into the cell in any suitable manner, for example by transfection. The construct comprising an hgRNA expression cassette may be introduced into the cell in any suitable manner, for example by transfection. Suitable transfection reagents and methods are routinely practiced in the art and can be identified by the skilled person. Optionally, the construct is a viral vector, optionally a lentiviral vector, and is introduced into the cell by transduction. Suitable transduction methods are routinely practiced in the art and can be identified by the skilled person.

For generating a targeted genetic deletion, the hgRNA may also be introduced into the cell by introducing an hgRNA expression cassette as described herein. Accordingly, a related aspect of the disclosure includes a method of generating a targeted genetic deletion, the method comprising: a) introducing into a cell a construct comprising an hgRNA expression cassette, wherein the proximal guide has been designed to target a site on a chromosome at one end of the desired deletion and the distal guide has been designed to target a target site on the chromosome at the other end of the desired deletion, and wherein the cell expresses a type II Cas protein and a type V Cas protein; b) culturing the cell under suitable conditions such that: i) the hgRNA is expressed and processed into mature guide RNAs, ii) the mature guide RNAs associate with their respective Cas protein and guide the Cas proteins to their respective target sites; iii) the Cas proteins each introduce a double-stranded break at the target site on the chromosome; and iv) the double-stranded breaks are repaired by a DNA repair process such that a targeted genetic deletion is generated.

Optionally the type II Cas protein expressed in the cell is a nuclear localized Cas9. Optionally the type V Cas protein expressed in the cell is a nuclear localized Cas12a protein, optionally an Lb-Cas12a protein or an As-Cas12a protein. In some embodiments the type II Cas protein and/or the type V Cas protein comprise a nuclear localization signal, optionally a nucleoplasmin nuclear localization signal and/or an SV40 nuclear localization signal.

A further aspect of the disclosure is a cell expressing a nuclear localized Cas9 protein, a nuclear localized Cas12a protein, and an hgRNA of the disclosure. In some embodiments the Cas12a protein is Lb-Cas12a. In some embodiments the Cas9 protein and/or the Cas12a protein comprise one or more nuclear localization signals, optionally a nucleoplasmin nuclear localization signal and/or an SV40 nuclear localization signal.

Any suitable cell may be used in the methods described herein, and can be determined by the skilled person on the basis of the desired application. The cell may be from any organism. Optionally the cell is a mammalian cell such as a human cell or a mouse cell. Optionally the cell is a cell line. The cell line may be any suitable cell line. Optionally the cell line is selected from the list consisting of HAP1, hTERT, RPE1, Neuro2a, and CGR8.

In some embodiments the cell is stably transduced with virus carrying a Cas9 and/or a Cas12a expression cassette.

As demonstrated herein, an optimized genome-scale, high-complexity hgRNA library that targets 672 human paralog pairs representing 1344 genes, or >90% of predicted paralogs in the human genome can be used to identify genetic interactions and chemical-genetic interactions.

Accordingly, one aspect of the disclosure is a method of genetic interaction screening, the method comprising: a) introducing into a plurality of cells the hgRNA library as described herein, wherein the plurality of cells each express a nuclear localized type II Cas protein and a nuclear localized type V Cas protein; b) culturing the plurality of cells such that: i) the multiplicity of hgRNAs are processed into mature guide RNAs, ii) the mature guide RNAs associate with their respective Cas protein and guide the Cas proteins to their respective target sites; c) culturing the plurality of cells for a period of time to allow for hgRNA dropout or enrichment; d) collecting the plurality of cells; and e) identifying one or more hgRNAs that are over- or under-represented in the plurality of cells.

A related aspect of the disclosure is a chemical-genetic interaction screening method, the method comprising: a) introducing into a plurality of cells the hgRNA library as described herein, wherein the plurality of cells each express a nuclear localized type II Cas protein and a nuclear localized type V Cas protein; b) culturing the plurality of cells such that: i) the multiplicity of hgRNAs are processed into mature guide RNAs, ii) the mature guide RNAs associate with their respective Cas protein and guide the Cas proteins to their respective target sites; c) treating with an amount of a test; d) culturing the plurality of cells under drug selection for a period of time to allow for hgRNA dropout; e) collecting the plurality of cells; and f) identifying one or more targets that suppress or sensitize the plurality of cells to the test drug.

The test drug can be for example a compound that affects cell growth, cell cycle, protein trafficking, splicing, protein turnover or modification, metabolism and/or any other cell function. For example, the drug can be a mTOR kinase inhibitor, a cell cycle inhibitor or the like.

It will be understood that CRISPR-Cas proteins may possess DNA endonuclease activity, or may be modified in such a way as to generate altered activities. For example, the CRISPR-Cas protein may generate a double-stranded DNA break at the target site. In another example, the CRISPR-Cas protein may be a modified CRISPR-Cas protein that binds the CRISPR-Cas target DNA and inhibits transcription. In another example, the CRISPR-Cas protein may be a modified CRISPR-Cas protein that acts as a base editor. Other modified CRISPR-Cas proteins can be used within the scope of the present disclosure. Suitable modified CRISPR-Cas proteins will depend on the application and can be determined by the skilled person.

Accordingly, in some embodiments of the genetic interaction screening method and/or the chemical-genetic interaction screening method, the CRISPR-Cas proteins each introduce a double-stranded break at the target site on the chromosome, and the double-stranded breaks are repaired by a DNA repair process such that a genetic alteration is generated at the target site. In other embodiments, one or more of the CRISPR-Cas proteins is modified to alter transcription of the CRISPR-Cas target DNA. In a further embodiment, one or more of the CRISPR-Cas proteins is modified to act as a base editor such that a genetic alteration is generated at the target site.

In some embodiments of the genetic interaction screening method and or the chemical-genetic interaction screening method at least or about a 200-fold, 250-fold, or more library coverage is retained over the time course of the screen.

A variety of scoring methods can be used in scoring the genetic interaction and/or the chemical-genetic interaction screening, for example the methods described herein. Appropriate scoring methods can be determined by the skilled person according to the desired application.

As demonstrated herein, a convolutional neural network can be trained to optimize guide design. Accordingly, one aspect of the disclosure includes a method of training a convolutional neural network for optimizing guide design, the method comprising: a) collecting a set of guide target region sequences and corresponding activity category from a database, wherein each guide target region sequence is n nucleotides in length and comprises a spacer sequence, PAM sequence, and flanking upstream and downstream sequences, and the activity category is either "active" or "inactive"; b) applying one or more transformations to each guide target region sequence, including generating a 4 by n binary matrix E such that element $e_{ij}$ represents the indicator variable for nucleotide i at position j, to create a training set; c) training the neural network using the training set by: i) passing the first training set into a convolutional layer of 52 filters of length 4 to generate an activated score set; ii) passing the activated score set through a pooling layer to generate an average score set; iii) passing the average score set through a dropout layer to generate a summarized feature score set; iv) passing the summarized feature score set through a fully connected hidden layer and another dropout layer; and v) passing the set generated in step iv) through an output layer.

In some embodiments, the activity category is active when the False Discovery Rate (FDR)<5% and the Log Fold Change (FC)<−1; or inactive where FDR>=5% and FC=(−0.5 to 0.5).

The trained convolutional neural network described herein can be used to generate prediction scores to aid in the design of a guide RNA. Accordingly, one aspect of the disclosure includes a method of designing a guide RNA, the method comprising: a) identifying a PAM sequence in a target region; b) determining a guide target region sequence for each PAM sequence, wherein the guide target region sequence is n nucleotides in length and comprises a spacer sequence, PAM sequence, and flanking upstream and downstream sequences; c) submitting the guide target regions sequence through the trained convolutional neural network described herein to obtain one or more prediction scores; and d) identifying a guide RNA sequence on the basis of the one or more prediction scores obtained in step c).

A further aspect of the disclosure is a spacer library comprising a multiplicity of CRISPR-Cas12a spacers designed using a method described herein that are capable of targeting a multiplicity of target regions or genes in a genome, wherein each of the multiplicity of CRISPR-Cas12a spacers are 15-28, 16 to 27, 17 to 26, 18 to 25, or 19 to 24 nucleotides in length, optionally 20, 21, 22, or 23 nucleotides in length. The spacer library can comprise the distal spacer or distal spacers where there is more than one Cas12a spacer. In an embodiment, the spacer library comprises a multiplicity of spacers that are capable of targeting 100, 200, 300, 400, 500, 600, 750, 1,000, 1,500, 2,000, 2,500, 3,000, 3,500, 4,000 or 4,500 genomic loci, for example at least 4,993 genes, or any number of genes or other genomic loci, or for example each gene in the genome or a desired subset thereof, wherein the library comprises one, two, three, four, five, or more spacers per target gene or genomic locus. In an embodiment, the library is capable of (e.g. designed for) targeting a desired subset of genes or genomic loci in the genome and comprises one, two, three, four, five, or more different spacers per gene or genomic locus.

In an embodiment, the spacer library is selected from an exon-targeting library, an intron-targeting library, a 5' and/or 3' UTR targeting library, a paralog targeting library, a chromosome targeting library, gene pair targeting library, dual-targeting of individual genes library, enhancer targeting library, promoter targeting library and/or a non-coding RNA (ncRNA) targeting library and the like.

Also described herein are the CRISPR-Cas12a spacers listed in Tables 1, 2, 3, 4, 5, and 6 as "Cas12a.Guide" and in Table 9 as "Cas12a Guide". In an embodiment, the library comprises at least or about 1,000, 2,000, 3,000, 4,000, 5,000, 10,000, 15,000, 20,000, 25,000, 30,000, 35,000, 40,000, 45,000, 50,000, or 55,000 Cas12a spacers, optionally each spacer capable of targeting a target region having a prediction score of greater than 0.6, greater than 0.7, greater than 0.8, or greater than 0.9 as determined by a method described herein (e.g. CNN/CHyMErA-Net) and/or as listed in Table 5 or 6 as "CNN.Score" or in Table 9 as "Cas12a Score". These libraries are disclosed in priority GB provisional application GB1907733.8 entitled "Methods and compositions for multiplex gene editing", filed 31 May 2019, in the Tables filed therein.

As shown herein, active Cas12a guides are neutral with respect to GC content, with a preference for G at the first position proximal to the PAM sequence, depletion of T at the first nine positions, and depleted for a C at the PAM-distal 23rd nucleotide. Similar nucleotide preferences were observed in the filters learned by the CNN classifier.

Accordingly, in an embodiment, the multiplicity of spacers, or a subset of the multiplicity, each spacer having a sequence of 23 nucleotides or longer, is designed or selected preferentially to include spacers that have one or more of the following properties: are neutral for GC content (e.g. have 40-60%, 45-55% or approximately 50% GC content), have a G at the first nucleotide (position one), do not have a T at one or more of each of the first nine nucleotides (positions 1 to 9), and/or do not have a C at the 23rd nucleotide (position 23).

By "designed or selected preferentially to include" or "preferential inclusion", it is meant that a spacer having one or more of the indicated properties are more likely to be selected or included than a spacer lacking one or more of the indicated properties. For example, spacers that have a GC content of between 40-60% are preferred, spacers that have a G at position one are preferred for example at a ratio of greater than 1:3, spacers that have any nucleotide that is not T at one or more of positions 1, 2, 3, 4, 5, 6, 7, 8 or 9 are preferred for example at a ratio of greater than 3:1 and/or spacers that have any nucleotide that is not C at position 23 are preferred for example at a ratio of greater than 3:1.

The multiplicity of spacers, or subset thereof, may therefore be neutral for GC content, enriched for G at position 1, depleted for T at each of positions 1 to 9, and/or depleted for C at position 23. Taking into account the above preferences, it may be that each of the multiplicity of spacers has for example a greater than 25% likelihood of nucleotide G being at position 1, has for example less than 25% likelihood of nucleotide T being at positions 1-9, independently, and/or for example has less than 25% likelihood of nucleotide C being at position 23. Overall GC content of each of the multiplicity of spacers can be about 40-60%, 45-55%, or preferentially approximately 50% (see FIG. 2*c*).

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Figure 7B:
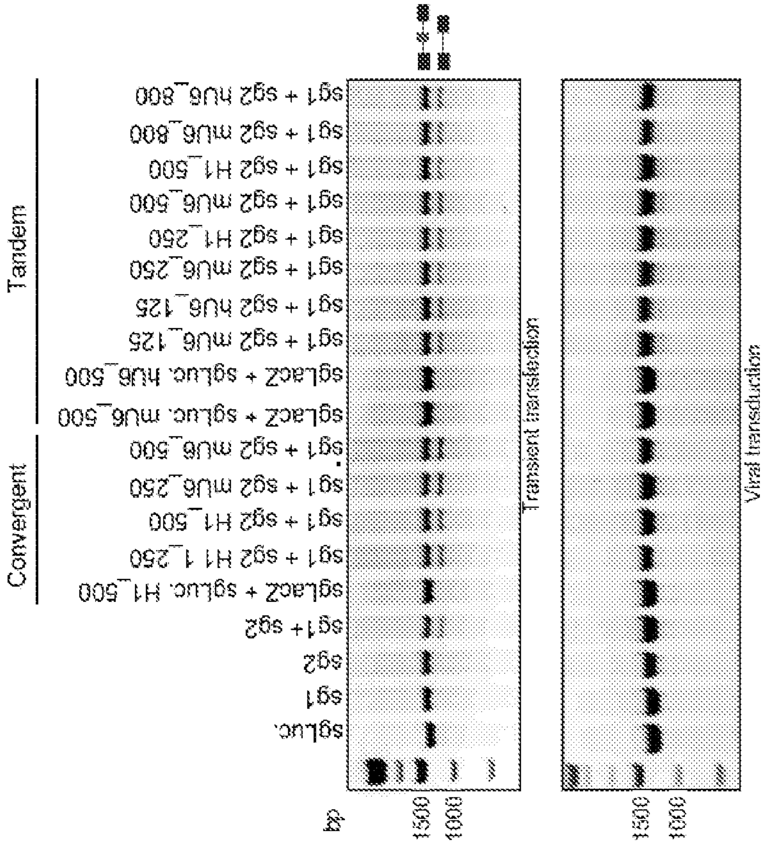
Figure 7A:
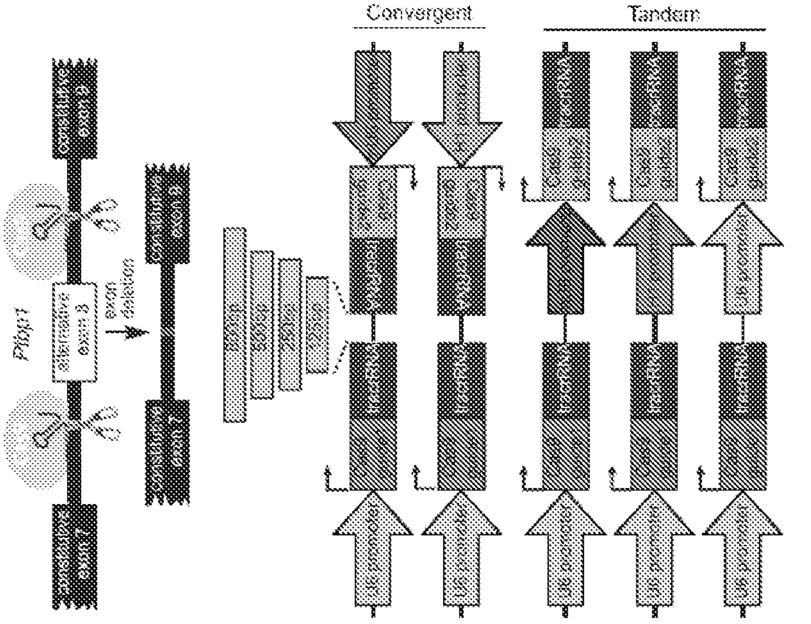
Figure 7C:
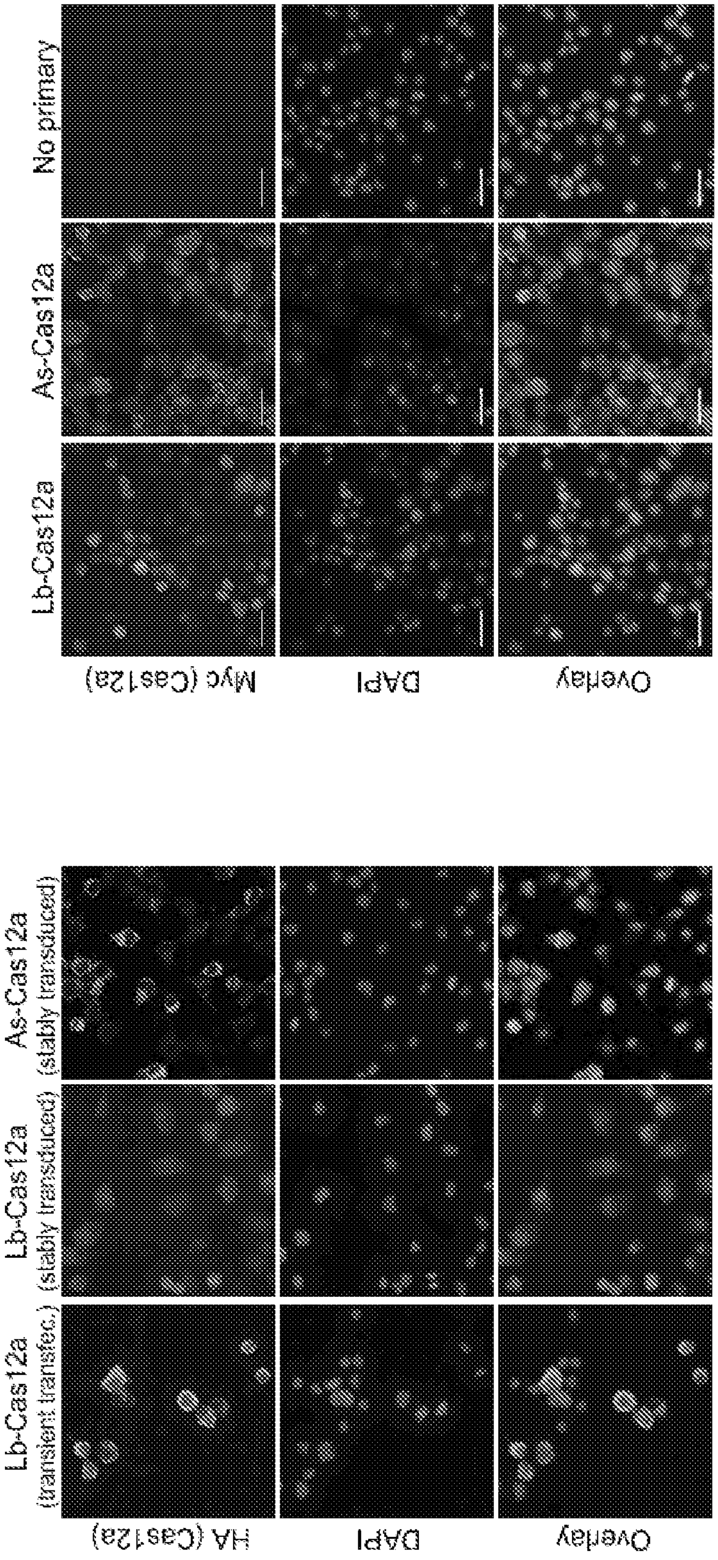
Figure 7D:
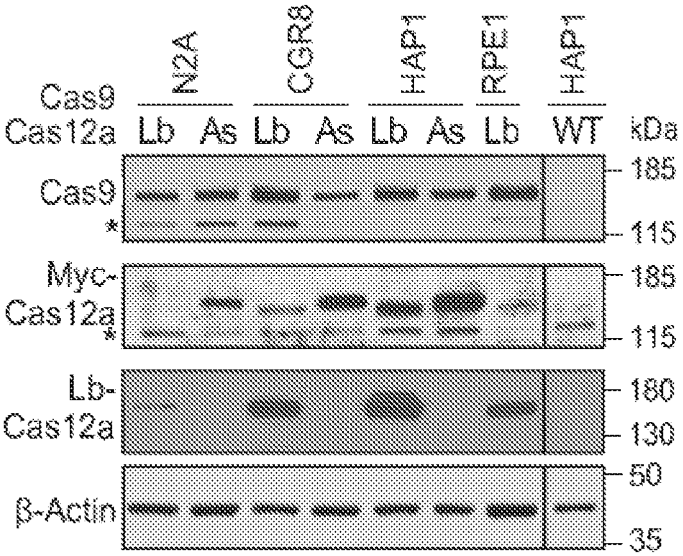
Figure 7E:
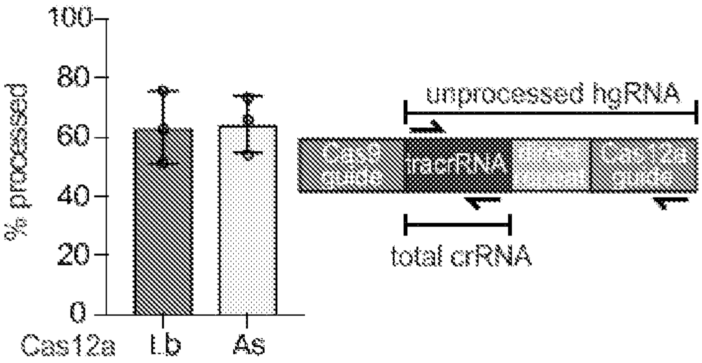

Example 1: Development of a Hybrid CRISPR-Cas System for Programmable Multi-Site Genome Editing Different lentiviral-based approaches employing gRNAs designed to direct deletion of exon 8 of the mouse Ptbp1 gene, by targeting intronic sequences flanking this exon (see Methods in Example 9) were compared. Employing single Cas enzymes generally resulted in poor deletion efficiencies (FIGS. 7A-B and FIG. 13). Cell lines co-expressing *S. pyogenes* Cas9 and Cas12a, either *Lachnospiraceae bacterium* ND2006 (Lb)-Cas12a or *Acidaminococcus* sp. BV3L6 (As)-Cas12a, together with hybrid guide (hg) RNAs that fuse Cas9 and Cas12a guides (FIGS. 1A and 7C-D) were generated. These hgRNAs are processed by intrinsic Cas12a RNAse activity (FIG. 7E) (Fonfara et al., 2016; Zetsche et al., 2016), liberating the individual Cas9 and Cas12a gRNAs for loading into their respective nucleases (FIG. 1A). The utility of combining Cas9 and Cas12a through expression of programmable hgRNAs, is demonstrated below. The system was named CHyMErA (Cas Hybrid for Multiplexed Editing and Screening Applications).

Figure 1B:
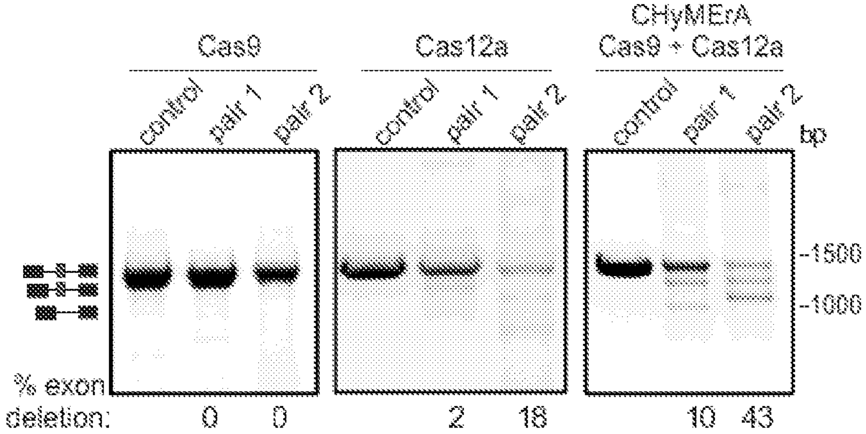
Figure 7F:
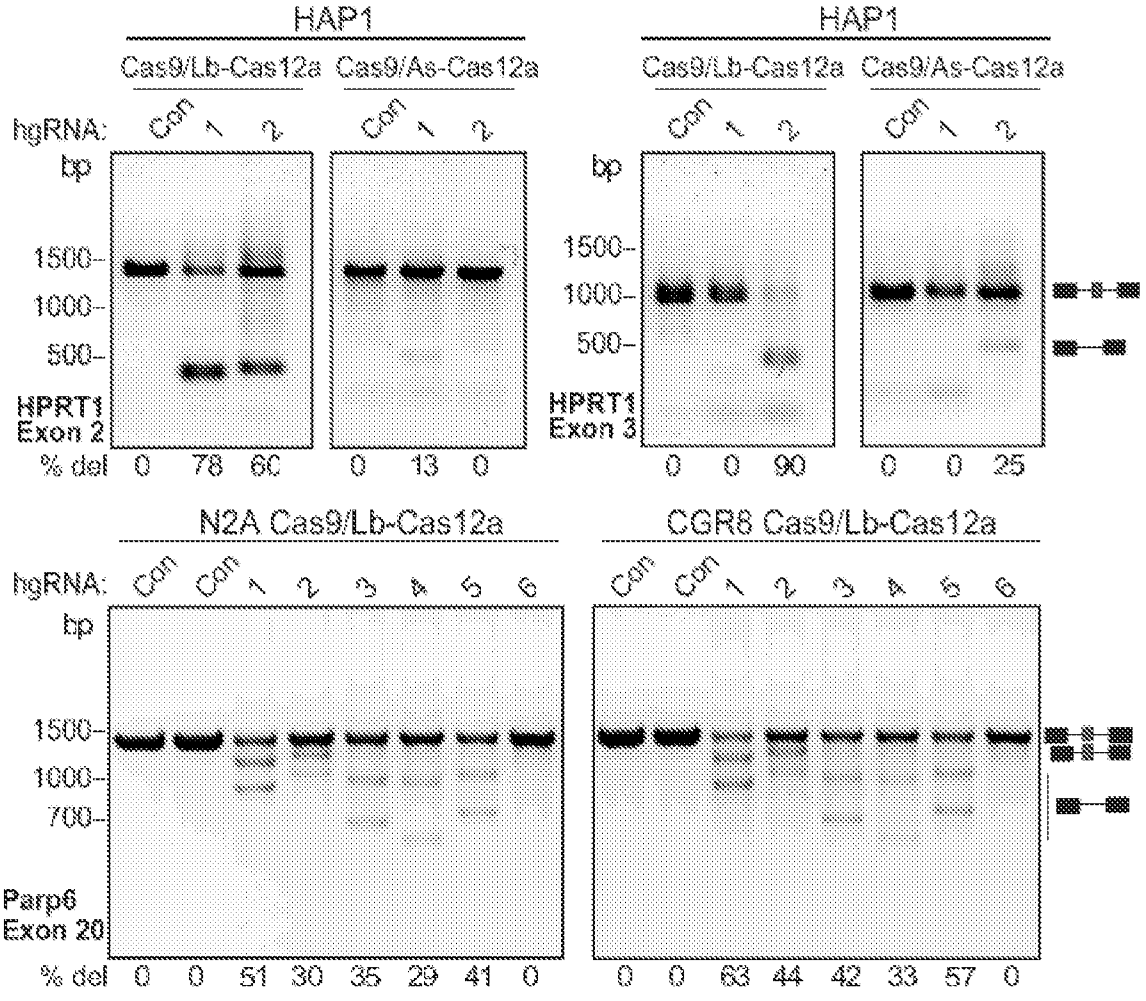
Figure 7G:
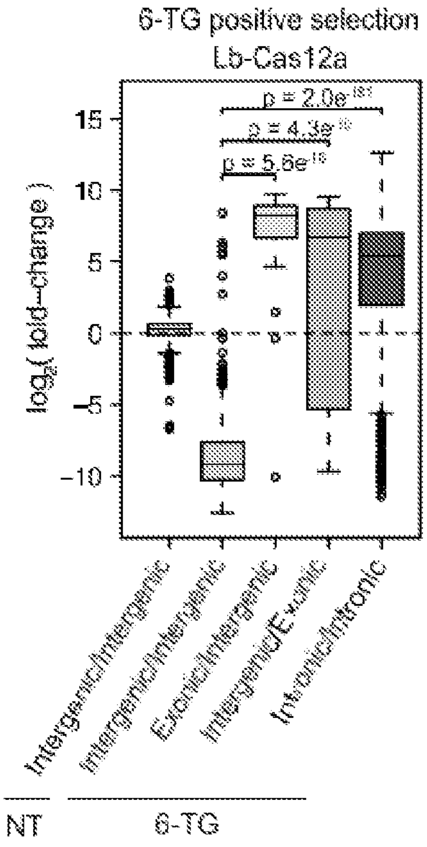

Cas9 and Cas12a hgRNA pairs targeting sequences flanking Ptbp1 exon 8 yield editing efficiencies of 10% to 43% following transduction in mouse CGR8 embryonic stem cells (FIG. 1B). These efficiencies are substantially higher than observed for any other tested combination of Cas nucleases (FIG. 1B and FIG. 13). The relatively high editing efficiency achieved with hgRNA pairs targeting flanking intronic regions was also observed for other tested alternative exons and in both mouse and human cell lines (FIG. 7F). Next, combinations of Cas9 and Cas12a hgRNAs targeting HPRT1 and TK1 genes were tested, which when knocked out result in cells becoming resistant to 6-thioguanine (6-TG) or thymidine block, respectively. A strong resistance to both drug treatments was observed (FIG. 1C), confirming that the dual targeting of HPRT1 and TK1 using CHyMErA is effective.

Figure 1C:
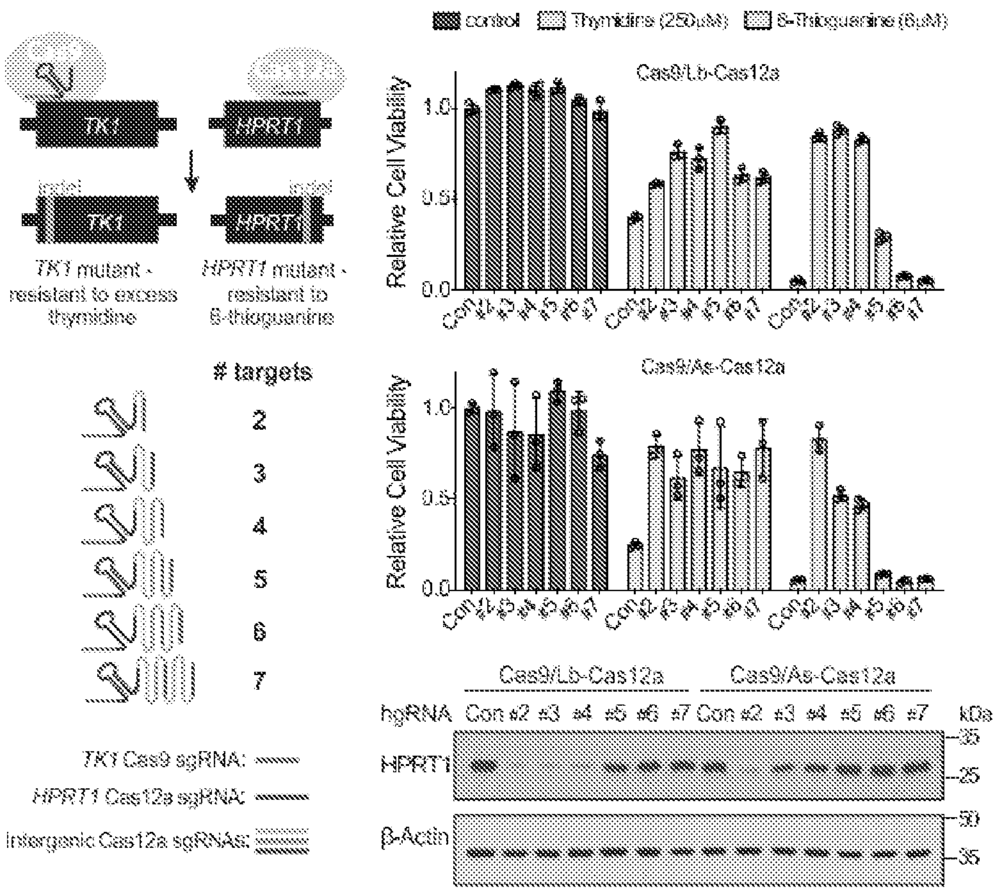

It was also tested whether CHyMErA is suitable for further multiplexing by increasing the number of guides for both Lb-Cas12a and As-Cas12a. Importantly, by adding intergenic guides at internal positions while keeping an HPRT1-targeting guide at the last position of a multi-targeting hgRNA construct, it was observed that multiplexing of up to three Cas12a guides results in robust editing (FIG. 1C), and also that Lb-Cas12a guides are more efficient at editing compared to As-Cas12a guides in this system. (FIG. 1C).

Figure 1D:
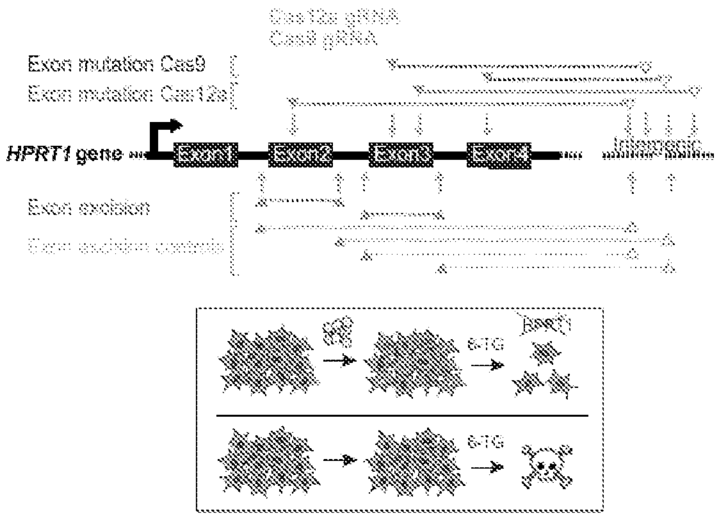

The efficiency of the CHyMErA system was tested in a pooled screen setting when targeting exons for deletion. Lentiviral-based positive selection pooled hgRNA screens were performed, and the human HPRT1 and TK1 genes were targeted using guide pairs that either target within exonic regions, which are expected to result in gene knockout, or intronic loci flanking constitutive exons in these genes, which are expected to result in exon deletion (FIG. 1D). All of the exon-flanking hgRNAs in the library were designed to introduce double-strand DNA breaks at intronic sites that are at least 100 bps distal from splice sites flanking the target exons. In parallel, a similar mouse lentiviral-based pooled hgRNA library targeting Hprt and Tk1 was built and used to perform positive selection screens in mouse cells (FIG. 15). As expected, when cells were treated with 6-TG, 95.8% of all library constructs were undetectable, indicating strong negative selection driven by the drug treatment. Importantly, strong enrichment of hgRNAs targeting human HPRT1 or mouse Hprt exonic sequences was observed, as well as hgRNAs comprising Cas9 and Cas12a pairs targeting HPRT1/Hprt exons for deletion, in 6-TG-treated human HAP1 and mouse N2A cells (FIG. 1E, Wilcoxon Rank-Sum Test; $p<2.2\times10^{-16}$; and FIG. 15). Of the 530 hgRNA pairs designed to delete exons 2 or 3 of HPRT1, 465 (88%) were enriched (FIGS. 1E and 7G; Wilcoxon Rank-Sum Test; $p<2.2\times10^{-182}$) Furthermore, 94% and 67% of exon-targeting hgRNAs (i.e. where Cas9 or Cas12a sequences target the exon) were also enriched (FIGS. 1E and 7G; Wilcoxon Rank-Sum Test; $p<2.2\times10^{-11}$). In contrast, only 2.5-3.5% of control guides were enriched in HAP1 cells.

Figure 1E:
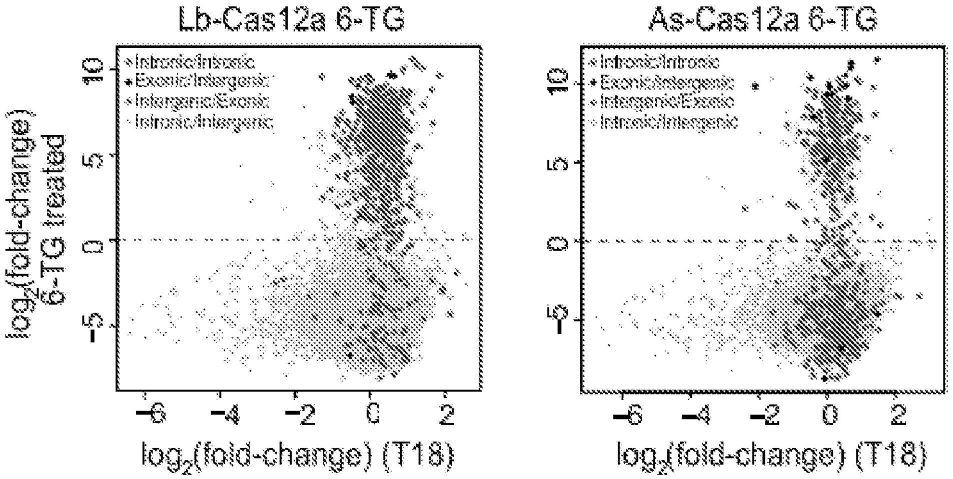
Figure 7H:
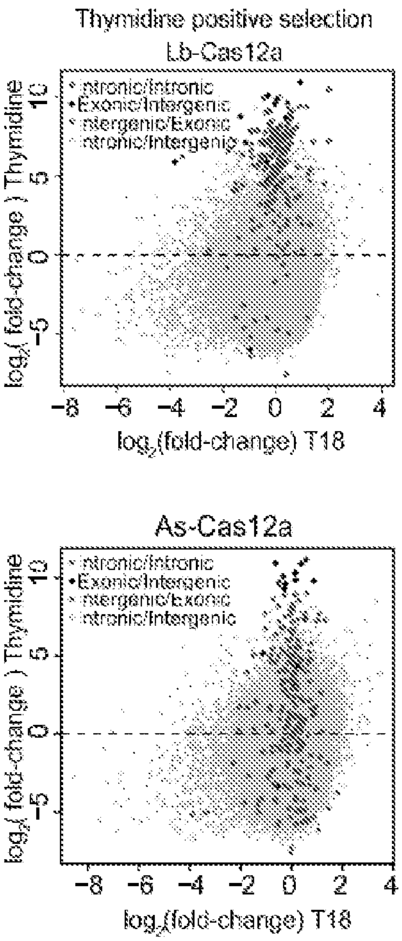
Figure 7I:
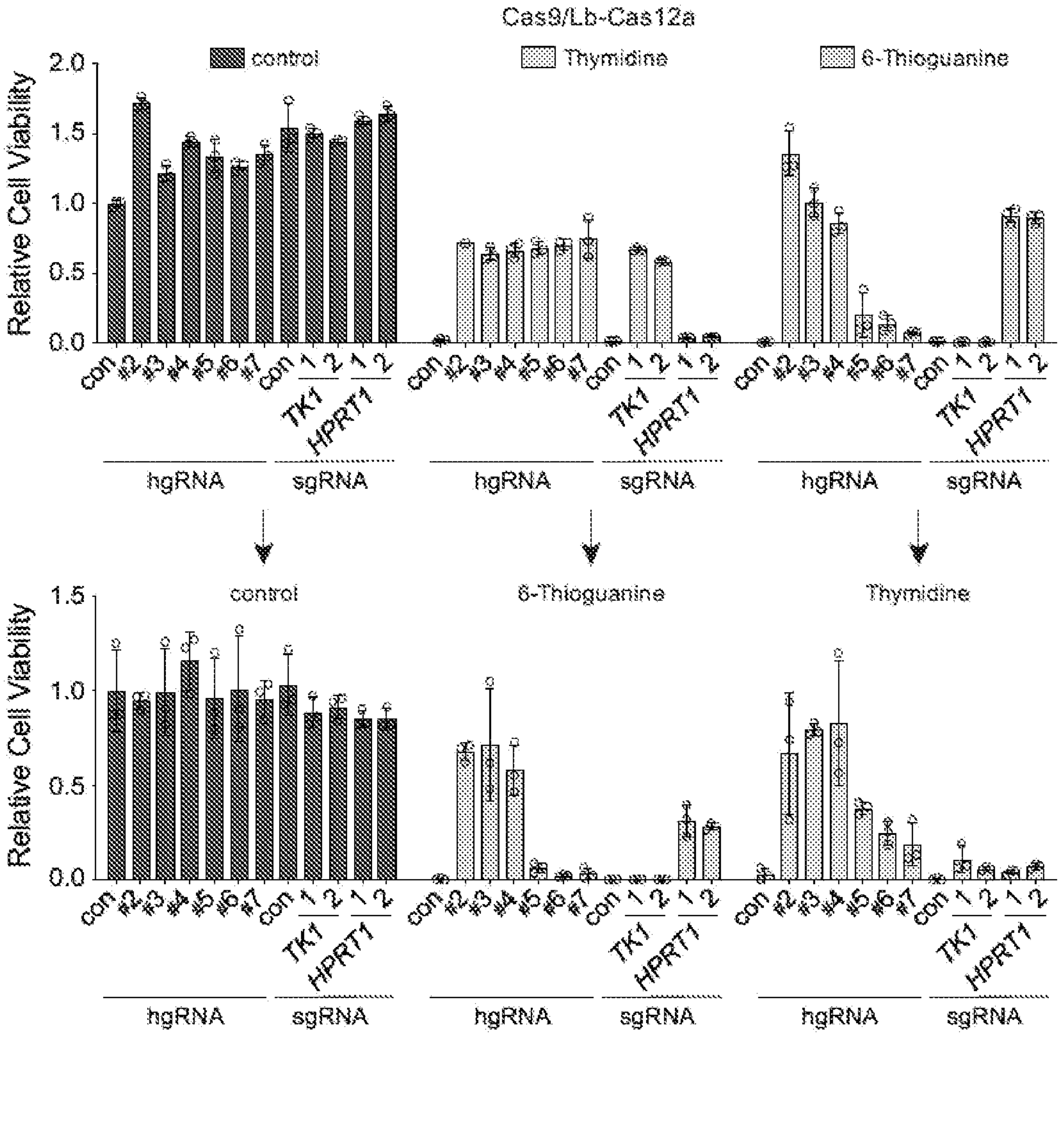

Similarly, targeting of TK1/Tk1 exonic sequences, or TK1/Tk1 exons for deletion using flanking targeting sequences, results in resistance to cell cycle arrest induced by double-thymidine block (FIG. 7H). Overall, 31.1% of all library hgRNAs are still detectable in the selected population (40% in N2A). Despite the weaker selection pressure, 86.4% of the TK1 exon-deletion hgRNAs enrich past the $97.5^{th}$ percentile of the negative control population and 82.5% of Tk1 exon-deletion hgRNAs in N2A, while 93.5% of the Cas9 exon-targeting hgRNAs and 50% of the Cas12a exon-targeting hgRNAs are enriched. Furthermore, in agreement with the HPRT1/Hprt and TK1/Tk1 hgRNA editing results in FIG. 1C, the exon-targeting positive selections display more efficient editing with Lb-Cas12a compared to As-Cas12a (FIGS. 1E and 7H). Collectively, these data demonstrate that co-expression of Cas9, Cas12a, and an hgRNA represents an effective alternative system for combinatorial genetic perturbation, including deletion of sizeable genetic elements such as exons.

Method Details: The methods used are those as described in Example 9.

Example 2: Optimization of Cas12a gRNAs Employed by CHyMErA

While models for designing Cas9 gRNAs that efficiently cut genomic DNA are established (Doench et al., 2016; Hart et al., 2017; Listgarten et al., 2018; Xu et al., 2015), the parameters that govern the editing efficiency of Cas12a guides are less well understood, particularly for genome-scale screening applications. To identify design rules for efficient Cas12a editing and broaden the utility of the CHyMErA system, human and mouse hgRNA ‘optimization’ libraries targeting core essential genes for inactivation, and exons for deletion were generated. To control for toxicity induced by double-stranded (ds)DNA breaks from the hgRNA system, each gRNA sequence was also paired with a gRNA targeting a non-coding intergenic sequence (FIG. 8A; Tables 1 and 2). To target constitutive exons of mouse core essential genes, all one-to-one orthologs of the human Core Essential Gene 2 (CEG2) set were first identified (Hart et al., 2017). From all possible 23-nt Cas12a guides (aka the spacer sequence of the guide) targeting these constitutive exons and adjacent to a TTTV 5'-end PAM sequence, up to 15 Cas12a guides per target exon were randomly selected. 20-nt Cas9 gRNAs were selected based on previously defined rules (Hart et al., 2017). Collectively, the optimization libraries target over 450 CEG2 essential genes, including>6,000 Cas9 and Cas12a exon-targeting guides and >35,000 exon-flanking guides, as well as 1,000 control constructs targeting intergenic regions (Tables 1 and 2).

Figure 1F:
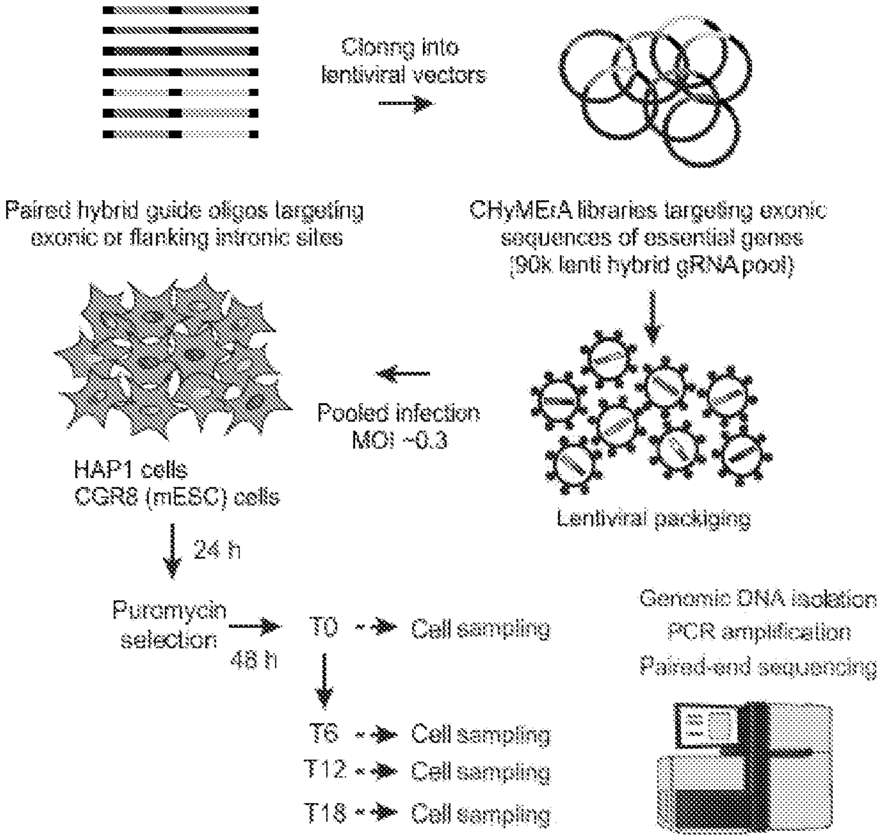

To construct pooled, multiplexed human and mouse hgRNA libraries, a two-step cloning strategy was developed using the pLCHKO lentiviral vector (FIG. 8B; see Methods in Example 9), and high-titer lentiviral stocks were generated for each library. Each library was separately transduced at a low multiplicity of infection (MOI less than 0.4) into human HAP1 cells and mouse CGR8 stem cells (FIG. 1F). Following selection with puromycin for 2 days, an aliquot of cells was collected for the reference T0 timepoint, the remaining cells were split into three parallel replicates, and the populations were passaged independently every three days for a total of 18 days (i.e. T18) while retaining a 250-fold library coverage. Genomic DNA was extracted from the T0, T6, T12 and T18 time points and hgRNA barcode sequences were quantified by paired-end sequencing (see Methods in Example 9).

Figure 1G:
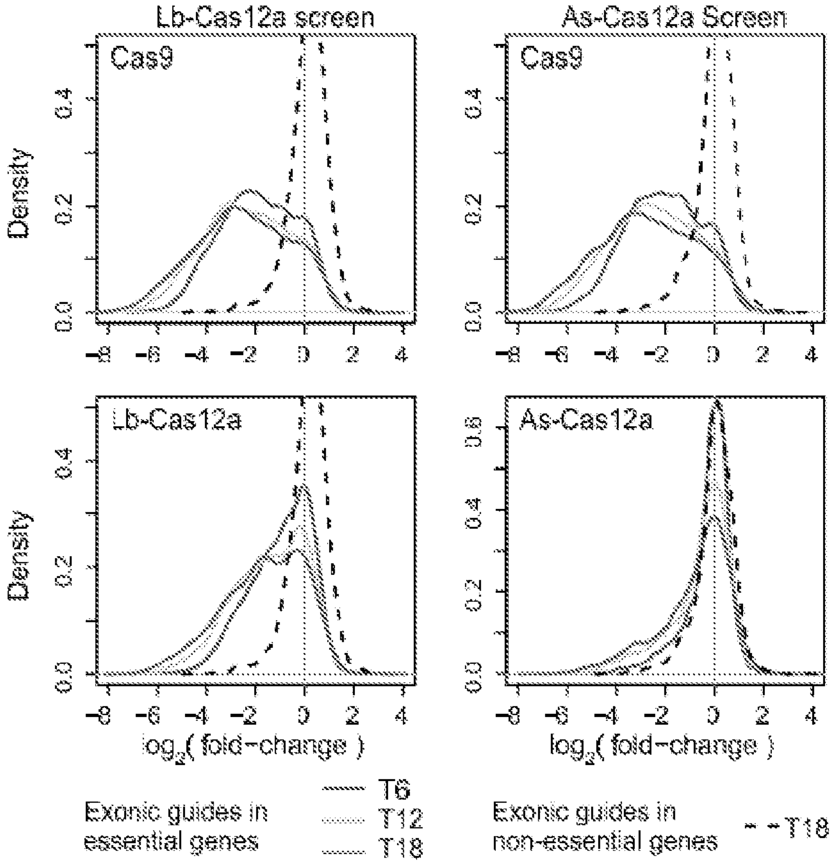
Figure 8A:
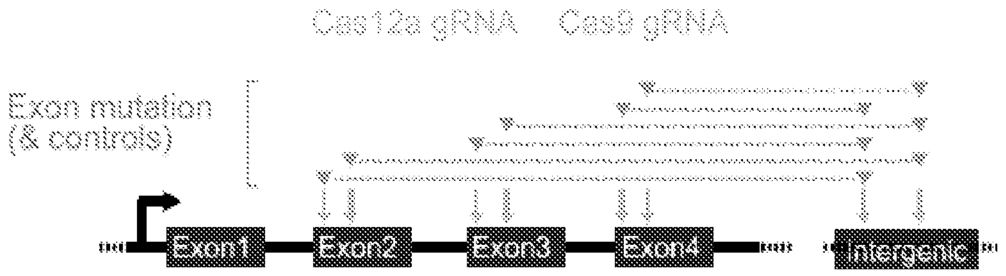
Figure 8B:
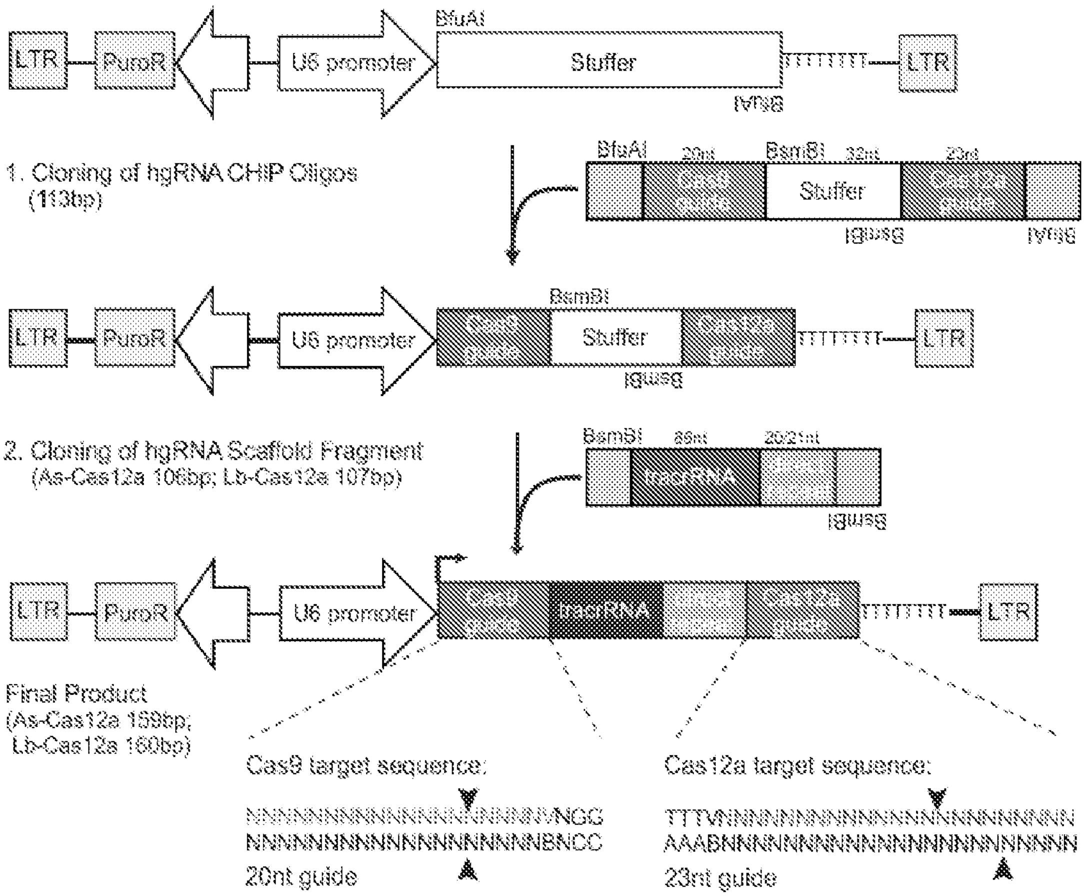
Figure 8C:
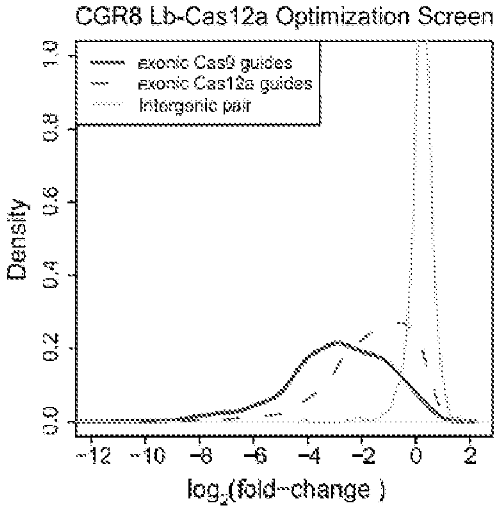
Figure 8C:
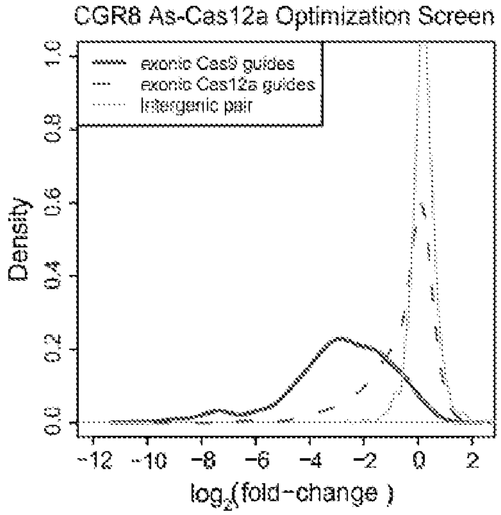

As expected, the log fold-change (LFC) distributions for each of the time points showed strong depletion of hgRNAs where the Cas9 guide portion is targeting core fitness genes and the Cas12a guide portion is targeting a non-functional intergenic sequence, for each of the Lb- and As-Cas12a libraries, and in both HAP1 and CGR8 cells (FIGS. 1G and 8C; Tables 3-4). LFC distributions indicating strong depletion of hgRNAs were also observed where the Cas12a guide is targeting essential genes and the Cas9 guide is targeting a non-functional intergenic sequence, an effect that is much stronger using the Lb-Cas12a nuclease compared to the As-Cas12a nuclease, and consistent with observations described above (FIGS. 1G and 8C). These results demonstrate the potential for Lb-Cas12a and hgRNA-containing libraries in performing negative selection screens, while the multi-targeting potential of the dual-guide constructs (FIGS. 1C and 1E) allows for the phenotypic assessment of genetic interactions and sizeable genetic segments using a single construct. In these experiments, Lb-Cas12a outperformed As-Cas12a. Lb-Cas12a was used in later Examples and is referred to as Cas12a onwards for simplicity.

Method Details: The methods used are those as described in Example 9.

Example 3: Deep Learning Framework for Predicting Efficient Cas12a Guides

Figure 2A:
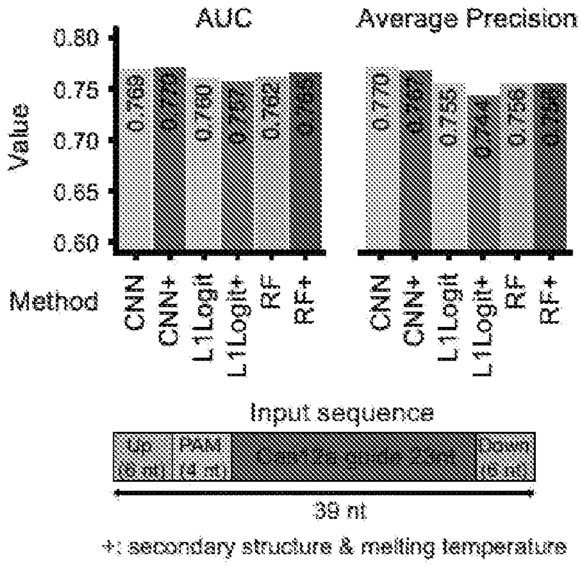
Figure 2B:
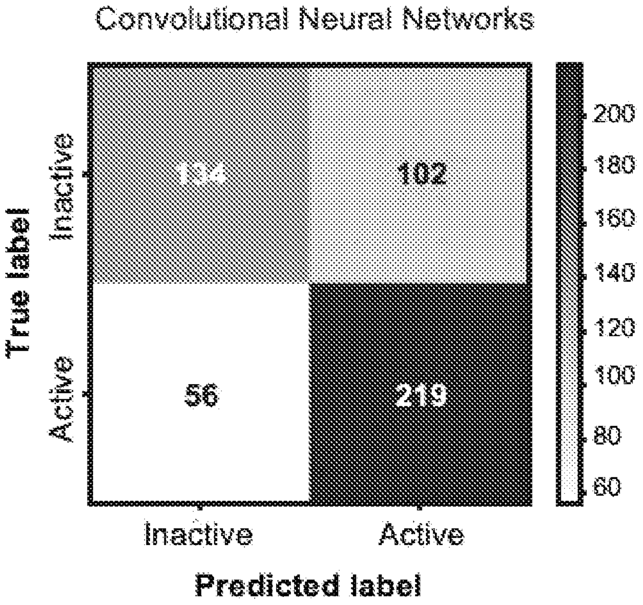
Figure 8D:
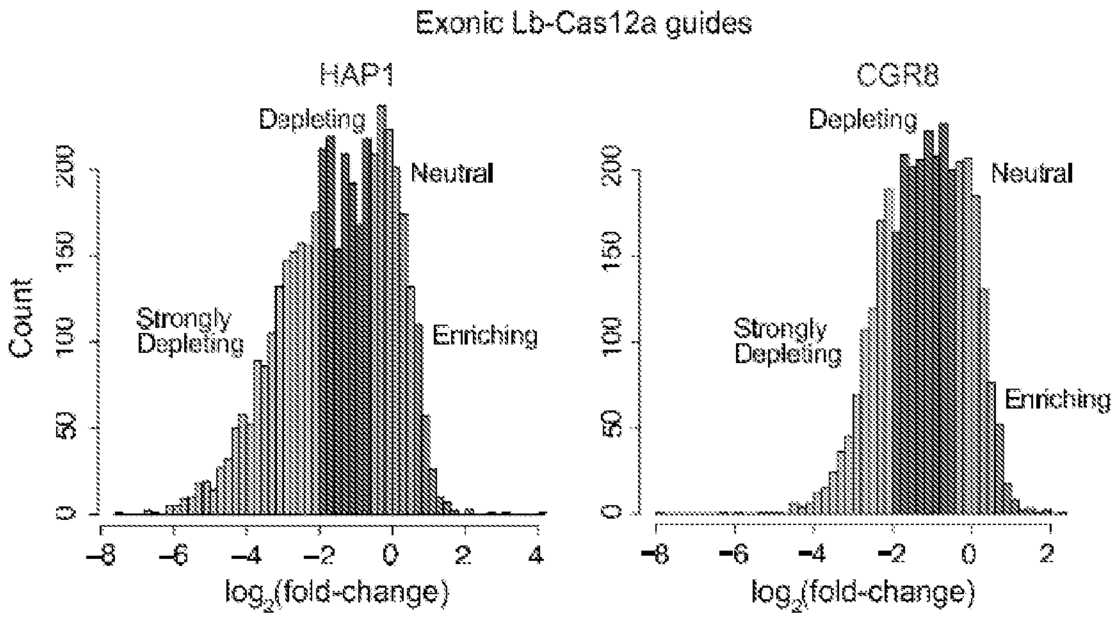
Figure 8E:
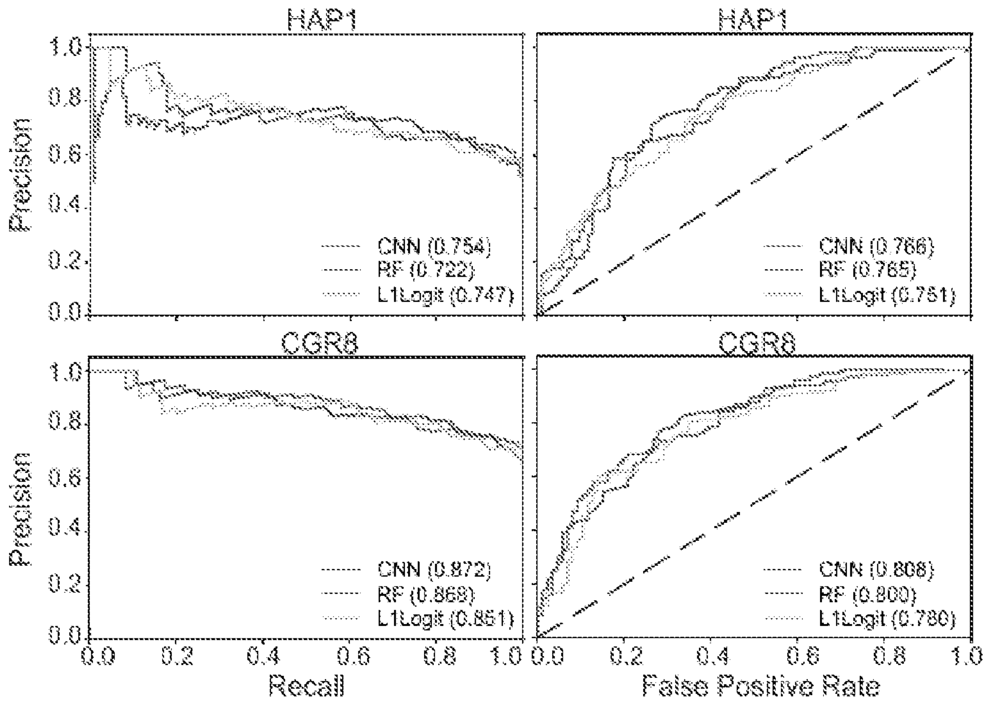

The data collected from the human and mouse Cas12a optimization libraries targeting essential genes were subsequently used to identify features associated with active Cas12a guides to infer Cas12a gRNA design rules. Machine learning algorithms were applied to the prediction of efficient Cas12a guides as follows. Cas12a guides targeting exons of core fitness genes were first binned into ‘active’ or ‘inactive’ categories based on their observed depletion, as determined by the LFC scores in HAP1 and CGR8 cells (FIG. 8D). For each guide, features were assembled based on single, di- and trinucleotide composition, PAM sequence, upstream and downstream sequences, as well as genomic accessibility at the target site. Using a deep-learning framework based on convolutional neural networks (CNNs), a model was trained that predicts Cas12a activity with an area under the receiver operating characteristic curve (AUROC) of 77%, for both human and mouse cells (FIGS. 2A-B and 8E), despite having a relatively modest set of training data. Other conventional machine learning approaches, including LASSO regression and random forests, performed similarly but with slightly reduced predictive power, at 76% accuracy by cross-validation (FIGS. 2A-B and 8E).

Figure 2C:
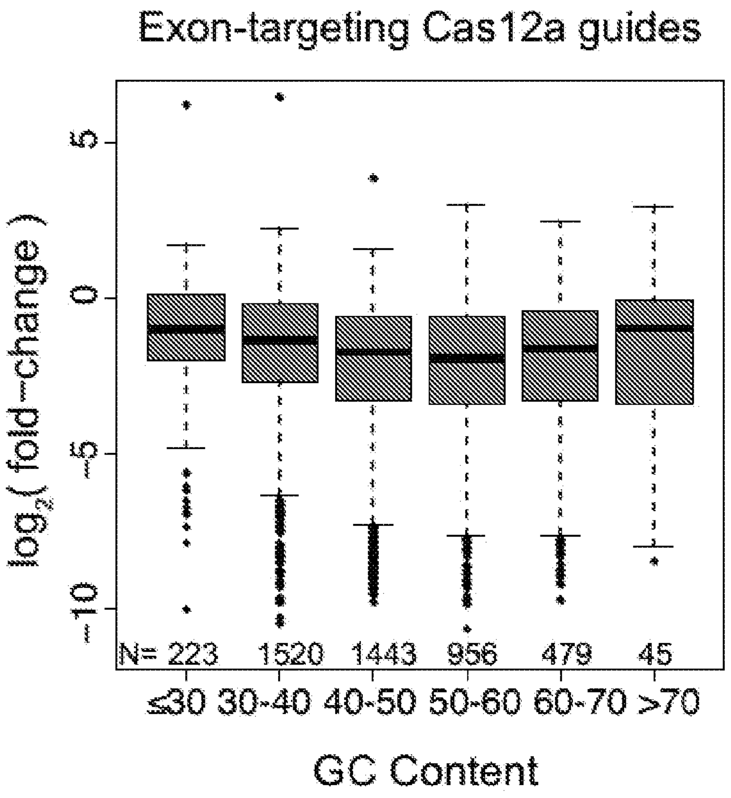
Figure 2D:
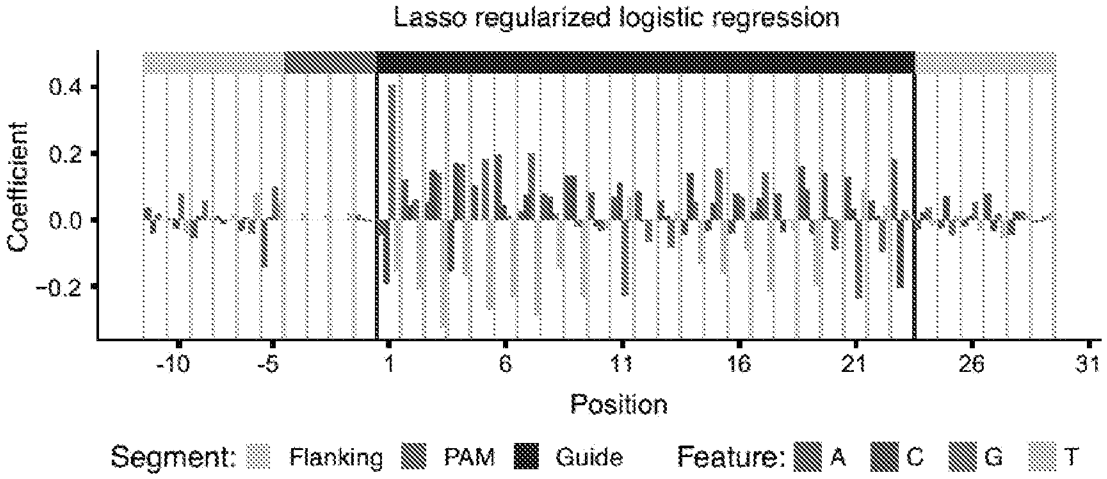
Figure 2E:
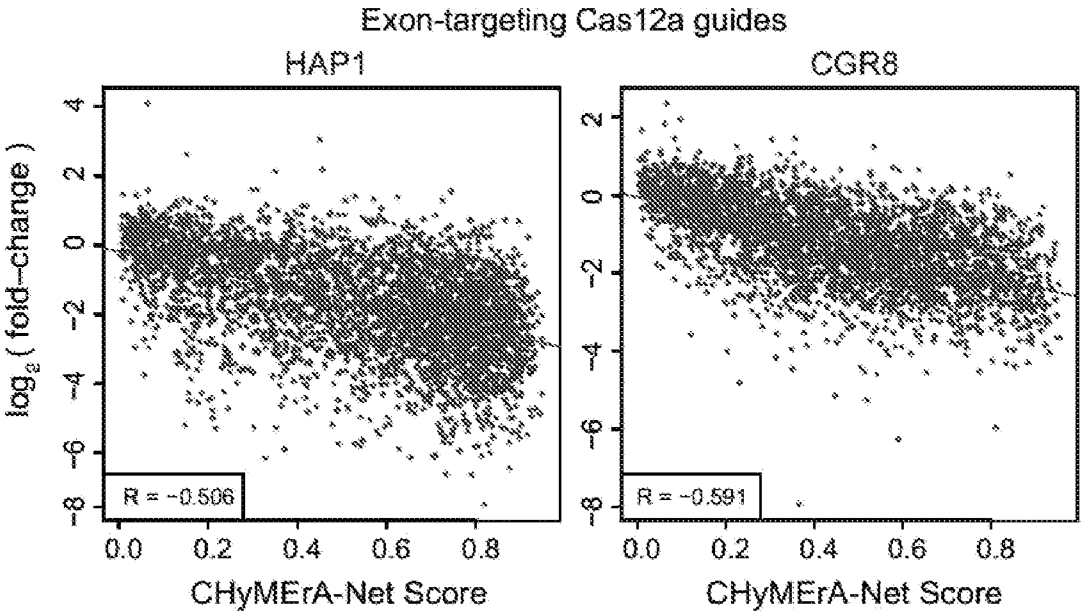
Figure 2F:
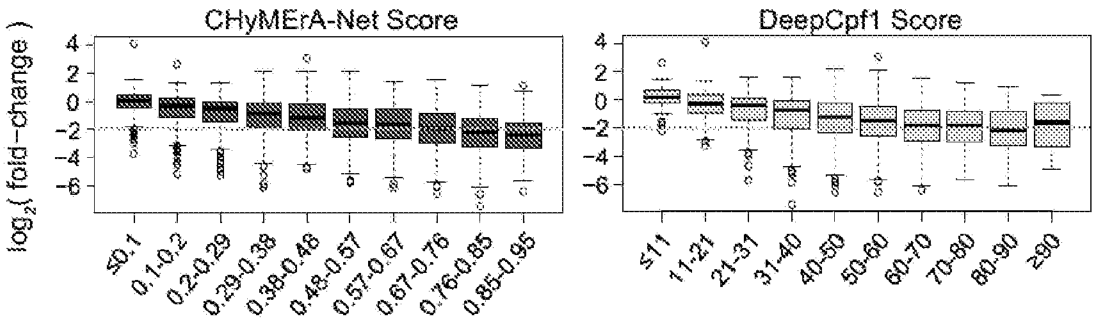
Figure 8F:
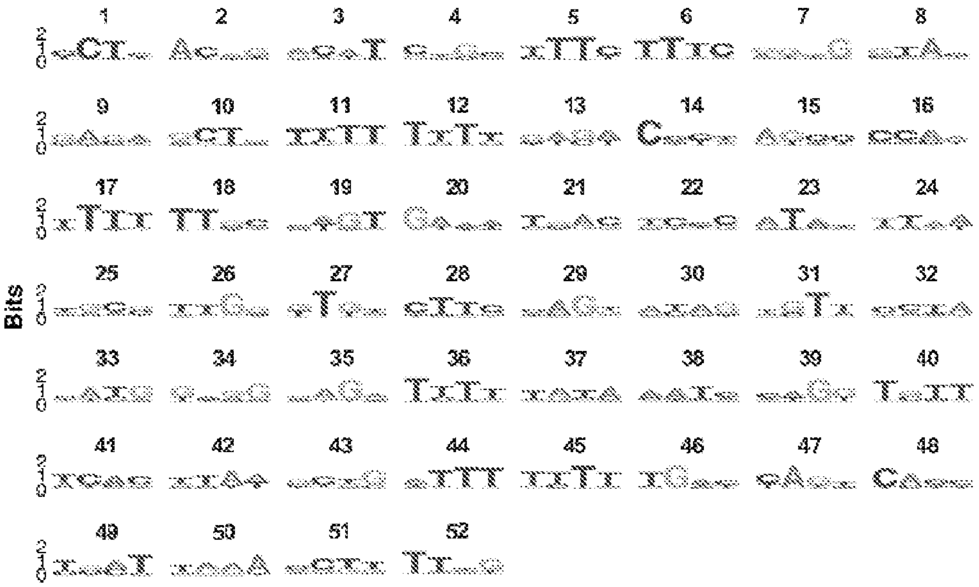
Figure 8G:
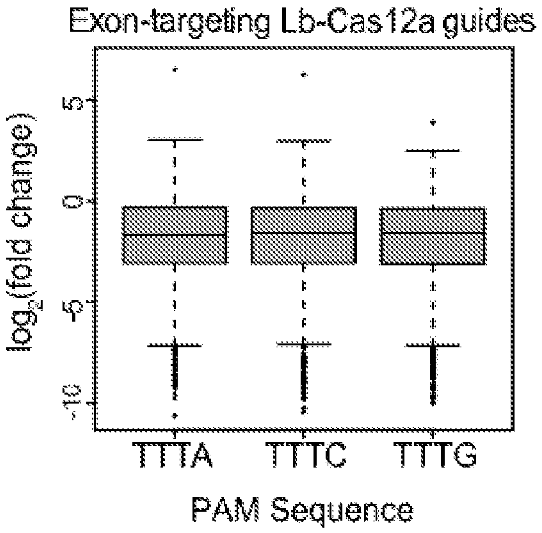
Figure 8H:
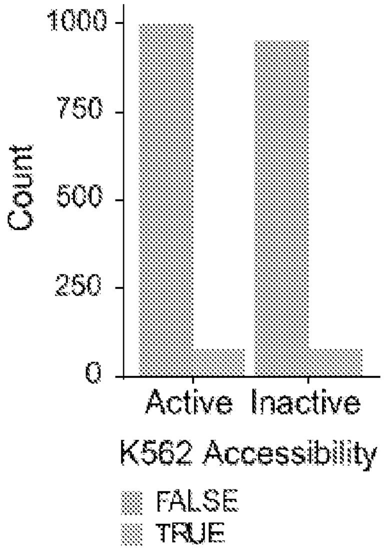

The most informative features for the CNN classifier were determined to involve the nucleotide composition of the Cas12a guide and target site. Specifically, active guides generally are neutral with respect to GC content, tend to have a 'G' in the first position proximal to the PAM sequence, and are depleted for "T" in the first 9 positions, and for 'C' at the PAM-distal 23$^{rd}$ nucleotide (FIGS. 2C-D). Similar nucleotide preferences were observed in the filters learned by the CNN classifier (FIG. 8F). Little predictive information is attributed to secondary structure, melting temperature, the 6 nt regions flanking the target site, or the 4 nt PAM sequence (FIGS. 2C and 8G). In contrast to previous studies (Kim et al., 2017, 2018), enrichment of active guides in regions with chromatin accessibility in a related cell line was not detected (FIG. 8H). A strong negative correlation between the CNN score for hgRNAs targeting essential genes and the LFC guide scores between T0 and T18 was also observed, supporting the efficacy of the CNN predictions (FIGS. 2E-F). Lastly, Cas12a guide scores were calculated using deepCpf1 (Kim et al, PMID: 29431740), an independent deep learning algorithm that predicts Cas12a guide activities, and LFC trends were compared by binning CNN scores and deepCpf1 scores into deciles. A strong negative slope was observed for CNN scores but not for deepCpf1 scores (FIG. 2G), indicating the CNN scoring approach is an improved quantitative metric for predicting Cas12a guide activities at endogenous loci.

Method Details: The methods used are those as described in Example 9.

Example 4: Dual Targeting Gene Inactivation Outperforms Conventional Single Targeting Perturbations Using the Lb-Cas12a gRNA design principles inferred by the CNN algorithm, a second generation 'optimized' hgRNA library targeting human genes was designed. This library comprises the following sets of Cas9 and Cas12a hgRNA expression cassettes: (1) 58332 hgRNAs where one or two guides target one of 4993 genes, defined as having the highest expression levels across a panel of five commonly used human cell lines (see Methods in Example 9); (2) 3566 control hgRNAs targeting intergenic or exogenous sequences for assessing single-versus dual-cutting effects; (3) 30848 combinatorial- and single-targeting hgRNAs directed at 1344 human paralogs and 22 hand-selected gene-gene pairs of interest (Table 5).

Figure 9A:
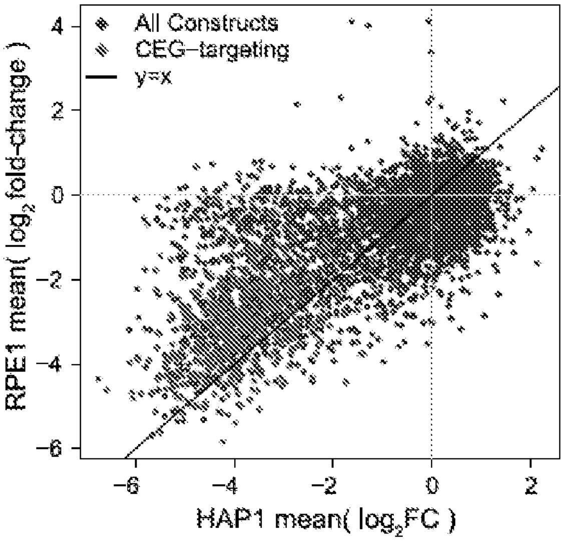

Fitness screens were performed in both HAP1 and hTERT-immortalized retinal pigment epithelial (RPE1) cells constitutively expressing Cas9 and Cas12a, as described above (FIG. 7D). Quantification of the hgRNA abundance showed correlated depletion of hgRNAs targeting core fitness genes compared to controls in both cell lines (FIG. 9A). Notably, CNN optimized Cas12a guides (i.e. individual Cas12a guides paired with intergenic control guides) were more efficiently depleted than Cas12a guides tested in the optimization screen (FIG. 3A; P=$1.4\times10^{28}$, Wilcoxon rank-sum test). This observation provides evidence that the CNN algorithm reliably improves the activity of Lb-Cas12a guides.

Figure 3A:
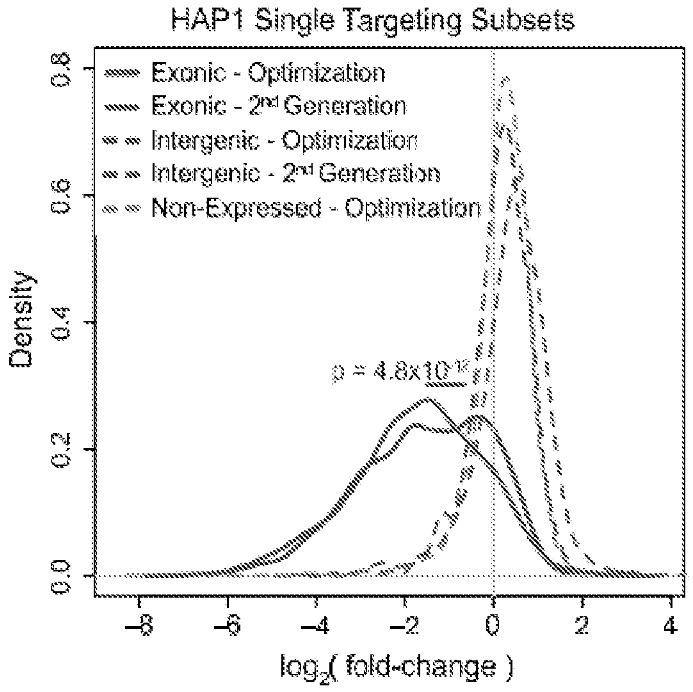
Figure 3B:
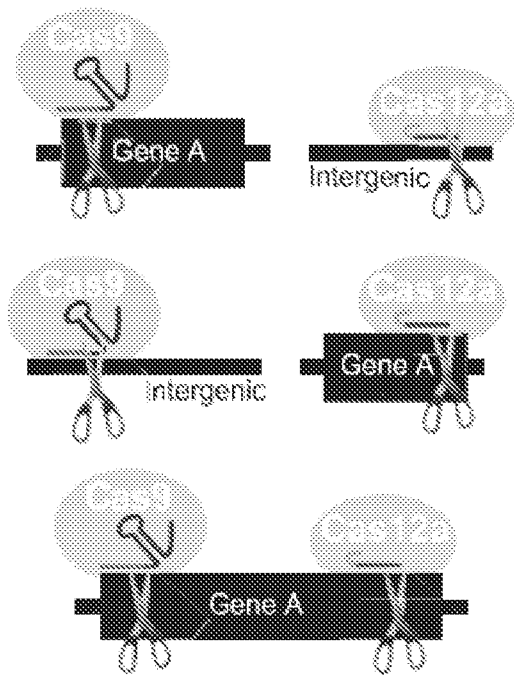

Having observed increased activity of the CNN optimized Cas12a gRNA designs, it was assessed whether the combination with Cas9 guides in the hgRNA format (i.e. dual-targeting mode) results in increased signal in phenotypic screens (FIG. 3A). Thus, it was considered that the probability that loss-of-function indel frequencies caused by a single Cas9 or Cas12a gRNA targeting a given gene [i.e. Pr(A) or Pr(B)] would be enhanced if a second indel event could be introduced in the same gene and in the same cell. Theoretically, this can be modelled as [$Pr(x)=Pr(A)+Pr(B)-Pr(A)Pr(B)$], where Pr(x) is the probability of a loss-of-function indel resulting from the combined editing in the dual-guide context. LFC distributions for non-targeting (NT) and intergenic targeting control hgRNAs were compared as controls.

Figure 9B:
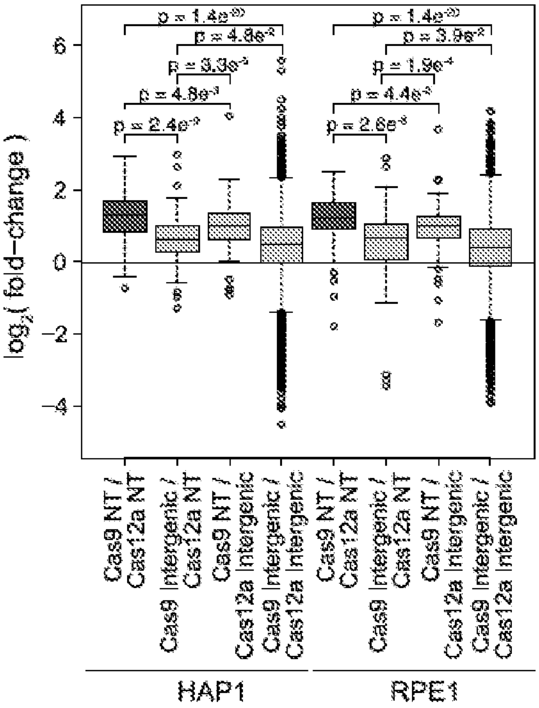

The dual genomic cuts introduced by the hgRNA do not cause toxicity as indicated by the observation that hgRNAs that introduce two genomic cuts have only a slightly lower positive LFC compared to those that introduce a single cut (i.e. intergenic-NT) in both HAP1 and RPE1 cells (FIG. 9B). Overall, the average hgRNA constructs targeting intergenic regions show no net LFC (FIG. 3C), but there does appear to be a correlation between the number of genomic cuts and a mild reduction in fitness (FIG. 9B), even in HAP1 cells harbouring a mutant TP53 gene. While non-targeting guides are slightly enriched relative to the total population, dual-cutting constructs show a mean LFC that is approximately two-fold lower, while single-cutting constructs show an intermediate phenotype in both HAP1 and RPE1 cells (FIG. 9B). With these observations in mind, when comparing single-vs. double-targeting of genes, single-targeting constructs were always paired with an intergenic-targeting control in order to control for this effect.

Figure 3C:
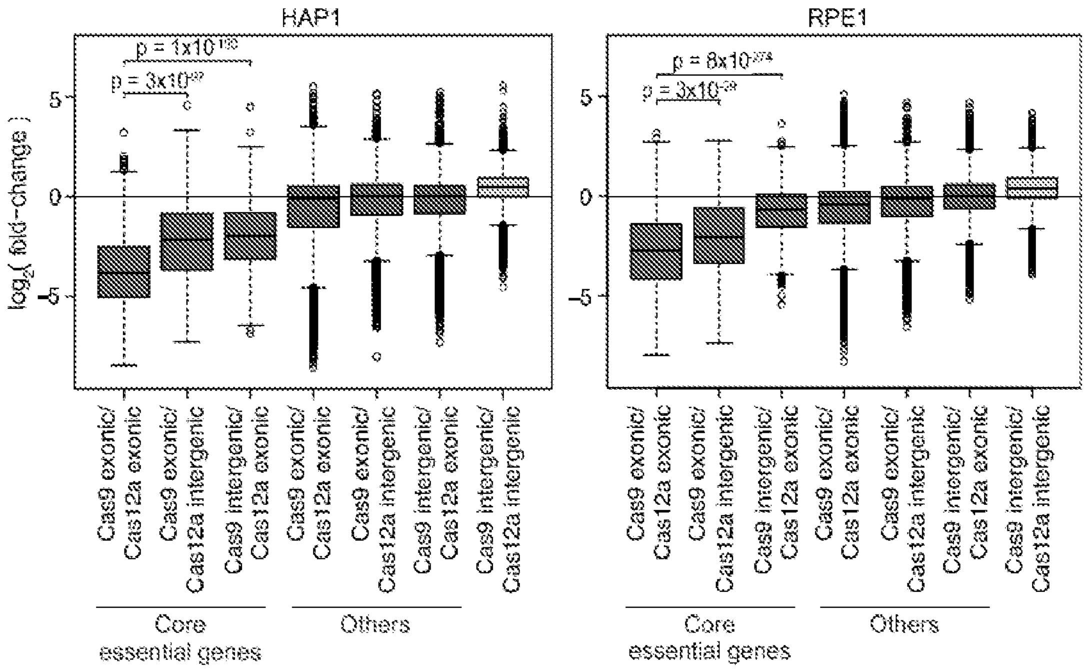
Figure 3D:
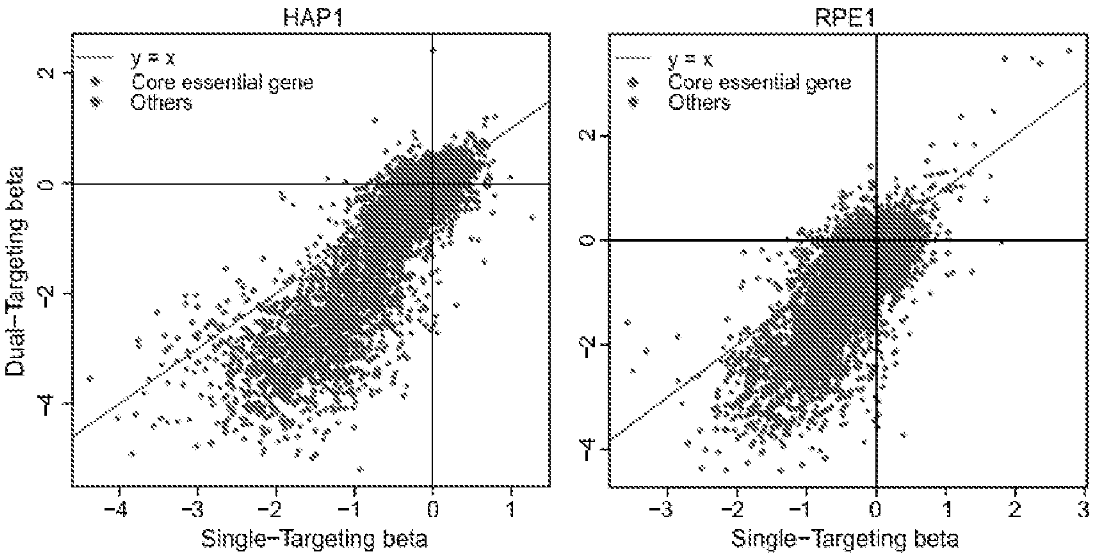
Figure 3E:
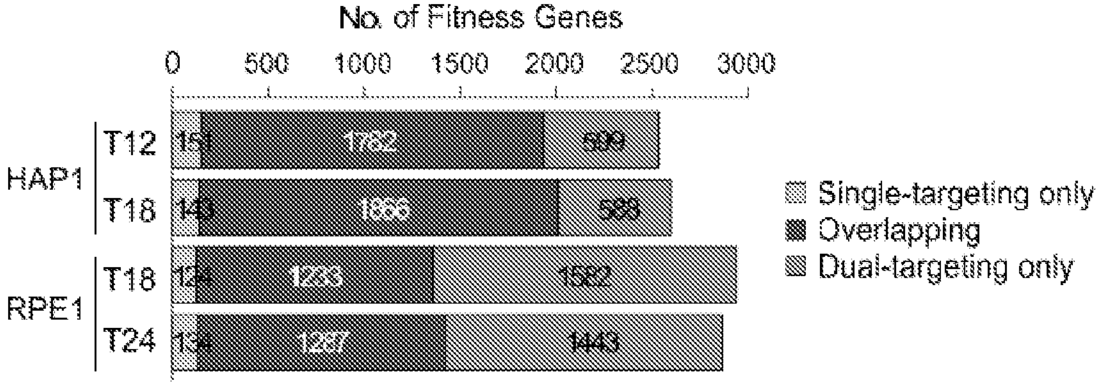
Figure 9C:
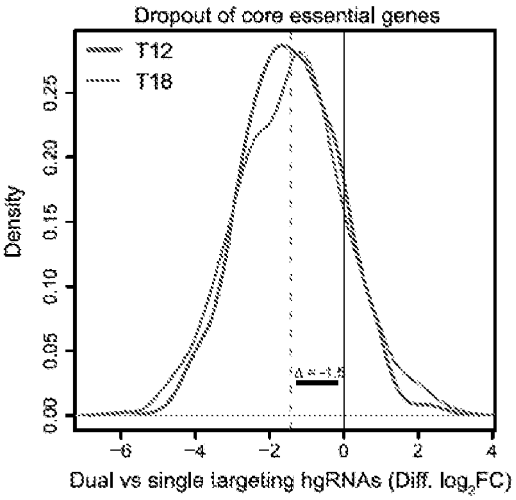
Figure 9D:
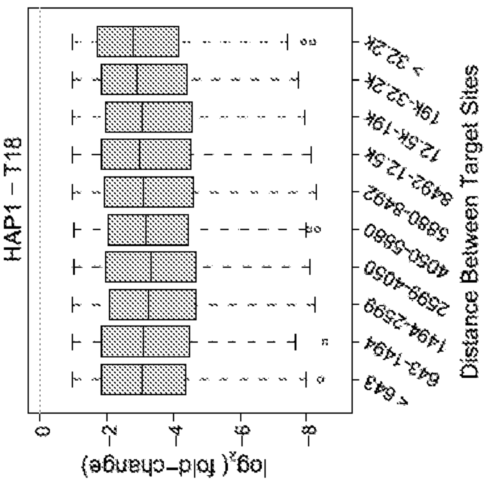
Figure 9E:
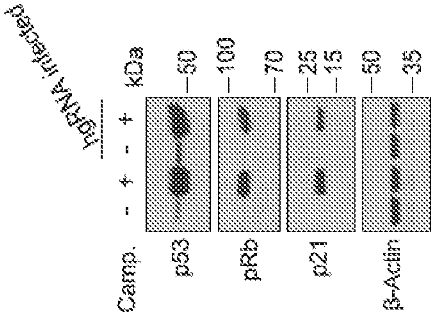
Figure 9F:
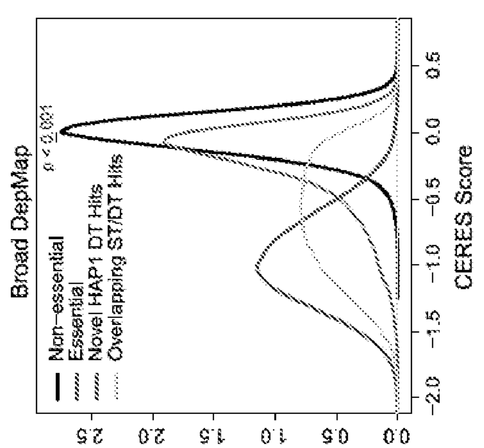

After taking this effect into consideration, targeting essential genes with two cuts via hgRNAs results in significantly higher hgRNA depletion in both HAP1 (2.8×) and RPE1 (2.6×) cells, compared to when essential genes are targeted with Cas9 or Cas12 targeting guides alone in the context of an hgRNA ($p<2.2\times10^{-16}$) (FIG. 3C-D, 9C). Importantly, the number of fitness genes identified by dual-targeting manipulations exceeds those captured by single-targeting and yields nearly 600 and 1500 additional fitness genes for HAP1 and RPE1, respectively (FIGS. 3E-G). It is noteworthy that RPE1 cells harbor a wild-type TP53 gene while HAP1 cells have a loss-of-function mutation in TP53, yet the efficiency of targeting CEGs between these lines is comparable. In agreement with the recent observations in (Brown et al., 2019), this suggests that expression of wild-type TP53 does not appreciably reduce the performance of CRISPR knockout screens as has been recently proposed (Haapaniemi et al., 2018). In summary, these results reveal that CHyMErA employing CNN-optimized hgRNAs affords increased multi-site targeting efficiency, and thus offers an effective platform for combinatorial gene perturbation.

Method Details: The methods used are those as described in Example 9.

Example 5: CHyMErA Accurately Detects Di-Genic Interactions

Figure 4A:
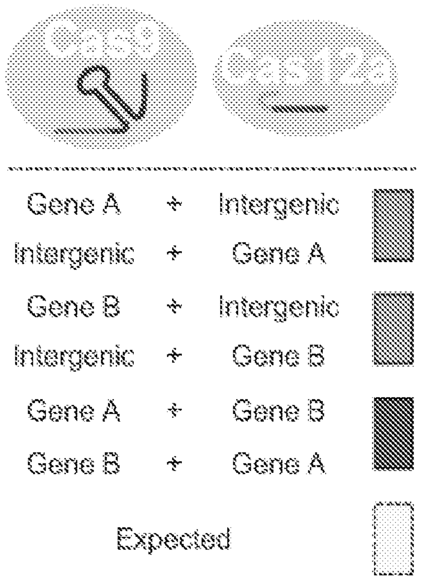

CHyMErA was applied to systematically map genetic interactions including epistatic relationships. To initially assess the efficacy of CHyMErA in mapping genetic interactions, the performance of CNN-optimized hgRNAs designed to test known di-genic interactions was analysed including: TP53-MDM2, TP53-MDM4, BCL2L1-MCL1, APC-CTNNB1, MAP2K1-BRAF, CDK2-CCNE1, PEA15-BRAF, CBFB-RUNX1, KDM4C-BRD4 and KDM6B-BRD4 (Tables 5-6). Genes comprising these pairs were targeted individually or in combination by both Cas9 and Cas12a gRNAs (FIG. 4A). The LFC of these pairs was used to score di-genic interactions by comparing if the observed LFC values for a double-knockout significantly differs from the sum of single-knockout LFCs (see Methods in Example 9).

Figure 4B:
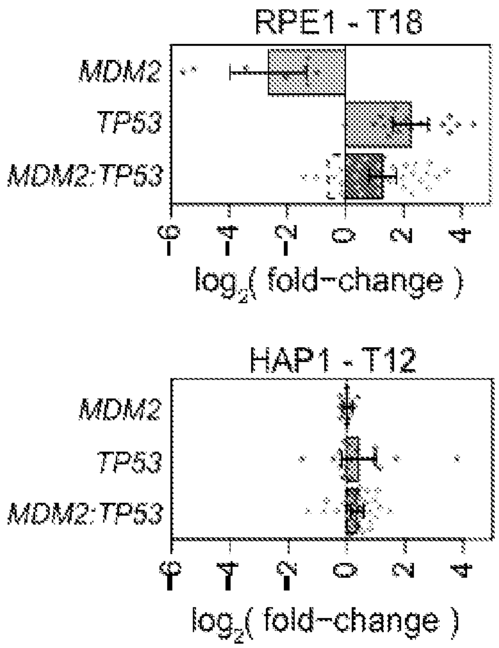
Figure 4C:
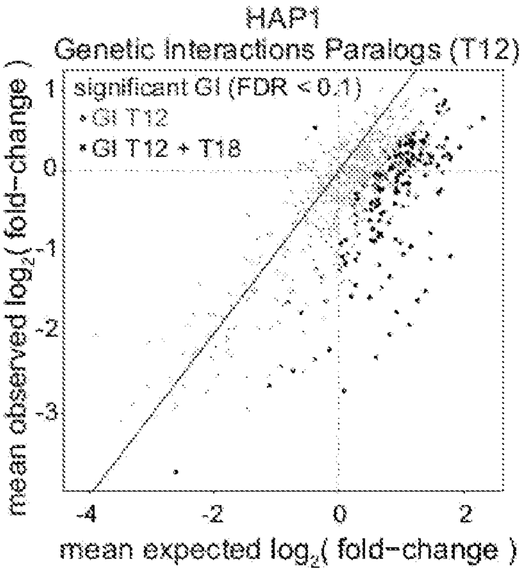
Figure 4D:
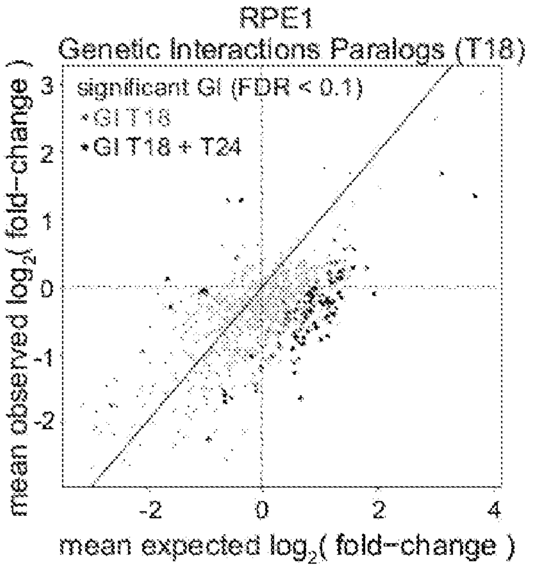
Figure 4E:
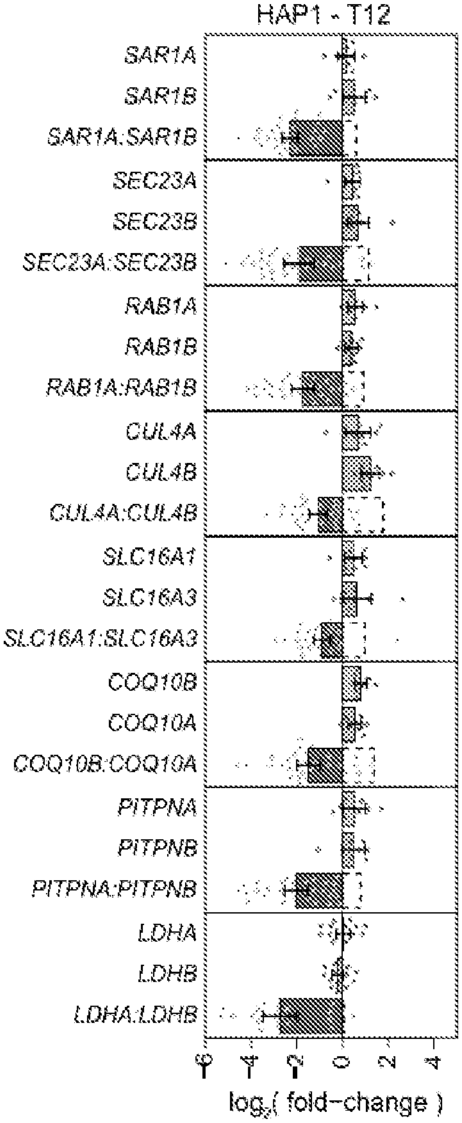
Figure 4F:
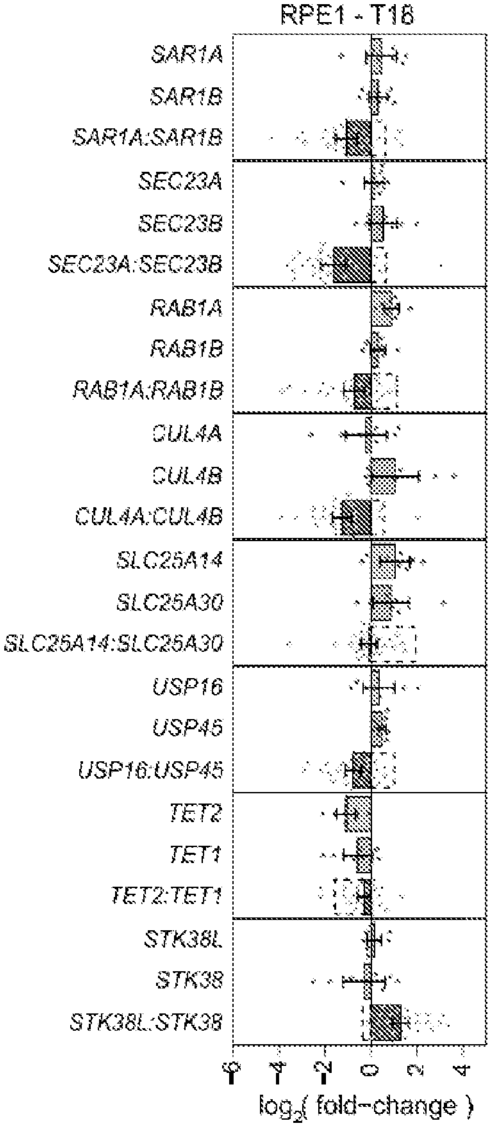
Figure 10A:
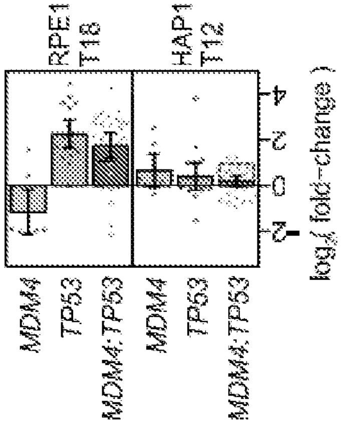
Figure 10B:
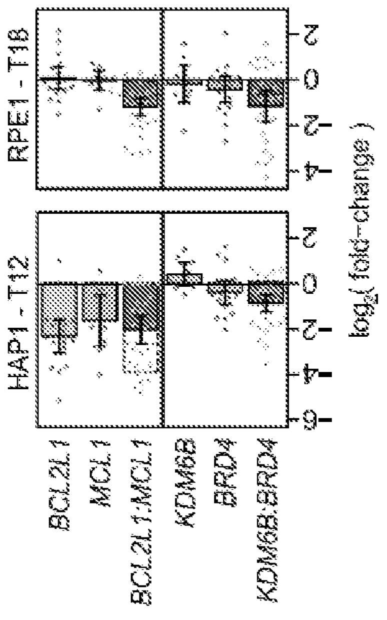
Figure 10C:
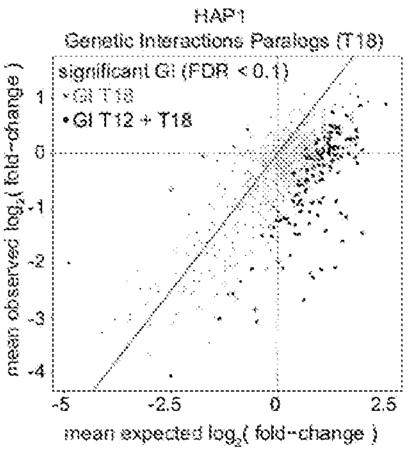
Figure 10D:
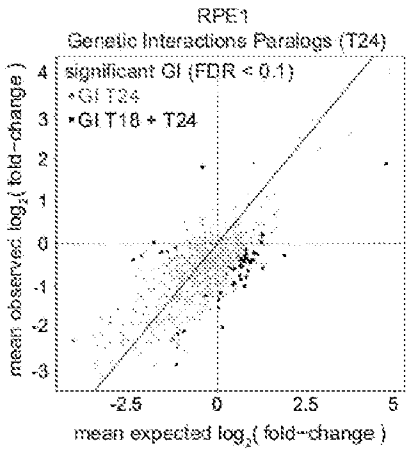
Figure 10E:
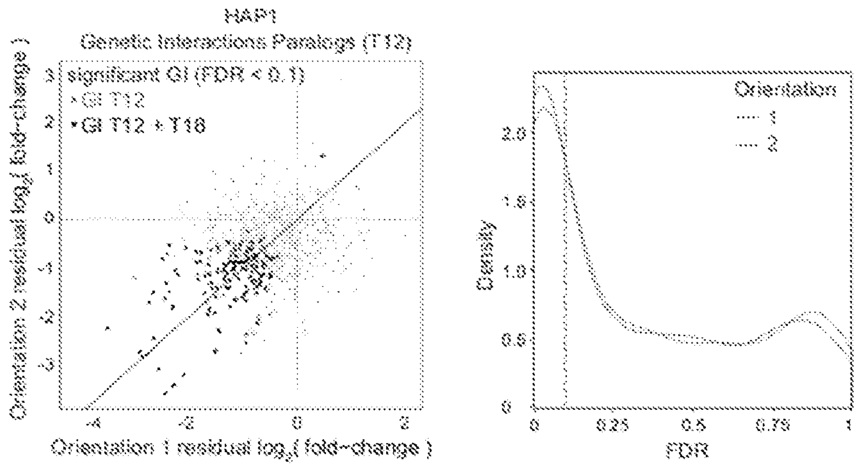
Figure 10F:
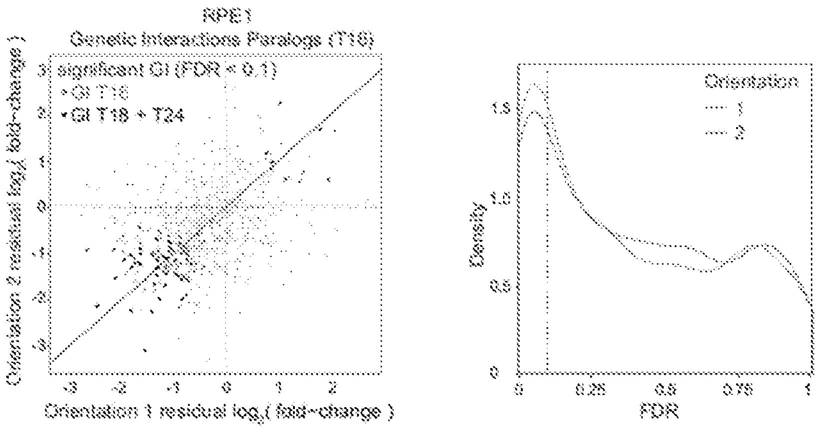
Figure 10G:
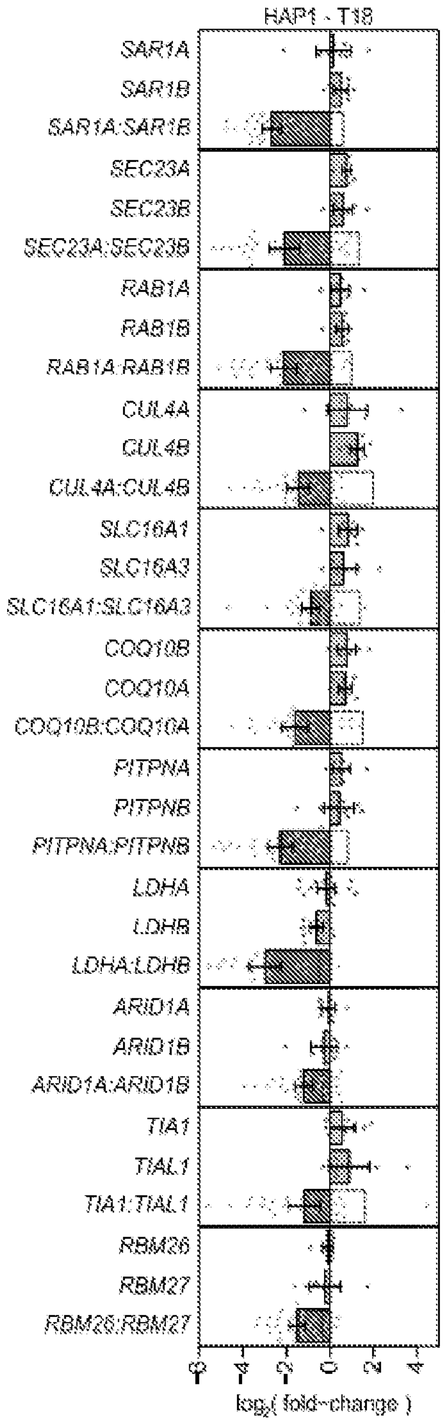
Figure 10H:
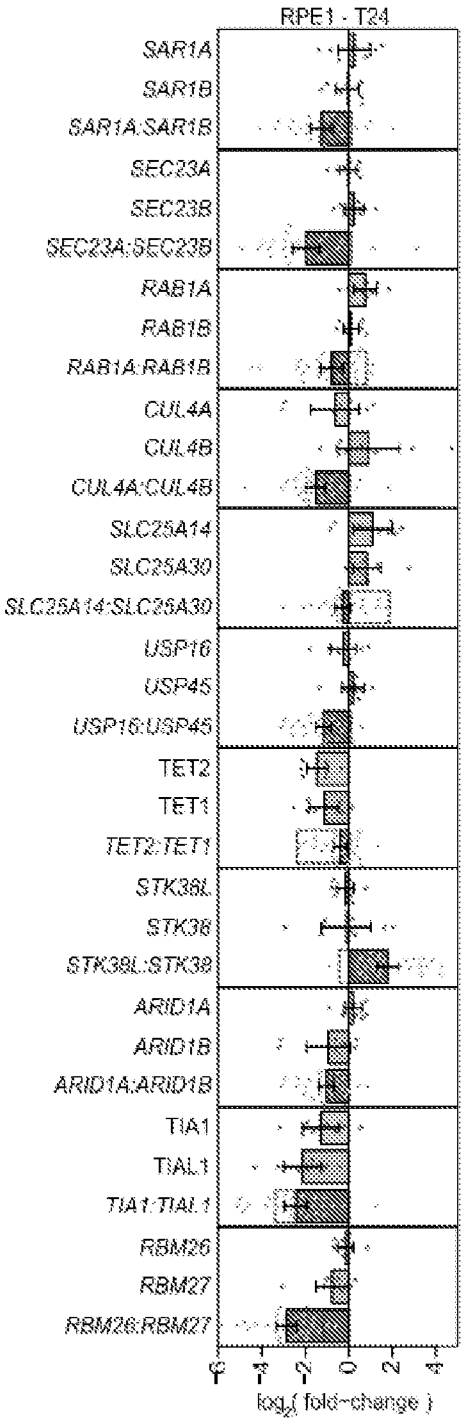

Using the additive model of genetic interactions, the screen detected expected genetic interactions and epistatic relationships between TP53 and its regulators MDM4 and MDM2 in RPE1 cells, which express wild-type TP53 (FIGS. 4B and 10A). These same interactions were not detected in HAP1 cells, which harbour a mutant version of TP53 (i.e. TP53-S215G) that is expressed, but predicted to be inactive (FIGS. 4B and 10A) (SLOVACKOVA et al., 2012). Furthermore, CHyMErA also accurately captured known negative genetic interactions between MCL1 and BCL2L1 (FIG. 10B), previously observed using Cas9-based dual gRNA systems (Han et al., 2017; Najm et al., 2017b) as well as between KDM6B and BRD4 (Wong et al., 2016) (FIG. 10B). These results thus support the application of CHyMErA in the systematic mapping of genetic interactions in mammalian cells.

Method Details: The methods used are those as described in Example 9.

Example 6: CHyMErA Screens Uncover Functional Relationships Between Paralogous Genes It is well accepted that genetic redundancy helps ensure phenotypic robustness (Gu et al., 2003). Yet, genetic redundancy also presents a major challenge for characterizing gene functions using loss of function approaches (Ewen-Campen et al., 2017). The multi-site targeting capability of CHyMErA was therefore used to systematically investigate the function of pairs of paralogous genes. There are 1381 strict human ohnolog families that have arisen from whole genome duplications of vertebrate genomes (Singh et al., 2015). 1344 paralogs were selected from this set that represent a near complete list of strict gene pairs (i.e. avoiding gene families with more than two paralogs), and these pairs were targeted either individually or in combination using the second generation CHyMErA library described above (Table 5). This set of paralogs represents genes involved in a broad range of biological processes such as the cell cycle, protein trafficking, splicing, protein turnover and modification, and metabolism (Table 5).

Following the same strategy for scoring combinatorial hgRNAs targeting known di-genic interactions described above, the effects of targeting paralogs (i.e. single versus both paralogs) on cellular fitness, was examined in HAP1 and RPE1 cells. 33% (219 pairs) of tested paralog pairs in HAP1 cells and 18% (122 pairs) in RPE1 cells display a non-additive fitness phenotype when targeted in combination and in both orientations, compared to what would be expected based on targeting a single paralog (FIGS. 4C-D, 10C-D, 10G-H and Table 7). The majority of these effects represent negative genetic interactions, although examples of positive interactions that result in masking of individual fitness phenotypes were also detected (FIGS. 4E-F and 10E-F).

Figure 10I:
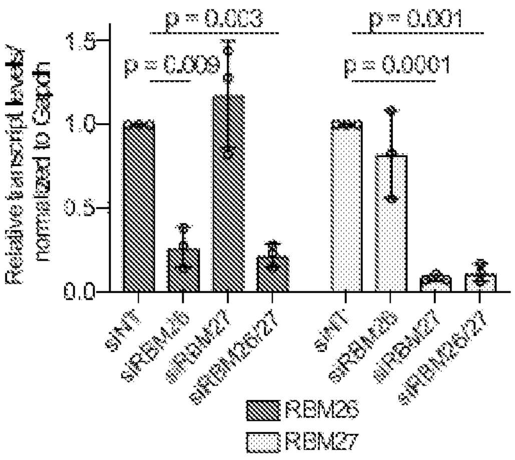
Figure 10J:
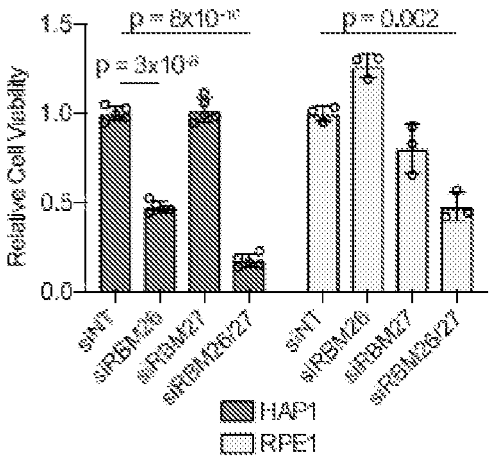
Figure 10K:
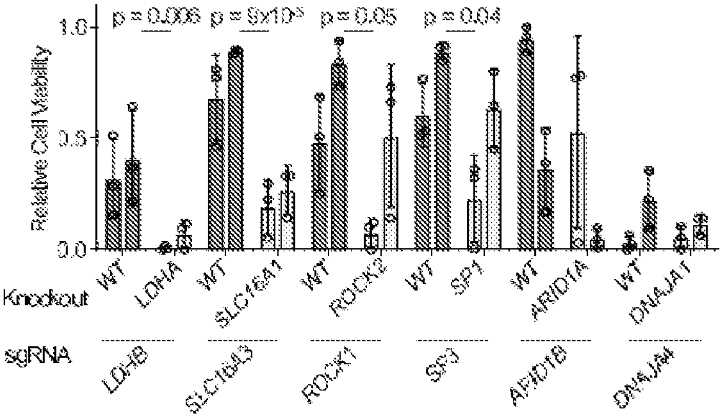

This analysis revealed negative GIs between several of the targeted paralog pairs that are known to exhibit functional redundancy; for example SEC23A-SEC23B, AR1D1A-AR1D1B and TIA1-TIAL1 (FIGS. 4E-F, 10E-F and Table 7) (Bassik et al., 2013a; Meyer et al., 2018; Viswanathan et al., 2018). A number of previously uncharacterized strong negative interactions between paralog pairs were also observed including SAR1A-SAR1B, RAB1A-RAB1B, LDHA-LDHB, RBM26-RBM27 and hnRNPF-hnRNPH3, as well as positive genetic interactions between paralogs such as STK38-STK38L and TET1-TET2 (FIGS. 4E-F, 10E-F and Table 7). Six interactions across a selected set of paralog pairs (i.e. LDHA-LDHB, SLC16A1-SLC16A3, ROCK1-ROCK2, SP1-SP3, ARID1A-ARID1B, and DNAJA1-DNAJA4) were validated using HAP1 clonal knockout cell lines, where a clear fitness defect was observed in double knockouts compared to single knockouts (FIG. 10K).

Figure 4G:
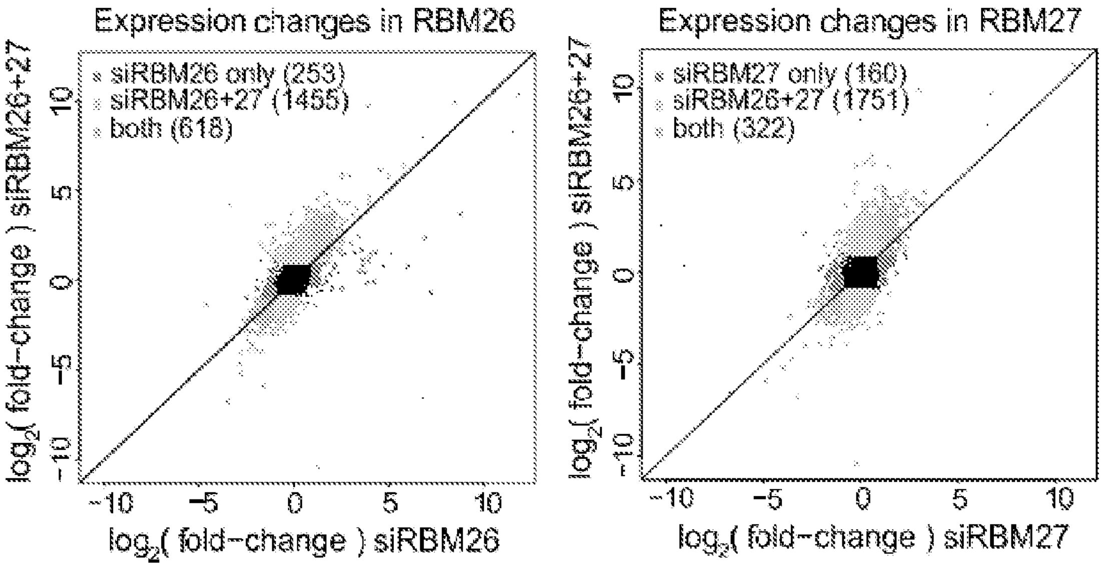
Figure 4H:
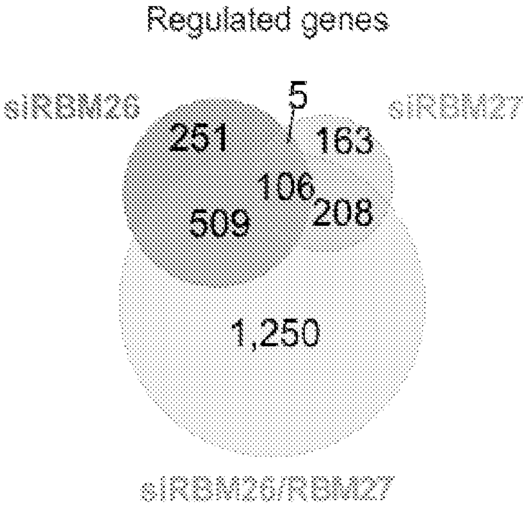
Figure 10L:
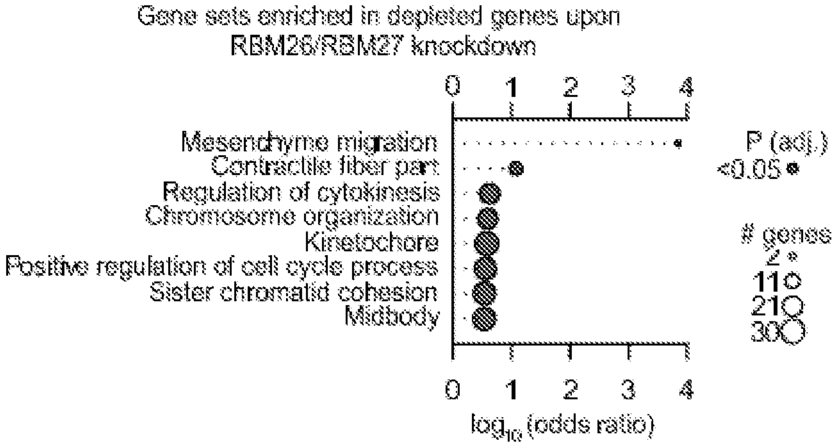

To explore functional roles of some of the stronger GIs shared between HAP1 and RPE1 cells, the RBM26-RBM27 paralog pair were further characterized, since RBM26 and RBM27 remain uncharacterized. These genes encode RNA binding proteins that contain RNA recognition motifs (RRMs). To further investigate functional interactions between this pair of paralogous genes, individual and combinatorial depletion of RBM26 and RBM27 using siRNAs was performed and cell fitness was measured. First, knockdown of each gene alone or in combination was confirmed by qPCR. Knockdown of RBM27 on its own has little effect on proliferation in either HAP or RPE1 cells. However, the combined knockdown of RBM26 and RBM27 results in a more than additive effect on cell viability, validating the interaction between these genes detected in the CHyMErA screen (FIG. 10J). Similarly, several additional pairwise interactions tested between paralogous genes were validated in HAP1 clonal knockout cell lines, where a clear fitness defect was observed in double knockouts relative to the single knockouts (FIG. 10K). To validate and further investigate the functional interaction between RBM26 and RBM27, single and double small interfering (si)RNA knockdowns were performed (FIG. 10I). Depletion of RBM27 has little effect on the proliferation of HAP1 or RPE1 cells, whereas their combined depletion results in a more than additive effect on cell viability (FIG. 10J). Moreover, RNA-sequencing (RNA-seq) profiling of HAP1 cells following siRNA knockdown of RBM26 and RBM27 reveals that their co-depletion results in a 72% increase in the number of genes with altered expression compared to that of both single-knockdowns (2,073 versus 1,204 genes, P<2.2x10-16, Fisher's exact test; FIG. 4G,H). Interestingly, genes downregulated following RBM26 and/or RBM27 co-depletion are enriched in terms related to the cell cycle (FIG. 10L). Collectively, these analyses demonstrate the efficacy of CHyMErA in detecting known and new GIs between pairs of paralogous genes, including a previously unknown interaction between RBM26 and RBM27 that shapes the human transcriptome.

Method Details: The methods used are those as described in Example 9.

Figure 11B:
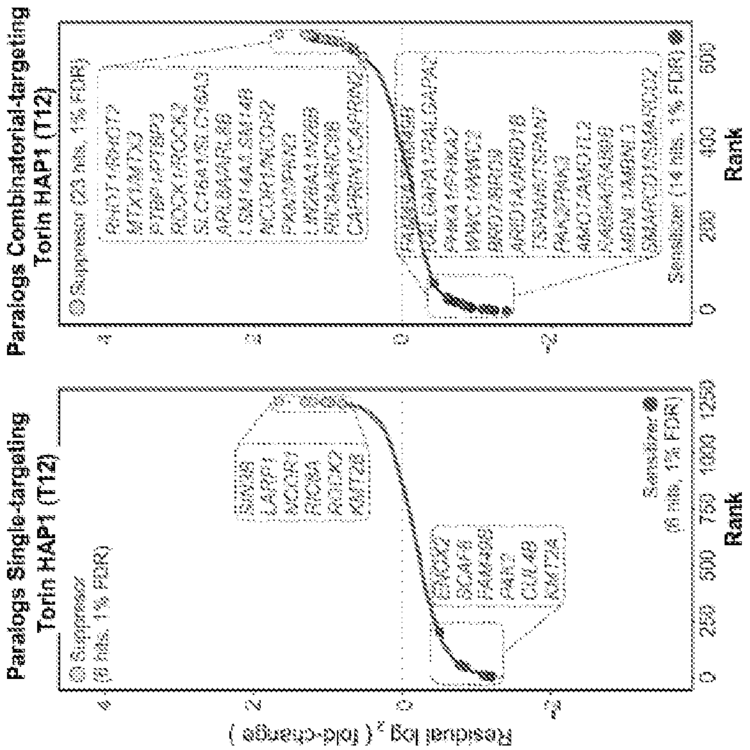
Figure 11A:
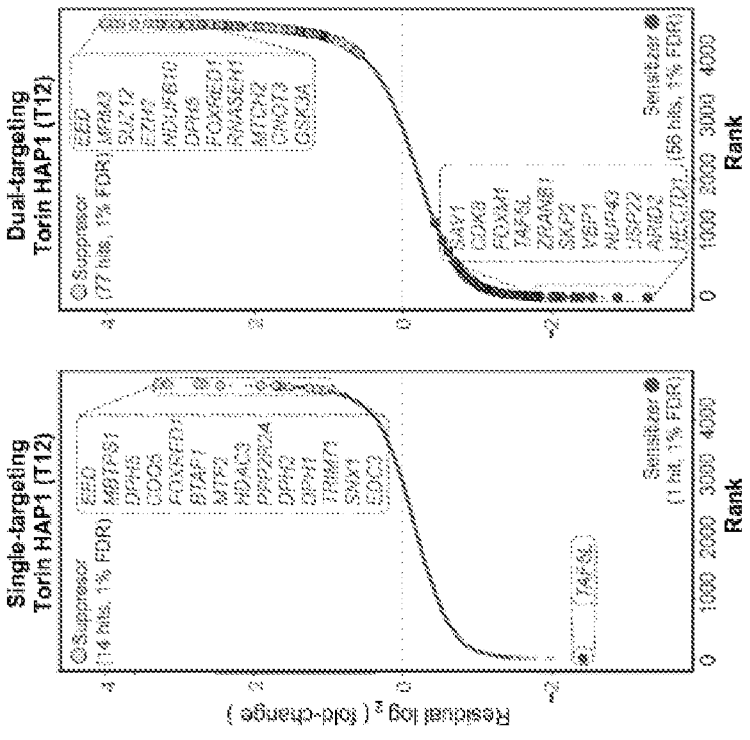

Example 7: Dual Gene Targeting Increases the Sensitivity of Chemogenetic Screens A powerful application of CRISPR screens is the identification of chemogenetic interactions that uncover molecular mechanisms of drug action, as well as novel targets for combinatorial treatment strategies. For instance, mTOR plays a central role in the regulation of fundamental processes including protein synthesis, autophagy and cell growth, and targeting this pathway is of considerable interest in clinical applications (Saxton and Sabatini, 2017; Valvezan and Manning, 2019). Therefore, to test the efficacy of CHyMErA for chemogenetic screens, HAP1 cells transduced with the dual gene and paralog-targeting hgRNA library were treated with the catalytic mTOR inhibitor Torin1, which targets both mTORC1 and mTORC2 kinase complexes (Thoreen et al., 2009), in order to identify mediators of sensitivity or resistance to mTOR inhibition. Perturbed HAP1 cell population was treated with a concentration of Torin1 that causes a 60% reduction in cell growth from day 3 through to day 18 (i.e. the assay end-point). To identify genes whose depletion significantly alter response to Torin1, the hgRNA LFC distributions+/− drug treatment were compared. This analysis identifies 17 and 8 single-guide-targeted genes as Torin1 suppressors and sensitizers, respectively (FIG. 5A,B; FDR<0.01; Table 8). Importantly, the number of genes detected is substantially increased by the dual-targeting approach, which identifies 77 suppressors and 56 sensitizers at the same FDR (FIG. 5A,B; Table 8). Additionally, 20 suppressor and 20 sensitizer paralog pairs were also identified, which are not identified by targeting either gene alone (FIG. 5C; Table 8, FDR<0.01). These data further underscore the power of CHyMErA for discovering new genetic relationships. Similar results were obtained from the analysis of additional time points (FIG. 11A,B and Table 8).

Figure 5A:
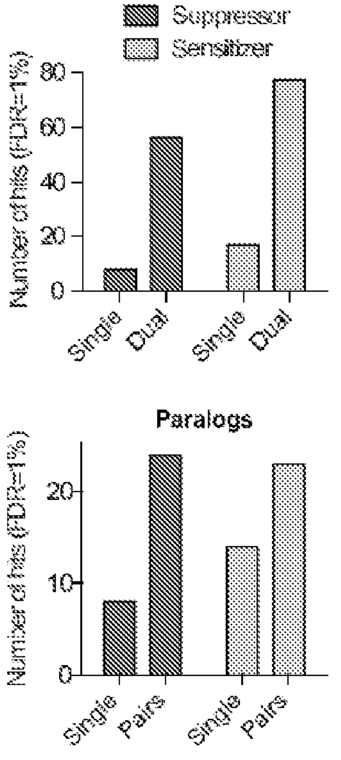
Figure 5B:
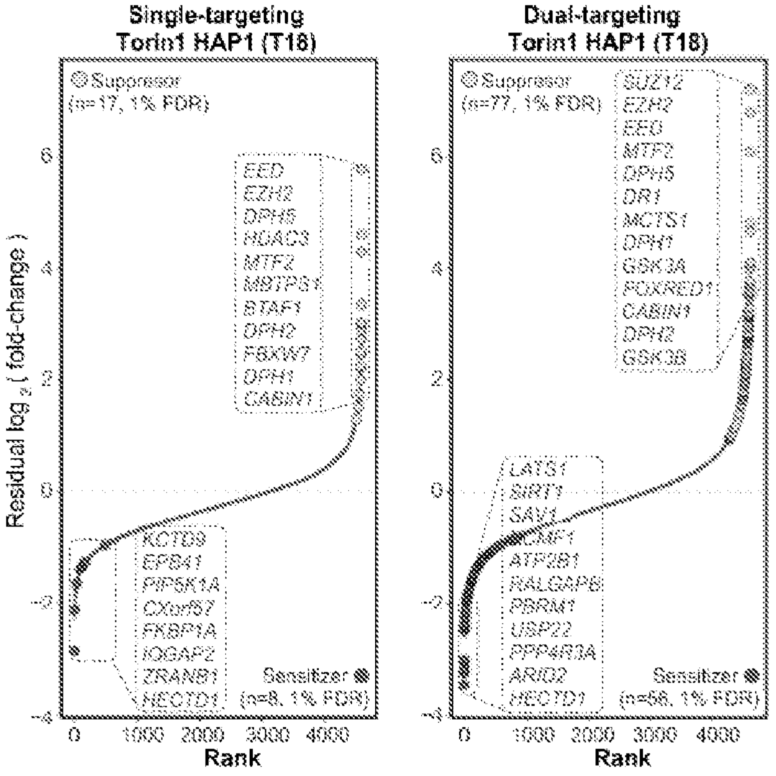
Figure 5C:
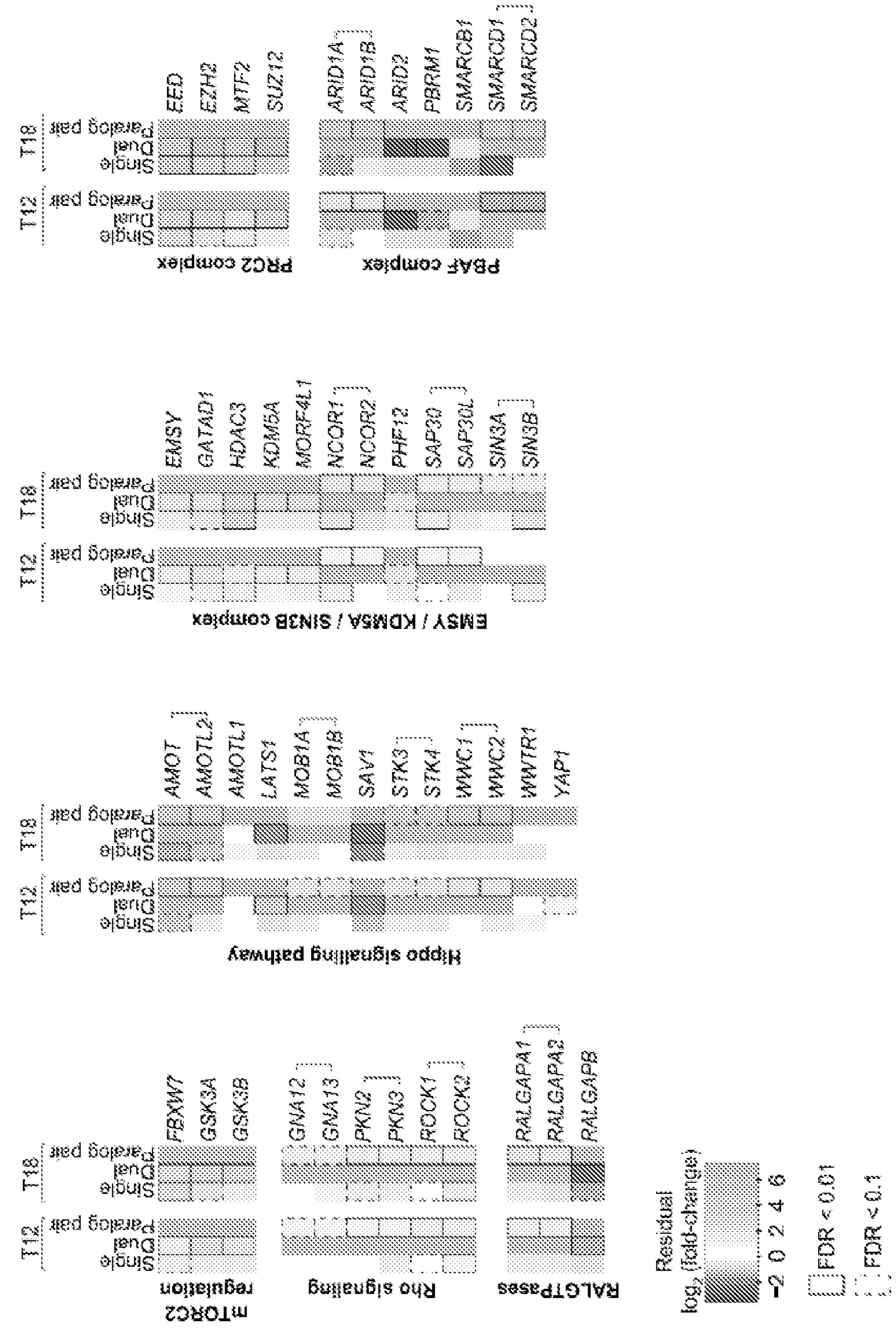
Figure 5D:
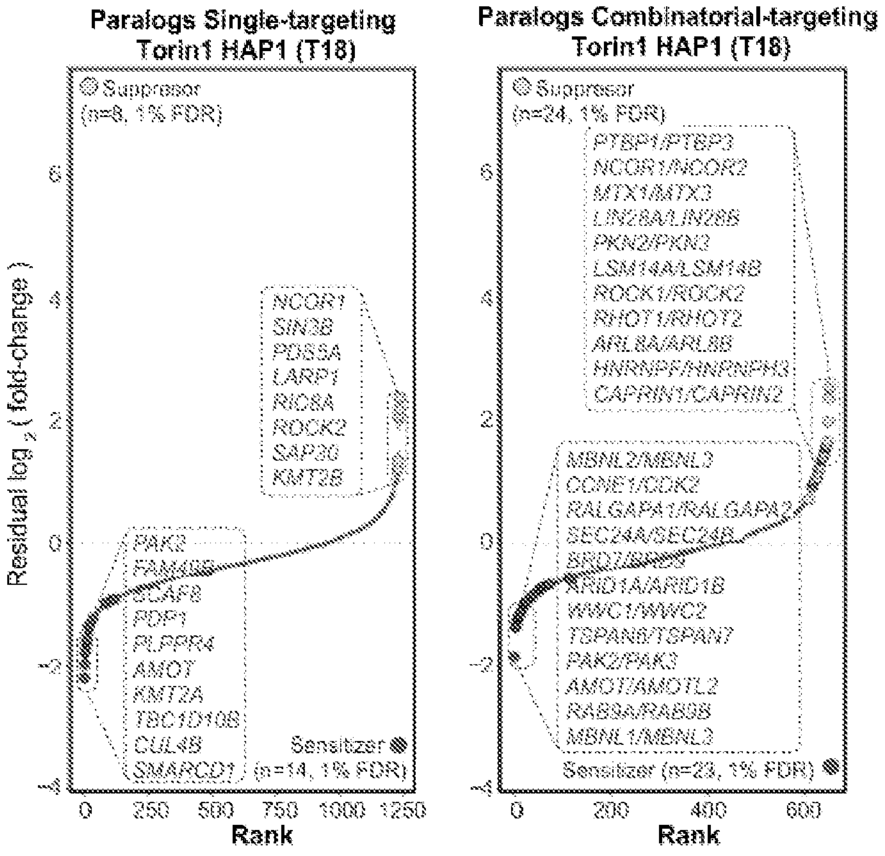
Figure 11C:
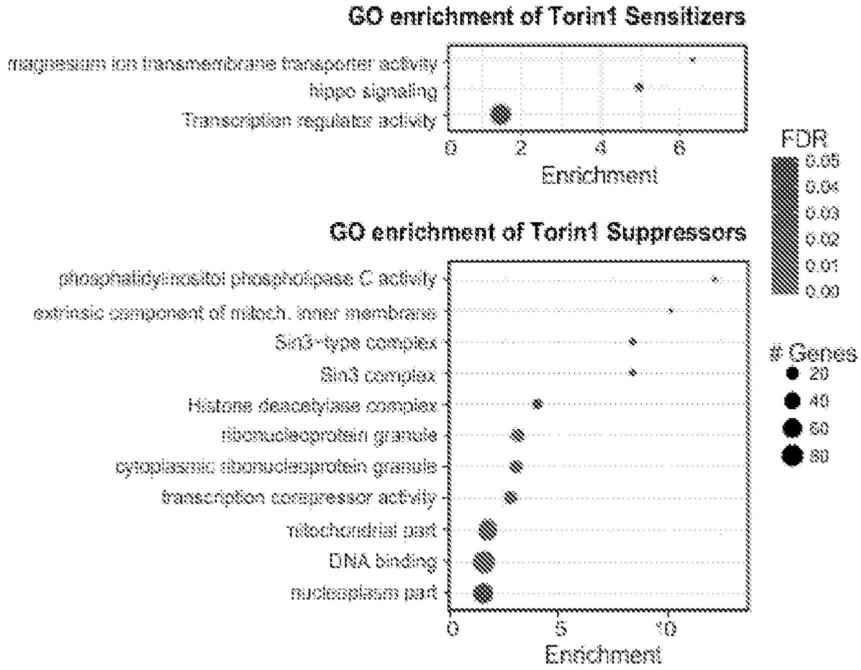
Figure 11D:
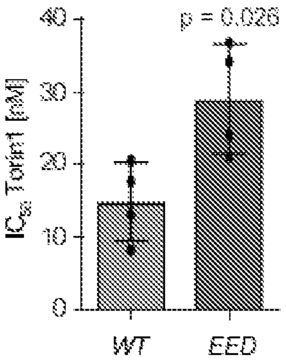
Figure 11E:
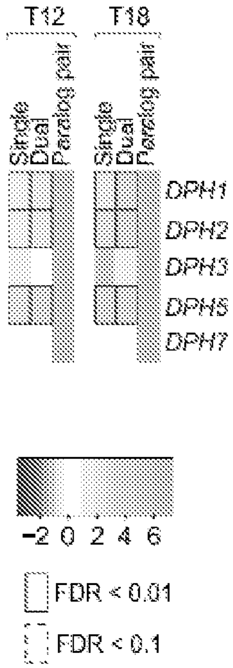

The Torinl screen identified several genes previously described as regulators and downstream effectors of mTOR signalling; for example, GSK3A, GSK3B, FBXW7 (Koo et al., 2014, 2015), RAL GTPases (Martin et al., 2014) and Rho signaling components such as ROCK1 and ROCK2 (Peterson et al., 2015; Shu and Houghton, 2009) (FIG. 5D). Gene ontology analysis of the sensitizer genes revealed an enrichment of Hippo signaling pathway genes and a BAF-type complex (FIGS. 5E and 11C). Strikingly, among these hits several paralog pairs were identified indicating redundant function of the gene pairs in the respective pathways. Among the suppressors, a strong enrichment was also found for chromatin regulators that negatively regulate gene expression, such as the polycomb repressive complex 2 (PRC2) and the EMSY/KDM5A/SIN3B complex (FIGS. 5E and 11C) (Varier et al., 2016). The PRC2 complex member encoded by the EED gene was identified as the top positive chemical-GI with both single- and dual-targeting hgRNAs. This finding was validated by treating HAP1 wild type and EED knockout cells with Torin1, where an increased tolerance of mTOR inhibition was observed in PRC2-deficient cells (FIG. 11D). In addition, multiple members of the pBAF complex were also detected as sensitizers to Torin1, including the paralogs ARID1A-ARID1B and SMARCD1-SMARCD2 (FIG. 5E). The increased signal afforded by the CHyMErA system captured multiple chemical-GIs linking mTOR inhibition to chromatin regulation and cell signalling proteins (FIGS. 5E and 11E and Table 8).

Collectively, these data demonstrate that dual-targeting of genes using CHyMErA provides a sensitive and effective screening method for the identification of chemical-GIs. Moreover, the combination of CHyMErA with the paralog-targeting hgRNA library identified novel interactions that were not detected by single gene knockout, likely due to functional redundancy between paralog pairs.

Method Details: The methods used are those as described in Example 9.

Example 8: Application of CHyMErA to Exon Deletion Screens

Having established the multisite targeting and exon deletion capabilities of CHyMErA (FIGS. 1B-E and 7F,H), its potential as a method for the large-scale screening of exon function was explored. To this end, CNN-optimized hgRNA libraries were designed targeting 2157 alternative cassette exons for deletion in RPE1 cells. These exons were selected on the basis of being detected in transcripts expressed across a panel of human cell lines (see Methods in Example 9), belonging to functionally diverse genes with a range of fitness profiles, and representing different levels of conservation (Table 9; see Methods in Example 9). Among the targeted exons, 132 are frame-altering and predicted to result in gene ablation via truncation of coding sequence and/or introduction of a premature stop codon capable of eliciting nonsense mediated mRNA decay. A further 2025 are frame-preserving. The frame-altering category includes exons in both fitness and non-fitness genes, and therefore targeting these two subsets of exons affords a comparative measure of the efficiency for hgRNAs that cause exon deletion and guide depletion in cell fitness screens.

As before, each exon was targeted by multiple Cas9-Cas12a hgRNAs. Where possible (depending on the availability of target sites), two individual Cas9 guides were paired with up to four Cas12a guides for each exon, in each case targeting both down- and up-stream intronic sequence flanking the targeted exon, resulting in a total of 16 pairs of deletion-targeting hgRNA constructs. Furthermore, each intronic Cas9 and Cas12a gRNA was also paired with two intergenic gRNAs to control for non-specific toxicity, adding 24 control guide pairs per exon. Finally, the library also included Cas9 gRNAs designed to target within constitutive exons of all the genes targeted in the library, in order to assess the phenotypic impact of inactivating genes harboring an alternative cassette exon (Table 9).

Figure 6A:
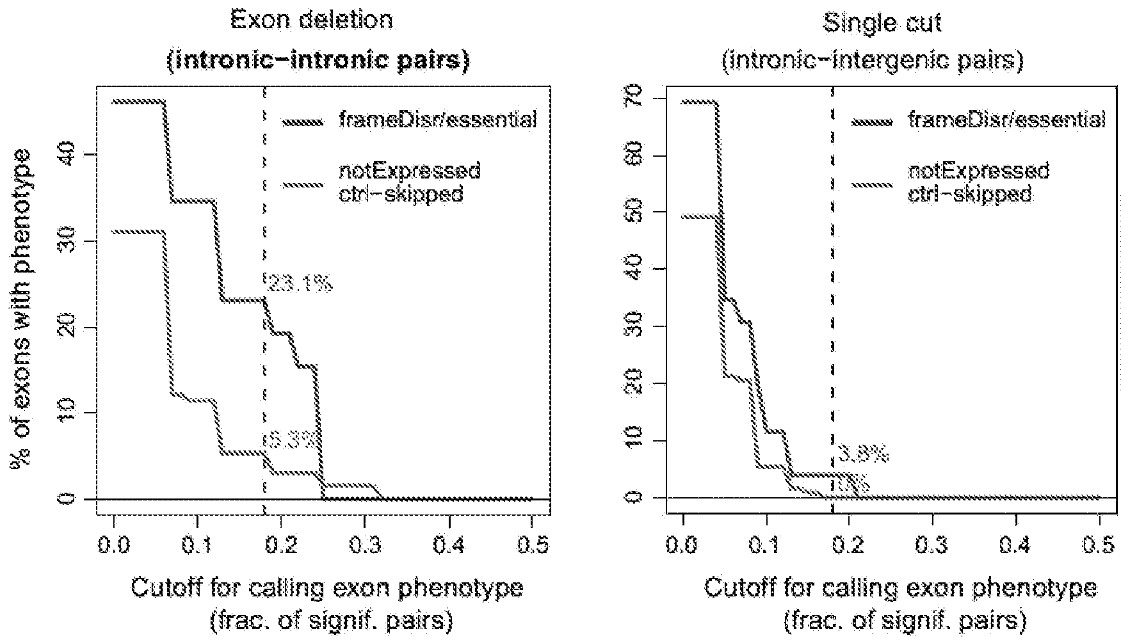
Figure 6B:
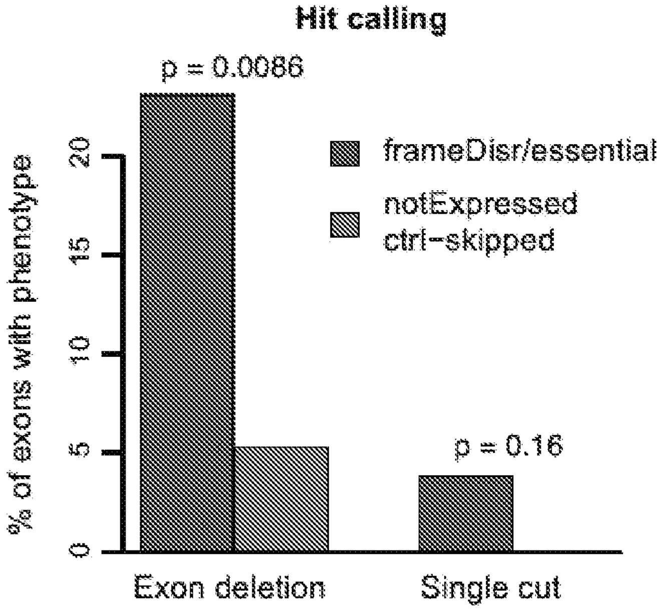
Figure 6C:
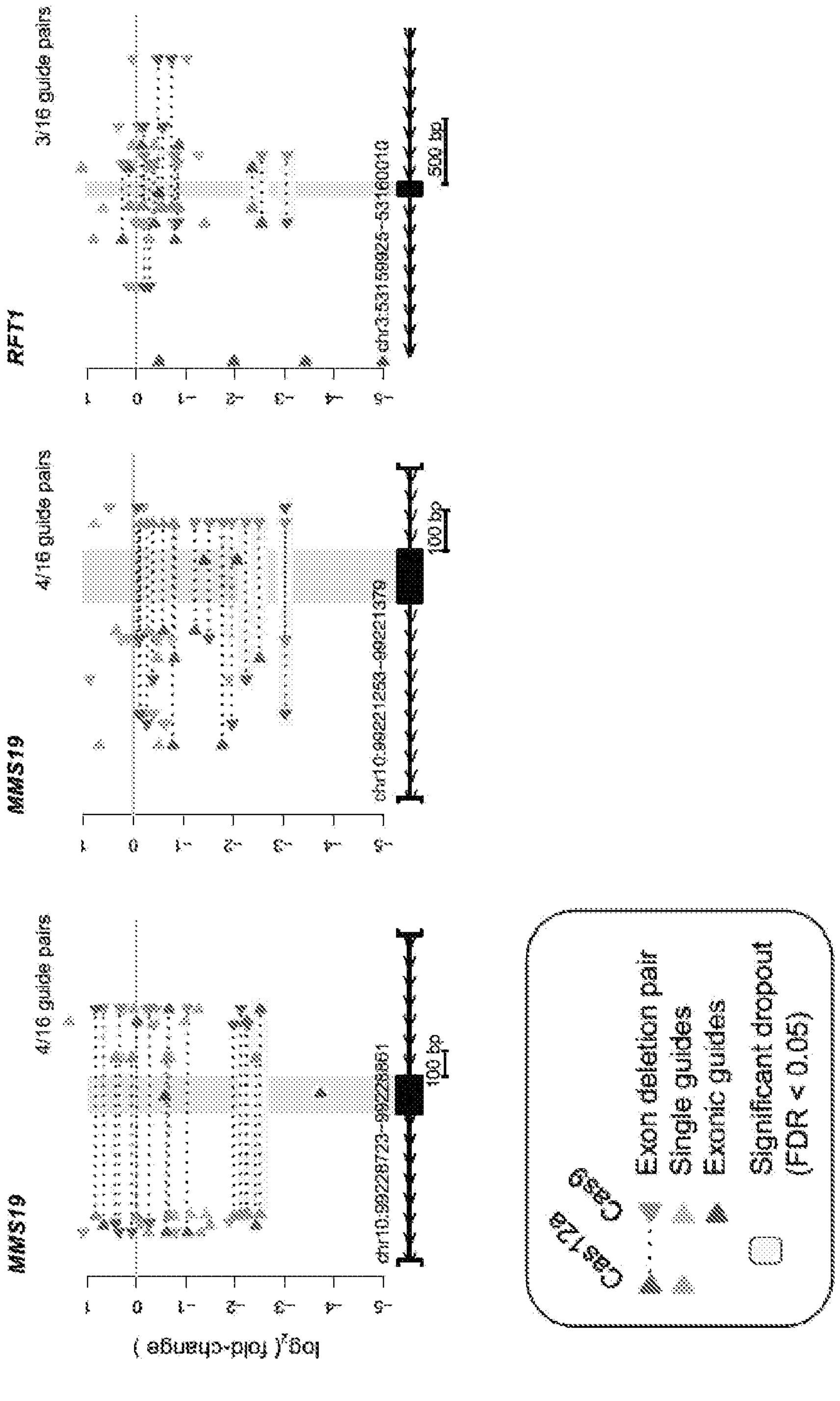

To assess the efficiency of exon deletion, the abundance of hgRNAs targeting frame-altering exons in fitness and non-fitness genes were compared. The guide pairs that displayed significant dropout or enrichment compared to the 1647 intergenic-intergenic control guide pairs included in the hgRNA library were first determined. The cumulative distribution for all targeted frame-disrupting exons in fitness and non-fitness genes based on the fraction of significantly depleted guide pairs was then determined. As expected, among the guide pairs displaying a significant dropout phenotype, strong enrichment was observed for frame-disruptive exons residing in fitness genes compared to exons residing in non-fitness genes (FIGS. 6A-C). Importantly, this enrichment was not detected for single cutting intronic-intergenic control guide pairs (FIGS. 6A-B). The strongest separation (~4.5-fold) between fitness and non-fitness genes was observed for exons for which there is a significant dropout of at least 18% of tested hgRNA exon-deletion pairs (FIGS. 6A-B). These results demonstrate that CHyMErA is capable of scoring the phenotypic consequences of exon deletion in the context of large-scale screens.

Method Details: The methods used are those as described in Example 9.

Example 9: CHyMErA Reveals Splicing Events that Regulate Cell Fitness

Figure 6D:
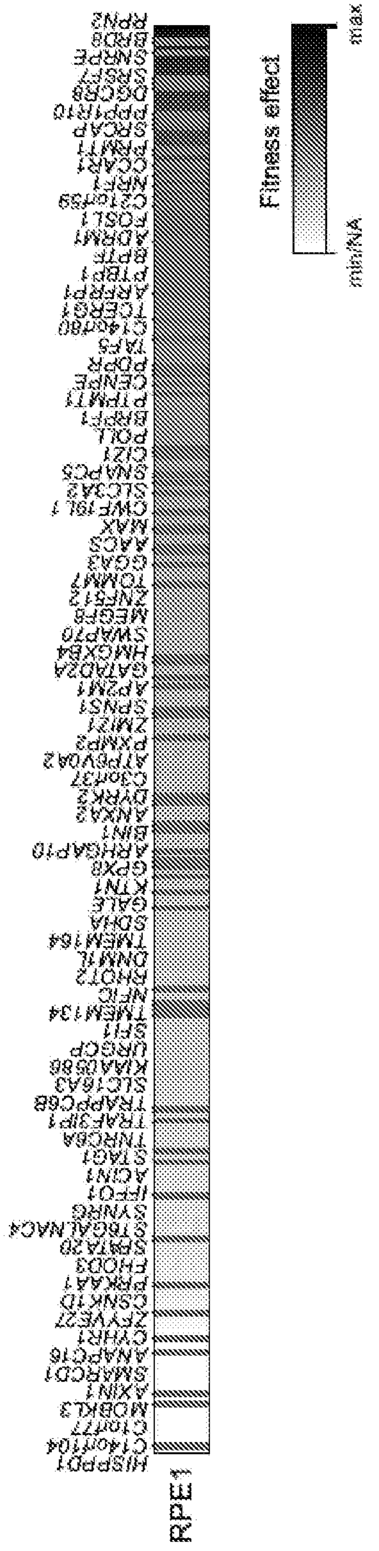
Figure 6E:
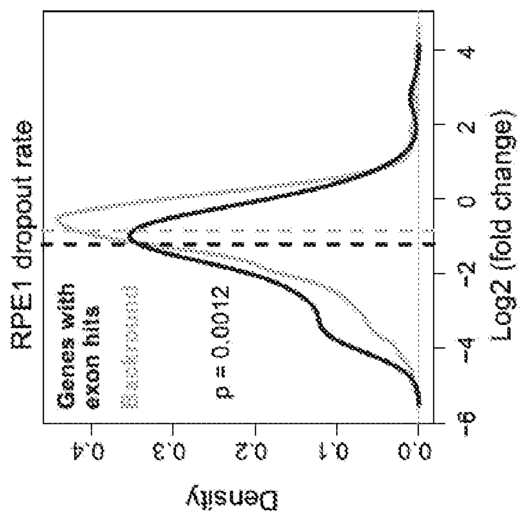
Figure 12A:
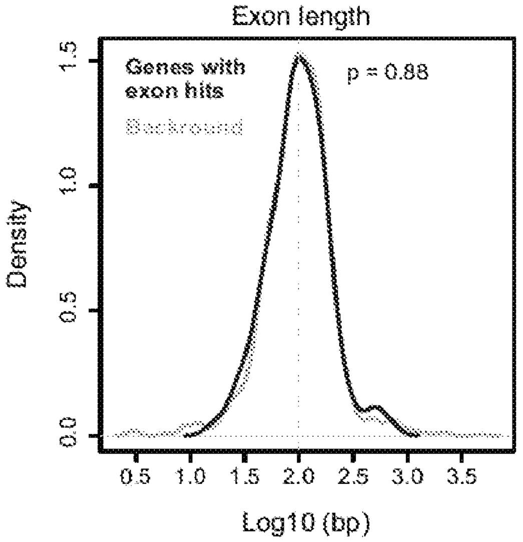
Figure 12B:
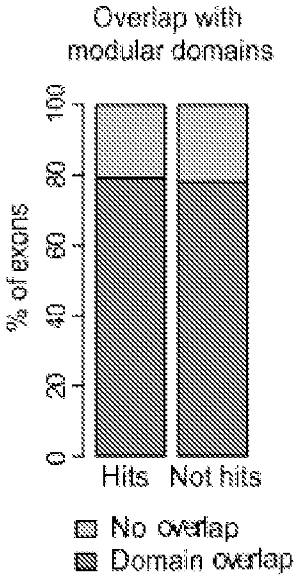
Figure 12C:
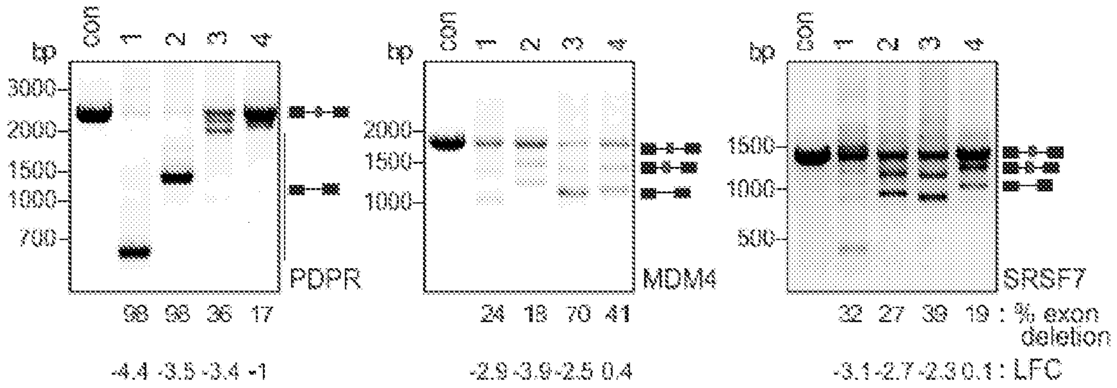

With the ability to perform targeted deletion of specific exons, CHyMErA was applied to investigate the consequences of deleting frame-preserving cassette exons on cell fitness. Of 2,025 frame-preserving cassette exons targeted for deletion in the hgRNA library, 124 result in significant depletion of guides in RPE1 cells (FIG. 6D and Table 10). As expected, these fitness exons are significantly enriched in essential genes (FIG. 6D; p<0.00012, Mann-Whitney U test). However, no apparent differences were detected between the exons impacting fitness versus those that do not in terms of their length or overlap with functional domains (FIGS. 12A-B). Validating the specificity of CHyMErA for exon deletion, the hgRNAs with detected strong LFC differences display higher editing efficiency than hgRNAs targeting the same exons but having marginal LFC values (FIG. 12C).

Figure 12D:
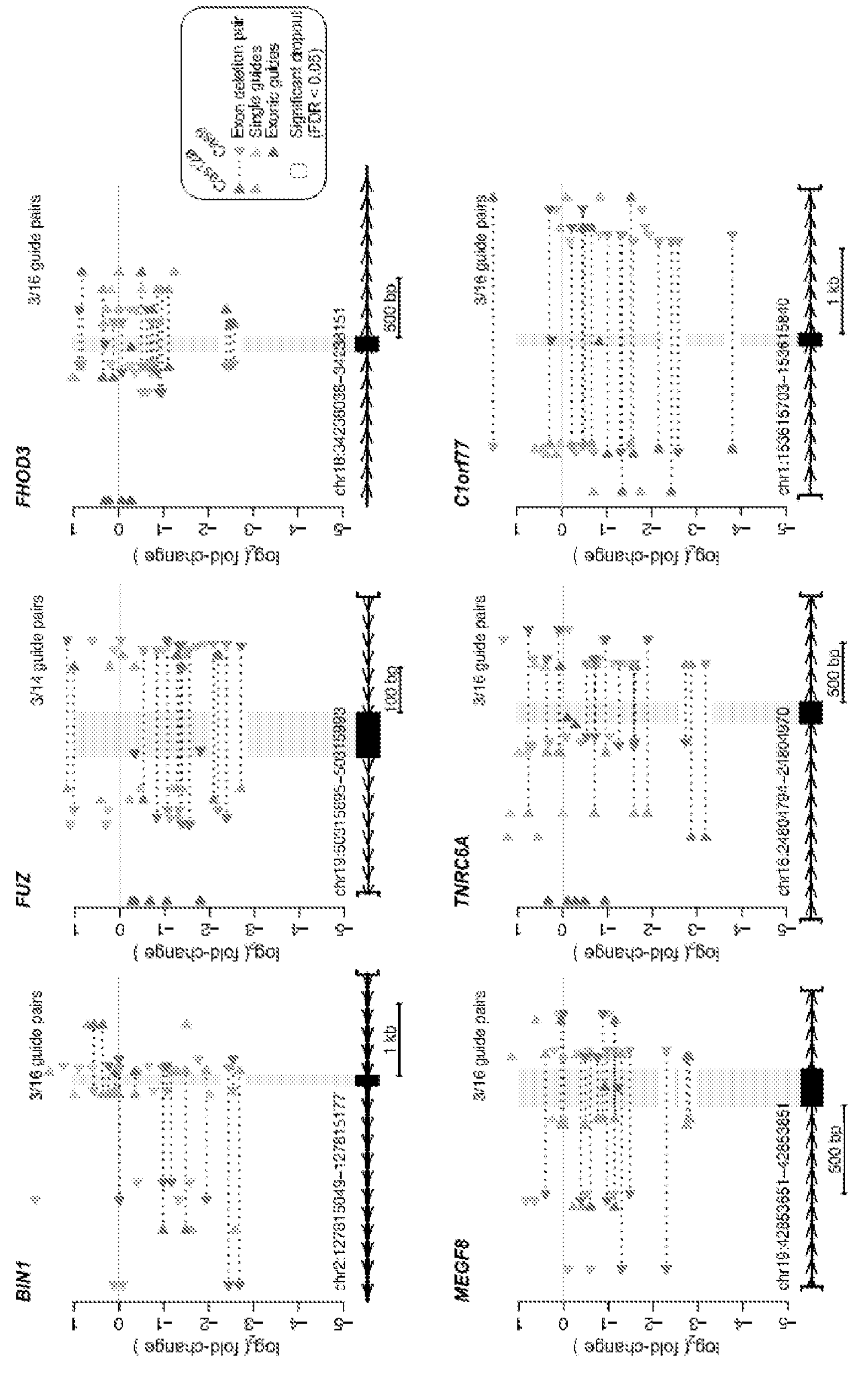
Figure 12E:
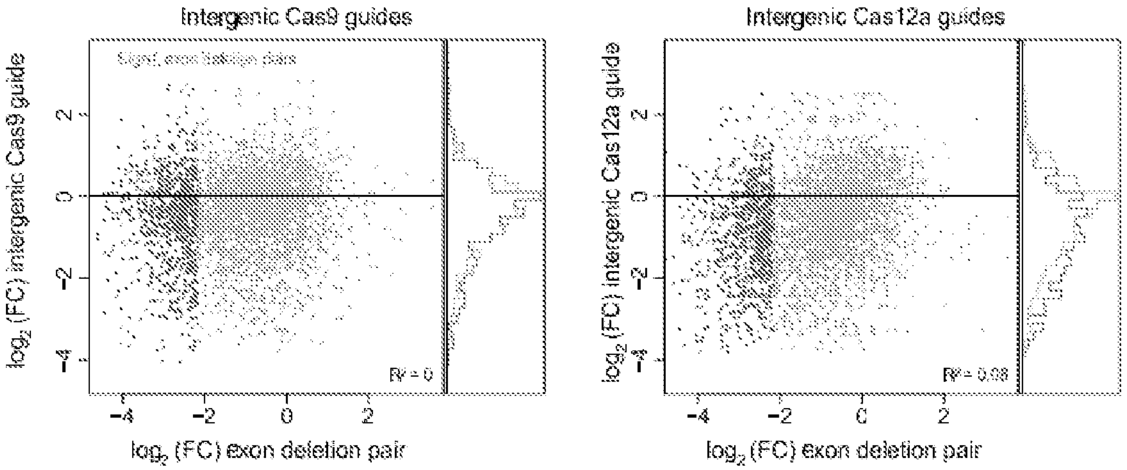
Figure 12F:
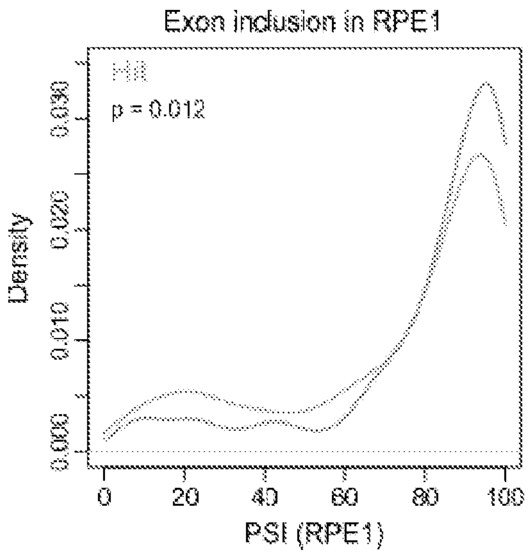

The exon deletion CHyMErA screen identified dozens of frame-preserving exons that are predicted to impact cellular fitness. For example, BIN1 exon 12A was identified as being critical for cell fitness (FIGS. 6D and 12D). BIN1 is a tumor suppressor that interacts with MYC and inhibits MYC-dependent transformation (Sakamuro et al., 1996). Exon 12A abolishes BIN1 tumor suppressor activity by generating a protein isoform that no longer binds to MYC (Pineda-Lucena et al., 2005), and aberrant splicing of this exon has been observed in melanoma cells (Ge et al., 1999).

Another hit from the exon library screen is PTBP1 exon 9, which has previously been shown to display reduced inclusion during neuronal differentiation, which contributes to the de-repression of a splicing network underlying neuronal differentiation that is negatively regulated by PTBP1 (Gueroussov et al., 2015). Furthermore, the exon deletion screen captured additional alternative exons that underlie cell fitness and which represent attractive examples for future studies. These results thus demonstrate that CHyMErA affords the systematic investigation of the function of alterative exons when coupled to biological assays.

Method Details

Cell line maintenance. HAP1 cells were obtained from Horizon Genomics (clone C631, sex: male with lost Y chromosome, RRID: CVCL_Y019). hTERT-RPE1 or RPE1 cells were obtained from ATCC (cat. #CRL-4000). Neuro-2A (N2A) cells were obtained from ATCC (cat. #CCL-131). Mouse CGR8 embryonic stem cells were obtained from the European Collection of Authenticated Cell Cultures. Human HAP1 cells were maintained in low glucose (10 mM), low glutamine (1 mM) DMEM (Wisent, 319-162-CL) supplemented with 10% FBS (Life Technologies) and 1% Penicillin/Streptomycin (Life Technologies). Human hTERT RPE1 cells were maintained in DMEM with high glucose and pyruvate (Life Technologies) supplemented with 10% FBS (Life Technologies) and 1% Penicillin/Streptomycin (Life Technologies). Mouse neuroblastoma Neuro-2A (N2A) cells were grown in DMEM (high glucose; Sigma-Aldrich) supplemented with 10% FBS, sodium pyruvate, non-essential amino acids, and penicillin/streptomycin. CGR8 mouse embryonic stem cells (mESC) were grown in gelatin coated plates in GMEM supplemented with 100 μM p-mercaptoethanol, 0.1 mM nonessential amino acids, 2 mM sodium pyruvate, 2.0 mM L-glutamine, 5,000 units/mL penicillin/streptomycin, 1000 units/mL recombinant mouse LIF (all Life Technologies) and 15% ES fetal calf serum (ATCC). Cells were maintained at sub-confluent conditions. Cells were dissociated using Trypsin (Life Technologies) and all cells were maintained at 37° C. and 5% CO2. Cells were regularly monitored for absence of *mycoplasma* infection.

Lenti-Cas12a vector construction. A nucleoplasmin nuclear localization signal (NLS) (SEQ ID NO: 23) was added at the C-terminus of an N-terminal SV40 NLS-tagged (SEQ ID NO: 22) Cas12a followed by a Myc tag (SEQ ID NO: 24) using conventional restriction enzyme cloning to generate As- or Lb-Cas12a-NLS-MYV-2A-NeoR lentiviral-based expression vectors named plenti-As-Cas12a-2×NLS and plenti-Lb-Cas12a-2×NLS, respectively. In embodiments where the DNA target is in the nucleus, the Cas protein comprises a nuclear localization moiety such as a nuclear localization signal.

TOPO-Cas9 tracr-Cas12a direct repeat vector construction. The tracrRNA-DR fragment was cloned into a TOPO vector by annealing and ligating oligos encoding for BsmBI-tracrRNA-DR-BsmBI following manufacturer's recommendation.

pLCKO hgRNA vector construction. The pLCHKO vector for hgRNA expression was derived from the pLCKO vector (Addgene #73311) by inverting the U6 expression cassette consisting of a stuffer sequence containing BfuAI/BveI sites followed by a RNA polymerase III transcription termination signal (AAAAAAA) of pLCKO vectors. Cloning of hgRNAs into the vector was performed in two steps, whereby the Cas9 and Cas12a guides, separated by a 32 nt spacer containing BsmBI/Esp31 sites, were first cloned into the pLCKO vector by ligating annealed oligos with appropriate overhangs and BsmBI digested vectors following manufacturer's recommendations. Separately, the tracrRNA-Direct Repeat (DR) fragment was cloned into a TOPO vector by annealing and ligating oligos encoding BsmBI-tracrRNA-DR BsmBI (see FIG. 14).

In a second step pLCKO vectors containing the dual guides were digested using BsmBI following manufacturer's recommendation and then the Cas9 tracrRNA—Cas12a DR fragment (with the corresponding overhangs) was ligated in the digested pLCKO vectors to reconstitute functional hgRNAs. The tracrRNA-DR fragment was generated by digesting TOPO vectors containing tracrRNA-DR between BsmBI sites.

pPapi constructs were cloned using oligos (generated by Twist Biosciences) as described previously (Cong et al. 2013; Wang et al. 2014)

Cas9/Cas12a cell line generation. Previously generated HAP1 and hTERT-RPE1 clonal cell lines expressing Cas9 (Hart et. al. 2015; Hart et al. 2017) were transduced with lentivirus carrying the As- or Lb-Cas12a-2A-NeoR expression cassette, and transduced cells were selected with G418 (500 μg ml-1) for 2 weeks. HAP1 and RPE1 Cas9-Cas12a cells were not subjected to single-cell isolation but were used as pools in CHyMErA screens. HAP1 Cas9-Cas12a cells became diploid during the selection process, as determined by ploidy analysis using flow cytometry.

Neuro-2A and CGR8 cells were transduced with lentivirus carrying the Cas9-2A-BlasticidinR-expressing cassette (Addgene, no. 73310) and selected with blasticidin (10 μg ml-1 for N2A and 6 μg ml-1 for CGR8) for 10 d. Cas9-expressing cell lines were then transduced with lentivirus carrying the As- or Lb-Cas12a2A-NeoR expression cassette and selected with G418 (500 μg ml-1). After 14 d of selection, N2A single cells were sorted by manual seeding of a single-cell suspension at 0.6 cells per well in 96-well plates. A cell clone with high editing efficiency was selected for subsequent CHyMErA screens. CGR8 Cas9-Cas12a cells were not subjected to single-cell isolation but instead were used as pools in CHyMErA screens.

Assessment of Cas9/Cas12a editing by 6-thioguanine toxicity assay. To determine Cas9 and Cas12a editing efficiency, HAP1 and RPE1 cells expressing Cas9 and Cas12a were transduced with hgRNAs targeting TK1 (by Cas9) and HPRT1 (by Cas12a). After selection for transduced cells using 1 microgram/ml puromycin for 2 days, cells were reseeded for proliferation assays and after 18 hours cells were either treated with 2.5 mM thymidine, 6 μM 6-thioguanine or mock treated for 4 days. Cell viability was assessed at the end of the assay using Alamar Blue according to the manufacturer's instructions. 6-TG results in cell death whereas thymidine block causes cell cycle arrest. As such, both drugs strongly affect cell fitness.

siRNA transfections. HAP1 and RPE1 cell lines were transfected with 10 nM of siGENOME siRNA pools targeting RBM26 and RBM27 (Dharmacon) using RNAiMax (Life Technologies), as recommended by the manufacturer. A non-targeting siRNA pool was used as control. Cells were harvested 48 hours post transfection for RNA extraction. For cell viability assays, knock-down was performed for 72 hours and the viability was monitored by Alamar Blue according to the manufacturer's instructions.

Validation of the Torin1-EED chemical genetic interaction. For validation of the Torin1 suppressor, HAP1 WT and an EED knockout cells were treated with a titration of Torin1 ranging between 0 and 100 nM. Cell viability was measured four days post-treatment and IC50 values were calculated using GraphPad Prism software.

Validation of genetic interactions between paralog pairs. HAP1 WT and knockout clones were transduced with lentiviruses derived from lentiCRISPRv2 Cas9 and sgRNA expression cassettes targeting an intergenic site in the AAVS1 locus or the corresponding paralog pair. Each gene was targeted with two independent sgRNAs. 24 hours after transduction cells were selected with 1 μmg/ml puromycin for 48 hours and seeded for proliferation assays. After 6 days, cell viability was measured by Alamar blue according to the manufacturer's instruction. The average viability of cells transduced with the two sgRNAs was calculated and normalized to the intergenic control sgRNAs.

Assessment of Cas9/Cas12a editing by PCR. To determine Cas9 and Cas12a editing efficiency, cells expressing Cas9 and Cas12a were transduced with lentiviruses derived from dual pLCKO (see FIG. 7*a*), pLCHKO or pPapi constructs targeting intronic regions flanking exons. Transduced cells were selected with 1 μg ml-1 of puromycin for 48 h, and gDNA was extracted using the PureLink® Genomic DNA Kit (Thermo Fisher Scientific™). Successful editing was assessed by PCR using primers flanking the targeted regions, and PCR products were resolved by agarose gel electrophoresis.

Percentage exon deletion was calculated using ImageJ software. Exon-included and -excluded band intensities were corrected by subtracting the background, and values were normalized by product size. Intensity of the exon-included band was divided by the sum of the exon-included and -excluded bands; the result was then multiplied by 100 to obtain percentage exon deletion, which was rounded to the nearest integer.

Immunofluorescence. Cells were seeded on cover slips and fixed with 4% paraformaldehyde in PBS for 10 minutes at room temperature. Cells were permeabilized with 1% NP-40 in antibody dilution solution (PBS, 0.2% BSA, 0.02% sodium azide) for 10 minutes and blocked with 1% goat serum for 45 minutes. Cells were incubated with anti-HA (1:1,000, Sigma) and anti-Myc antibodies (1:1,00, Sigma M4439) for 1 hour at room temperature. Subsequently, cells were incubated with Alexa Fluor488 goat anti rabbit antibodies (Invitrogen, A-1108, 1:500) and counterstained with 1 g/ml DAPI (Cell Signaling, 4083S) for 45 minutes in the dark. Cells were visualized by microscopy (WaveFX confocal microscope from Quorum Technologies).

Immunoblotting. Cells were lysed in buffer F (10 mM Tris pH 7.05, 50 mM NaCl, 30 mM Na pyrophosphate, 50 mM NaF, 10% Glycerol, 0.5% Triton X-100) and centrifuged at 14,000 rpm for 10 minutes. The supernatant was collected and protein concentration was determined using Bradford reagent (BioRad). 10-25 μg protein was resolved on 4-12% Bis-Tris gels (Life Technologies) and transferred to Immobilon-P nitrocellulose membrane (Millipore) at 66V for 90 minutes. Subsequently, proteins were detected using the following antibodies: anti-Beta-Actin (1:10,000, Abcam ab8226), anti-Cas9 (1:4,000, Diagenode C15200229), anti-Cpf1 (1:1000, Sigma SAB4200777), anti-P53 (1:2,000, Life Technologies, no. AH00152), anti-pRb S807/811 (1:500, Cell Signaling, no. 9308), anti-p21 (1:500, Cell Signaling, no. 2946), or anti-Myc (1:1,000, Sigma M4439). After binding with HRP-conjugated secondary antibodies (1:5,000; anti-Mouse Jackson ImmunoResearch 715-035-151; anti-Rabbit, Cell Signaling Technology 7074), proteins were visualized on X-ray film using Super Signal chemiluminescence reagent (Thermo Scientific) according to manufacturer's instructions.

Cas12a RNA processing activity. HAP1 cells expressing both Cas9 and Cas12a or Cas9 alone were transduced with a lentiviral hgRNA expression cassette. RNA was extracted using TRIzol (Thermo Fisher Scientific™) following manufacturer's recommendations. Subsequently, RNA was converted to cDNA using Maxima H cDNA synthesis kit (Thermo Fisher Scientific™) and random primers. Total and unprocessed Cas9 and Cas12a guides were amplified and quantified by quantitative PCR using SensiFAST real-time PCR kit (Bioline). The full-length (unprocessed) hgRNA was quantified by primers annealing to the beginning of the TracrRNA and to the end of the Cas12a guide. To quantify total levels of the Cas9 guide (processed and unprocessed), primers annealing to the beginning and end of the TracrRNA were used. The Cas12a processing activity was estimated by normalizing the levels of unprocessed hgRNA to total levels of the Cas9 guide.

Surveyor assays. ON-target genomic editing efficiency was estimated using the surveyor assay, essentially as previously described (Guschin et al., 2010). In brief, N2A cells were transduced with multiple independent Cas9 and sgRNA-expressing viruses targeting Ptbp1 intronic regions. Cells were selected in Puromycin (2.5 μg/ml) for 48 hours and 4 days post-selection genomic DNA was extracted using the PureLink® Genomic DNA Kit (Thermo Fisher Scientific™), as per the manufacturer's recommendations. After amplification of the targeted loci by PCR (Table 11), PCR products were denatured and re-annealed to form heteroduplexes. The re-annealed PCR products were incubated with T7 endonuclease (NEB) for 20 minutes at 37° C., and the cleavage efficiency was determined by agarose gel electrophoresis.

Lentiviral hgRNA library construction. For construction of CHyMErA libraries, Cas9 and Cas12a spacer sequences were cloned into a lentiviral vector via two rounds of Golden Gate assembly. 113-nt oligo pools were designed carrying 20 nt Cas9 and 23nt Cas12a spacers intervened by a 32 nt stuffer sequence harbouring BsmBI restriction sites, and flanked by short sequences harbouring BfuAI restriction sites. The oligo pools were synthesized on 90k microarray chips (CustomArray Inc., a member of GenScript, USA), each with a density of ~94,000 sequences. Oligos were amplified by PCR over 10 cycles using Q5 polymerase (1. 98° C. 30s, 2. 98° C. 10s, 3. 53° C. 30s, 4. 72° C. 10s, 5. 72° C. 2 min; steps 2-4 repeated for 9 cycles). Amplified oligos were purified on a PCR purification column and an aliquot was run on a 2% agarose gel to check purity. The pLCHKO hgRNA vector backbone was digested with BfuAI (NEB) overnight at 37° C. and with BspMI (NEB) for 2 h. The digested backbone was dephosphorylated with rSAP (NEB) for 1 h at 37° C. and gel purified using the GeneJet gel extraction kit (ThermoScientific). The amplified oligos were digested with BveI (Thermo Fisher™, FastDigest) and ligated into the digested pLCHKO backbone using T4 ligase (NEB) in a combined reaction overnight over 12 cycles (1.

37° C. 30 min, 2. 16° C. 30 min, 3. 24° C. 60 min, 4. 37° C. 15 min, 5. 65° C. 10 min; steps 1-3 were repeated for 11 cycles) using an empirically determined vector: insert ratio for example approximately 1:25. The ratio was determined on a case-by-case basis based on the number of colonies obtained in a small scale test ligation. The ligation mix was precipitated using sodium acetate and ethanol. The purified ligation reaction was transformed into Endura competent cells (Lucigen) by electroporation (1 mm cuvette, 25uF, 2000, 1600V) and plated on 15 cm ampicillin LB agar plates to reach a library coverage of 500 to 1,000-fold. Bacterial colonies were scrapped from the plates, pooled and bacterial pellets were collected. The Ligation 1 library plasmid was extracted using a Mega-prep plasmid purification kit (Qiagen).

In a second step, the Cas9 tracrRNA and the Cas12a direct repeat was inserted into the pooled library. The Ligation 1 plasmid library was digested overnight using Esp31 (Thermo Fisher™, FastDigest) and BsmBI (2h, 55° C.), dephosphorylated using rSAP (1h, 37° C.) and purified on a PCR purification column. A TOPO vector carrying the Cas9 tracrRNA and the Cas12a direct repeat was digested using Esp31 and subsequently ligated into the digested pLCHKO-Ligation 1 vector overnight over 12 cycles (1. 37° C. 30 min, 2. 16° C. 30 min, 3. 24° C. 60 min, 4. 37° C. 15 min, 5. 65° C. 10 min, steps 1-3 were repeat for 11 cycles) using a vector: insert ratio of 1:25. The ligation mix was precipitated using sodium acetate and ethanol. The purified ligation reaction was transformed into Endura competent cells (Lucigen) by electroporation (1 mm cuvette, 25uF, 2000, 1600V) and plated on 15 cm ampicillin LB agar plates to reach a library coverage of 500 to 1,000-fold. Bacterial colonies were scrapped from the plates, pooled and bacterial pellets were collected. The Ligation 2 library plasmid was extracted using a Mega-prep plasmid purification kit (Qiagen).

Library virus production and MOI determination. For library virus production, 8 million HEK293T cells were seeded per 15 cm plate in high glucose, pyruvate DMEM medium+10% FBS. Twenty-four hours after seeding the cells were transfected with a mix of 6 μg lentiviral pLCHKO vector containing the hgRNA library, 6.5 μg packaging vector psPAX2, 4 μg envelope vector pMD2. G, 48 μl X-treme Gene transfection reagent (Roche) and 1.4 ml Opti-MEM medium (LifeTechnologies) as per manufacturer's instructions. 24 hours post-transfection the medium was replaced with serum-free, high-BSA growth medium (DMEM, 1.1 g/100 ml BSA, 1% Penicillin/Streptomycin). The virus-containing medium was harvested 48 hours after transfection, centrifuged at 1,500 rpm for 5 minutes, aliquoted and frozen at −80° C.

For determination of viral titers, cells were transduced with a titration of the lentiviral hgRNA library along with polybrene (8 μg/ml). After 24 hours, the virus-containing medium was replaced with fresh medium containing puromycin (1-2 μg/ml) and cells were incubated for an additional 48 hours. Multiplicity of infection (MOI) of the titrated virus was determined 72 hours post-infection by comparing percent survival of puromycin-selected cells to infected but non-selected control cells. Due to pre-existing puromycin resistance, hTERT RPE1 cells were lifted and reseeded in medium containing puromycin (20 μg/ml) in order to achieve efficient selection of cells transduced with the lentiviral hgRNA library.

Pooled hgRNA dropout screens. For pooled screens 3 million cells were seeded in 15 cm plates. A total of 90 million cells were transduced with lentiviral libraries at a MOI-0.3, such that each hgRNA is represented in about 250-300 cells. 24 h after infection, transduced cells were selected with 1-2 μg/ml puromycin for 48 hours. 72 hours after transduction cells were harvested and pooled (day 0/T0). 30 million cells were collected for subsequent gDNA extraction and determination of day 0 hgRNA distribution (i.e. T0 reference). Furthermore, cells from the pool were seeded into three replicates, each containing 21 million cells (>200-fold library coverage), which were passaged every three days and maintained at >200-fold library coverage until T18. gDNA pellets were collected at each day of cell passage.

Pooled positive hgRNA screens for resistance to 6-thioguanine and thymidine block. For positive selection screens, three replicates of 20 million (10 million cells/15 cm plate seeded) HAP1 and CGR8 cells transduced with human or mouse hgRNA optimization libraries were seeded at T6 and treated with 2.5 mM thymidine or 6 μM 6-Thioguanine on the next day. After 16 h, thymidine-treated cells were washed and released into normal medium and 10 h later treated with thymidine for a second time. Cells were maintained in medium containing thymidine or 6-thioguanine for the rest of the screen. At T18 15 million cells were collected for genomic DNA extraction, and hgRNA expression cassettes were amplified and subjected to high-throughput sequencing as described below.

Torin1 CHyMErA Chemogenetic screen. After transducing HAP1 cells with the CHyMErA library, the population was continuously treated with Torin1 (Selleckchem; S2827) at a concentration that causes a 60% reduction in cell growth (i.e. $IC_{60}$) from day 3 through day 18 (i.e. the assay end-point).

Preparation of sequencing libraries and Illumina sequencing. Genomic DNA was extracted using the Wizard Genomic DNA Purification Kit (Promega) according to manufacturer's recommendations. The gDNA pellets were resuspended in buffer TE and concentration was estimated by Qubit using dsDNA Broad Range Assay reagents (Invitrogen). Sequencing libraries were prepared from the extracted gDNA (55 μg for HAP1, RPE1 and CGR8; 87.5 μg for N2A cells) in two PCR reactions to (1) enrich guide-RNA regions in the genome and (2) amplify guide-RNA and attach Illumina TruSeq adapters with i5 and i7 indices. Barcoded libraries were gel purified, run on bioanalyzer and final concentrations were estimated by qRT-PCR. Sequencing libraries were sequenced on an Illumina NextSeq500 or NovaSeq using paired-end sequencing. The first 29 reads were dark cycles that were followed by 31 cycles for reading the Cas12a guide and an index read of 8 cycles. For the paired read, 20 dark cycles were followed by 30 cycles for reading the Cas9 guide and an index read of 8 cycles.

Dual-guide Mapping and Quantification. FASTQ files from paired-end sequencing were first processed to trim off flanking sequence upstream and downstream of the guide sequence using a custom Perl script. Reads that did not contain the expected 3' sequence, allowing up to two mismatches, were discarded. Pre-processed paired reads were then aligned to a FASTA file containing the library sequences using Bowtie (v0.12.7) with the following parameters: -v 3 -l 18 --chunkmbs 256 -t<library_name>. The number of mapped read pairs for each dual-guide construct was then counted and merged, along with annotations, into a matrix.

Human and mouse hgRNA optimization library design. Human and mouse hgRNA libraries were designed in which exonic regions of reference core essential genes (CEG2) (Hart et al., 2017) and non-essential genes were targeted either with Cas9 (paired with an intergenic-targeting Lb-Cas12a) or Cas12a (paired with an intergenic-targeting Cas9). To target constitutive exons of mouse core essential genes, all one-to-one orthologs of the CEG2 set were first identified. From all possible 23-nt Cas12a guides targeting these constitutive exons and adjacent to a TTTV 5'-end PAM sequence, up to 15 Cas12a guides per target exon were randomly selected. 20-nt Cas9 gRNAs were selected based on previously defined rules. Collectively, the optimization libraries target over 450 CEG2 essential genes, and include up to 5 Cas12a and 3 Cas9 exon-targeting guides per exon, up to 15 Cas12a and 2 Cas9 exon-flanking guides per exon, as well as 1000 control constructs targeting intergenic regions with similar spacing between target sites as the exon-targeting guide pairs (Tables 1 and 2). To control for toxicity induced by hgRNA-directed dsDNA breaks, each gRNA sequence was paired with a gRNA targeting a non-coding intergenic sequence.

In addition, thymidine kinase 1 (TK1) and HPRT1 were also targeted the same way. Furthermore, exon-deletion constructs targeting TK1 and HPRT1 were designed by pairing guides targeting intronic regions upstream and downstream of selected exons with target sites located at least 100 nucleotides away from splice sites. The full contents of the human and mouse optimization libraries can be found in Tables 1 and 2, respectively.

Second generation human dual cutting and paralog hgRNA library design. A 2nd generation hgRNA library was designed in which the ~5,000 highest expressed genes across a panel of human cell lines (HAP1, RPE1, HEK293T, HCT116, HeLa, A375) were targeted either with Cas9 (paired with an intergenic-targeting Lb-Cas12a), Lb-Cas12a (paired with an intergenic-targeting Cas9) or with both Cas9 and Lb-Cas12a guides (dual-targeting). Target sites for the dual-targeting constructs were spaced between 107 base pairs (bp) and >946 kb (median distance, 6,863 bp). In addition, hgRNAs targeting intergenic and non-targeting sites were included as controls. This portion of the library included 61,888 hgRNA constructs.

As a second part of the library, paralogue gene pairs (Singh et al., 2015) for gene families with two expressed pairs across a panel of human cell lines (HAP1, RPE1, HEK293T, HCT116, HeLa, A375) were targeted. Of 1,381 strict human ohnolog families that have arisen from whole-genome duplications of vertebrate genomes, 1,344 paralogs were selected (avoiding gene families with more than two paralogs). In addition, selected gene pairs of interest were targeted, some of which have been previously reported to genetically interact. All these gene pairs were either targeted individually by Cas9 (paired with an intergenic-targeting Lb-Cas12a) and Lb-Cas12a (paired with an intergenic-targeting Cas9) or with both Cas9 and Lb-Cas12a guides in both possible orientations (dual-targeting). This portion of the library comprised 30,848 hgRNA constructs. The full contents of the human single gene dual targeting and paralog targeting library can be found in Table 5.

Exon-deletion hgRNA library design. For the first generation exon-deletion guide pair library, murine exons with a minimum host gene expression in N2A cells≥5 cRPKM and that are alternatively spliced in neural cells were selected according to any of the following criteria: (1) inclusion>10 PSI in N2A and dynamically regulated during neuronal differentiation (Hubbard et al., 2013); (2) more highly included in neural compared to non-neural cells and tissues by an average of 10 PSI and also more highly included in N2A versus non-neural cells by an average of 10 PSI (Raj et al., 2014), (3) microexons up to 27 nt in length with >10 PSI in N2A and differentially spliced between neural and non-neural cells by an average of 10 PSI.

For the second generation exon-targeting library for use in human cells, alternative exons were selected as follows: Alternative splicing and host gene expression in HAP1 cells was first quantified from RNA-Seq data using vast-tools 1.2.0 (Tapial et al., 2017). Exons were selected through two complementary streams. In the first stream, exons were selected that had a PSI range>30 across 108 diverse tissues and cell types in VASTDB, and were at least moderately included (PSI≥15) in either HAP1, HeLa, 293T, or MCF7 cells and whose host genes were expressed at >5 cRPKM in the same cell line. 4,290 candidate exons from stream 1 and 466 from stream 2 were combined, and events were prioritized according to essentiality in HAP1 cells (Hart et al., 2015, 2017) and whether they preserve the open reading frame. After guide design, this selection resulted in 324 frame preserving events in essential genes, 2,942 frame preserving exons not in essential genes, 118 frame disrupting events in essential genes, and 40 events that were neither frame preserving nor within essential genes. A group of control exons was designed that were skipped in HAP1 cells (PSI<3) but included in at least one other cell type or tissue at PSI>20, and whose host genes were expressed in HAP1 cells (CRPKM>5), irrespective of gene essentiality. For all exons, hgRNAs targeting intronic sites flanking the exon of interest were designed to introduce dsDNA breaks at intronic sites at least 100 bp distal from splice sites flanking the target exons. Each exon was targeted by multiple Cas9-Cas12a hgRNAs. Where possible (that is, depending on the availability of target sites), two individual Cas9 guides were paired with up to four Cas12a guides targeting both up- and downstream flanking intronic sequences, resulting in a total of 16 pairs of deletion-targeting hgRNA constructs for each exon. To control for toxicity of single guides each intronic guide was also paired with two intergenic-targeting guides, adding 24 control hgRNA pairs per exon. Furthermore, each gene targeted by exon deletion hgRNAs was also targeted by exon-targeting Cas9 guides. The full contents of the human exon targeting library can be found in Table 9.

RNA-seq. RNA was extracted from HAP1 cells transfected with nontargeting siRNA, siRBM26 and/or siRBM27, as described above, using the RNeasy extraction kit (Qiagen) following the manufacturer's recommendations. Two independent biological samples for each condition were generated, resulting in a total of eight samples. DNase-treated RNA samples were submitted for RNA-seq at the Donnelly Sequencing Center at the University of Toronto. Total RNA was quantified using Qubit RNA BR (catalog. no. Q10211, Thermo Fisher Scientific™) fluorescent chemistry, and 1 ng was used to obtain RNA integrity number (RIN) using the Bioanalyzer RNA 6000 Pico kit (catalog. no. 5067-1513, Agilent). The lowest RIN was 8.7, and median was 9.6.

Total RNA (2.5 μg) per sample was processed using the MGIEasy Directional RNA Library Prep Set v.2.0 (protocol v. A0, catalog. no. 1000006385, Shenzhen) including mRNA enrichment with the Dynabeads mRNA Purification Kit (catalog. no. 61006, Thermo Fisher Scientific™). RNA was fragmented at 87° C. for 6 min following the addition of 75% of the recommended volume of fragmentation buffer, to produce longer fragments. Libraries were amplified with 12 cycles of PCR.

The top stock (1 μl) of each purified final library was run on an Agilent Bioanalyzer™ dsDNA High Sensitivity chip (catalog. no. 5067-4626, Agilent) to determine an average library size of 581 bp, and to confirm the absence of dimers.

Libraries were quantified using the Quant-iT dsDNA High Sensitivity fluorometry kit (catalog. no. Q33120, Thermo Fisher™), pooled equimolarly and libraries in each of four replicate pools were then circularized using the MGIEasy Circularization Module (catalog no. 1000005260, Shenzhen).

From each of the four pools, 40 fmol of circularized library was sequenced 2×150 bp on a single lane of an FCL flowcell on the MGISEQ-2000 platform (also known as the DNBSEQ-G400 platform, Shenzhen), for a total of four lanes of sequencing.

Quantification and Statistical Analysis

Analysis of CHyMErA optimization screen. Depletion of the dual-guide constructs was assessed with the Bioconductor package edgeR (v.3.18.1). After depth normalization, only constructs with more than 1 count per million ('cpm') in at least two samples were retained. Exon-targeting constructs that result in significant depletion overtime ('active guides') were identified from the T18 triplicate samples using the likelihood ratio test, with a $\log_2$(fold-change) less than zero and FDR<0.05. There were 1073 guide constructs that were significantly active at this threshold in the HAP1 screen. In addition, 1026 inactive ('neutral') guides were identified where the $\log_2$(fold-change) was between −0.5 and 0.5. These 'active' and 'inactive' sets were used to train the machine learning classifiers.

Of note, 4-6% of reads from plasmid pool samples map to recombined guide constructs. The level of recombination strongly increased following lentiviral transduction of cell lines (to >19%). This suggests that the predominant source of recombination occurs as a result of template switching by viral reverse transcriptase during production of the lentiviral library or viral transduction, and not as the result of template switching during PCR amplification.

Analysis of nucleotide composition of active Cas12a guides. The physical properties of Cas12a guides targeting exons of the "gold-standard essential" gene were examined in order to optimize guide design. The log-fold-change at the screen end-point was as the measure of "activity". Single-, di- and tri-nucleotide composition, GC content, PAM sequence, and upstream and downstream sequences were examined for the full set of exon-targeting guides, and also for the significantly depleted guides. Significantly depleted guides were defined as those with a $\log_2$(fold-change)<0, and an FDR<0.05 (HAP1 n=1073; CGR8 n=1749; N2A n=1063). The parameters examined were associated PAM sequence, GC content, and base composition at each position in the Cas12a guide sequence.

Training classifiers to predict Cas12a guide activity. To better understand the differences between Cas12a active and inactive guide sequences and to help identify effective guides, a classifier was trained using data from the pilot screen to predict guide activity (active versus inactive). Models were trained using three different approaches: L1-regularized logistic regression (L1Logit), random forests (RF), and convolutional neural networks (CNNs).

To construct the dataset for modelling, Cas9 guide sequences from Cas9-intergenic/Cas12a-exonic hgRNAs from optimization screens performed in human and mouse cell lines were combined (2,096 HAP1 sequences, 2,401 CGR8, and 600 N2A), totaling 5,097 unique sequences. Each 23 bp guide sequence was extended by adding the upstream PAM sequence (4 bp) and flanking upstream and downstream sequences (6 bp each), resulting in a total sequence length of 39 bp. Next, discrete labels were assigned to each guide according to its guide activity from the initial screen: active (FDR<0.05, FC<−1) and inactive (FDR>=0.05, FC=(−0.5, 0.5). To construct the features for model training, each sequence was transformed into a set of numerical features using one-hot encoding, resulting in a 4 by 39 binary matrix E such that element $e_{ij}$ represents the indicator variable for nucleotide i (A, T, C, and G) at position j. This representation serves as the main input to the CNN. In order to be amenable for the conventional algorithms, this binary matrix was converted into individual nucleotide- and position-specific binary features, resulting in 156 binary features. Binary features representing the 2-mer occurrences at every position (16 features per position) were also included, adding another 608 binary features for a total of 764 sequence-based features.

In addition to one-hot encoding of the guide sequences, additional hand-crafted features were created: the predicted minimum free energy (MFE) secondary structure of the guide sequence, and melting temperatures for various segments of the guide sequence. For secondary structure prediction, RNAfold (Lorenz et al., 2011) was used to calculate minimum free energy values for each 23 bp guide sequence. For melting temperatures, the MeltingTemp.Tm_NN( ) function from Biopython (Cock et al., 2009) was used to calculate melting temperatures for the guide sequence, seed (positions 1-6), trunk (7-18), and promiscuous region (19-23). In total, an additional five hand-crafted features were generated. Together these features were used to augment the sequence-based features.

Predicting with chromatin accessibility information. To investigate the use of chromatin information in predicting Cas12a guide activity DNAse hypersensitive sites from K562 (GSM736629) were used. The chromatin status of each guide in the dataset were identified and 92% of the guides were found to be inaccessible. Due to this imbalance, this suggested that this feature would not be an informative feature in the model. Thus, it was not included in the final model.

Convolutional Neural Network (CNN) Architecture for predicting efficient Cas12a guides. To identify features associated with the most active Cas12a guides, machine learning algorithms were applied to predict efficient Cas12a guides as follows: Cas12a guides targeting exons of core fitness genes were first binned into active or inactive categories based on their observed relative depletion levels, as determined by LFC scores in HAP1 and CGR8 cells (Supplementary FIG. 2*d*). For each guide, features were assembled based on single, di- and trinucleotide composition, PAM sequence, up- and downstream sequences as well as genomic accessibility at the target site. The CNN consists of three main components: convolutional-pool layers, fully connected layers, and an output layer. First, E was passed into a convolutional layer consisting of 52 filters of length four. Each filter is a four by four matrix that represents a motif to be learn from the data. In other words, a filter is a position weight matrix (PWM). During training, each filter scans along the input sequence computes a score for each 4-mer, followed by a rectified linear unit (ReLU) activation. These activated scores are then passed through a pooling layer, where the average score is computed over a sliding window of 3. Next, to prevent the model from overfitting, the scores proceed through a dropout layer with a dropout rate of 0.22. At this stage, the convolution step has produced a set of summarized feature scores representing the input sequence. Before proceeding to the next fully connected layer, the features set was extended by concatenating the hand-crafted features described above. This new feature set is then passed to a single fully connected hidden layer with 12 units, followed by another dropout layer. Finally, the scores proceed through an output layer consisting of a sigmoid function. Training was carried out using the Adam optimizer with learning rate of 0.0001 and minimizing the binary cross-entropy loss function. By the end of training, the filters in the convolutional layer will have learned a set of motifs that are predictive of guide activity. All hyperparameters were chosen through cross-validation as described below, with the exception for the pooling size for the pooling layers, which were fixed.

Deep learning Model selection. To implement the conventional algorithms, the scikit-learn framework (Pedregosa et al., 2011) was used. To implement the CNN, Keras (Chollet and others, 2015) with TensorFlow (Abadi et al., 2015) backend was used. 90% of the data were randomly selected for training, while the remaining 10% were withheld for testing. The sampling was stratified such that the relative proportions of each cell line were maintained.

| Sample | Train | Test |
|---|---|---|
| HAP1 | 1886 | 210 |
| CGR8 | 2160 | 241 |
| N2A | 540 | 60 |

To determine the optimal hyperparameters, five-fold cross-validation was performed on the training data. For the conventional methods, a grid search was performed for the following parameters:

L1Logit: alpha

RF: number of trees

For CNN, a random sampling search was performed (Bergstra and Bengio, 2012) for the number of filters, filter size, and batch size.

Evaluation of deep learning models. The performance of the classifiers were evaluated by predicting on held out test data. For each algorithm, models with and without the additional secondary structure and melting temperature features were compared. Performance was measured based on area under the receiver operating characteristic curve (AUC) and average precision using the scikit-learn's functions auc( ) and average_precision_score( ).

To compare CHyMErA-Net scores with DeepCpf136, the scores of Cas12a guides in the libraries were calculated using DeepCpf1 and compared LFC trends by binning CHyMErA-Net and DeepCpf1 scores into ten bins of approximately equal size. Although the CNN predictions and DeepCpf1 were trained using different readouts (proliferation versus indel frequencies), nucleases (Lb- versus As-Cas12a) and with different amounts of data (5,097 training sequences versus 15,000 sequences for DeepCpf1), strong negative slopes were observed for scores from both classifiers.

Scoring of genetic interactions in the "optimized" library. Data were scored for genetic interactions (GIs) by comparing the observed log FC values for dual-targeting constructs to a null model derived from exonic-intergenic guides. An additive model of genetic interactions was assumed (Equation 1), where GIs occur when the observed log 2-fold change (LFC) values for a double-knockout (Equation 2) significantly differs from the sum of single-knockout LFCs (Equation 3). Each gene pair's set of double-knockout LFCs was compared to the set of all sums of single-knockout LFCs using Wilcoxon-rank sum tests followed by Benjamini-Hochberg FDR corrections. Significance testing was only performed on expected and observed sets with matching orientations, where Cas9 targets gene A and Cas12a targets gene B or vice versa, resulting in two p-values per gene pair. Most Cas9 guides had three replicates, and most Cas12a guides had five replicates, but the number of replicates varied slightly across gene pairs (Table 5). To avoid false positives, significant GIs were only called on a gene-pair level if both orientations were significant at a 0.1 FDR threshold with the same sign. If both orientations for a specific gene pair were significant GIs but one was positive and the other was negative, for example, that gene pair was not called as a significant GI. All scored data is contained Table 7.

$$LFC_{AB}=LFC_A+LFC_B+GI_{AB}$$

Equation 1. Additive model of genetic interactions for genes A and B.

$$\text{Observed}_1 = \{A_{CAS9_i}B_{CAS12A_j} \mid i \in 1 \ldots 3 \text{ and } j \in 1 \ldots 5\}$$

$$\text{Observed}_2 = \{A_{CAS9_i}B_{CAS12A_j} \mid i \in 1 \ldots 3 \text{ and } j \in 1 \ldots 5\}$$

Equation 2. Gene pair-specific set of observed LFCs for testing genetic interactions. The set of all exonic-exonic LFCs where one guide's Cas9 targets gene A and its Cas12a targets gene B for orientation 1, and vice versa for orientation 2.

$$\text{Expected}_1 = \{A_{CAS9_i} + B_{CAS12A_j} \mid i \in 1 \ldots 3 \text{ and } j \in 1 \ldots 5\}$$

$$\text{Expected}_2 = \{A_{CAS9_i} + B_{CAS12A_j} \mid i \in 1 \ldots 3 \text{ and } j \in 1 \ldots 5\}$$

Equation 3. Gene pair-specific set of expected LFCs for testing genetic interactions. The set of all sums of exonic-intergenic LFCs where one guide's Cas9 targets gene A and the other guide's Cas12a targets gene B for orientation 1, and vice versa for orientation 2.

MAGeCK scoring of dual-targeting library. Because the dual-targeting library lacked the gold-standard negative genes required by the BAGEL algorithm, a model-based analysis of genome-wide CRISPR-Cas9 knockout (MAGeCK) was employed to score these data. Input matrices were prepared using a bespoke R script. A matrix of read counts was prepared separately for each single- and dual-targeting subset, along with a design matrix. Single-targeting constructs were identified as having one exon-targeting guide (either Cas9 or Cas12a) paired with an intergenic-targeting guide, while dual-targeting constructs comprise two exon-targeting guides. Each extracted matrix was filtered to remove guide constructs that had zero reads in all samples. MAGeCK was run using the following command line: mageck mle --count-table<count_file>-<design-matrix>-norm-method median -output-prefix<sampleName>.mle. Significantly depleted genes were called where beta score<0 and FDR<0.05.

Analysis of DepMap data. Data from the DepMap screening platform (DepMap Public 19Q1) were downloaded. The matrix consisted of CERES-adjusted, gene-level fitness scores for 558 screened cell lines. Gene annotations were parsed to gene symbols in R, and analyzed with no further adjustments. CERES scores for the four gene sets (CEG2, gold-standard negatives, dual-targeting only and single-targeting-dual-targeting overlap) were aggregated and plotted together.

Scoring of differential response to mTOR inhibition. Data were scored for differential response to mTOR inhibition by comparing log fold-change (LFC) values for the HAP1 screen +/− Torin1 drug treatment across four different types of guides and two timepoints. The types of guides analysed include (1) single-targeting guides targeting a single gene, (2) dual-targeting guides targeting a single gene, (3) single-targeting guides targeting a single paralogous gene, and (4) dual-targeting guides targeting paralogous gene pairs in a combinatorial manner. All LFC values +/− Torin1 treatment were compared separately at T12 and T18 using Wilcoxon-rank sum tests between the treated and the untreated LFCs for each gene followed by Benjamini-Hochberg FDR correction.

Data were processed as follows. For (1), each gene was targeted by three Cas12a guides and two Cas9 guides with three replicates per guide. To measure Torin1 response for each gene, these guide LFCs were aggregated, including replicates, to test sets of 15 LFCs—Torin1 against corresponding sets of 15 LFCs+Torin1. For (2), each gene was dual-targeted by six guides with three replicates per guide. To ensure that the statistical power of this analysis was equivalent to the statistical power for (1), one of the six dual-targeting guides was randomly dropped for each contrast before comparing sets of 15 guides with replicates +/−Torin1 as in (1). For (3), each gene was targeted by five Cas12a guides and three Cas9 guides with three replicates per guide. These guide LFCs were aggregated, including replicates, to test sets of 24 LFCs—Torin1 against corresponding sets of 24 LFCs+Torin1. For (4), each paralog pair was combinatorial targeted by fifteen guides in each orientation with three replicates per guide. To ensure that the statistical power of this analysis was equivalent to the statistical power of (3), the mean of each replicate was taken, and 6 of the remaining 30 guides across both orientations were randomly dropped before testing for differential Torin1 response.

For gene ontology analysis the GOrilla tool was used. Hits that were called at a 0.1 FDR at the early and late time points were included in the target list and all targeted genes were used as background. For data visualization, terms with less than 900 members and enriched at an FDR of less than 0.05 were displayed.

RNA-seq analysis of RBM26 and/or RBM27 knockdown experiments. To quantify gene expression, pretrimmed reads were pseudoaligned to the GENCODE human gene annotation v.29. Transcript-level quantifications were aggregated per gene using the R package tximport, and differential expression between control non-targeting and RBM26 and/or RBM27 knockdown was assessed using the classic mode (exactTest) in edgeR. Genes changing more than two-fold and with FDR<0.05 were deemed significantly different. To compare overlaps in changes between treatments, only genes expressed at RPKM>5 in at least one treatment were considered.

Gene Ontology analysis of genes with LFC>1, FDR<0.05 and RPKM>5 was performed with FuncAssociate87 using all detected genes (RPKM>5) as background. For plotting, overlapping categories were removed when>70% of changing genes overlapped with another category with a more significant enrichment.

Analysis of exon deletion screens. Dropout rates were scored for significant exonic deletion events by comparing them to a null distribution derived from intergenic-intergenic guides. Each intronic-intronic guide pair's log fold-change (LFC) was compared to the distribution of LFCs of all intergenic-intergenic guide pairs, and called intronic-intronic pairs as significant if they satisfied p<0.05 for a two-tailed test against the empirical null distribution.

A targeted exon was subsequently called successfully targeted (i.e., a 'hit') if >18% of the intronic-intronic pairs targeting the exon were called significant, including at least one pair for which neither the Cas9 guide nor the Cas12a guide in combination with an intergenic guide resulted in significant dropout, measured similarly as described for intronic-introinc pairs above. This threshold was chosen to maximize the difference in hit rates for frame disrupting exons in expressed genes whose deletion is known to cause a growth defect, compared to exons that are skipped or within non-expressed genes in the given cell line. Growth-related fitness in RPE1 cells was derived from previous studies (Hart et al., 2015) and gene expression as well as exon inclusion was scored from RNA-seq data (Hart et al., 2015) using vast-tools.

Example 10: Comparison of CHyMErA with Other Dual Targeting Systems

Assessment of Cas9-Cas12a editing by PCR. To determine Cas9 and Cas12a editing efficiency, cells expressing Cas9 and Cas12a were transduced with lentiviruses derived from dual pLCKO (as above), pLCHKO or pPapi constructs targeting intronic regions flanking exons. Transduced cells were selected with 1 μg/ml of puromycin for 48 h, and gDNA was extracted using the PureLink Genomic DNA Kit (Thermo Fisher Scientific™). Successful editing was assessed by PCR using primers flanking the targeted regions, and PCR products were resolved by agarose gel electrophoresis.

Percentage exon deletion was calculated using ImageJ software. Exon-included and -excluded band intensities were corrected by subtracting the background, and values were normalized by product size. Intensity of the exon-included band was divided by the sum of the exon-included and -excluded bands; the result was then multiplied by 100 to obtain percentage exon deletion, which was rounded to the nearest integer.

Additional method details are described in Example 9.

TABLE 12

Sequences

| SEQ ID NO | Description | Sequence |
|---|---|---|
| 1 | Cas9 PAM | NGG |
| 2 | Generic Cas9 target sequence | $N_1$NGG (N1 is 15 to 25, 16 to 24, 17 to 23, 18 to 22, or 19 to 21 nucleotides, optionally 20 nucleotides) |

TABLE 12-continued

| SEQ ID NO | Description | Sequence |
|---|---|---|
| 3 | Cas12a PAM | TTTV |
| 4 | Generic Cas12a target sequence | TTTV$N_1$ (N1 is 15 to 28, 16 to 27, 17 to 26, 18 to 25, or 19 to 24 nucleotides, optionally 20, 21, 22, or 23 nucleotides) |
| 5 | Modified *S. pyogenes* tracrRNA sequence (DNA) | gtttcagagctatgctggaaacagcatagcaagttgaaataaggctagtccgttatcaacttgaaaaagtggcaccgagtcggtgc |
| 6 | Lb-Cas12a direct repeat sequence (DNA) | taatttctactcttgtagat |
| 7 | As-Cas12a direct repeat sequence (DNA) | Taatttctactaagtgtagat |
| 8 | Generic hgRNA for Lb-Cas12a | $N_1$gtttcagagctatgctggaaacagcatagcaagttgaaataaggctagtccgttatcaacttgaaaaagtggcaccgagtcggtgctaatttctactaagtgtagat$N_2$ (N1 is 15 to 25, 16 to 24, 17 to 23, 18 to 22, or 19 to 21 nucleotides, optionally 20 nucleotides; N2 is 15 to 28, 16 to 27, 17 to 26, 18 to 25, or 19 to 24 nucleotides, optionally 20, 21, 22, or 23 nucleotides) |
| 9 | Generic hgRNA for As-Cas12a | $N_1$gtttcagagctatgctggaaacagcatagcaagttgaaataaggctagtccgttatcaacttgaaaaagtggcaccgagtcggtgctaatttctactcttgtagat$N_2$ (N1 is 15 to 25, 16 to 24, 17 to 23, 18 to 22, or 19 to 21 nucleotides, optionally 20 nucleotides; N2 is 15 to 28, 16 to 27, 17 to 26, 18 to 25, or 19 to 24 nucleotides, optionally 20, 21, 22, or 23 nucleotides) |
| 10 | Generic stuffer sequence | gtttagagacggctaaatccgcgtctcgagat |
| 11 | Generic/degenerate stuffer sequence | gtttDGAGACGaDDDDDDDDcCGTCTCDagat |
| 12 | Generic paired guide oligonucleotide | $N_1$gtttagagacggctaaatccgcgtctcgagat$N_2$ (N1 is 15 to 25, 16 to 24, 17 to 23, 18 to 22, or 19 to 21 nucleotides, optionally 20 nucleotides; N2 is 15 to 28, 16 to 27, 17 to 26, 18 to 25, or 19 to 24 nucleotides, optionally 20, 21, 22, or 23 nucleotides) |
| 13 | Generic/degenerate paired guide oligonucleotide | $N_1$gtttDGAGACGaDDDDDDDDcCGTCTCDagat$N_2$ (N1 is 15 to 25, 16 to 24, 17 to 23, 18 to 22, or 19 to 21 nucleotides, optionally 20 nucleotides; N2 is 15 to 28, 16 to 27, 17 to 26, 18 to 25, or 19 to 24 nucleotides, optionally 20, 21, 22, or 23 nucleotides) |
| 14 | pLCHKO | Sequence listing |
| 15 | second oligo: 5' truncated tracrRNA and 3' truncated Lb-Cas12a direct repeat | cagagctatgctggaaacagcatagcaagttgaaataaggctagtccgttatcaacttgaaaaagtggcaccgagtcggtgctaatttctactaagtgt |
| 16 | second oligo: 5' truncated tracrRNA and 3' truncated | cagagctatgctggaaacagcatagcaagttgaaataaggctagtccgttatcaacttgaaaaagtggcaccgagtcggtgctaatttctactcttgt |

TABLE 12-continued

Sequences

| SEQ ID NO | Description | Sequence |
|---|---|---|
| | As-Cas12a direct repeat | |
| 17 | BsmBl-tracrRNA-Lb-Cas12a_DR BsmBl | cgtctctGTTTCAGAGCTATGCTGGAAACAGCATAGCAAGTTGAAATAAGGCTAGTCCGTTATCAACTTGAAAAAGTGGCACCGAGTCGGTGCT**TAATTTCTACTAAGTGTAGAT**agagacg |
| 18 | BsmBl-tracrRNA-As-Cas12a_DR-BsmBl | cgtctctGTTTCAGAGCTATGCTGGAAACAGCATAGCAAGTTGAAATAAGGCTAGTCCGTTATCAACTTGAAAAAGTGGCACCGAGTCGGTGCT**TAATTTCTACTCTTGTAGAT**agagacg |
| 19 | Sp-Cas9 | Sequence listing |
| 20 | Lb-Cpf1 | Sequence listing |
| 21 | As-Cpf1: | Sequence listing |
| 22 | SV40 NLS | ccaaagaagaagcggaaggtc |
| 23 | Nucleoplasmin NLS | AAAAGGCCGGCGGCCACGAAAAAGGCCGGCCAGGCAAAAAAGAAAAAG |
| 24 | Myc tag | GAACAAAAACTCATCTCAGAAGAGGATCTG |
| 25 | CHIP Oligo | agaga**ACCTGC**agagaccg**NNNNNNNNNNNNNNNNNNNN**gtttaGAGACGgctaaatccgCGTCTCgagat**NNNNNNNNNNNNNNNNNNNNNNNNN**ttttagag**GCAGGT**agaga |
| 26 | CHIP Oligo with degenerate nucleotide code | agaga**ACCTGC**agagaccg**NNNNNNNNNNNNNNNNNNNN**gtttDGAGACGaDDDDDDDDcCGTCTCDagat**NNNNNNNNNNNNNNNNNNNNNNNNN**ttttagag**GCAGGT**agaga |
| 27 | TOPO fragment As-Cas12a | **CGTCTC**tgtttcagagctatgctggaaacagcatagcaagttgaaataaggctagtccgttatcaacttgaaaaagtggcaccgagtcggtgctaatttctactcttgtagata**GAGACG** |
| 28 | TOPO fragment Lb-Cas12a | **CGTCTC**tgtttcagagctatgctggaaacagcatagcaagttgaaataaggctagtccgttatcaacttgaaaaagtggcaccgagtcggtgctaatttctactaagtgtagata**GAGACG** |
| 29 | As-Cas12a hgRNA insert | ggacgaggtaccg**NNNNNNNNNNNNNNNNNNNN**gtttcagagctatgctggaaacagcatagcaagttgaaataaggctagtccgttatcaacttgaaaaagtggcaccgagtcggtgctaatttctactcttgtagat**NNNNNNNNNNNNNNNNNNNNNNNNN**tttttttt |
| 30 | Lb-Cas12a hgRNA insert | ggacgaggtaccg**NNNNNNNNNNNNNNNNNNNN**gtttcagagctatgctggaaacagcatagcaagttgaaataaggctagtccgttatcaacttgaaaaagtggcaccgagtcggtgctaatttctactaagtgtagat**NNNNNNNNNNNNNNNNNNNNNNNNN**tttttttt |

REFERENCES

Adamson, B., Norman, T. M., Jost, M., Cho, M. Y., Nunez, J. K., Chen, Y., Villalta, J. E., Gilbert, L. A., Horlbeck, M. A., Hein, M. Y., et al. (2016). A Multiplexed Single-Cell CRISPR Screening Platform Enables Systematic Dissection of the Unfolded Protein Response. Cell 167, 1867-1882.e21.

Ashworth, A., Lord, C. J., and Reis-Filho, J. S. (2011). Genetic Interactions in Cancer Progression and Treatment. Cell 145, 30-38.

Bassik, M. C., Kampmann, M., Lebbink, R. J., Wang, S., Hein, M. Y., Poser, I., Weibezahn, J., Horlbeck, M. A., Chen, S., Mann, M., et al. (2013a). A systematic mammalian genetic interaction map reveals pathways underlying ricin susceptibility. Cell 152, 909-922.

Bassik, M. C., Kampmann, M., Lebbink, R. J., Wang, S., Hein, M. Y., Poser, I., Weibezahn, J., Horlbeck, M. A., Chen, S., Mann, M., et al. (2013b). A Systematic Mammalian Genetic Interaction Map Reveals Pathways Underlying Ricin Susceptibility. Cell 152, 909-922.

Berriz, G. F., King, O. D., Bryant, B., Sander, C. & Roth, F. P. Characterizing gene sets with FuncAssociate. Bioinformatics 19, 2502-2504 (2003)

Boettcher, M., Tian, R., Blau, J. A., Markegard, E., Wagner, R. T., Wu, D., Mo, X., Biton, A., Zaitlen, N., Fu, H., et al. (2018). Dual gene activation and knockout screen reveals directional dependencies in genetic networks. Nat. Biotechnol. 36, 170-178.

Brake, O. ter, Hooft, K. 't, Liu, Y. P., Centlivre, M., Jasmijn von Eije, K., and Berkhout, B. (2008). Lentiviral Vector Design for Multiple shRNA Expression and Durable HIV-1 Inhibition. Mol. Ther. 16, 557-564.

Breinig, M., Schweitzer, A. Y., Herianto, A. M., Revia, S., Schaefer, L., Wendler, L., Cobos Galvez, A., and Tschaharganeh, D. F. (2019). Multiplexed orthogonal genome editing and transcriptional activation by Cas12a. Nat. Methods 16, 51-54.

Chow, R. D., Wang, G., Codina, A., Ye, L., and Chen, S. (2017). Mapping in vivo genetic interactomics through Cpf1 crRNA array screening. bioRxiv 153486.

Cock, P. J. A., Antao, T., Chang, J. T., Chapman, B. A., Cox, C. J., Dalke, A., Friedberg, I., Hamelryck, T., Kauff, F., Wilczynski, B., et al. (2009). Biopython: freely available Python tools for computational molecular biology and bioinformatics. Bioinformatics 25, 1422-1423.

Cong, L., Ran, F. A., Cox, D., Lin, S., Barretto, R., Habib, N., Hsu, P. D., Wu, X., Jiang, W., Marraffini, L. A., et al. (2013). Multiplex genome engineering using CRISPR/Cas systems. Science 339, 819-823.

Costanzo, M., VanderSluis, B., Koch, E. N., Baryshnikova, A., Pons, C., Tan, G., Wang, W., Usaj, M., Hanchard, J., Lee, S. D., et al. (2016). A global genetic interaction network maps a wiring diagram of cellular function. Science 353, aaf1420-aaf1420.

Costanzo, M., Kuzmin, E., van Leeuwen, J., Mair, B., Moffat, J., Boone, C., and Andrews, B. (2019). Global Genetic Networks and the Genotype-to-Phenotype Relationship. Cell 177, 85-100. Dang, Y. et al. Optimizing sgRNA structure to improve CRISPR-Cas9 knockout efficiency. Genome Biol. 16, 280 (2015).

Doench, J. G. (2018). Am i ready for CRISPR? A user's guide to genetic screens. Nat. Rev. Genet. 19, 67-80.

Doench, J. G., Fusi, N., Sullender, M., Hegde, M., Vaimberg, E. W., Donovan, K. F., Smith, I., Tothova, Z., Wilen, C., Orchard, R., et al. (2016). Optimized sgRNA design to maximize activity and minimize off-target effects of CRISPR-Cas9. Nat. Biotechnol. 34, 184-191.

Dominguez, D., Tsai, Y.-H., Weatheritt, R., Wang, Y., Blencowe, B. J., and Wang, Z. (2016). An extensive program of periodic alternative splicing linked to cell cycle progression. Elife 5.

Dvinge, H., Kim, E., Abdel-Wahab, O., and Bradley, R. K. (2016). RNA splicing factors as oncoproteins and tumour suppressors. Nat. Rev. Cancer 16, 413-430.

Ewen-Campen, B., Mohr, S. E., Hu, Y., and Perrimon, N. (2017). Accessing the Phenotype Gap: Enabling Systematic Investigation of Paralog Functional Complexity with CRISPR. Dev. Cell 43, 6-9.

Fonfara, I., Richter, H., Bratovič, M., Le Rhun, A., and Charpentier, E. (2016). The CRISPR-associated DNA-cleaving enzyme Cpf1 also processes precursor CRISPR RNA. Nature 532, 517-521.

Ge, K., DuHadaway, J., Du, W., Herlyn, M., Rodeck, U., and Prendergast, G. C. (1999). Mechanism for elimination of a tumor suppressor: aberrant splicing of a brain-specific exon causes loss of function of Bin1 in melanoma. Proc. Natl. Acad. Sci. U.S.A 96, 9689-9694.

Gonatopoulos-Pournatzis, T., Wu, M., Braunschweig, U., Roth, J., Han, H., Best, A. J., Raj, B., Aregger, M., O'Hanlon, D., Ellis, J. D., et al. (2018). Genome-wide CRISPR-Cas9 Interrogation of Splicing Networks Reveals a Mechanism for Recognition of Autism-Misregulated Neuronal Microexons. Mol. Cell 72, 510-524.e12.

Gu, Z., Steinmetz, L. M., Gu, X., Scharfe, C., Davis, R. W., and Li, W.-H. (2003). Role of duplicate genes in genetic robustness against null mutations. Nature 421, 63-66.

Gueroussov, S., Gonatopoulos-Pournatzis, T., Irimia, M., Raj, B., Lin, Z.-Y., Gingras, A.-C., and Blencowe, B. J. (2015). An alternative splicing event amplifies evolutionary differences between vertebrates. Science 349, 868-873.

Guschin, D. Y., Waite, A. J., Katibah, G. E., Miller, J. C., Holmes, M. C., and Rebar, E. J. (2010). A rapid and general assay for monitoring endogenous gene modification. Methods Mol. Biol. 649, 247-256.

Haapaniemi, E., Botla, S., Persson, J., Schmierer, B., and Taipale, J. (2018). CRISPR-Cas9 genome editing induces a p53-mediated DNA damage response. Nat. Med. 24, 927-930.

Han, K., Jeng, E. E., Hess, G. T., Morgens, D. W., Li, A., and Bassik, M. C. (2017). Synergistic drug combinations for cancer identified in a CRISPR screen for pairwise genetic interactions. Nat. Biotechnol. 35, 463-474.

Haney, M. S., Bohlen, C. J., Morgens, D. W., Ousey, J. A., Barkal, A. A., Tsui, C. K., Ego, B. K., Levin, R., Kamber, R. A., Collins, H., et al. (2018). Identification of phagocytosis regulators using magnetic genome-wide CRISPR screens. Nat. Genet. 50, 1716-1727.

Hart, T., Chandrashekhar, M., Aregger, M., Steinhart, Z., Brown, K. R., MacLeod, G., Mis, M., Zimmermann, M., Fradet-Turcotte, A., Sun, S., et al. (2015). High-Resolution CRISPR Screens Reveal Fitness Genes and Genotype-Specific Cancer Liabilities. Cell 163, 1515-1526.

Hart, T., Tong, A. H. Y., Chan, K., Van Leeuwen, J., Seetharaman, A., Aregger, M., Chandrashekhar, M., Hustedt, N., Seth, S., Noonan, A., et al. (2017). Evaluation and Design of Genome-Wide CRISPR/SpCas9 Knockout Screens. G3: 7, 2719-2727.

Horlbeck, M. A., Xu, A., Wang, M., Bennett, N. K., Park, C. Y., Bogdanoff, D., Adamson, B., Chow, E. D., Kampmann, M., Peterson, T. R., et al. (2018). Mapping the Genetic Landscape of Human Cells. Cell 174, 953-967.e22.

Hubbard, K. S., Gut, I. M., Lyman, M. E., and McNutt, P. M. (2013). Longitudinal RNA sequencing of the deep transcriptome during neurogenesis of cortical glutamatergic neurons from murine ESCs. F1000Research 2, 35.

Jinek, M., Chylinski, K., Fonfara, I., Hauer, M., Doudna, J. A., and Charpentier, E. (2012). A Programmable Dual-RNA-Guided DNA Endonuclease in Adaptive Bacterial Immunity. Science 337, 816-821.

Kafri, R., Springer, M., and Pilpel, Y. (2009). Genetic Redundancy: New Tricks for Old Genes. Cell 136, 389-392.

Ke, M., Mo, L., Li, W., Zhang, X., Li, F., and Yu, H. (2017). Ubiquitin ligase SMURF1 functions as a prognostic marker and promotes growth and metastasis of clear cell renal cell carcinoma. FEBS Open Bio 7, 577-586.

Kim, H. K., Song, M., Lee, J., Menon, A. V., Jung, S., Kang, Y.-M., Choi, J. W., Woo, E., Koh, H. C., Nam, J.-W., et al. (2017). In vivo high-throughput profiling of CRISPR-Cpf1 activity. Nat. Methods 14, 153-159.

Kim, H. K., Min, S., Song, M., Jung, S., Choi, J. W., Kim, Y., Lee, S., Yoon, S., and Kim, H. H. (2018). Deep learning improves prediction of CRISPR-Cpf1 guide RNA activity. Nat. Biotechnol. 36, 239-241.

Koo, J., Yue, P., Gal, A. A., Khuri, F. R., and Sun, S.-Y. (2014). Maintaining Glycogen Synthase Kinase-3 Activity Is Critical for mTOR Kinase Inhibitors to Inhibit Cancer Cell Growth. Cancer Res. 74, 2555-2568.

Koo, J., Yue, P., Deng, X., Khuri, F. R., and Sun, S.-Y. (2015). mTOR Complex 2 Stabilizes Mcl-1 Protein by Suppressing Its Glycogen Synthase Kinase 3-Dependent and SCF-FBXW7-Mediated Degradation. Mol. Cell. Biol. 35, 2344-2355.

Kuzmin, E., VanderSluis, B., Wang, W., Tan, G., Deshpande, R., Chen, Y., Usaj, M., Balint, A., Mattiazzi Usaj, M., van Leeuwen, J., et al. (2018). Systematic analysis of complex genetic interactions. Science 360, eaao1729.

Li, M., Yu, J. S. L., Tilgner, K., Ong, S. H., Koike-Yusa, H., and Yusa, K. (2018). Genome-wide CRISPR-KO Screen Uncovers mTORC1-Mediated Gsk3 Regulation in Naive Pluripotency Maintenance and Dissolution. Cell Rep. 24, 489-502.

Listgarten, J., Weinstein, M., Kleinstiver, B. P., Sousa, A. A., Joung, J. K., Crawford, J., Gao, K., Hoang, L., Elibol, M., Doench, J. G., et al. (2018). Prediction of off-target activities for the end-to-end design of CRISPR guide RNAs. Nat. Biomed. Eng. 2, 38-47.

Liu, Y., Yu, C., Daley, T. P., Wang, F., Cao, W. S., Bhate, S., Lin, X., Still, C., Liu, H., Zhao, D., et al. (2018). CRISPR Activation Screens Systematically Identify Factors that Drive Neuronal Fate and Reprogramming. Cell Stem Cell 23, 758-771.e8.

Lorenz, R., Bernhart, S. H., Höner zu Siederdissen, C., Tafer, H., Flamm, C., Stadler, P. F., and Hofacker, I. L. (2011). ViennaRNA Package 2.0. Algorithms Mol. Biol. 6, 26.

Lynch, M., and Conery, J. S. (2000). The evolutionary fate and consequences of duplicate genes. Science 290, 1151-1155.

Mali, P., Yang, L., Esvelt, K. M., Aach, J., Guell, M., DiCarlo, J. E., Norville, J. E., and Church, G. M. (2013). RNA-Guided Human Genome Engineering via Cas9. Science 339, 823-826.

Martin, T. D., Chen, X.-W., Kaplan, R. E. W., Saltiel, A. R., Walker, C. L., Reiner, D. J., and Der, C. J. (2014). Ral and Rheb GTPase Activating Proteins Integrate mTOR and GTPase Signaling in Aging, Autophagy, and Tumor Cell Invasion. Mol. Cell 53, 209-220.

Meyer, C., Garzia, A., Mazzola, M., Gerstberger, S., Molina, H., and Tuschl, T. (2018). The TIA1 RNA-Binding Protein Family Regulates EIF2AK2-Mediated Stress Response and Cell Cycle Progression. Mol. Cell 69, 622-635.e6.

Najm, F. J., Strand, C., Donovan, K. F., Hegde, M., Sanson, K. R., Vaimberg, E. W., Sullender, M. E., Hartenian, E., Kalani, Z., Fusi, N., et al. (2017a). Orthologous CRISPR-Cas9 enzymes for combinatorial genetic screens. Nat. Biotechnol. 36, 179-189.

Najm, F. J., Strand, C., Donovan, K. F., Hegde, M., Sanson, K. R., Vaimberg, E. W., Sullender, M. E., Hartenian, E., Kalani, Z., Fusi, N., et al. (2017b). Orthologous CRISPR-Cas9 enzymes for combinatorial genetic screens. Nat. Biotechnol.

Park, R. J., Wang, T., Koundakjian, D., Hultquist, J. F., Lamothe-Molina, P., Monel, B., Schumann, K., Yu, H., Krupzcak, K. M., Garcia-Beltran, W., et al. (2016). A genome-wide CRISPR screen identifies a restricted set of HIV host dependency factors. Nat. Genet. 49, 193-203.

Patel, S. J., Sanjana, N. E., Kishton, R. J., Eidizadeh, A., Vodnala, S. K., Cam, M., Gartner, J. J., Jia, L., Steinberg, S. M., Yamamoto, T. N., et al. (2017). Identification of essential genes for cancer immunotherapy. Nature 548, 537-542.

Peterson, T. R., Laplante, M., Van Veen, E., Van Vugt, M., Thoreen, C. C., and Sabatini, D. M. (2015). mTORC1 regulates cytokinesis through activation of Rho-ROCK signaling.

Pineda-Lucena, A., Ho, C. S. W., Mao, D. Y. L., Sheng, Y., Laister, R. C., Muhandiram, R., Lu, Y., Seet, B. T., Katz, S., Szyperski, T., et al. (2005). A Structure-based Model of the c-Myc/Bin1 Protein Interaction Shows Alternative Splicing of Bin1 and c-Myc Phosphorylation are Key Binding Determinants. J. Mol. Biol. 351, 182-194.

Quesnel-Valliées, M., Weatheritt, R. J., Cordes, S. P., and Blencowe, B. J. (2019). Autism spectrum disorder: insights into convergent mechanisms from transcriptomics. Nat. Rev. Genet. 20, 51-63.

Raj, B., Irimia, M., Braunschweig, U., Sterne-Weiler, T., O'Hanlon, D., Lin, Z.-Y., Chen, G. I., Easton, L. E., Ule, J., Gingras, A.-C., et al. (2014). A Global Regulatory Mechanism for Activating an Exon Network Required for Neurogenesis. Mol. Cell 56, 90-103.

Sack, L. M., Davoli, T., Xu, Q., Li, M. Z., and Elledge, S. J. (2016). Sources of Error in Mammalian Genetic Screens. G3: 6, 2781-2790.

Sakamuro, D., Elliott, K. J., Wechsler-Reya, R., and Prendergast, G. C. (1996). BIN1 is a novel MYC-interacting protein with features of a tumour suppressor. Nat. Genet. 14, 69-77.

Saxton, R. A., and Sabatini, D. M. (2017). mTOR Signaling in Growth, Metabolism, and Disease. Cell 168, 960-976.

Scotti, M. M., and Swanson, M. S. (2016). RNA mis-splicing in disease. Nat. Rev. Genet. 17, 19-32.

Shalem, O., Sanjana, N. E., Hartenian, E., Shi, X., Scott, D. A., Mikkelsen, T. S., Heckl, D., Ebert, B. L., Root, D. E., Doench, J. G., et al. (2014). Genome-scale CRISPR-Cas9 knockout screening in human cells. Science 343, 84-87.

Shen, J. P., Zhao, D., Sasik, R., Luebeck, J., Birmingham, A., Bojorquez-Gomez, A., Licon, K., Klepper, K., Pekin, D., Beckett, A. N., et al. (2017a). Combinatorial CRISPR-Cas9 screens for de novo mapping of genetic interactions. Nat. Methods 14, 573-576.

Shen, J. P., Zhao, D., Sasik, R., Luebeck, J., Birmingham, A., Bojorquez-Gomez, A., Licon, K., Klepper, K., Pekin, D., Beckett, A. N., et al. (2017b). Combinatorial CRISPR-Cas9 screens for de novo mapping of genetic interactions. Nat. Methods.

Shifrut, E., Carnevale, J., Tobin, V., Roth, T. L., Woo, J. M., Bui, C. T., Li, P. J., Diolaiti, M. E., Ashworth, A., and Marson, A. (2018). Genome-wide CRISPR Screens in Primary Human T Cells Reveal Key Regulators of Immune Function. Cell 175, 1958-1971.e15.

Shu, L., and Houghton, P. J. (2009). The mTORC2 Complex Regulates Terminal Differentiation of C2C12 Myoblasts. Mol. Cell. Biol. 29, 4691-4700.

Singh, P. P., Arora, J., and Isambert, H. (2015). Identification of Ohnolog Genes Originating from Whole Genome Duplication in Early Vertebrates, Based on Synteny Comparison across Multiple Genomes. PLOS Comput. Biol. 11, e1004394.

SLOVACKOVA, J., SMARDA, J., and SMARDOVA, J. (2012). Roscovitine-induced apoptosis of H1299 cells depends on functional status of p53. Neoplasma 59, 606-612.

Stockman, V. B., Ghamsari, L., Lasso, G., Honig, B., Shapira, S. D., and Wang, H. H. (2016). A High-Throughput Strategy for Dissecting Mammalian Genetic Interactions. PLoS One 11, e0167617.

Tapial, J., Ha, K. C. H., Sterne-Weiler, T., Gohr, A., Braunschweig, U., Hermoso-Pulido, A., Quesnel-Valliéres, M., Permanyer, J., Sodaei, R., Marquez, Y., et al. (2017). An atlas of alternative splicing profiles and functional associations reveals new regulatory programs and genes that simultaneously express multiple major isoforms. Genome Res. 27, 1759-1768.

Thoreen, C. C., Kang, S. a, Chang, J. W., Liu, Q., Zhang, J., Gao, Y., Reichling, L. J., Sim, T., Sabatini, D. M., and Gray, N. S. (2009). An ATP-competitive mammalian target of rapamycin inhibitor reveals rapamycin-resistant functions of mTORC1. J. Biol. Chem. 284, 8023-8032.

Tsang, C. K., Bertram, P. G., Ai, W., Drenan, R., and Zheng, X. F. S. (2003). Chromatin-mediated regulation of nucleolar structure and RNA Pol I localization by TOR. EMBO J. 22, 6045-6056.

Valvezan, A. J., and Manning, B. D. (2019). Molecular logic of mTORC1 signalling as a metabolic rheostat. Nat. Metab. 1, 321-333.

Varier, R. A., de Santa Pau, E. C., van der Groep, P., Lindeboom, R. G. H., Matarese, F., Mensinga, A., Smits, A. H., Edupuganti, R. R., Baltissen, M. P., Jansen, P. W. T. C., et al. (2016). Recruitment of the Mammalian Histone-modifying EMSY Complex to Target Genes Is Regulated by ZNF131. J. Biol. Chem. 291, 7313-7324.

Vidigal, J. A., and Ventura, A. (2015). Rapid and efficient one-step generation of paired gRNA CRISPR-Cas9 libraries. Nat. Commun. 6, 8083.

Viswanathan, S. R., Nogueira, M. F., Buss, C. G., Krill-Burger, J. M., Wawer, M. J., Malolepsza, E., Berger, A. C., Choi, P. S., Shih, J., Taylor, A. M., et al. (2018). Genome-scale analysis identifies paralog lethality as a vulnerability of chromosome 1 p loss in cancer. Nat. Genet. 50, 937-943.

Wang, G., Zimmermann, M., Mascall, K., Lenoir, W. F., Moffat, J., Angers, S., Durocher, D., and Hart, T. (2017). Identifying drug-gene interactions from CRISPR knockout screens with drugZ. bioRxiv 232736.

Wang, T., Wei, J. J., Sabatini, D. M., and Lander, E. S. (2014). Genetic screens in human cells using the CRISPR-Cas9 system. Science 343, 80-84.

Wang, T., Birsoy, K., Hughes, N. W., Krupczak, K. M., Post, Y., Wei, J. J., Lander, E. S., and Sabatini, D. M. (2015). Identification and characterization of essential genes in the human genome. Science 350, 1096-1101.

Wong, A. S. L., Choi, G. C. G., Cui, C. H., Pregernig, G., Milani, P., Adam, M., Perli, S. D., Kazer, S. W., Gaillard, A., Hermann, M., et al. (2016). Multiplexed barcoded CRISPR-Cas9 screening enabled by CombiGEM. Proc. Natl. Acad. Sci. 113, 2544-2549.

Wright, A. V., Nunez, J. K., and Doudna, J. A. (2016). Biology and Applications of CRISPR Systems: Harnessing Nature's Toolbox for Genome Engineering. Cell 164, 29-44.

Xu, H., Xiao, T., Chen, C.-H., Li, W., Meyer, C. A., Wu, Q., Wu, D., Cong, L., Zhang, F., Liu, J. S., et al. (2015). Sequence determinants of improved CRISPR sgRNA design. Genome Res. 25, 1147-1157.

Zetsche, B., Gootenberg, J. S., Abudayyeh, O. O., Slaymaker, I. M., Makarova, K. S., Essletzbichler, P., Volz, S. E., Joung, J., van der Oost, J., Regev, A., et al. (2015). Cpf1 Is a Single RNA-Guided Endonuclease of a Class 2 CRISPR-Cas System. Cell 163, 759-771.

Zetsche, B., Heidenreich, M., Mohanraju, P., Fedorova, I., Kneppers, J., DeGennaro, E. M., Winblad, N., Choudhury, S. R., Abudayyeh, O. O., Gootenberg, J. S., et al. (2016). Multiplex gene editing by CRISPR-Cpf1 using a single crRNA array. Nat. Biotechnol. 35, 31-34.

Zhu, H., Shyh-Chang, N., Segré, A. V, Shinoda, G., Shah, S. P., Einhorn, W. S., Takeuchi, A., Engreitz, J. M., Hagan, J. P., Kharas, M. G., et al. (2011). The Lin28/let-7 axis regulates glucose metabolism. Cell 147, 81-94.

Zhu, S., Li, W., Liu, J., Chen, C.-H., Liao, Q., Xu, P., Xu, H., Xiao, T., Cao, Z., Peng, J., et al. (2016). Genome-scale deletion screening of human long non-coding RNAs using a paired-guide RNA CRISPR-Cas9 library. Nat. Biotechnol. 34, 1279-1286.

The invention claimed is:

1. A hybrid guide RNA (hgRNA) comprising, from 5' to 3', a proximal spacer RNA, a type II CRISPR-Cas tracrRNA, a type V CRISPR-Cas direct repeat, and a distal spacer RNA, wherein the proximal spacer targets a type II CRISPR target site, and the distal spacer targets a type V CRISPR target site, wherein the hgRNA is capable of being processed by a type V Cas protein into a first and a second mature guide RNA.

2. The hgRNA of claim 1, wherein the hgRNA is capable of being processed by a type V Cas protein into a first and a second mature guide RNA and/or wherein the proximal spacer targets a Cas9 target site and/or the distal spacer targets a Cas12a target site.

3. The hgRNA of claim 1, further comprising one or more additional direct repeats and one or more additional spacers, wherein the one or more additional spacers are capable of being processed into mature guide RNAs by a type V Cas protein and/or wherein the proximal spacer targets a Cas9 target site and/or the distal spacer targets a Cas12a target site.

4. The hgRNA of claim 1, wherein the proximal spacer is 15 to 25, 16 to 24, 17 to 23, 18 to 22, or 19 to 21 nucleotides in length, and/or wherein the distal spacer is 15 to 28, 16 to 27, 17 to 26, 18 to 25, or 19 to 24 nucleotides in length, and/or wherein the tracrRNA has the sequence as set out in SEQ ID NO: 5, wherein the type V CRISPR-Cas direct repeat is a Lb-Cas12a direct repeat or an As-Cas12a direct repeat, and/or the hgRNA has a sequence as set out in SEQ ID NO: 8 or SEQ ID NO: 9.

5. A construct comprising an hgRNA expression cassette, the expression cassette comprising a DNA sequence encoding the hgRNA of claim 1, wherein the DNA sequence is operably linked to a promoter and a transcription termination site.

6. A method of generating a targeted genetic deletion, the method comprising:

I)
- a) introducing into a cell the hgRNA of claim 1, wherein the proximal-spacer targets a CRISPR target site on a chromosome at one end of the desired deletion and the distal spacer targets another CRISPR target site on the chromosome at the other end of the desired deletion, and wherein the cell expresses a nuclear localized type II Cas protein and a nuclear localized type V Cas protein;
- b) culturing the cell under suitable conditions such that:
  - i) the hgRNA is processed into mature guide RNAs,
  - ii) the mature guide RNAs associate with their respective Cas protein and guide the Cas proteins to their respective CRISPR target sites;
  - iii) the Cas proteins each introduce a double-stranded break at the target site on the chromosome; and
  - iv) the double-stranded breaks are repaired by a DNA repair process such that a targeted genetic deletion is generated; or II)
- a) introducing into a cell a construct comprising an hgRNA expression cassette, the expression cassette comprising a DNA sequence encoding the hgRNA of claim 1, wherein the DNA sequence is operably linked to a promoter, optionally a U6 promoter, and a transcription termination site, optionally wherein the construct is a lentiviral vector having a (+) strand and a (−) strand and the hgRNA expression cassette is inverted so as to be encoded on the (−) strand, wherein the proximal spacer has been designed to target a site on a chromosome at one end of the desired deletion and the distal spacer has been designed to target a target site on the chromosome at the other end of the desired deletion, and wherein the cell expresses a nuclear localized type II Cas protein and a nuclear localized type V Cas protein;
- b) culturing the cell under suitable conditions such that:
  - i) the hgRNA is expressed and processed into mature guide RNAs,
  - ii) the mature guide RNAs associate with their respective Cas protein and guide the Cas proteins to their respective target sites;
  - iii) the Cas proteins each introduce a double-stranded break at the target site on the chromosome; and
  - iv) the double-stranded breaks are repaired by a DNA repair process such that a targeted genetic deletion is generated.

7. The method of claim 6, wherein the type II Cas protein is Cas9 and/or the type V Cas protein is Cas12a, optionally wherein the type V Cas protein is Lb-Cas12a or As-Cas12a; and/or wherein the type II Cas protein and/or the type V Cas protein comprises one or more nuclear localization signals, optionally two nuclear localization signals, optionally a nucleoplasmin nuclear localization signal and/or an SV40 nuclear localization signal.

8. The hgRNA of claim 4, wherein the proximal spacer is 20 nucleotides in length;

the distal spacer is 20, 21, 22, or 23 nucleotides in length; and/or the distal spacer has one or more of the following properties: is neutral with respect to GC content, has a G at the first nucleotide, does not have a T at one or more of the first nine nucleotides, and/or does not have a C at the 23rd nucleotide.

9. The hgRNA of claim 4, wherein the Lb-Cas12a direct repeat has a sequence as set out in SEQ ID NO: 6 or the As-Cas12a direct repeat has a sequence as set out in SEQ ID NO: 7.

10. The construct of claim 5, wherein the promoter is a U6 promoter and/or wherein the construct is a lentiviral vector having a (+) strand and a (−) strand and the hgRNA expression cassette is inverted so as to be encoded on the (−) strand.

* * * * *

SEQUENCE LISTING

```
<160> NUMBER OF SEQ ID NOS: 30

<210> SEQ ID NO 1
<211> LENGTH: 3
<212> TYPE: DNA
<213> ORGANISM: Artificial Sequence
<220> FEATURE:
<223> OTHER INFORMATION: Cas9 PAM
<220> FEATURE:
<221> NAME/KEY: misc_feature
<222> LOCATION: (1)..(1)
<223> OTHER INFORMATION: n is a, c, g, or t

<400> SEQUENCE: 1

ngg                                                                 3


<210> SEQ ID NO 2
<211> LENGTH: 28
<212> TYPE: DNA
<213> ORGANISM: Artificial Sequence
<220> FEATURE:
<223> OTHER INFORMATION: Generic Cas9 target sequence
<220> FEATURE:
<221> NAME/KEY: misc_feature
<222> LOCATION: (1)..(15)
<223> OTHER INFORMATION: n is a, c, g, or t
<220> FEATURE:
<221> NAME/KEY: misc_feature
<222> LOCATION: (16)..(25)
<223> OTHER INFORMATION: n is a, c, g, or t and can be present or absent
<220> FEATURE:
<221> NAME/KEY: misc_feature
<222> LOCATION: (26)..(26)
```

<223> OTHER INFORMATION: n is a, c, g, or t

<400> SEQUENCE: 2
nnnnnnnnnn nnnnnnnnnn nnnnnngg 28

<210> SEQ ID NO 3
<211> LENGTH: 4
<212> TYPE: DNA
<213> ORGANISM: Artificial Sequence
<220> FEATURE:
<223> OTHER INFORMATION: Cas12a PAM

<400> SEQUENCE: 3 tttv 4

<210> SEQ ID NO 4
<211> LENGTH: 32
<212> TYPE: DNA
<213> ORGANISM: Artificial Sequence
<220> FEATURE:
<223> OTHER INFORMATION: Generic Cas12a target sequence
<220> FEATURE:
<221> NAME/KEY: misc_feature
<222> LOCATION: (5)..(19)
<223> OTHER INFORMATION: n is a, c, g, or t
<220> FEATURE:
<221> NAME/KEY: misc_feature
<222> LOCATION: (20)..(32)
<223> OTHER INFORMATION: n is a, c, g, or t and can be present or absent

<400> SEQUENCE: 4
tttvnnnnnn nnnnnnnnnn nnnnnnnnnn nn 32

<210> SEQ ID NO 5
<211> LENGTH: 86
<212> TYPE: DNA
<213> ORGANISM: Artificial Sequence
<220> FEATURE:
<223> OTHER INFORMATION: Modified S. pyogenes tracrRNA sequence (DNA)

<400> SEQUENCE: 5
gtttcagagc tatgctggaa acagcatagc aagttgaaat aaggctagtc cgttatcaac 60
ttgaaaaagt ggcaccgagt cggtgc 86

<210> SEQ ID NO 6
<211> LENGTH: 20
<212> TYPE: DNA
<213> ORGANISM: Unknown
<220> FEATURE:
<223> OTHER INFORMATION: Lachnospiraceae bacterium

<400> SEQUENCE: 6
taatttctac tcttgtagat 20

<210> SEQ ID NO 7
<211> LENGTH: 21
<212> TYPE: DNA
<213> ORGANISM: Acidaminococcus sp. BV3L6

<400> SEQUENCE: 7
taatttctac taagtgtaga t 21

<210> SEQ ID NO 8
<211> LENGTH: 160
<212> TYPE: DNA
<213> ORGANISM: Artificial Sequence
<220> FEATURE:
<223> OTHER INFORMATION: Generic hgRNA for Lb-Cas12a
<220> FEATURE:
<221> NAME/KEY: misc_feature
<222> LOCATION: (1)..(15)
<223> OTHER INFORMATION: n is a, c, g, t or u
<220> FEATURE:
<221> NAME/KEY: misc_feature
<222> LOCATION: (16)..(25)
<223> OTHER INFORMATION: n is a, c, g, or t and can be present or absent
<220> FEATURE:
<221> NAME/KEY: misc_feature
<222> LOCATION: (133)..(147)
<223> OTHER INFORMATION: n is a, c, g, t or u
<220> FEATURE:
<221> NAME/KEY: misc_feature
<222> LOCATION: (148)..(160)
<223> OTHER INFORMATION: n is a, c, g, or t and can be present or absent

<400> SEQUENCE: 8
nnnnnnnnnn nnnnnnnnnn nnnnngtttc agagctatgc tggaaacagc atagcaagtt 60
gaaataaggc tagtccgtta tcaacttgaa aaagtggcac cgagtcggtg ctaatttcta 120
ctaagtgtag atnnnnnnnn nnnnnnnnnn nnnnnnnnnn 160

<210> SEQ ID NO 9
<211> LENGTH: 159
<212> TYPE: DNA
<213> ORGANISM: Artificial Sequence
<220> FEATURE:
<223> OTHER INFORMATION: Generic hgRNA for As-Cas12a
<220> FEATURE:
<221> NAME/KEY: misc_feature
<222> LOCATION: (1)..(15)
<223> OTHER INFORMATION: n is a, c, g, t or u
<220> FEATURE:
<221> NAME/KEY: misc_feature
<222> LOCATION: (16)..(25)
<223> OTHER INFORMATION: n is a, c, g, or t and can be present or absent
<220> FEATURE:
<221> NAME/KEY: misc_feature
<222> LOCATION: (132)..(146)
<223> OTHER INFORMATION: n is a, c, g, t or u
<220> FEATURE:
<221> NAME/KEY: misc_feature
<222> LOCATION: (147)..(159)
<223> OTHER INFORMATION: n is a, c, g, or t and can be present or absent

<400> SEQUENCE: 9
nnnnnnnnnn nnnnnnnnnn nnnnngtttc agagctatgc tggaaacagc atagcaagtt 60
gaaataaggc tagtccgtta tcaacttgaa aaagtggcac cgagtcggtg ctaatttcta 120
ctcttgtaga tnnnnnnnnn nnnnnnnnnn nnnnnnnnn 159

<210> SEQ ID NO 10
<211> LENGTH: 32
<212> TYPE: DNA
<213> ORGANISM: Artificial Sequence
<220> FEATURE:
<223> OTHER INFORMATION: Generic stuffer sequence

<400> SEQUENCE: 10
gtttagagac ggctaaatcc gcgtctcgag at 32

<210> SEQ ID NO 11
<211> LENGTH: 32
<212> TYPE: DNA
<213> ORGANISM: Artificial Sequence
<220> FEATURE:
<223> OTHER INFORMATION: Generic/degenerate stuffer sequence

<400> SEQUENCE: 11
gtttdgagac gadddddddd ccgtctcdag at 32

<210> SEQ ID NO 12
<211> LENGTH: 85
<212> TYPE: DNA
<213> ORGANISM: Artificial Sequence
<220> FEATURE:
<223> OTHER INFORMATION: Generic paired guide oligonucleotide
<220> FEATURE:
<221> NAME/KEY: misc_feature
<222> LOCATION: (1)..(15)
<223> OTHER INFORMATION: n is a, c, g, or t
<220> FEATURE:
<221> NAME/KEY: misc_feature
<222> LOCATION: (16)..(25)
<223> OTHER INFORMATION: n is a, c, g, or t and can be present or absent
<220> FEATURE:
<221> NAME/KEY: misc_feature
<222> LOCATION: (58)..(72)
<223> OTHER INFORMATION: n is a, c, g, or t
<220> FEATURE:
<221> NAME/KEY: misc_feature
<222> LOCATION: (73)..(85)
<223> OTHER INFORMATION: n is a, c, g, or t and can be present or absent

<400> SEQUENCE: 12
nnnnnnnnnn nnnnnnnnnn nnnnngttta gagacggcta aatccgcgtc tcgagatnnn 60
nnnnnnnnnn nnnnnnnnnn nnnnn 85

<210> SEQ ID NO 13
<211> LENGTH: 85
<212> TYPE: DNA
<213> ORGANISM: Artificial Sequence
<220> FEATURE:
<223> OTHER INFORMATION: Generic/degenerate paired guide oligonucleotide
<220> FEATURE:
<221> NAME/KEY: misc_feature
<222> LOCATION: (1)..(15)
<223> OTHER INFORMATION: n is a, c, g, or t
<220> FEATURE:
<221> NAME/KEY: misc_feature
<222> LOCATION: (16)..(25)
<223> OTHER INFORMATION: n is a, c, g, or t and can be present or absent
<220> FEATURE:
<221> NAME/KEY: misc_feature
<222> LOCATION: (58)..(72)
<223> OTHER INFORMATION: n is a, c, g, or t
<220> FEATURE:
<221> NAME/KEY: misc_feature
<222> LOCATION: (73)..(85)
<223> OTHER INFORMATION: n is a, c, g, or t and can be present or absent

<400> SEQUENCE: 13
nnnnnnnnnn nnnnnnnnnn nnnnngtttd gagacgaddd dddddccgtc tcdagatnnn 60
nnnnnnnnnn nnnnnnnnnn nnnnn 85

<210> SEQ ID NO 14
<211> LENGTH: 9371
<212> TYPE: DNA
<213> ORGANISM: Artificial Sequence
<220> FEATURE:
<223> OTHER INFORMATION: pLCHKO

<400> SEQUENCE: 14
cccgggttgc gccttttcca aggcagccct gggtttgcgc agggacgcgg ctgctctggg 60
cgtggttccg ggaaacgcag cggcgccgac cctgggtctc gcacattctt cacgtccgtt 120
cgcagcgtca cccggatctt cgccgctacc cttgtgggcc ccccggcgac gcttcctgct 180

```
ccgcccctaa gtcgggaagg ttccttgcgg ttcgcggcgt gccggacgtg acaaacggaa    240
gccgcagctc acactagtac cctcgcagac ggacagcgcc agggagcaat ggcagcgcgc    300
cgaccgcgat gggctgtggc caatagcggc tgctcagcag ggcgcgccga gagcagcggc    360
cgggaagggg cggtgcggga ggcggggtgt ggggcggtag tgtgggccct gttcctgccc    420
gcgcggtgtt ccgcattctg caagcctccg gagcgcacgt cggcagtcgg ctccctcgtt    480
gaccgaatca ccgacctctc tccccagggg gatccaccgg agcttaccat gaccgagtac    540
aagcccacgg tgcgcctcgc cacccgcgac gacgtcccca gggccgtacg caccctcgcc    600
gccgcgttcg ccgactaccc cgccacgcgc cacaccgtcg atccggaccg ccacatcgag    660
cgggtcaccg agctgcaaga actcttcctc acgcgcgtcg ggctcgacat cggcaaggtg    720
tgggtcgcgg acgacggcgc cgccgtggcg gtctggacca cgccggagag cgtcgaagcg    780
ggggcggtgt tcgccgagat cggcccgcgc atggccgagt tgagcggttc ccggctggcc    840
gcgcagcaac agatggaagg cctcctggcg ccgcaccggc ccaaggagcc cgcgtggttc    900
ctggccaccg tcggtgtttc gcccgaccac cagggcaagg gtctgggcag cgccgtcgtg    960
ctccccggag tggaggcggc cgagcgcgcc ggggtgcccg ccttcctgga gacctccgcg   1020
ccccgcaacc tccccttcta cgagcggctc ggcttcaccg tcaccgccga cgtcgaggtg   1080
cccgaaggac cgcgcacctg gtgcatgacc cgcaagcccg gtgcctgaac gcgttaagtc   1140
gacaatcaac ctctggatta caaaatttgt gaaagattga ctggtattct taactatgtt   1200
gctcctttta cgctatgtgg atacgctgct ttaatgcctt tgtatcatgc tattgcttcc   1260
cgtatggctt tcattttctc ctccttgtat aaatcctggt tgctgtctct ttatgaggag   1320
ttgtggcccg ttgtcaggca acgtggcgtg gtgtgcactg tgtttgctga cgcaaccccc   1380
actggttggg gcattgccac cacctgtcag ctcctttccg ggactttcgc tttccccctc   1440
cctattgcca cggcggaact catcgccgcc tgccttgccc gctgctggac aggggctcgg   1500
ctgttgggca ctgacaattc cgtggtgttg tcggggaaat catcgtcctt tccttggctg   1560
ctcgcctgtg ttgccacctg gattctgcgc gggacgtcct tctgctacgt cccttcggcc   1620
ctcaatccag cggaccttcc ttcccgcggc ctgctgccgg ctctgcggcc tcttccgcgt   1680
cttcgccttc gccctcagac gagtcggatc tccctttggg ccgcctcccc gcgtcgactt   1740
taagaccaat gacttacaag gcagctgtag atcttagcca ctttttaaaa gaaaaggggg   1800
gactggaagg gctaattcac tcccaacgaa gacaagatct gctttttgct tgtactgggt   1860
ctctctggtt agaccagatc tgagcctggg agctctctgg ctaactaggg aacccactgc   1920
ttaagcctca ataaagcttg ccttgagtgc ttcaagtagt gtgtgcccgt ctgttgtgtg   1980
actctggtaa ctagagatcc ctcagaccct tttagtcagt gtggaaaatc tctagcagta   2040
cgtatagtag ttcatgtcat cttattattc agtatttata acttgcaaag aaatgaatat   2100
cagagagtga gaggaacttg tttattgcag cttataatgg ttacaaataa agcaatagca   2160
tcacaaattt cacaaataaa gcattttttt cactgcattc tagttgtggt ttgtccaaac   2220
tcatcaatgt atcttatcat gtctggctct agctatcccg cccctaactc cgcccatccc   2280
gcccctaact ccgcccagtt ccgcccattc tccgccccat ggctgactaa ttttttttat   2340
ttatgcagag gccgaggccg cctcggcctc tgagctattc cagaagtagt gaggaggctt   2400
ttttggaggc ctagggacgt acccaattcg ccctatagtg agtcgtatta cgcgcgctca   2460
ctggccgtcg ttttacaacg tcgtgactgg gaaaaccctg gcgttaccca acttaatcgc   2520
```

cttgcagcac atccccccttt cgccagctgg cgtaatagcg aagaggcccg caccgatcgc 2580
ccttcccaac agttgcgcag cctgaatggc gaatgggacg cgccctgtag cggcgcatta 2640
agcgcggcgg gtgtggtggt tacgcgcagc gtgaccgcta cacttgccag cgccctagcg 2700
cccgctcctt tcgctttctt cccttccttt ctcgccacgt tcgccggctt tccccgtcaa 2760
gctctaaatc gggggctccc tttagggttc cgatttagtg ctttacggca cctcgacccc 2820
aaaaaacttg attagggtga tggttcacgt agtgggccat cgccctgata gacggttttt 2880
cgccctttga cgttggagtc cacgttcttt aatagtggac tcttgttcca aactggaaca 2940
acactcaacc ctatctcggt ctattctttt gatttataag ggattttgcc gatttcggcc 3000
tattggttaa aaaatgagct gatttaacaa aaatttaacg cgaattttaa caaaatatta 3060
acgcttacaa tttaggtggc acttttcggg gaaatgtgcg cggaacccct atttgtttat 3120
ttttctaaat acattcaaat atgtatccgc tcatgagaca ataaccctga taaatgcttc 3180
aataatattg aaaaaggaag agtatgagta ttcaacattt ccgtgtcgcc cttattccct 3240
tttttgcggc attttgcctt cctgtttttg ctcacccaga aacgctggtg aaagtaaaag 3300
atgctgaaga tcagttgggt gcacgagtgg gttacatcga actggatctc aacagcggta 3360
agatccttga gagttttcgc cccgaagaac gttttccaat gatgagcact tttaaagttc 3420
tgctatgtgg cgcggtatta tcccgtattg acgccgggca agagcaactc ggtcgccgca 3480
tacactattc tcagaatgac ttggttgagt actcaccagt cacagaaaag catcttacgg 3540
atggcatgac agtaagagaa ttatgcagtg ctgccataac catgagtgat aacactgcgg 3600
ccaacttact tctgacaacg atcggaggac cgaaggagct aaccgctttt ttgcacaaca 3660
tgggggatca tgtaactcgc cttgatcgtt gggaaccgga gctgaatgaa gccataccaa 3720
acgacgagcg tgacaccacg atgcctgtag caatggcaac aacgttgcgc aaactattaa 3780
ctggcgaact acttactcta gcttcccggc aacaattaat agactggatg gaggcggata 3840
aagttgcagg accacttctg cgctcggccc ttccggctgg ctggtttatt gctgataaat 3900
ctggagccgg tgagcgtggg tctcgcggta tcattgcagc actggggcca gatggtaagc 3960
cctcccgtat cgtagttatc tacacgacgg ggagtcaggc aactatggat gaacgaaata 4020
gacagatcgc tgagataggt gcctcactga ttaagcattg gtaactgtca gaccaagttt 4080
actcatatat actttagatt gatttaaaac ttcattttta atttaaaagg atctaggtga 4140
agatcctttt tgataatctc atgaccaaaa tcccttaacg tgagttttcg ttccactgag 4200
cgtcagaccc cgtagaaaag atcaaaggat cttcttgaga tccttttttt ctgcgcgtaa 4260
tctgctgctt gcaaacaaaa aaaccaccgc taccagcggt ggtttgtttg ccggatcaag 4320
agctaccaac tctttttccg aaggtaactg gcttcagcag agcgcagata ccaaatactg 4380
ttcttctagt gtagccgtag ttaggccacc acttcaagaa ctctgtagca ccgcctacat 4440
acctcgctct gctaatcctg ttaccagtgg ctgctgccag tggcgataag tcgtgtctta 4500
ccgggttgga ctcaagacga tagttaccgg ataaggcgca gcggtcgggc tgaacggggg 4560
gttcgtgcac acagcccagc ttggagcgaa cgacctacac cgaactgaga tacctacagc 4620
gtgagctatg agaaagcgcc acgcttcccg aagggagaaa ggcggacagg tatccggtaa 4680
gcggcagggt cggaacagga gagcgcacga gggagcttcc agggggaaac gcctggtatc 4740
tttatagtcc tgtcgggttt cgccacctct gacttgagcg tcgatttttg tgatgctcgt 4800
caggggggcg gagcctatgg aaaaacgcca gcaacgcggc ctttttacgg ttcctggcct 4860
tttgctggcc ttttgctcac atgttctttc ctgcgttatc ccctgattct gtggataacc 4920

```
gtattaccgc ctttgagtga gctgataccg ctcgccgcag ccgaacgacc gagcgcagcg   4980
agtcagtgag cgaggaagcg gaagagcgcc caatacgcaa accgcctctc cccgcgcgtt   5040
ggccgattca ttaatgcagc tggcacgaca ggtttcccga ctggaaagcg ggcagtgagc   5100
gcaacgcaat taatgtgagt tagctcactc attaggcacc ccaggcttta cactttatgc   5160
ttccggctcg tatgttgtgt ggaattgtga gcggataaca atttcacaca ggaaacagct   5220
atgaccatga ttacgccaag cgcgcaatta accctcacta aagggaacaa aagctggagc   5280
tgcaagctta atgtagtctt atgcaatact cttgtagtct tgcaacatgg taacgatgag   5340
ttagcaacat gccttacaag gagagaaaaa gcaccgtgca tgccgattgg tggaagtaag   5400
gtggtacgat cgtgccttat taggaaggca acagacgggt ctgacatgga ttggacgaac   5460
cactgaattg ccgcattgca gagatattgt atttaagtgc ctagctcgat acataaacgg   5520
gtctctctgg ttagaccaga tctgagcctg ggagctctct ggctaactag ggaacccact   5580
gcttaagcct caataaagct tgccttgagt gcttcaagta gtgtgtgccc gtctgttgtg   5640
tgactctggt aactagagat ccctcagacc cttttagtca gtgtggaaaa tctctagcag   5700
tggcgcccga acagggactt gaaagcgaaa gggaaaccag aggagctctc tcgacgcagg   5760
actcggcttg ctgaagcgcg cacggcaaga ggcgaggggc ggcgactggt gagtacgcca   5820
aaaattttga ctagcggagg ctagaaggag agagatgggt gcgagagcgt cagtattaag   5880
cgggggagaa ttagatcgcg atgggaaaaa attcggttaa ggccaggggg aaagaaaaaa   5940
tataaattaa aacatatagt atgggcaagc agggagctag aacgattcgc agttaatcct   6000
ggcctgttag aaacatcaga aggctgtaga caaatactgg gacagctaca accatccctt   6060
cagacaggat cagaagaact tagatcatta tataatacag tagcaaccct ctattgtgtg   6120
catcaaagga tagagataaa agacaccaag gaagctttag acaagataga ggaagagcaa   6180
aacaaaagta agaccaccgc acagcaagcg gccgctgatc ttcagacctg gaggaggaga   6240
tatgagggac aattggagaa gtgaattata taaatataaa gtagtaaaaa ttgaaccatt   6300
aggagtagca cccaccaagg caaagagaag agtggtgcag agagaaaaaa gagcagtggg   6360
aataggagct ttgttccttg ggttcttggg agcagcagga agcactatgg gcgcagcgtc   6420
aatgacgctg acggtacagg ccagacaatt attgtctggt atagtgcagc agcagaacaa   6480
tttgctgagg gctattgagg cgcaacagca tctgttgcaa ctcacagtct ggggcatcaa   6540
gcagctccag gcaagaatcc tggctgtgga aagataccta aaggatcaac agctcctggg   6600
gatttggggt tgctctggaa aactcatttg caccactgct gtgccttgga atgctagttg   6660
gagtaataaa tctctggaac agatttggaa tcacacgacc tggatggagt gggacagaga   6720
aattaacaat tacacaagct taatacactc cttaattgaa gaatcgcaaa accagcaaga   6780
aaagaatgaa caagaattat tggaattaga taaatgggca agtttgtgga attggtttaa   6840
cataacaaat tggctgtggt atataaaatt attcataatg atagtaggag gcttggtagg   6900
tttaagaata gtttttgctg tactttctat agtgaataga gttaggcagg gatattcacc   6960
attatcgttt cagacccacc tcccaacccc gaggggaccc agagaattca aaaaaaactc   7020
tgcaggtcta caaaaaagag caagaagcta aaaaagattt aaaaattatt tttagcgcag   7080
ttaatggaac aggaactaaa tttaccccaa aaatattacg tgaatcagga tataacgtta   7140
ttgaggttga agagcatgca tttgaagatg aaacatttaa aaatgttgta aatccaaatc   7200
cagaatttga tcctgcatga aaaataccgc ttgaatatgg tattaaacat gatgcagata   7260
```

```
ttattattat gaatgaccca gatgctgaca gatttggaat ggcaataaaa catgatggtc   7320
attttgtaag attagatgga aatcaaacag gaccaatttt aattgattga aaattatcaa   7380
atctaaaacg cttaaatagc attccaaaaa atccggctct atattcaagt tttgtaacaa   7440
gtgatttggg tgatagaatc gctcatgaaa aatatggagt taatattgta aaaactttaa   7500
ctggatttaa atgaatgggt agagaaattg ctaaagaaga agataacgga ttaaattttg   7560
tttttgctta tgaagaaagt tatggatatg taattgatga ctcagctaga gataaagatg   7620
gaatacaagc ttctatatta atagcagagg ctgcttgatt ttataaaaaa caaaataaaa   7680
cattagtaga ctatttagaa gatttattta aagaaatggg tgcatattac actttcactt   7740
taaacttgaa ttttaaacca gaagaaaaga aattaaaaat tgaaccatta atgaaatcat   7800
tgagagcaac acccttaact caaattgctg gacttaaagt tgttaatgtt gaagactaca   7860
tcgatggaat gtataatatg ccaggacaag acttactaaa attttattta gaagataagt   7920
catgatttgc tgttcgccca agtggaactg aacctaaact aaaaatttat tttataggtg   7980
ttggtgaatc tgttcaaaac gctaaagtta aagtagacga aattattaaa gaattaaaat   8040
taaaaatgaa tatataggag aaaaaatgaa actaaacaaa tatatagatc acacattatt   8100
aaaacaagat gctacgaaag ctgaaattaa acaattatgt gatgaagcaa ttgaatttga   8160
ttttgcaaca gtttgtgtta attcatattg aacaagctat tgtaaagaat tattaaaagg   8220
cacaaatgta ggaataacaa atgttgtagg ttttcctcta ggtgcatgca caacagctac   8280
aaaagcattc gaagtttctg aagcaattaa agatggtgca acagaaattg atatggtatt   8340
aaatattggt gcattaaaag acaaaaatta tgaattagtt ttagaagaca tgaaagctgt   8400
aaaaaaagca gctggatcac atgttgttaa atgtattatg gaaaattgtt tattaacaaa   8460
agaagaaatc atgaaagctt gtgaaatagc tgttgaagct ggattagaat ttgttaaaac   8520
atcaacagga ttttcaaaat caggtgcaac atttgaagat gttaaactaa tgaagtcagt   8580
tgttaaagac aatgctttag ttaaagcagc tggtggagtt agaacatttg aagatgctca   8640
aaaaatgatt gaagcaggag ctgaccgctt aggaacaagt ggtggagtag ctattattaa   8700
aggtgaagaa aacaacgcga gttactaaaa ctagcgtttt tttattttgc tcatttttat   8760
taaaagtttg caaaaaggaa cataaaaatt ctaattattg atactaaagt tattaaaaag   8820
aagattttgg ttgattttat aaaggtcata gaatataata ttttagcatg tgtattttgt   8880
gtgctcattt acaacacacc tgcctaccgg tacctcgtcc tttccacaag atatataaag   8940
ccaagaaatc gaaatacttt caagttacgg taagcatatg atagtccatt ttaaaacata   9000
attttaaaac tgcaaactac ccaagaaatt attactttct acgtcacgta ttttgtacta   9060
atatctttgt gtttacagtc aaattaattc taattatctc tctaacagcc ttgtatcgta   9120
tatgcaaata tgaaggaatc atgggaaata ggccctctct gaattctaga tcttgagaca   9180
aatggcagta ttcatccaca attttaaaag aaaagggggg attggggggt acagtgcagg   9240
ggaaagaata gtagacataa tagcaacaga catacaaact aaagaattac aaaaacaaat   9300
tacaaaaatt caaaattttc gggtttatta cagggacagc agagatccac tttggcgccg   9360
gctcgagggg g                                                         9371
```

<210> SEQ ID NO 15
<211> LENGTH: 99
<212> TYPE: DNA
<213> ORGANISM: Artificial Sequence
<220> FEATURE:
<223> OTHER INFORMATION: second oligo: 5' truncated tracrRNA and 3' truncated Lb-Cas12a direct repeat

<400> SEQUENCE: 15
cagagctatg ctggaaacag catagcaagt tgaaataagg ctagtccgtt atcaacttga 60
aaaagtggca ccgagtcggt gctaatttct actaagtgt 99

<210> SEQ ID NO 16
<211> LENGTH: 98
<212> TYPE: DNA
<213> ORGANISM: Artificial Sequence
<220> FEATURE:
<223> OTHER INFORMATION: second oligo: 5 truncated tracrRNA and 3' truncated As-Cas12a direct repeat

<400> SEQUENCE: 16
cagagctatg ctggaaacag catagcaagt tgaaataagg ctagtccgtt atcaacttga 60
aaaagtggca ccgagtcggt gctaatttct actcttgt 98

<210> SEQ ID NO 17
<211> LENGTH: 122
<212> TYPE: DNA
<213> ORGANISM: Artificial Sequence
<220> FEATURE:
<223> OTHER INFORMATION: BsmBI - tracrRNA - Lb-Cas12a_DR - BsmBI

<400> SEQUENCE: 17
cgtctctgtt tcagagctat gctggaaaca gcatagcaag ttgaaataag gctagtccgt 60
tatcaacttg aaaaagtggc accgagtcgg tgcttaattt ctactaagtg tagatagaga 120
cg 122

<210> SEQ ID NO 18
<211> LENGTH: 121
<212> TYPE: DNA
<213> ORGANISM: Artificial Sequence
<220> FEATURE:
<223> OTHER INFORMATION: BsmBI - tracrRNA - As-Cas12a_DR - BsmBI

<400> SEQUENCE: 18
cgtctctgtt tcagagctat gctggaaaca gcatagcaag ttgaaataag gctagtccgt 60
tatcaacttg aaaaagtggc accgagtcgg tgcttaattt ctactcttgt agatagagac 120
g 121

<210> SEQ ID NO 19
<211> LENGTH: 4128
<212> TYPE: DNA
<213> ORGANISM: Streptococcus pyogenes

<400> SEQUENCE: 19
atgggtatcc acggagtccc agcagccgac aagaagtaca gcatcggcct ggacatcggc 60
accaactctg tgggctgggc cgtgatcacc gacgagtaca aggtgcccag caagaaattc 120
aaggtgctgg gcaacaccga ccggcacagc atcaagaaga acctgatcgg agccctgctg 180
ttcgacagcg gcgaaacagc cgaggccacc cggctgaaga gaaccgccag aagaagatac 240
accagacgga agaaccggat ctgctatctg caagagatct tcagcaacga gatggccaag 300
gtggacgaca gcttcttcca cagactggaa gagtccttcc tggtggaaga ggataagaag 360
cacgagcggc accccatctt cggcaacatc gtggacgagg tggcctacca cgagaagtac 420
cccaccatct accacctgag aaagaaactg gtggacagca ccgacaaggc cgacctgcgg 480

-continued

```
ctgatctatc tggccctggc ccacatgatc aagttccggg gccacttcct gatcgagggc    540
gacctgaacc ccgacaacag cgacgtggac aagctgttca tccagctggt gcagacctac    600
aaccagctgt tcgaggaaaa ccccatcaac gccagcggcg tggacgccaa ggccatcctg    660
tctgccagac tgagcaagag cagacggctg gaaaatctga tcgcccagct gcccggcgag    720
aagaagaatg gcctgttcgg caacctgatt gccctgagcc tgggcctgac ccccaacttc    780
aagagcaact tcgacctggc cgaggatgcc aaactgcagc tgagcaagga cacctacgac    840
gacgacctgg acaacctgct ggcccagatc ggcgaccagt acgccgacct gtttctggcc    900
gccaagaacc tgtccgacgc catcctgctg agcgacatcc tgagagtgaa caccgagatc    960
accaaggccc ccctgagcgc ctctatgatc aagagatacg acgagcacca ccaggacctg   1020
accctgctga aagctctcgt gcggcagcag ctgcctgaga agtacaaaga gatttttcttc   1080
gaccagagca agaacggcta cgccggctac attgacggcg gagccagcca ggaagagttc   1140
tacaagttca tcaagcccat cctggaaaag atggacggca ccgaggaact gctcgtgaag   1200
ctgaacagag aggacctgct gcggaagcag cggaccttcg acaacggcag catcccccac   1260
cagatccacc tgggagagct gcacgccatt ctgcggcggc aggaagattt ttacccattc   1320
ctgaaggaca accgggaaaa gatcgagaag atcctgacct tccgcatccc ctactacgtg   1380
ggccctctgg ccaggggaaa cagcagattc gcctggatga ccagaaagag cgaggaaacc   1440
atcaccccct ggaacttcga ggaagtggtg gacaagggcg cttccgccca gagcttcatc   1500
gagcggatga ccaacttcga taagaacctg cccaacgaga aggtgctgcc caagcacagc   1560
ctgctgtacg agtacttcac cgtgtataac gagctgacca aagtgaaata cgtgaccgag   1620
ggaatgagaa agcccgcctt cctgagcggc gagcagaaaa aggccatcgt ggacctgctg   1680
ttcaagacca accggaaagt gaccgtgaag cagctgaaag aggactactt caagaaaatc   1740
gagtgcttcg actccgtgga aatctccggc gtggaagatc ggttcaacgc ctccctgggc   1800
acataccacg atctgctgaa aattatcaag gacaaggact tcctggacaa tgaggaaaac   1860
gaggacattc tggaagatat cgtgctgacc ctgacactgt ttgaggacag agagatgatc   1920
gaggaacggc tgaaaaccta tgcccacctg ttcgacgaca aagtgatgaa gcagctgaag   1980
cggcggagat acaccggctg gggcaggctg agccggaagc tgatcaacgg catccgggac   2040
aagcagtccg gcaagacaat cctggatttc ctgaagtccg acggcttcgc caacagaaac   2100
ttcatgcagc tgatccacga cgacagcctg acctttaaag aggacatcca gaaagcccag   2160
gtgtccggcc agggcgatag cctgcacgag cacattgcca atctggccgg cagccccgcc   2220
attaagaagg gcatcctgca gacagtgaag gtggtggacg agctcgtgaa agtgatgggc   2280
cggcacaagc ccgagaacat cgtgatcgaa atggccagag agaaccagac cacccagaag   2340
ggacagaaga acagccgcga gagaatgaag cggatcgaag agggcatcaa agagctgggc   2400
agccagatcc tgaaagaaca ccccgtggaa aacacccagc tgcagaacga gaagctgtac   2460
ctgtactacc tgcagaatgg gcgggatatg tacgtggacc aggaactgga catcaaccgg   2520
ctgtccgact acgatgtgga ccatatcgtg cctcagagct ttctgaagga cgactccatc   2580
gacaacaagg tgctgaccag aagcgacaag aaccggggca agagcgacaa cgtgccctcc   2640
gaagaggtcg tgaagaagat gaagaactac tggcggcagc tgctgaacgc caagctgatt   2700
acccagagaa agttcgacaa tctgaccaag gccgagagag gcggcctgag cgaactggat   2760
aaggccggct tcatcaagag acagctggtg gaaacccggc agatcacaaa gcacgtggca   2820
cagatcctgg actcccggat gaacactaag tacgacgaga atgacaagct gatccgggaa   2880
```

gtgaaagtga tcaccctgaa gtccaagctg gtgtccgatt tccggaagga tttccagttt 2940
tacaaagtgc gcgagatcaa caactaccac cacgcccacg acgcctacct gaacgccgtc 3000
gtgggaaccg ccctgatcaa aaagtaccct aagctggaaa gcgagttcgt gtacggcgac 3060
tacaaggtgt acgacgtgcg gaagatgatc gccaagagcg agcaggaaat cggcaaggct 3120
accgccaagt acttcttcta cagcaacatc atgaactttt tcaagaccga gattaccctg 3180
gccaacggcg agatccggaa gcggcctctg atcgagacaa acggcgaaac cggggagatc 3240
gtgtgggata agggccggga ttttgccacc gtgcggaaag tgctgagcat gccccaagtg 3300
aatatcgtga aaaagaccga ggtgcagaca ggcggcttca gcaaagagtc tatcctgccc 3360
aagaggaaca gcgataagct gatcgccaga aagaaggact gggaccctaa gaagtacggc 3420
ggcttcgaca gccccaccgt ggcctattct gtgctggtgg tggccaaagt ggaaaagggc 3480
aagtccaaga aactgaagag tgtgaaagag ctgctgggga tcaccatcat ggaaagaagc 3540
agcttcgaga agaatcccat cgactttctg gaagccaagg gctacaaaga agtgaaaaag 3600
gacctgatca tcaagctgcc taagtactcc ctgttcgagc tggaaaacgg ccggaagaga 3660
atgctggcct ctgccggcga actgcagaag ggaaacgaac tggccctgcc ctccaaatat 3720
gtgaacttcc tgtacctggc cagccactat gagaagctga agggctcccc cgaggataat 3780
gagcagaaac agctgtttgt ggaacagcac aagcactacc tggacgagat catcgagcag 3840
atcagcgagt tctccaagag agtgatcctg gccgacgcta atctggacaa agtgctgtcc 3900
gcctacaaca agcaccggga taagcccatc agagagcagg ccgagaatat catccacctg 3960
tttaccctga ccaatctggg agcccctgcc gccttcaagt actttgacac caccatcgac 4020
cggaagaggt acaccagcac caaagaggtg ctggacgcca ccctgatcca ccagagcatc 4080
accggcctgt acgagacacg gatcgacctg tctcagctgg gaggcgac 4128

<210> SEQ ID NO 20
<211> LENGTH: 3684
<212> TYPE: DNA
<213> ORGANISM: Unknown
<220> FEATURE:
<223> OTHER INFORMATION: Lachnospiraceae bacterium

<400> SEQUENCE: 20
atgagcaagc tggagaagtt tacaaactgc tactccctgt ctaagaccct gaggttcaag 60
gccatccctg tgggcaagac ccaggagaac atcgacaata agcggctgct ggtggaggac 120
gagaagagag ccgaggatta taagggcgtg aagaagctgc tggatcgcta ctatctgtct 180
tttatcaacg acgtgctgca cagcatcaag ctgaagaatc tgaacaatta catcagcctg 240
ttccggaaga aaaccagaac cgagaaggag aataaggagc tggagaacct ggagatcaat 300
ctgcggaagg agatcgccaa ggccttcaag ggcaacgagg gctacaagtc cctgtttaag 360
aaggatatca tcgagacaat cctgccagag ttcctggacg ataaggacga gatcgccctg 420
gtgaacagct tcaatggctt taccacagcc ttcaccggct tctttgataa cagagagaat 480
atgttttccg aggaggccaa gagcacatcc atcgccttca ggtgtatcaa cgagaatctg 540
acccgctaca tctctaatat ggacatcttc gagaaggtgg acgccatctt tgataagcac 600
gaggtgcagg agatcaagga gaagatcctg aacagcgact atgatgtgga ggatttcttt 660
gagggcgagt tctttaactt tgtgctgaca caggagggca tcgacgtgta taacgccatc 720
atcggcggct tcgtgaccga gagcggcgag aagatcaagg gcctgaacga gtacatcaac 780
ctgtataatc agaaaaccaa gcagaagctg cctaagttta agccactgta taagcaggtg 840
ctgagcgatc gggagtctct gagcttctac ggcgagggct atacatccga tgaggaggtg 900
ctggaggtgt ttagaaacac cctgaacaag aacagcgaga tcttcagctc catcaagaag 960
ctggagaagc tgttcaagaa ttttgacgag tactctagcg ccggcatctt tgtgaagaac 1020
ggccccgcca tcagcacaat ctccaaggat atcttcggcg agtggaacgt gatccgggac 1080
aagtggaatg ccgagtatga cgatatccac ctgaagaaga aggccgtggt gaccgagaag 1140
tacgaggacg atcggagaaa gtccttcaag aagatcggct ccttttctct ggagcagctg 1200
caggagtacg ccgacgccga tctgtctgtg gtggagaagc tgaaggagat catcatccag 1260
aaggtggatg agatctacaa ggtgtatggc tcctctgaga agctgttcga cgccgatttt 1320
gtgctggaga agagcctgaa gaagaacgac gccgtggtgg ccatcatgaa ggacctgctg 1380
gattctgtga agagcttcga gaattacatc aaggccttct ttggcgaggg caaggagaca 1440
aacagggacg agtccttcta tggcgatttt gtgctggcct acgacatcct gctgaaggtg 1500
gaccacatct acgatgccat ccgcaattat gtgacccaga agccctactc taaggataag 1560
ttcaagctgt attttcagaa ccctcagttc atgggcggct gggacaagga taaggagaca 1620
gactatcggg ccaccatcct gagatacggc tccaagtact atctggccat catggataag 1680
aagtacgcca agtgcctgca gaagatcgac aaggacgatg tgaacggcaa ttacgagaag 1740
atcaactata agctgctgcc cggccctaat aagatgctgc caaaggtgtt cttttctaag 1800
aagtggatgg cctactataa ccccagcgag gacatccaga agatctacaa gaatggcaca 1860
ttcaagaagg gcgatatgtt taacctgaat gactgtcaca agctgatcga cttctttaag 1920
gatagcatct cccggtatcc aaagtggtcc aatgcctacg atttcaactt ttctgagaca 1980
gagaagtata aggacatcgc cggcttttac agagaggtgg aggagcaggg ctataaggtg 2040
agcttcgagt ctgccagcaa gaaggaggtg gataagctgg tggaggaggg caagctgtat 2100
atgttccaga tctataacaa ggacttttcc gataagtctc acggcacacc caatctgcac 2160
accatgtact tcaagctgct gtttgacgag aacaatcacg gacagatcag gctgagcgga 2220
ggagcagagc tgttcatgag gcgcgcctcc ctgaagaagg aggagctggt ggtgcaccca 2280
gccaactccc ctatcgccaa caagaatcca gataatccca agaaaaccac aaccctgtcc 2340
tacgacgtgt ataaggataa gaggttttct gaggaccagt acgagctgca catcccaatc 2400
gccatcaata agtgccccaa gaacatcttc aagatcaata cagaggtgcg cgtgctgctg 2460
aagcacgacg ataaccccta tgtgatcggc atcgataggg gcgagcgcaa tctgctgtat 2520
atcgtggtgg tggacggcaa gggcaacatc gtggagcagt attccctgaa cgagatcatc 2580
aacaacttca acggcatcag gatcaagaca gattaccact ctctgctgga caagaaggag 2640
aaggagaggt tcgaggcccg ccagaactgg acctccatcg agaatatcaa ggagctgaag 2700
gccggctata tctctcaggt ggtgcacaag atctgcgagc tggtggagaa gtacgatgcc 2760
gtgatcgccc tggaggacct gaactctggc tttaagaata gccgcgtgaa ggtggagaag 2820
caggtgtatc agaagttcga gaagatgctg atcgataagc tgaactacat ggtggacaag 2880
aagtctaatc cttgtgcaac aggcggcgcc ctgaagggct atcagatcac caataagttc 2940
gagagcttta agtccatgtc tacccagaac ggcttcatct tttacatccc tgcctggctg 3000
acatccaaga tcgatccatc taccggcttt gtgaacctgc tgaaaaccaa gtataccagc 3060
atcgccgatt ccaagaagtt catcagctcc tttgacagga tcatgtacgt gcccgaggag 3120
gatctgttcg agtttgccct ggactataag aacttctctc gcacagacgc cgattacatc 3180
aagaagtgga agctgtactc ctacggcaac cggatcagaa tcttccggaa tcctaagaag 3240
aacaacgtgt tcgactggga ggaggtgtgc ctgaccagcg cctataagga gctgttcaac 3300
aagtacggca tcaattatca gcagggcgat atcagagccc tgctgtgcga gcagtccgac 3360
aaggccttct actctagctt tatggccctg atgagcctga tgctgcagat gcggaacagc 3420
atcacaggcc gcaccgacgt ggattttctg atcagccctg tgaagaactc cgacggcatc 3480
ttctacgata gccggaacta tgaggcccag gagaatgcca tcctgccaaa gaacgccgac 3540
gccaatggcg cctataacat cgccagaaag gtgctgtggg ccatcggcca gttcaagaag 3600
gccgaggacg agaagctgga taaggtgaag atcgccatct ctaacaagga gtggctggag 3660
tacgcccaga ccagcgtgaa gcac 3684

<210> SEQ ID NO 21
<211> LENGTH: 3921
<212> TYPE: DNA
<213> ORGANISM: Acidaminococcus sp. BV3L6

<400> SEQUENCE: 21
atgacacagt tcgagggctt taccaacctg tatcaggtga gcaagacact gcggtttgag 60
ctgatcccac agggcaagac cctgaagcac atccaggagc agggcttcat cgaggaggac 120
aaggcccgca atgatcacta caaggagctg aagcccatca tcgatcggat ctacaagacc 180
tatgccgacc agtgcctgca gctggtgcag ctggattggg agaacctgag cgccgccatc 240
gactcctata gaaaggagaa aaccgaggag acaaggaacg ccctgatcga ggagcaggcc 300
acatatcgca atgccatcca cgactacttc atcggccgga cagacaacct gaccgatgcc 360
atcaataaga gacacgccga gatctacaag ggcctgttca aggccgagct gtttaatggc 420
aaggtgctga agcagctggg caccgtgacc acaaccgagc acgagaacgc cctgctgcgg 480
agcttcgaca agtttacaac ctacttctcc ggcttttatg agaacaggaa gaacgtgttc 540
agcgccgagg atatcagcac agccatccca caccgcatcg tgcaggacaa cttccccaag 600
tttaaggaga attgtcacat cttcacacgc ctgatcaccg ccgtgcccag cctgcgggag 660
cactttgaga acgtgaagaa ggccatcggc atcttcgtga gcacctccat cgaggaggtg 720
ttttccttcc ctttttataa ccagctgctg acacagaccc agatcgacct gtataaccag 780
ctgctgggag gaatctctcg ggaggcaggc accgagaaga tcaagggcct gaacgaggtg 840
ctgaatctgg ccatccagaa gaatgatgag acagcccaca tcatcgcctc cctgccacac 900
agattcatcc ccctgtttaa gcagatcctg tccgatagga acaccctgtc tttcatcctg 960
gaggagttta agagcgacga ggaagtgatc cagtccttct gcaagtacaa gacactgctg 1020
agaaacgaga acgtgctgga gacagccgag gccctgttta acgagctgaa cagcatcgac 1080
ctgacacaca tcttcatcag ccacaagaag ctggagacaa tcagcagcgc cctgtgcgac 1140
cactgggata cactgaggaa tgccctgtat gagcggagaa tctccgagct gacaggcaag 1200
atcaccaagt ctgccaagga gaaggtgcag cgcagcctga agcacgagga tatcaacctg 1260
caggagatca tctctgccgc aggcaaggag ctgagcgagg ccttcaagca gaaaaccagc 1320
gagatcctgt cccacgcaca cgccgccctg gatcagccac tgcctacaac cctgaagaag 1380
caggaggaga aggagatcct gaagtctcag ctggacagcc tgctgggcct gtaccacctg 1440
ctggactggt ttgccgtgga tgagtccaac gaggtggacc ccgagttctc tgcccggctg 1500
accggcatca agctggagat ggagccttct ctgagcttct acaacaaggc cagaaattat 1560
gccaccaaga agccctactc cgtggagaag ttcaagctga actttcagat gcctacactg 1620
gcctctggct gggacgtgaa taaggagaag aacaatggcg ccatcctgtt tgtgaagaac 1680
ggcctgtact atctgggcat catgccaaag cagaagggca ggtataaggc cctgagcttc 1740
gagcccacag agaaaaccag cgagggcttt gataagatgt actatgacta cttccctgat 1800
gccgccaaga tgatcccaaa gtgcagcacc cagctgaagg ccgtgacagc ccactttcag 1860
acccacacaa cccccatcct gctgtccaac aatttcatcg agcctctgga gatcacaaag 1920
gagatctacg acctgaacaa tcctgagaag gagccaaaga agtttcagac agcctacgcc 1980
aagaaaaccg gcgaccagaa gggctacaga gaggccctgt gcaagtggat cgacttcaca 2040
agggattttc tgtccaagta taccaagaca acctctatcg atctgtctag cctgcggcca 2100
tcctctcagt ataaggacct gggcgagtac tatgccgagc tgaatcccct gctgtaccac 2160
atcagcttcc agagaatcgc cgagaaggag atcatggatg ccgtggagac aggcaagctg 2220
tacctgttcc agatctataa caaggacttt gccaagggcc accacggcaa gcctaatctg 2280
cacacactgt attggaccgg cctgttttct ccagagaacc tggccaagac aagcatcaag 2340
ctgaatggcc aggccgagct gttctaccgc cctaagtcca ggatgaagag gatggcacac 2400
cggctgggag agaagatgct gaacaagaag ctgaaggatc agaaaacccc aatccccgac 2460
accctgtacc aggagctgta cgactatgtg aatcacagac tgtcccacga cctgtctgat 2520
gaggccaggg ccctgctgcc caacgtgatc accaaggagg tgtctcacga gatcatcaag 2580
gataggcgct ttaccagcga caagttcttt ttccacgtgc ctatcacact gaactatcag 2640
gccgccaatt ccccatctaa gttcaaccag agggtgaatg cctacctgaa ggagcacccc 2700
gagacaccta tcatcggcat cgatcggggc gagagaaacc tgatctatat cacagtgatc 2760
gactccaccg gcaagatcct ggagcagcgg agcctgaaca ccatccagca gtttgattac 2820
cagaagaagc tggacaacag ggagaaggag agggtggcag caaggcaggc ctggtctgtg 2880
gtgggcacaa tcaaggatct gaagcagggc tatctgagcc aggtcatcca cgagatcgtg 2940
gacctgatga tccactacca ggccgtggtg gtgctggaga acctgaattt cggctttaag 3000
agcaagagga ccggcatcgc cgagaaggcc gtgtaccagc agttcgagaa gatgctgatc 3060
gataagctga attgcctggt gctgaaggac tatccagcag agaaagtggg aggcgtgctg 3120
aacccatacc agctgacaga ccagttcacc tcctttgcca agatgggcac ccagtctggc 3180
ttcctgtttt acgtgcctgc cccatataca tctaagatcg atcccctgac cggcttcgtg 3240
gacccettcg tgtggaaaac catcaagaat cacgagagcc gcaagcactt cctggagggc 3300
ttcgactttc tgcactacga cgtgaaaacc ggcgacttca tcctgcactt taagatgaac 3360
agaaatctgt ccttccagag gggcctgccc ggctttatgc ctgcatggga tatcgtgttc 3420
gagaagaacg agacacagtt tgacgccaag ggcacccctt tcatcgccgg caagagaatc 3480
gtgccagtga tcgagaatca cagattcacc ggcagatacc gggacctgta tcctgccaac 3540
gagctgatcg ccctgctgga ggagaagggc atcgtgttca gggatggctc caacatcctg 3600
ccaaagctgc tggagaatga cgattctcac gccatcgaca ccatggtggc cctgatccgc 3660
agcgtgctgc agatgcggaa ctccaatgcc gccacaggcg aggactatat caacagcccc 3720
gtgcgcgatc tgaatggcgt gtgcttcgac tcccggtttc agaacccaga gtggcccatg 3780
gacgccgatg ccaatggcgc ctaccacatc gccctgaagg gccagctgct gctgaatcac 3840
ctgaaggaga gcaaggatct gaagctgcag aacggcatct ccaatcagga ctggctggcc 3900
tacatccagg agctgcgcaa c 3921

<210> SEQ ID NO 22
<211> LENGTH: 21
<212> TYPE: DNA
<213> ORGANISM: Artificial Sequence
<220> FEATURE:
<223> OTHER INFORMATION: SV40 NLS

<400> SEQUENCE: 22
ccaaagaaga agcggaaggt c 21

<210> SEQ ID NO 23
<211> LENGTH: 48
<212> TYPE: DNA
<213> ORGANISM: Artificial Sequence
<220> FEATURE:
<223> OTHER INFORMATION: Nucleoplasmin NLS

<400> SEQUENCE: 23
aaaaggccgg cggccacgaa aaaggccggc caggcaaaaa agaaaaag 48

<210> SEQ ID NO 24
<211> LENGTH: 30
<212> TYPE: DNA
<213> ORGANISM: Artificial Sequence
<220> FEATURE:
<223> OTHER INFORMATION: Myc tag

<400> SEQUENCE: 24
gaacaaaaac tcatctcaga agaggatctg 30

<210> SEQ ID NO 25
<211> LENGTH: 113
<212> TYPE: DNA
<213> ORGANISM: Artificial Sequence
<220> FEATURE:
<223> OTHER INFORMATION: CHIP Oligo
<220> FEATURE:
<221> NAME/KEY: misc_feature
<222> LOCATION: (20)..(39)
<223> OTHER INFORMATION: n is a, c, g, or t
<220> FEATURE:
<221> NAME/KEY: misc_feature
<222> LOCATION: (72)..(94)
<223> OTHER INFORMATION: n is a, c, g, or t

<400> SEQUENCE: 25
agagaacctg cagagaccgn nnnnnnnnnn nnnnnnnnng tttagagacg gctaaatccg 60
cgtctcgaga tnnnnnnnnn nnnnnnnnnn nnnnttttag aggcaggtag aga 113

<210> SEQ ID NO 26
<211> LENGTH: 113
<212> TYPE: DNA
<213> ORGANISM: Artificial Sequence
<220> FEATURE:
<223> OTHER INFORMATION: CHIP Oligo with degenerate nucleotide code
<220> FEATURE:
<221> NAME/KEY: misc_feature
<222> LOCATION: (20)..(39)
<223> OTHER INFORMATION: n is a, c, g, or t
<220> FEATURE:
<221> NAME/KEY: misc_feature
<222> LOCATION: (72)..(94)
<223> OTHER INFORMATION: n is a, c, g, or t

<400> SEQUENCE: 26
agagaacctg cagagaccgn nnnnnnnnnn nnnnnnnnng tttdgagacg adddddddc 60 cgtctcdaga tnnnnnnnnn nnnnnnnnnn nnnnttttag aggcaggtag aga 113

<210> SEQ ID NO 27
<211> LENGTH: 120
<212> TYPE: DNA
<213> ORGANISM: Artificial Sequence
<220> FEATURE:
<223> OTHER INFORMATION: TOPO fragment As-Cas12a

<400> SEQUENCE: 27
cgtctctgtt tcagagctat gctggaaaca gcatagcaag ttgaaataag gctagtccgt 60
tatcaacttg aaaaagtggc accgagtcgg tgctaatttc tactcttgta gatagagacg 120

<210> SEQ ID NO 28
<211> LENGTH: 121
<212> TYPE: DNA
<213> ORGANISM: Artificial Sequence
<220> FEATURE:
<223> OTHER INFORMATION: TOPO fragment Lb-Cas12a

<400> SEQUENCE: 28
cgtctctgtt tcagagctat gctggaaaca gcatagcaag ttgaaataag gctagtccgt 60
tatcaacttg aaaaagtggc accgagtcgg tgctaatttc tactaagtgt agatagagac 120
g 121

<210> SEQ ID NO 29
<211> LENGTH: 171
<212> TYPE: DNA
<213> ORGANISM: Artificial Sequence
<220> FEATURE:
<223> OTHER INFORMATION: As-Cas12a hgRNA insert
<220> FEATURE:
<221> NAME/KEY: misc_feature
<222> LOCATION: (14)..(33)
<223> OTHER INFORMATION: n is a, c, g, t or u
<220> FEATURE:
<221> NAME/KEY: misc_feature
<222> LOCATION: (140)..(162)
<223> OTHER INFORMATION: n is a, c, g, t or u

<400> SEQUENCE: 29
ggacgaggta ccgnnnnnnn nnnnnnnnnn nnngtttcag agctatgctg gaaacagcat 60
agcaagttga aataaggcta gtccgttatc aacttgaaaa agtggcaccg agtcggtgct 120
aatttctact cttgtagatn nnnnnnnnnn nnnnnnnnnn nntttttttt t 171

<210> SEQ ID NO 30
<211> LENGTH: 172
<212> TYPE: DNA
<213> ORGANISM: Artificial Sequence
<220> FEATURE:
<223> OTHER INFORMATION: Lb-Cas12a hgRNA insert
<220> FEATURE:
<221> NAME/KEY: misc_feature
<222> LOCATION: (14)..(33)
<223> OTHER INFORMATION: n is a, c, g, t or u
<220> FEATURE:
<221> NAME/KEY: misc_feature
<222> LOCATION: (141)..(163)
<223> OTHER INFORMATION: n is a, c, g, t or u

<400> SEQUENCE: 30
ggacgaggta ccgnnnnnnn nnnnnnnnnn nnngtttcag agctatgctg gaaacagcat 60

-continued

```
agcaagttga aataaggcta gtccgttatc aacttgaaaa agtggcaccg agtcggtgct    120

aatttctact aagtgtagat nnnnnnnnnn nnnnnnnnnn nnntttttttt tt           172
```